(12) United States Patent
Axten et al.

(10) Patent No.: US 8,598,156 B2
(45) Date of Patent: Dec. 3, 2013

(54) CHEMICAL COMPOUNDS

(75) Inventors: Jeffrey Michael Axten, Collegeville, PA (US); Seth Wilson Grant, Collegeville, PA (US); Dirk A. Heerding, Collegeville, PA (US); Jesus Rual Medina, Collegeville, PA (US); Stuart Paul Romeril, Collegeville, PA (US); Jun Tang, Research Triangle Park, NC (US)

(73) Assignee: GlaxoSmithKline LLC, Philadelphia, PA (US)

( * ) Notice: Subject to any disclaimer, the term of this patent is extended or adjusted under 35 U.S.C. 154(b) by 0 days.

(21) Appl. No.: 13/637,127

(22) PCT Filed: Mar. 23, 2011

(86) PCT No.: PCT/US2011/029511
§ 371 (c)(1),
(2), (4) Date: Sep. 25, 2012

(87) PCT Pub. No.: WO2011/119663
PCT Pub. Date: Sep. 29, 2011

(65) Prior Publication Data
US 2013/0018038 A1 Jan. 17, 2013

Related U.S. Application Data

(60) Provisional application No. 61/381,480, filed on Sep. 10, 2010, provisional application No. 61/352,863, filed on Jun. 9, 2010, provisional application No. 61/317,476, filed on Mar. 25, 2010.

(51) Int. Cl.
*A01N 43/62* (2006.01)
*A61K 31/55* (2006.01)

(52) U.S. Cl.
USPC ........... 514/210.21; 514/262.1; 514/265.1; 514/301; 514/407; 514/260.1; 514/302; 544/280; 544/117; 544/262; 546/115; 546/119

(58) Field of Classification Search
None
See application file for complete search history.

(56) References Cited

U.S. PATENT DOCUMENTS

| | | | |
|---|---|---|---|
| 5,342,947 A | 8/1994 | Lackey et al. |
| 5,491,237 A | 2/1996 | Fang et al. |
| 5,559,235 A | 9/1996 | Luzzio et al. |
| 5,681,835 A | 10/1997 | Wilson |
| 5,877,219 A | 3/1999 | Wilson |
| 5,977,134 A | 11/1999 | Ciccarone et al. |
| 6,063,923 A | 5/2000 | Fang et al. |
| 6,207,716 B1 | 3/2001 | Wilson |
| 6,268,391 B1 | 7/2001 | Dickerson et al. |
| 6,329,416 B1 | 12/2001 | Grubb et al. |
| 6,391,882 B1 | 5/2002 | Moltzen et al. |
| 2002/0032204 A1 | 3/2002 | Moon et al. |
| 2005/0032871 A1 | 2/2005 | Tang et al. |
| 2005/0058035 A1 | 3/2005 | Kim |
| 2006/0014768 A1 | 1/2006 | Kawasaki et al. |
| 2006/0074102 A1 | 4/2006 | Cusack et al. |
| 2006/0128689 A1 | 6/2006 | Gomtsyan et al. |
| 2007/0179122 A1 | 8/2007 | Urmann et al. |
| 2007/0185097 A1 | 8/2007 | Zhao |
| 2007/0225269 A1 | 9/2007 | Cassayre et al. |
| 2008/0000864 A1 | 1/2008 | Shapiro |
| 2008/0025946 A1 | 1/2008 | Sivakumar et al. |

(Continued)

FOREIGN PATENT DOCUMENTS

EP 0359418 B1 10/1994
EP 0684231 A1 5/1995

(Continued)

OTHER PUBLICATIONS

Accession No. 1935:1160 CAPLUS, 1934.*

(Continued)

*Primary Examiner* — Brandon Fetterolf
*Assistant Examiner* — Jean Cornet
(74) *Attorney, Agent, or Firm* — Wayne J. Dustman; Edward R. Gimmi

(57) ABSTRACT

The invention is directed to substituted indoline derivatives. Specifically, the invention is directed to compounds according to Formula I:

(I)

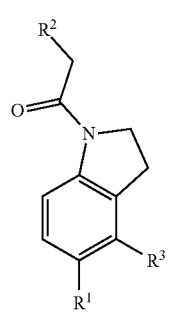

wherein $R^1$, $R^2$, and $R^3$ are defined herein.
The compounds of the invention are inhibitors of PERK and can be useful in the treatment of cancer, ocular diseases, and diseases associated with activated unfolded protein response pathways, such as Alzheimer's disease, stroke, Type 1 diabetes Parkinson disease, Huntington's disease, amyotrophic lateral sclerosis, myocardial infarction, cardiovascular disease, atherosclerosis, and arrhythmias, and more specifically cancers of the breast, colon, pancreatic, and lung. Accordingly, the invention is further directed to pharmaceutical compositions comprising a compound of the invention. The invention is still further directed to methods of inhibiting PERK activity and treatment of disorders associated therewith using a compound of the invention or a pharmaceutical composition comprising a compound of the invention.

17 Claims, No Drawings

(56) References Cited

U.S. PATENT DOCUMENTS

| | | |
|---|---|---|
| 2009/0221548 A1 | 9/2009 | Zhao |
| 2011/0124858 A1 | 5/2011 | Iwata et al. |
| 2012/0077828 A1* | 3/2012 | Axten et al. .............. 514/265.1 |

FOREIGN PATENT DOCUMENTS

| | | |
|---|---|---|
| JP | 2001072662 A1 | 3/2001 |
| JP | 2003237233 | 8/2003 |
| KR | 20100086745 | 8/2010 |
| WO | WO9312085 A1 | 6/1993 |
| WO | WO9827058 | 6/1998 |
| WO | WO9847885 | 10/1998 |
| WO | WO9850358 | 11/1998 |
| WO | WO 99/28313 | 6/1999 |
| WO | WO9943672 A1 | 9/1999 |
| WO | WO0015612 | 3/2000 |
| WO | WO 00/66166 | 11/2000 |
| WO | WO0112600 A1 | 2/2001 |
| WO | WO 02/051836 | 7/2002 |
| WO | WO02/059110 | 8/2002 |
| WO | WO02072549 A1 | 9/2002 |
| WO | WO2005/110410 | 11/2005 |
| WO | WO2005/121142 | 12/2005 |
| WO | WO2006032987 A1 | 3/2006 |
| WO | WO2006075152 | 7/2006 |
| WO | WO2006113864 A2 | 10/2006 |
| WO | WO2007024944 | 3/2007 |
| WO | WO2007026920 A2 | 3/2007 |
| WO | WO2007/056625 | 5/2007 |
| WO | WO2007076070 | 7/2007 |
| WO | WO2007146230 A2 | 12/2007 |
| WO | WO2008046083 A2 | 4/2008 |
| WO | WO2008060789 A2 | 5/2008 |
| WO | WO 2008/098104 | 8/2008 |
| WO | WO2009054914 | 4/2009 |
| WO | WO2009/062118 A2 | 5/2009 |
| WO | WO2009/062118 A3 | 5/2009 |
| WO | WO2009105504 | 8/2009 |
| WO | WO2009/151621 | 12/2009 |
| WO | WO 2010008777 | 2/2010 |
| WO | WO2010/045542 | 4/2010 |
| WO | WO2010/075561 | 7/2010 |
| WO | WO 2010093535 | 8/2010 |
| WO | WO2010/107765 | 9/2010 |
| WO | WO2010112124 | 10/2010 |
| WO | WO2010115491 | 10/2010 |
| WO | WO2010/129964 | 11/2010 |
| WO | WO2010129467 | 11/2010 |
| WO | PCT/US2011/029511 | 5/2011 |

OTHER PUBLICATIONS

Abraham, et al., *Current Opinion in Immunology*, 8(3):412-418 (1996).
Adams, et al., *Cancer Invest.*, 22(2):304-311 (2004).
Ameri, et al., *Blood*, 103:1876-82 (2004).
Ashby, et al., *Current Opinion in Lipidology*, 9(2):99-102 (1998).
Balasubramanian, et al., *Cancer Letters*, 280:211-221 (2009).
Ball, et al., *Progress in Cell Cycle Res.*, 3:125 (1997).
Bertrand, *European Journal of Medicinal Chemistry*, 45:2095-2116 (2010).
Bi, et al., *EMBO J*, 24:3470-81 (2005).
Blais, et al., *Cell Cycle*, 5:2874-7 (2006).
Bolen, et al., *Annual Review of Immunology*, 15:371-404 (1997).
Bouma, et al., *J. Antimicrob. Chemother.*, 42(6):817-820 (1998).
Brekken, et al., *Cancer Res.*, 60:5117-5124 (2000).
Brewer, et al., *Proc. National Academy of Science*, 97:12625-30 (2000).
Brodt, et al., *Biochemical Pharmacology*, 60:1101-1107 (2000).
Brown, et al., *National Rev. Cancer*, 4:437-47 (2004).
Bruns, et al., *Cancer Research*, 60:2926-2935 (2000).
Canman, et al., *Oncogene*, 17(25):3301-3308 (1998).
Chen, et al., *Cancer Research*, 58:1965-1971 (1998).
Cullinan, et al., *J. Biological Chemistry*, 279:20108-17 (2004).
Dar, et al., *Cell*, 122:887-900 (2005).
Davies, et al., *Int. J. Cancer*, 123:85-8 (2008).
Delepine, et al., *National Genetology*, 25:406-9 (2000).
Einzig, et al., *Proc. Am. Soc. Clin. Oncol.*, 20:46.
Feldman, et al., *Molecular Cancer Research*, 3:597-605 (2005).
Feling, et al., *Angew. Chem. Int. Ed. Engl.*, 42(3):355-357 (2003).
Forastiere, et al., *Sem. Oncol.*, 20:56 (1990).
Gerster, et al., *J. Het. Chem.*, 6:207-213 (1969).
Gottlicher, et al., *EMBO J.*, 20(24):6969-6978 (2001).
Green, et al., *Cancer Treat. Rev.*, 26(4):269-286 (2000).
Gupta, et al., *PLoS One*, Perk Regulates Proliferation, 4:e8008 (2009).
Hamanaka, et al., *Molecular Biology Cell*, 16:5493-501 (2005).
Hamanaka, et al., *Oncogene*, 28:910-20 (2009).
Harding, et al., *Molecular Cell*, 7:1153-63 (2001).
Holmes, et al., *J. Nat. Cancer Inst.*, 83:1797 (1991).
Iida, et al., *BMC Cell Biology*, 8:38 (2007).
Jackson, et al., *International Journal of Biochemistry and Cell Biology*, 29(7):935-938 (1997).
Jia, et al., *Blood*, 102(5):1824-1832 (2003).
Jorgensen, et al., *BMC Cancer*, 8:229 (2008).
Kanekura, et al., *Molecular Neurobiology*, 39(2):81-89 (2009).
Kath, John C., *Exp. Opinion Ther. Patents*, 10(6):803-818 (2000).
Kearns, et al., *Seminars in Oncology*, 3(6):16-23 (1995).
Kingston, et al., *Studies in Organic Chemistry*, 26:219-235 (1986).
Kitada, et al., *Antisense Res. Dev.*, 4:71-79 (1994).
Koumenis, et al., *Molecular Cell Biology*, 22:7405-16 (2002).
Koumenis, et al., *Molecular Cell Biology*, 4:423-36 (2006).
Kuhn, et al., *Blood*, 110:3281-3290 (2007).
Kumar, et al., *J. Biol. Chem.*, 256:10435-10441 (1981).
Lackey, et al., *Bioorganic and Medicinal Chemistry Letters*, 10:223-226 (2000).
Leder, et al., *Cancer Cell*, 425:9 (2006).
Lee, et al., *Mol. Cell. Endocrinol.*, 188:47-54 (2002).
Lenova, et al., *Chemistry of Heterocyclic Compounds*, 18(7):753-755 (1982).
Ma, et al., *Journal of Biology Chemistry*, 277:18728-35 (2002).
Ma, et al., *National Rev. Cancer*, 4:966-77 (2004).
Ma, et al., *Rapid Commun. Mass. Spectrom*, 15:1693-700 (2001).
Marciniak, et al., *J. Cellular Biology*, 172:201-9 (2006).
Markman, et al., *Yale Journal of Biology and Medicine*, 64:583 (1991).
Marks, et al., *Nature Biotechnology*, 25:84-90 (2007).
Martinez-Iacaci, et al., *Int. J. Cancer*, 88(1):44-52 (2000).
Massague, et al., *Cancer Surveys*, 27:41-64 (1996).
McAlpine, et al., *Drug Targets*, 10(2):151-157 (2010).
McGuire, et al., *Ann, Intern. Med.*, 111:273 (1989).
Melnikova, Irene, *Nature Reviews Drug Discovery*, 4:711-712 (2005).
Miyazaki, et al., *Bioorganic and Medicinal Chemistry Letters*, 17:250-254 (2007).
Nassif, et al., *Amyotrophic Lateral Sclerosis Pathogenesis*, 13(12):1955-1989 (2010).
O'Connor, et al., *Neuron*, 60(6):988-1009 (2008).
Oliff, BioChimica et Biophysica Acta, (1999) 1423(3):19-30.
Panobinostat, *Drugs of the Future*, 32(4):315-322 (2007).
Paschen, et al., *Current Neurovascular Research*, 1:173-181 (2004).
Pearce, et al., *Nature Reviews Molecular Cell Biology*, 11:9-22 (2010).
Philip, et al., *Cancer Treatment and Research*, 78:3-27 (1995).
Reilly, et al., *Cancer Research*, 60:3569-3576 (2000).
Richon, et al., *Proc. Nat. Acad. Sci.*, 97(18):10014-10019 (2000).
Romero-Ramirez, L., et al., *Cancer Research*, 64:5943-5947 (2004).
Rosania, et al., *Exp. Opin. Ther. Patents*, 10(2):215-230 (2000).
Rouschop, K.M., et al., *J. Clin. Invest.*, 120:127-141 (2010).
Salminen, A., et al., *Journal of Neuroinflammation*, 6:41 (2009).
Scharovsky, et al., *Journal of Biomedical Science*, 7(4):292-298 (2000).
Schreiber, et al., *Science*, 232:1250-1253 (1986).
Schiff, et al., *Nature*, 277:665-667 (1979).
Schiff, et al., *Proc. National Academy of Science USA*, 77:1561-1565 (1980).

(56) References Cited

OTHER PUBLICATIONS

Shawyer, et al., *DDT*, 2: Feb. 1997.
Shi, Y., et al., *Molecular Cell. Biol.*, 18:7499-509 (1998).
Sinh, et al., *Journal of Hematotherapy and Stem Cell Research*, 8(5):465-480 (1999).
Smithgall, let al., *Journal of Pharmacological and Toxicological Methods*, 34(3):125-132 (1995).
Sood, R., et al., *Biochem. J.*, 2:281-293 (2000).
Stenger, et al., *Community Oncology*, 4:384-386 (2007).
Su, Q., *J. Biol. Chem.*, 283:469-475 (2008).
Tabas, et al., *Annals of New York Academy of Sciences*, 1173(S1):E40-E45 (2009).
Tennant, et al., *Nature Reviews*, 267 (2010).
Vigushin, et al., *Anticancer Drugs*, 13(1):1-13 (2002).
Vinodhkumar, et al., *Biomedicine & Pharmacotherapy*, 62:85-93 (2008).
Water, et al., *J. Clinical Oncology*, 18:1812-1823 (2000).
Wani, et al., *J. American Chem. Soc.*, 93:2325 (1971).
Williamson, et al., *The Journal of Allergy and Clinical Immunology*, 118(6):1369-1374 (2006).
Woo, et al., *Nature*, 368:750 (1994).
Yamamoto, et al., *Journal of Biochemistry*, 126(5):799-803 (1999).
Yen, et al., *Oncogene*, 19:3460-3469 (2000).
Zhang, W., et al., *Cell Metab.*, 4:491-497 (2006).
Zhong, et al., *Cancer Research*, 60(6):1541-1545 (2000).
European Search Report dated Jul. 10, 2013.

\* cited by examiner

CHEMICAL COMPOUNDS

This application is a 371 of International Application No. PCT/US2011/029511, filed 23 Mar. 2011, which claims the benefit of: U.S. Provisional Application No. 61/419,068, filed 2 Dec. 2010; U.S. Provisional Application No. 61/388,151, filed 30 Sep. 2010; U.S. Provisional Application No. 61/381,480, filed 10 Sep. 2010; U.S. Provisional Application No. 61/352,863, filed 9 Jun. 2010; and U.S. Provisional Application No. 61/317,476, filed 25 Mar. 2010.

FIELD OF THE INVENTION

The present invention relates to substituted indoline derivatives that are inhibitors of the activity of the protein kinase R (PKR)-like ER kinase, PERK. The present invention also relates to pharmaceutical compositions comprising such compounds and methods of using such compounds in the treatment of cancer, ocular diseases and diseases associated with activated unfolded protein response pathways, such as Alzheimer's disease, stroke, Type 1 diabetes, Parkinson disease, Huntington's disease, amyotrophic lateral sclerosis, myocardial infarction, cardiovascular disease, atherosclerosis, and arrhythmias.

BACKGROUND OF THE INVENTION

The unfolded protein response (UPR) is a signal transduction pathway that allows cells to survive environmental stresses that perturb protein folding and maturation in the endoplasmic reticulum (ER) (Ma and Hendershot, 2004), (Feldman et al., 2005), (Koumenis and Wouters, 2006). Stress stimuli that activate UPR include hypoxia, disruption of protein glycosylation (glucose deprivation), depletion of luminal ER calcium, or changes in ER redox status (Ma and Hendershot, 2004), (Feldman et al., 2005). These perturbations result in the accumulation of unfolded or mis-folded proteins in the ER, which is sensed by resident ER membrane proteins. These proteins activate a coordinated cellular response to alleviate the impact of the stress and enhance cell survival. Responses include an increase in the level of chaperone proteins to enhance protein re-folding, degradation of the mis-folded proteins, and translational arrest to decrease the burden of proteins entering the ER. These pathways also regulate cell survival by modulating apoptosis (Ma and Hendershot, 2004), (Feldman et al., 2005), (Hamanaka et al., 2009) and autophagy (Rouschop et al.), and can trigger cell death under conditions of prolonged ER stress.

Three ER membrane proteins have been identified as primary effectors of the UPR: protein kinase R (PKR)-like ER kinase [PERK, also known as eukaryotic initiation factor 2A kinase 3 (EIF2AK3), or pancreatic eIF2α kinase (PEK)], inositol-requiring gene 1 α/β (IRE1), and activating transcription factor 6 (ATF6) (Ma and Hendershot, 2004). Under normal conditions these proteins are held in the inactive state by binding to the ER chaperone, GRP78 (BiP). Accumulation of unfolded proteins in the ER leads to release of GRP78 from these sensors resulting in their activation (Ma et al., 2002). PERK is a type I ER membrane protein containing a stress-sensing domain facing the ER lumen, a transmembrane segment, and a cytosolic kinase domain (Shi et al., 1998), (Sood et al., 2000). Release of GRP78 from the stress-sensing domain of PERK results in oligomerization and autophosphorylation at multiple serine, threonine and tyrosine residues (Ma et al., 2001), (Su et al., 2008). The major substrate for PERK is the eukaryotic initiation factor 2α (eIF2α) at serine-51 (Marciniak et al., 2006). This site is also phosphorylated by other PERK family members [(general control non-derepressed 2 (GCN2), PKR, and heme-regulated kinase (HRI)] in response to different stimuli, and by pharmacological inducers of ER stress such as thapsigargin and tunicamycin. Phosphorylation of eIF2α converts it to an inhibitor of eIF2B, which hinders the assembly of the 40S ribosome translation initiation complex and consequently reduces the rate of translation initiation. Among other effects, this leads to a loss of cyclin D1 in cells resulting in arrest in the G1 phase of the cell division cycle (Brewer and Diehl, 2000), (Hamanaka et al., 2005). Paradoxically, translation of certain messages encoding downstream effectors of eIF2α, ATF4 and CHOP (C/EBP homologous protein; GADD153), which modulate cellular survival pathways, is actually increased upon ER stress. A second PERK substrate, Nrf2, regulates cellular redox potential, contributes to cell adaptation to ER stress, and promotes survival (Cullinan and Diehl, 2004). The normal function of PERK is to protect secretory cells from ER stress. Phenotypes of PERK knockout mice include diabetes, due to loss of pancreatic islet cells, skeletal abnormalities, and growth retardation (Harding et al., 2001), (Zhang et al., 2006), (Iida et al., 2007). These features are similar to those seen in patients with Wolcott-Rallison syndrome, who carry germline mutations in the PERK gene (Delepine et al., 2000). IRE1 is a transmembrane protein with kinase and endonulease (RNAse) functions (Feldman et al., 2005) (Koumenis and Wouters, 2006). Under ER stress, it undergoes oligomerization and autophosphorylation, which activates the endonuclease to excise an intron from unspliced X-box binding protein 1 (XBP1) mRNA. This leads to the synthesis of truncated XBP1s, which activates transcription of UPR genes. The third effector of UPR, ATF6, is transported to the golgi upon ER stress, where it is cleaved by proteases to release the cytosolic transcription domain. This domain translocates to the nucleus and activates transcription of UPR genes (Feldman et al., 2005), (Koumenis and Wouters, 2006).

Tumor cells experience episodes of hypoxia and nutrient deprivation during their growth due to inadequate blood supply and aberrant blood vessel function (Brown and Wilson, 2004), (Blais and Bell, 2006). Thus, they are likely to be dependent on active UPR signaling to facilitate their growth. Consistent with this, mouse fibroblasts derived from PERK-/-, XBP1-/-, and ATF4-/- mice, and fibroblasts expressing mutant eIF2α show reduced clonogenic growth and increased apoptosis under hypoxic conditions in vitro and grow at substantially reduced rates when implanted as tumors in nude mice (Koumenis et al., 2002), (Romero-Ramirez et al., 2004), (Bi et al., 2005). Human tumor cell lines carrying a dominant negative PERK that lacks kinase activity also showed increased apoptosis in vitro under hypoxia and impaired tumor growth in vivo (Bi et al., 2005). In these studies, activation of the UPR was observed in regions within the tumor that coincided with hypoxic areas. These areas exhibited higher rates of apoptosis compared to tumors with intact UPR signaling. Further evidence supporting the role of PERK in promoting tumor growth is the observation that the number, size, and vascularity of insulinomas arising in transgenic mice expressing the SV40-T antigen in the insulin-secreting beta cells, was profoundly reduced in PERK -/- mice compared to wild-type control (Gupta et al., 2009). Activation of the UPR has also been observed in clinical specimens. Human tumors, including those derived from cervical carcinomas, glioblastomas (Bi et al., 2005), lung cancers (Jorgensen et al., 2008) and breast cancers (Ameri et al., 2004), (Davies et al., 2008) show elevated levels of proteins involved in UPR, compared to normal tissues. Therefore, inhibiting the unfolded protein response with compounds that block the activity of PERK and other components of the UPR is expected to have utility as anticancer agents and in the treatment of diseases associated with activated unfolded protein response pathways, such as Alzheimer's disease, stroke and Type 1 diabetes.

Loss of endoplasmic reticulum homeostasis and accumulation of misfolded proteins can contribute to a number of disease states including cardiovascular and degenerative diseases (Paschen, 2004) such as: Alzheimer's disease (Salminen et al., 2009 and O'Connor et. al. 2008), Parkinson disease, Huntington's disease, amyotrophic lateral sclerosis (Kanekura et. al., 2009 and Nassif et. al. 2010), myocardial infarction, cardiovascular disease, atherosclerosis (McAlpine et. al, 2010), and arrhythmias. A PERK inhibitor is expected to have utility in the treatment of such cardiovascular and degenerative diseases in which the underlying pathology and symptoms are associated with dysregulaton of the unfolded protein response.

REFERENCES

Ameh, K., Lewis, C. E., Raida, M., Sowter, H., Hai, T., and Harris, A. L. (2004). Anoxic induction of ATF-4 through HIF-1-independent pathways of protein stabilization in human cancer cells, Blood 103, 1876-82.

Bi, M., Naczki, C., Koritzinsky, M., Fels, D., Blais, J., Hu, N., Harding, H., Novoa, I., Varia, M., Raleigh, J., et al. (2005). ER stress-regulated translation increases tolerance to extreme hypoxia and promotes tumor growth, EMBO J. 24, 3470-81.

Blais, J., and Bell, J. C. (2006). Novel therapeutic target: the PERKs of inhibiting the integrated stress response, Cell Cycle 5, 2874-7.

Brewer, J. W., and Diehl, J. A. (2000). PERK mediates cell-cycle exit during the mammalian unfolded protein response, Proc Natl Acad Sci USA 97, 12625-30.

Brown, J. M., and Wilson, W. R. (2004). Exploiting tumour hypoxia in cancer treatment, Nat Rev Cancer 4, 437-47.

Cullinan, S. B., and Diehl, J. A. (2004). PERK-dependent activation of Nrf2 contributes to redox homeostasis and cell survival following endoplasmic reticulum stress, J Biol Chem 279, 20108-17.

Davies, M. P., Barraclough, D. L., Stewart, C., Joyce, K. A., Eccles, R. M., Barraclough, R., Rudland, P. S., and Sibson, D. R. (2008). Expression and splicing of the unfolded protein response gene XBP-1 are significantly associated with clinical outcome of endocrine-treated breast cancer, Int J Cancer 123, 85-8.

Delepine, M., Nicolino, M., Barrett, T., Golamaully, M., Lathrop, G. M., and Julier, C. (2000). EIF2AK3, encoding translation initiation factor 2-alpha kinase 3, is mutated in patients with Wolcott-Rallison syndrome, Nat Genet. 25, 406-9.

Feldman, D. E., Chauhan, V., and Koong, A. C. (2005). The unfolded protein response: a novel component of the hypoxic stress response in tumors, Mol Cancer Res 3, 597-605. Gupta, S., McGrath, B., and Cavener, D. R. (2009). PERK regulates the proliferation and development of insulin-secreting beta-cell tumors in the endocrine pancreas of mice, PLoS One 4, e8008.

Hamanaka, R. B., Bennett, B. S., Cullinan, S. B., and Diehl, J. A. (2005). PERK and GCN2 contribute to eIF2alpha phosphorylation and cell cycle arrest after activation of the unfolded protein response pathway, Mol Biol Cell 16, 5493-501.

Hamanaka, R. B., Bobrovnikova-Marjon, E., Ji, X., Liebhaber, S. A., and Diehl, J. A. (2009). PERK-dependent regulation of IAP translation during ER stress, Oncogene 28, 910-20.

Harding, H. P., Zeng, H., Zhang, Y., Jungries, R., Chung, P., Plesken, H., Sabatini, D. D., and Ron, D. (2001). Diabetes mellitus and exocrine pancreatic dysfunction in perk−/− mice reveals a role for translational control in secretory cell survival, Mol Cell 7, 1153-63.

Iida, K., Li, Y., McGrath, B. C., Frank, A., and Cavener, D. R. (2007). PERK eIF2 alpha kinase is required to regulate the viability of the exocrine pancreas in mice, BMC Cell Biol 8, 38.

Jorgensen, E., Stinson, A., Shan, L., Yang, J., Gietl, D., and Albino, A. P. (2008). Cigarette smoke induces endoplasmic reticulum stress and the unfolded protein response in normal and malignant human lung cells, BMC Cancer 8, 229.

Kanekura, K.; Suzuki, H.; Aiso, S.; Matsuoka, M. ER Stress and Unfolded Protein Response in Amyotrophic Lateral Sclerosis Molecular Neurobiology (2009), 39(2), 81-89.

Koumenis, C., Naczki, C., Koritzinsky, M., Rastani, S., Diehl, A., Sonenberg, N., Koromilas, A., and Wouters, B. G. (2002). Regulation of protein synthesis by hypoxia via activation of the endoplasmic reticulum kinase PERK and phosphorylation of the translation initiation factor eIF2alpha, Mol Cell Biol 22, 7405-16.

Koumenis, C., and Wouters, B. G. (2006). "Translating" tumor hypoxia: unfolded protein response (UPR)-dependent and UPR-independent pathways, Mol Cancer Res 4, 423-36.

Ma, K., Vattem, K. M., and Wek, R. C. (2002). Dimerization and release of molecular chaperone inhibition facilitate activation of eukaryotic initiation factor-2 kinase in response to endoplasmic reticulum stress, J Biol Chem 277, 18728-35.

Ma, Y., and Hendershot, L. M. (2004). The role of the unfolded protein response in tumour development: friend or foe?, Nat Rev Cancer 4, 966-77.

Ma, Y., Lu, Y., Zeng, H., Ron, D., Mo, W., and Neubert, T. A. (2001). Characterization of phosphopeptides from protein digests using matrix-assisted laser desorption/ionization time-of-flight mass spectrometry and nanoelectrospray quadrupole time-of-flight mass spectrometry, Rapid Commun Mass Spectrom 15, 1693-700.

Marciniak, S. J., Garcia-Bonilla, L., Hu, J., Harding, H. P., and Ron, D. (2006). Activation-dependent substrate recruitment by the eukaryotic translation initiation factor 2 kinase PERK, J Cell Biol 172, 201-9.

McAlpine, C. S.; Bowes, A. J.; and Werstuck, G. H. (2010) Diabetes, hyperglycemia and accelerated atherosclerosis: evidence supporting a role for endoplasmic reticulum (ER) stress signaling. Cardiovascular & Hematological Disorders: Drug Targets 10(2), 151-157.

Nassif, M.; Matus, S.; Castillo, K.; and Hetz, C. (2010) Amyotrophic Lateral Sclerosis Pathogenesis: A Journey Through the Secretory Pathway Antioxidants & Redox Signaling 13(12), 1955-1989.

O'Connor, T.; Sadleir, K. R.; Maus, E.; Velliquette, R. A.; Zhao, J.; Cole, S. L.; Eimer, W. A.; Hitt, B.; Bembinster, L. A.; Lammich, S. Lichtenthaler, S. F., Hebert, S. S., De Strooper, B., Haass, C., Bennett, D. A., Vassar, R. (2008) Phosphorylation of the translation initiation factor eIF2α increases BACE1 levels and promotes amyloidogenesis. Neuron, 60(6), 988-1009.

Paschen, W. (2004) Endoplasmic reticulum dysfunction in brain pathology: Critical role of protein synthesis Current Neurovascular Research, 1(2), 173-181.

Romero-Ramirez, L., Cao, H., Nelson, D., Hammond, E., Lee, A. H., Yoshida, H., Mori, K., Glimcher, L. H., Denko, N. C., Giaccia, A. J., et al. (2004). XBP1 is essential for survival under hypoxic conditions and is required for tumor growth, Cancer Res 64, 5943-7.

Rouschop, K. M., van den Beucken, T., Dubois, L., Niessen, H., Bussink, J., Savelkouls, K., Keulers, T., Mujcic, H., Landuyt, W., Voncken, J. W., et al. The unfolded protein response protects human tumor cells during hypoxia through regulation of the autophagy genes MAP1LC3B and ATG5, J Clin Invest 120, 127-41.

Salminen, A.; Kauppinen, A.; Suuronen, T.; Kaarniranta, K.; Ojala, J. ER stress in Alzheimer's disease: a novel neuronal trigger for inflammation and Alzheimer's pathology. Journal of Neuroinflammation (2009), 6:41.

Shi, Y., Vattem, K. M., Sood, R., An, J., Liang, J., Stramm, L., and Wek, R. C. (1998). Identification and characterization of pancreatic eukaryotic initiation factor 2 alpha-subunit kinase, PEK, involved in translational control, Mol Cell Biol 18, 7499-509.

Sood, R., Porter, A. C., Ma, K., Quilliam, L. A., and Wek, R. C. (2000). Pancreatic eukaryotic initiation factor-2alpha kinase (PEK) homologues in humans, *Drosophila melanogaster* and *Caenorhabditis elegans* that mediate translational control in response to endoplasmic reticulum stress, Biochem J 346 Pt 2, 281-93.

Su, Q., Wang, S., Gao, H. Q., Kazemi, S., Harding, H. P., Ron, D., and Koromilas, A. E. (2008). Modulation of the eukaryotic initiation factor 2 alpha-subunit kinase PERK by tyrosine phosphorylation, J Biol Chem 283, 469-75.

Tabas, I.; Seimon, T.; Timmins, J.; Li, G.; Lim, W. Macrophage apoptosis in advanced atherosclerosis Annals of the New York Academy of Sciences (2009), 1173(S1), E40-E45.

Zhang, W., Feng, D., Li, Y., Iida, K., McGrath, B., and Cavener, D. R. (2006). PERK EIF2AK3 control of pancreatic beta cell differentiation and proliferation is required for postnatal glucose homeostasis, *Cell Metab* 4, 491-7.

It is an object of the instant invention to provide novel compounds that are inhibitors of PERK.

It is also an object of the present invention to provide pharmaceutical compositions that comprise a pharmaceutical carrier and compounds useful in the methods of the invention.

It is also an object of the present invention to provide a method for treating cancer, and diseases associated with activated unfolded protein response pathways, such as Alzheimer's disease, stroke, Type 1 diabetes, Parkinson disease, Huntington's disease, amyotrophic lateral sclerosis, myocardial infarction, cardiovascular disease, atherosclerosis, and arrhythmias, that comprises administering such inhibitors of PERK activity.

SUMMARY OF THE INVENTION

In one aspect, the invention is directed to substituted indoline derivatives, specifically, to compounds according to Formula I:

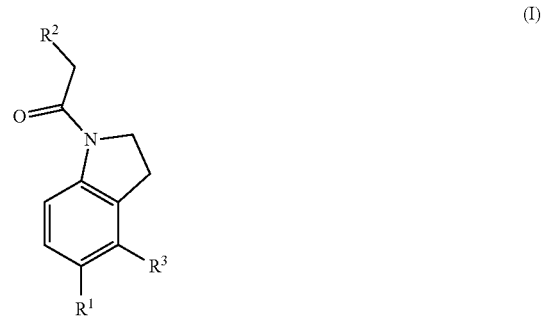

(I)

wherein $R^1$, $R^2$ and $R^3$ are defined below.

The present invention also relates to the discovery that the compounds of Formula (I) are active as inhibitors of PERK.

This invention also relates to a method of treating cancer, which comprises administering to a subject in need thereof an effective amount of a PERK inhibiting compound of Formula (I).

This invention also relates to a method of treating Alzheimer's disease, which comprises administering to a subject in need thereof an effective amount of a PERK inhibiting compound of Formula (I).

This invention also relates to a method of treating stroke, which comprises administering to a subject in need thereof an effective amount of a PERK inhibiting compound of Formula (I).

This invention also relates to a method of treating Type 1 diabetes, which comprises administering to a subject in need thereof an effective amount of a PERK inhibiting compound of Formula (I).

This invention also relates to a method of treating a disease state selected from: Parkinson disease, Huntington's disease, amyotrophic lateral sclerosis, myocardial infarction, cardiovascular disease, atherosclerosis, and arrhythmias, which comprises administering to a subject in need thereof an effective amount of a PERK inhibiting compound of Formula (I).

In a further aspect of the invention there is provided novel processes and novel intermediates useful in preparing the presently invented PERK inhibiting compounds.

Included in the present invention are pharmaceutical compositions that comprise a pharmaceutical carrier and compounds useful in the methods of the invention.

Also included in the present invention are methods of co-administering the presently invented PERK inhibiting compounds with further active ingredients.

DETAILED DESCRIPTION OF THE INVENTION

This invention relates to novel compounds of Formula (I):

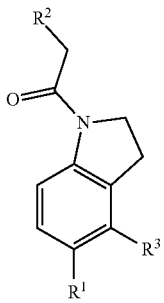

(I)

wherein:
R$^1$ is selected from:
bicycloheteroaryl, and
bicycloheteroaryl substituted with from one to five substituents independently selected from:
halo,
C$_{1-6}$alkyl,
C$_{1-4}$alkyloxy,
—OH,
hydroxyC$_{1-4}$alkyl,
—COOH,
—CONH$_2$,
tetrazole,
—CF$_3$,
—C$_{1-4}$alkylOC$_{1-4}$alkyl,
—CH$_2$CH$_2$N(H)C(O)OCH$_2$aryl,
diC$_{1-4}$alkylaminoC$_{1-4}$alkyl,
aminoC$_{1-4}$alkyl,
—NO$_2$,
—NH$_2$,
—CN,
aryl,
aryl substituted with from one to three substituents independently selected from: C$_{1-4}$alkyl, diC$_{1-4}$alkylaminoC$_{1-4}$alkyl, fluoro, chloro, bromo, iodo and —CF$_3$,
heterocycloalkyl,
heterocycloalkyl substituted with from one to three substituents independently selected from: C$_{1-4}$alkyl, diC$_{1-4}$alkylaminoC$_{1-4}$alkyl, fluoro, chloro, bromo, iodo and —CF$_3$,
_C$_{1-4}$alkylheterocycloalkyl,
_C$_{1-4}$alkylheterocycloalkyl substituted with from one to three substituents independently selected from: C$_{1-4}$alkyl,
diC$_{1-4}$alkylaminoC$_{1-4}$alkyl, fluoro, chloro, bromo, iodo and —CF$_3$, heteroaryl, and
heteroaryl substituted with from one to three substituents independently selected from: C$_{1-4}$alkyl, diC$_{1-4}$alkylaminoC$_{1-4}$alkyl, fluoro, chloro, bromo, iodo and —CF$_3$;
R$^2$ is selected from:
aryl,
aryl substituted with form one to five substituents independently selected from: fluoro, chloro, bromo, iodo, C$_{1-4}$alkyl, C$_{1-4}$alkyloxy, —OH, —COOH, —CONH$_2$, —CF$_3$, —C$_{1-4}$alkylOC$_{1-4}$alkyl, —NO$_2$, —NH$_2$ and CN,
heteroaryl,
heteroaryl substituted with from one to five substituents independently selected from: fluoro, chloro, bromo, iodo, C$_{1-4}$alkyl, C$_{1-4}$alkyloxy, —OH, —COOH, —CONH$_2$, —CF$_3$, —C$_{1-4}$alkylOC$_{1-4}$alkyl, —NO$_2$, —NH$_2$ and CN,
cycloalkyl, and
cycloalkyl substituted with from one to five substituents independently selected from: fluoro, chloro, bromo, iodo, C$_{1-4}$alkyl, C$_{1-4}$alkyloxy, —OH, —COOH, —CONH$_2$, —CF$_3$, —C$_{1-4}$alkylOC$_{1-4}$alkyl, —NO$_2$, —NH$_2$ and CN; and
R$^3$ is selected from: hydrogen, fluoro, chloro, bromo and iodo;
and salts thereof.

This invention also relates to pharmaceutically acceptable salts of the compounds of Formula (I).

Suitably the compound of Formula (I) is not 3-[1-(phenylacetyl)-2,3-dihydro-1H-indol-5-yl]-7-(3-pyridinyl)thieno[3,2-c]pyridin-4-amine.

For compounds of Formula (I), suitably R$^1$ is bicycloheteroaryl substituted with from one to three substituents independently selected from:
halo,
C$_{1-6}$alkyl,
C$_{1-4}$alkyloxy,
—OH,
hydroxyC$_{1-4}$alkyl,
—COOH,
—CONH$_2$,
tetrazole,
—CF$_3$,
—C$_{1-4}$alkylOC$_{1-4}$alkyl,
—CH$_2$CH$_2$N(H)C(O)OCH$_2$aryl,
diC$_{1-4}$alkylaminoC$_{1-4}$alkyl,
aminoC$_{1-4}$alkyl,
—NO$_2$,
—NH$_2$,
—CN,
aryl,
aryl substituted with from one to three substituents independently selected from: C$_{1-4}$alkyl, diC$_{1-4}$alkylaminoC$_{1-4}$alkyl, fluoro, chloro, bromo, iodo and —CF$_3$,
heterocycloalkyl,
heterocycloalkyl substituted with from one to three substituents independently selected from: C$_{1-4}$alkyl, diC$_{1-4}$alkylaminoC$_{1-4}$alkyl, fluoro, chloro, bromo, iodo and —CF$_3$,
_C$_{1-4}$alkylheterocycloalkyl,
_C$_{1-4}$alkylheterocycloalkyl substituted with from one to three substituents independently selected from: C$_{1-4}$alkyl,
diC$_{1-4}$alkylaminoC$_{1-4}$alkyl, fluoro, chloro, bromo, iodo and —CF$_3$, heteroaryl, and
heteroaryl substituted with from one to three substituents independently selected from: C$_{1-4}$alkyl, diC$_{1-4}$alkylaminoC$_{1-4}$alkyl, fluoro, chloro, bromo, iodo and —CF$_3$.

For compounds of Formula (I), suitably R$^1$ is bicycloheteroaryl substituted with from one to three substituents independently selected from:
halo,
C$_{1-6}$alkyl,
C$_{1-4}$alkyloxy,
—OH,
hydroxyC$_{1-4}$alkyl,
—COOH,
tetrazole,
—CF$_3$, —C$_{1-4}$alkylOC$_{1-4}$alkyl,
—CH$_2$CH$_2$N(H)C(O)OCH$_2$aryl,
diC$_{1-4}$alkylaminoC$_{1-4}$alkyl,
aminoC$_{1-4}$alkyl,
—NO$_2$,
—NH$_2$,
CN,
aryl,
aryl substituted with from one to three substituents independently selected from: C$_{1-4}$alkyl, diC$_{1-4}$alkylaminoC$_{1-4}$alkyl, fluoro, chloro, bromo, iodo and —CF$_3$,
heterocycloalkyl,
heterocycloalkyl substituted with from one to three substituents independently selected from: C$_{1-4}$alkyl, diC$_{1-4}$alkylaminoC$_{1-4}$alkyl, fluoro, chloro, bromo, iodo and —CF$_3$,
_C$_{1-4}$alkylheterocycloalkyl,
_C$_{1-4}$alkylheterocycloalkyl substituted with from one to three substituents independently selected from: C$_{1-4}$alkyl,
diC$_{1-4}$alkylaminoC$_{1-4}$alkyl, fluoro, chloro, bromo, iodo and —CF$_3$, heteroaryl, and
heteroaryl substituted with from one to three substituents independently selected from: C$_{1-4}$alkyl, diC$_{1-4}$alkylaminoC$_{1-4}$alkyl, fluoro, chloro, bromo, iodo and —CF$_3$.

For compounds of Formula (I), suitably R$^1$ is selected from the following bicycloheteroaryls, wherein the attachment position is designated with a wavy line:

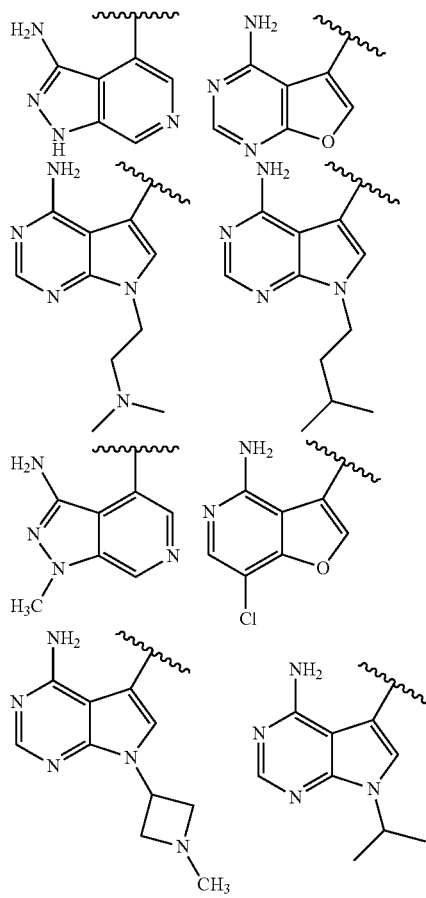

-continued

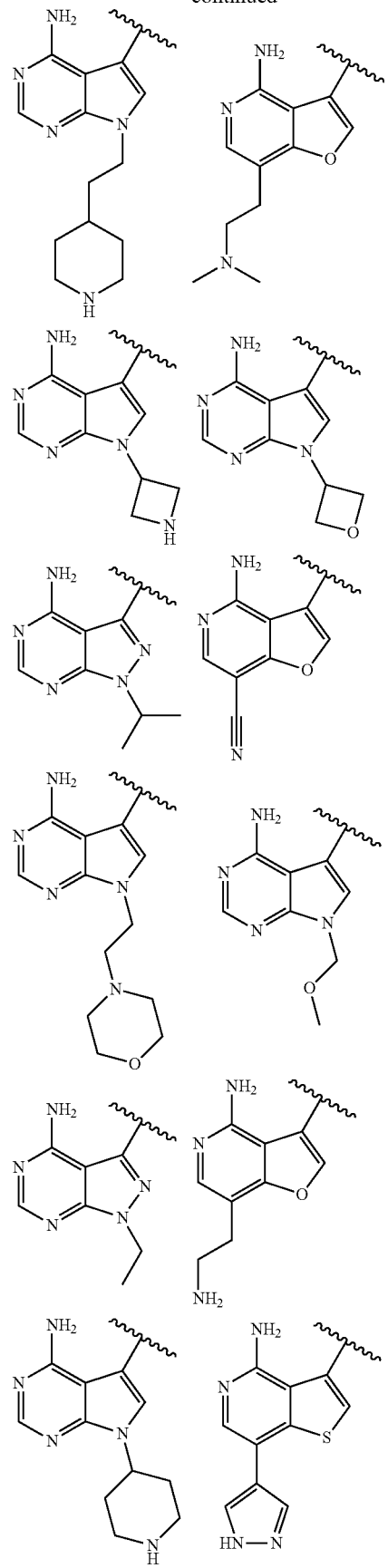

-continued
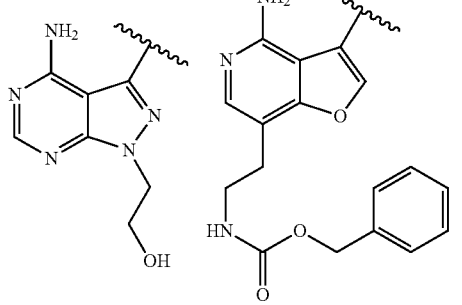
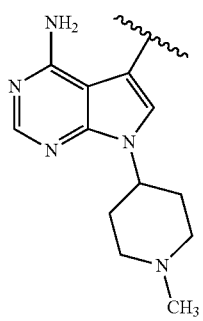
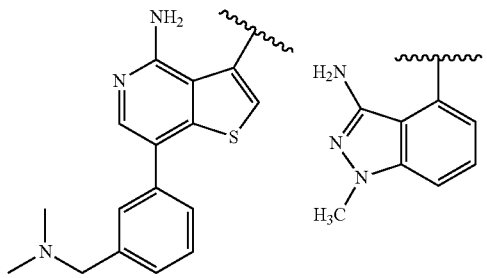
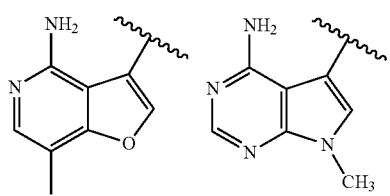
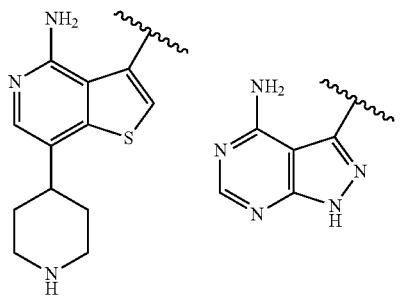
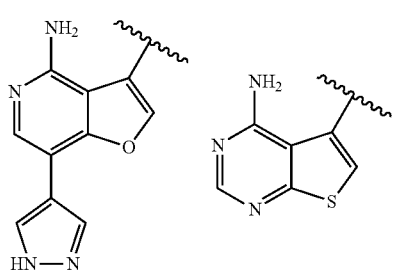
-continued
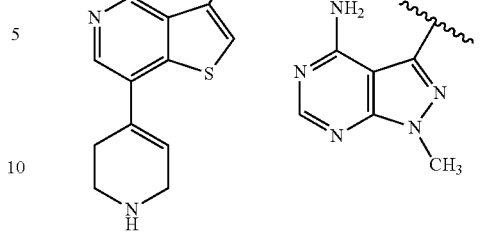
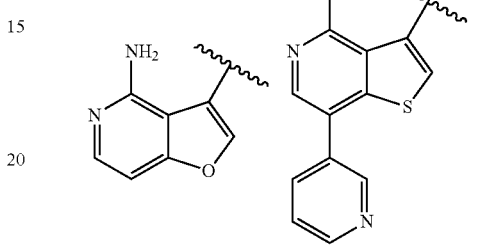
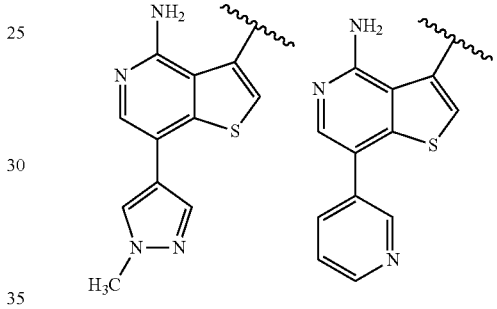
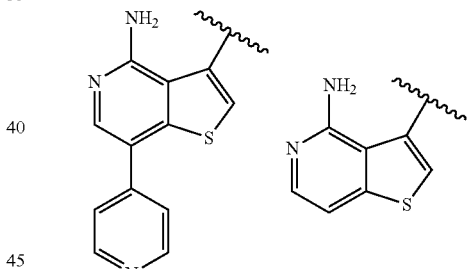
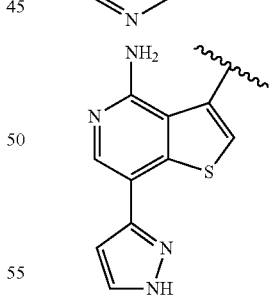
and
R² is selected from:
aryl,
aryl substituted with form one to three substituents independently selected from: halo, $C_{1-4}$alkyl, $C_{1-4}$alkyloxy, —OH, —COOH, —CF$_3$, —C$_{1-4}$alkylOC$_{1-4}$alkyl, —NO$_2$, —NH$_2$ and CN,
heteroaryl, heteroaryl substituted with from one to five substituents independently selected from: fluoro, chloro, bromo, iodo, $C_{1-4}$alkyl, $C_{1-4}$alkyloxy, —OH, —COOH, —CF$_3$, —$C_{1-4}$alkylOC$_{1-4}$alkyl, —NO$_2$, —NH$_2$ and CN; and
$R^3$ is selected from: hydrogen, fluoro and chloro.
Suitably, this invention relates to novel compounds of Formula (IA):

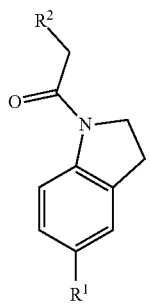

(IA)

wherein:
$R^1$ is selected from:
bicycloheteroaryl, and
bicycloheteroaryl substituted with form one to five substituents selected from:
halo,
$C_{1-4}$alkyl,
$C_{1-4}$alkyloxy,
—OH,
—COOH,
tetrazole,
—CF$_3$,
—$C_{1-4}$alkylOC$_{1-4}$alkyl,
—NO$_2$,
—NH$_2$,
CN,
aryl,
aryl substituted with from one to three substituents selected from: $C_{1-4}$alkyl, di$C_{1-4}$alkylamino$C_{1-4}$alkyl, fluoro, chloro, bromo, iodo and —CF$_3$,
heterocycloalkyl,
heterocycloalkyl substituted with from one to three substituents selected from: $C_{1-4}$alkyl, di$C_{1-4}$alkylamino$C_{1-4}$alkyl, fluoro, chloro, bromo, iodo and —CF$_3$,
heteroaryl, and
heteroaryl substituted with from one to three substituents selected from: $C_{1-4}$alkyl, di$C_{1-4}$alkylamino$C_{1-4}$alkyl, fluoro, chloro, bromo, iodo and —CF$_3$; and
$R^2$ is selected from:
aryl,
aryl substituted with form one to five substituents selected from: fluoro, chloro, bromo, iodo, $C_{1-4}$alkyl, $C_{1-4}$alkyloxy, —OH, —COOH, —CF$_3$, —$C_{1-4}$alkylOC$_{1-4}$alkyl, —NO$_2$, —NH$_2$ and CN,
cycloalkyl, and
cycloalkyl substituted with from one to five substituents selected from: fluoro, chloro, bromo, iodo, $C_{1-4}$alkyl, $C_{1-4}$alkyloxy, —OH, —COOH, —CF$_3$, —$C_{1-4}$alkylOC$_{1-4}$alkyl, —NO$_2$, —NH$_2$ and CN;
and salts thereof.
This invention also relates to pharmaceutically acceptable salts of the compounds of Formula (IA).
Suitably the compound of Formula (IA) is not 3-[1-(phenylacetyl)-2,3-dihydro-1H-indol-5-yl]-7-(3-pyridinyl)thieno[3,2-c]pyridin-4-amine.

For compounds of Formula (IA), suitably $R^1$ is bicycloheteroaryl substituted with from one to three substituents selected from:
halo,
$C_{1-4}$alkyl,
$C_{1-4}$alkyloxy,
—OH,
—COOH,
tetrazole,
—CF$_3$,
—$C_{1-4}$alkylOC$_{1-4}$alkyl,
—NO$_2$,
—NH$_2$,
—CN,
aryl,
aryl substituted with from one to three substituents selected from: $C_{1-4}$alkyl, di$C_{1-4}$alkylamino$C_{1-4}$alkyl, fluoro, chloro, bromo, iodo and —CF$_3$
heterocycloalkyl,
heterocycloalkyl substituted with from one to three substituents selected from: $C_{1-4}$alkyl, di$C_{1-4}$alkylamino$C_{1-4}$alkyl, fluoro, chloro, bromo, iodo and —CF$_3$,
heteroaryl, and
heteroaryl substituted with from one to three substituents selected from: $C_{1-4}$alkyl, di$C_{1-4}$alkylamino$C_{1-4}$alkyl, fluoro, chloro, bromo, iodo and —CF$_3$.
For compounds of Formula (IA), suitably $R^1$ is selected from:

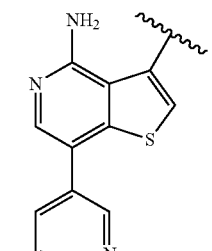
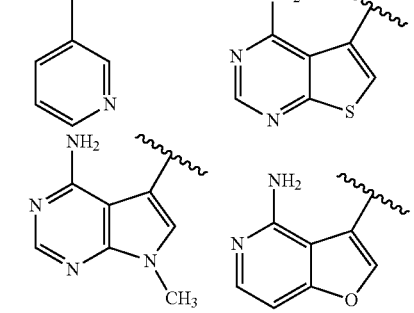
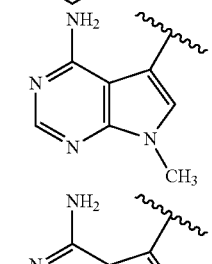
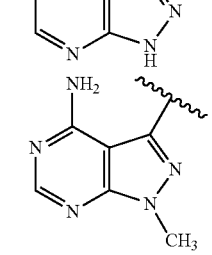
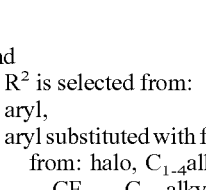

;

and
$R^2$ is selected from:
aryl,
aryl substituted with form one to three substituents selected from: halo, $C_{1-4}$alkyl, $C_{1-4}$alkyloxy, —OH, —COOH, —CF$_3$, —$C_{1-4}$alkylOC$_{1-4}$alkyl, —NO$_2$, —NH$_2$ and CN, cycloalkyl, and
cycloalkyl substituted with from one to three substituents selected from: halo, $C_{1-4}$alkyl, $C_{1-4}$alkyloxy, —OH, —COOH, —CF$_3$, —C$_{1-4}$alkylOC$_{1-4}$alkyl, —NO$_2$, —NH$_2$ and CN.

Suitably, this invention relates to novel compounds of Formula (IB):

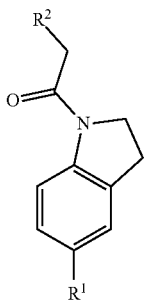

(IB)

wherein:
R$^1$ is selected from:
bicycloheteroaryl, and
bicycloheteroaryl substituted with form one to five substituents selected from: halo, $C_{1-4}$alkyl, $C_{1-4}$alkyloxy, —OH, —COOH, —CF$_3$, —C$_{1-4}$alkylOC$_{1-4}$alkyl, aryl, heteroaryl, —NO$_2$, —NH$_2$ and CN, and
R$^2$ is selected from:
aryl,
aryl substituted with form one to five substituents selected from: halo, $C_{1-4}$alkyl, $C_{1-4}$alkyloxy, —OH, —COOH, —CF$_3$, —C$_{1-4}$alkylOC$_{1-4}$alkyl, —NO$_2$, —NH$_2$ and CN,
cycloalkyl, and
cycloalkyl substituted with from one to five substituents selected from: halo, $C_{1-4}$alkyl, $C_{1-4}$alkyloxy, —OH, —COOH, —CF$_3$, C$_{1-4}$alkylOC$_{1-4}$alkyl, —NO$_2$, —NH$_2$ and CN;
and salts thereof.

This invention also relates to pharmaceutically acceptable salts of the compounds of Formula (IB).

Suitably the compound of Formula (IB) is not 3-[1-(phenylacetyl)-2,3-dihydro-1H-indol-5-yl]-7-(3-pyridinyl)thieno[3,2-c]pyridin-4-amine.

For compounds of Formula (1B), suitably R$^1$ is bicycloheteroaryl substituted with form one to three substituents selected from: halo, $C_{1-4}$alkyl, $C_{1-4}$alkyloxy, —OH, —COOH, —CF$_3$, —C$_{1-4}$alkylOC$_{1-4}$alkyl, aryl, heteroaryl, —NO$_2$, —NH$_2$ and CN.

For compounds of Formula (1B), suitably R$^1$ is selected from:

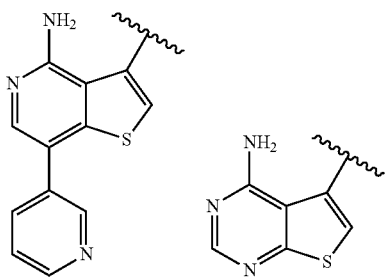

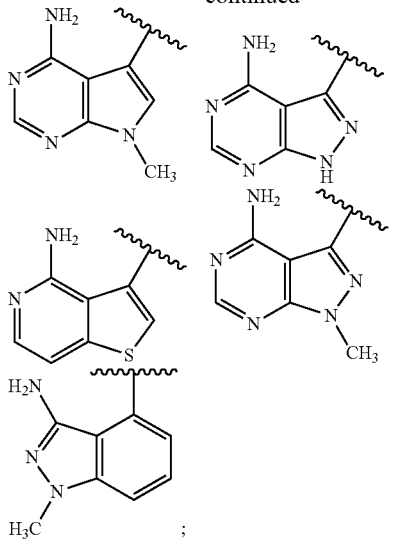

and
R$^2$ is selected from:
aryl,
aryl substituted with form one to three substituents selected from: halo, $C_{1-4}$alkyl, $C_{1-4}$alkyloxy, —OH, —COOH, —CF$_3$, —C$_{1-4}$alkylOC$_{1-4}$alkyl, —NO$_2$, —NH$_2$ and CN,
cycloalkyl, and
cycloalkyl substituted with from one to three substituents selected from: halo, $C_{1-4}$alkyl, $C_{1-4}$alkyloxy, —OH, —COOH, —CF$_3$, —C$_{1-4}$alkylOC$_{1-4}$alkyl, —NO$_2$, —NH$_2$ and CN.

Included in the presently invented compounds of Formula (I) are:
1-methyl-3-[1-(phenylacetyl)-2,3-dihydro-1H-indol-5-yl]-1H-pyrazolo[3,4-d]pyrimidin-4-amine;
3-{1-[(2,5-difluorophenyl)acetyl]-2,3-dihydro-1H-indol-5-yl}-1-methyl-1H-pyrazolo[3,4-d]pyrimidin-4-amine;
3-[1-(phenylacetyl)-2,3-dihydro-1H-indol-5-yl]-1H-pyrazolo[3,4-d]pyrimidin-4-amine;
7-methyl-5-[1-(phenylacetyl)-2,3-dihydro-1H-indol-5-yl]-7H-pyrrolo[2,3-d]pyrimidin-4-amine;
3-[1-(phenylacetyl)-2,3-dihydro-1H-indol-5-yl]thieno[3,2-c]pyridin-4-amine;
3-{1-[(2,5-difluorophenyl)acetyl]-2,3-dihydro-1H-indol-5-yl}thieno[3,2-c]pyridin-4-amine;
3-[1-(phenylacetyl)-2,3-dihydro-1H-indol-5-yl]-7-(3-pyridinyl)thieno[3,2-c]pyridin-4-amine;
1-methyl-4-{1-[(3-methylphenyl)acetyl]-2,3-dihydro-1H-indol-5-yl}-1H-indazol-3-amine;
3-[1-(phenylacetyl)-2,3-dihydro-1H-indol-5-yl]-7-(4-pyridinyl)thieno[3,2-c]pyridin-4-amine;
3-{1-[(2,5-difluorophenyl)acetyl]-2,3-dihydro-1H-indol-5-yl}-7-(3-pyridinyl)thieno[3,2-c]pyridin-4-amine;
3-{1-[(2,5-difluorophenyl)acetyl]-2,3-dihydro-1H-indol-5-yl}-7-(1H-pyrazol-3-yl)thieno[3,2-c]pyridin-4-amine;
4-{1-[(2,5-difluorophenyl)acetyl]-2,3-dihydro-1H-indol-5-yl}-1-methyl-1H-indazol-3-amine;
3-[1-(phenylacetyl)-2,3-dihydro-1H-indol-5-yl]-7-(1H-pyrazol-4-yl)thieno[3,2-c]pyridin-4-amine;
7-(1-methyl-1H-pyrazol-4-yl)-3-[1-(phenylacetyl)-2,3-dihydro-1H-indol-5-yl]thieno[3,2-c]pyridin-4-amine;
3-{1-[(2-fluorophenyl)acetyl]-2,3-dihydro-1H-indol-5-yl}-1-methyl-1H-pyrazolo[3,4-d]pyrimidin-4-amine;
3-{1-[(3-fluorophenyl)acetyl]-2,3-dihydro-1H-indol-5-yl}-1-methyl-1H-pyrazolo[3,4-d]pyrimidin-4-amine;

1-methyl-3-{1-[(2-methylphenyl)acetyl]-2,3-dihydro-1H-indol-5-yl}-1H-pyrazolo[3,4-d]pyrimidin-4-amine;
1-methyl-3-{1-[(3-methylphenyl)acetyl]-2,3-dihydro-1H-indol-5-yl}-1H-pyrazolo[3,4-d]pyrimidin-4-amine;
3-[1-(phenylacetyl)-2,3-dihydro-1H-indol-5-yl]-7-(1,2,3,6-tetrahydro-4-pyridinyl)thieno[3,2-c]pyridin-4-amine;
3-(1-{[3-(trifluoromethyl)phenyl]acetyl}-2,3-dihydro-1H-indol-5-yl)thieno[3,2-c]pyridin-4-amine;
3-{1-[(2-chlorophenyl)acetyl]-2,3-dihydro-1H-indol-5-yl}thieno[3,2-c]pyridin-4-amine;
3-{1-[(3-chlorophenyl)acetyl]-2,3-dihydro-1H-indol-5-yl}thieno[3,2-c]pyridin-4-amine;
3-(1-{[3-(methyloxy)phenyl]acetyl}-2,3-dihydro-1H-indol-5-yl)thieno[3,2-c]pyridin-4-amine;
3-(1-{[2-(methyloxy)phenyl]acetyl}-2,3-dihydro-1H-indol-5-yl)thieno[3,2-c]pyridin-4-amine;
3-[1-(2-naphthalenylacetyl)-2,3-dihydro-1H-indol-5-yl]thieno[3,2-c]pyridin-4-amine;
3-[1-(phenylacetyl)-2,3-dihydro-1H-indol-5-yl]-7-(4-piperidinyl)thieno[3,2-c]pyridin-4-amine;
7-{3-[(dimethylamino)methyl]phenyl}-3-[1-(phenylacetyl)-2,3-dihydro-1H-indol-5-yl]thieno[3,2-c]pyridin-4-amine;
3-{1-[(2,5-dimethylphenyl)acetyl]-2,3-dihydro-1H-indol-5-yl}-1-methyl-1H-pyrazolo[3,4-d]pyrimidin-4-amine;
3-{1-[(3-fluoro-5-methylphenyl)acetyl]-2,3-dihydro-1H-indol-5-yl}-1-methyl-1H-pyrazolo[3,4-d]pyrimidin-4-amine;
3-{1-[(3,5-dimethylphenyl)acetyl]-2,3-dihydro-1H-indol-5-yl}-1-methyl-1H-pyrazolo[3,4-d]pyrimidin-4-amine;
5-{1-[(2,5-difluorophenyl)acetyl]-2,3-dihydro-1H-indol-5-yl}thieno[2,3-d]pyrimidin-4-amine;
3-{1-[(2,3-difluorophenyl)acetyl]-2,3-dihydro-1H-indol-5-yl}-1-methyl-1H-pyrazolo[3,4-d]pyrimidin-4-amine;
7-methyl-5-{1-[(2-methylphenyl)acetyl]-2,3-dihydro-1H-indol-5-yl}-7H-pyrrolo[2,3-d]pyrimidin-4-amine;
5-{1-[(2-fluorophenyl)acetyl]-2,3-dihydro-1H-indol-5-yl}-7-methyl-7H-pyrrolo[2,3-d]pyrimidin-4-amine;
5-{1-[(3-fluorophenyl)acetyl]-2,3-dihydro-1H-indol-5-yl}-7-methyl-7H-pyrrolo[2,3-d]pyrimidin-4-amine;
3-{1-[(2,3-difluorophenyl)acetyl]-2,3-dihydro-1H-indol-5-yl}thieno[3,2-c]pyridin-4-amine;
7-methyl-5-{1-[(3-methylphenyl)acetyl]-2,3-dihydro-1H-indol-5-yl}-7H-pyrrolo[2,3-d]pyrimidin-4-amine;
3-{1-[(3-fluoro-2-methylphenyl)acetyl]-2,3-dihydro-1H-indol-5-yl}thieno[3,2-c]pyridin-4-amine;
3-{2-[5-(4-aminothieno[3,2-c]pyridin-3-yl)-2,3-dihydro-1H-indol-1-yl]-2-oxoethyl}benzonitrile;
3-{1-[(2-fluoro-5-methylphenyl)acetyl]-2,3-dihydro-1H-indol-5-yl}-1-methyl-1H-pyrazolo[3,4-d]pyrimidin-4-amine;
3-{1-[(2,3-dimethylphenyl)acetyl]-2,3-dihydro-1H-indol-5-yl}-1-methyl-1H-pyrazolo[3,4-d]pyrimidin-4-amine;
3-{1-[(3-chlorophenyl)acetyl]-2,3-dihydro-1H-indol-5-yl}-1-methyl-1H-pyrazolo[3,4-d]pyrimidin-4-amine;
1-methyl-3-(1-{[3-(trifluoromethyl)phenyl]acetyl}-2,3-dihydro-1H-indol-5-yl)-1H-pyrazolo[3,4-d]pyrimidin-4-amine;
7-methyl-5-(1-{[3-(trifluoromethyl)phenyl]acetyl}-2,3-dihydro-1H-indol-5-yl)-7H-pyrrolo[2,3-d]pyrimidin-4-amine;
5-{1-[(3-fluoro-5-methylphenyl)acetyl]-2,3-dihydro-1H-indol-5-yl}-7-methyl-7H-pyrrolo[2,3-d]pyrimidin-4-amine;
5-{1-[(3-chlorophenyl)acetyl]-2,3-dihydro-1H-indol-5-yl}-7-methyl-7H-pyrrolo[2,3-d]pyrimidin-4-amine;
5-{1-[(2-chlorophenyl)acetyl]-2,3-dihydro-1H-indol-5-yl}-7-methyl-7H-pyrrolo[2,3-d]pyrimidin-4-amine;
7-methyl-5-(1-{[2-(methyloxy)phenyl]acetyl}-2,3-dihydro-1H-indol-5-yl)-7H-pyrrolo[2,3-d]pyrimidin-4-amine;
1-methyl-3-(1-{[3-(methyloxy)phenyl]acetyl}-2,3-dihydro-1H-indol-5-yl)-1H-pyrazolo[3,4-d]pyrimidin-4-amine;
7-methyl-5-(1-{[3-(methyloxy)phenyl]acetyl}-2,3-dihydro-1H-indol-5-yl)-7H-pyrrolo[2,3-d]pyrimidin-4-amine;
3-{1-[(2-chlorophenyl)acetyl]-2,3-dihydro-1H-indol-5-yl}-1-methyl-1H-pyrazolo[3,4-d]pyrimidin-4-amine;
1-methyl-3-(1-{[2-(methyloxy)phenyl]acetyl}-2,3-dihydro-1H-indol-5-yl)-1H-pyrazolo[3,4-d]pyrimidin-4-amine;
5-{1-[(3-chloro-5-fluorophenyl)acetyl]-2,3-dihydro-1H-indol-5-yl}-7-methyl-7H-pyrrolo[2,3-d]pyrimidin-4-amine;
3-{1-[(2,5-difluorophenyl)acetyl]-2,3-dihydro-1H-indol-5-yl}furo[3,2-c]pyridin-4-amine;
1-methyl-3-{1-[(2,3,5-trifluorophenyl)acetyl]-2,3-dihydro-1H-indol-5-yl}-1H-pyrazolo[3,4-d]pyrimidin-4-amine;
5-{1-[(2,5-dimethylphenyl)acetyl]-2,3-dihydro-1H-indol-5-yl}-7-methyl-7H-pyrrolo[2,3-d]pyrimidin-4-amine;
3-{1-[(2,5-difluorophenyl)acetyl]-2,3-dihydro-1H-indol-5-yl}-7-(1H-pyrazol-4-yl)furo[3,2-c]pyridin-4-amine;
3-{1-[(3,5-dichlorophenyl)acetyl]-2,3-dihydro-1H-indol-5-yl}-1-methyl-1H-pyrazolo[3,4-d]pyrimidin-4-amine;
5-{1-[(2,5-difluorophenyl)acetyl]-2,3-dihydro-1H-indol-5-yl}-7-methyl-7H-pyrrolo[2,3-d]pyrimidin-4-amine;
3-{1-[(2,5-difluorophenyl)acetyl]-2,3-dihydro-1H-indol-5-yl}-7-(1H-pyrazol-4-yl)thieno[3,2-c]pyridin-4-amine;
3-{1-[(3,5-difluorophenyl)acetyl]-2,3-dihydro-1H-indol-5-yl}-1-methyl-1H-pyrazolo[3,4-d]pyrimidin-4-amine;
5-{1-[(3-methylphenyl)acetyl]-2,3-dihydro-1H-indol-5-yl}-7-(4-piperidinyl)-7H-pyrrolo[2,3-c]pyrimidin-4-amine;
5-{1-[(3-methyl phenyl)acetyl]-2,3-dihydro-1H-indol-5-yl}-7-(1-methyl-4-piperidinyl)-7H-pyrrolo[2,3-d]pyrimidin-4-amine;
5-{1-[(3-methylphenyl)acetyl]-2,3-dihydro-1H-indol-5-yl}thieno[2,3-d]pyrimidin-4-amine;
3-{1-[(3-fluoro-5-methylphenyl)acetyl]-2,3-dihydro-1H-indol-5-yl}furo[3,2-c]pyridin-4-amine;
3-{1-[(3-chloro-5-fluorophenyl)acetyl]-2,3-dihydro-1H-indol-5-yl}furo[3,2-c]pyridin-4-amine;
3-{1-[(2-fluoro-5-methylphenyl)acetyl]-2,3-dihydro-1H-indol-5-yl}furo[3,2-c]pyridin-4-amine;
1-methyl-3-{1-[(1-methyl-1H-pyrrol-2-yl)acetyl]-2,3-dihydro-1H-indol-5-yl}-1H-pyrazolo[3,4-d]pyrimidin-4-amine;
3-{1-[(3-chlorophenyl)acetyl]-2,3-dihydro-1H-indol-5-yl}furo[3,2-c]pyridin-4-amine;
5-{1-[(2,3-difluorophenyl)acetyl]-2,3-dihydro-1H-indol-5-yl}-7-methyl-7H-pyrrolo[2,3-c]pyrimidin-4-amine;
5-{1-[(2-fluoro-3-methylphenyl)acetyl]-2,3-dihydro-1H-indol-5-yl}-7-methyl-7H-pyrrolo[2,3-c]pyrimidin-4-amine;
5-{1-[(3-fluoro-2-methylphenyl)acetyl]-2,3-dihydro-1H-indol-5-yl}-7-methyl-7H-pyrrolo[2,3-d]pyrimidin-4-amine;
5-{1-[(2-fluoro-5-methylphenyl)acetyl]-2,3-dihydro-1H-indol-5-yl}-7-methyl-7H-pyrrolo[2,3-c]pyrimidin-4-amine;
3-{1-[(2-fluoro-3-methylphenyl)acetyl]-2,3-dihydro-1H-indol-5-yl}-1-methyl-1H-pyrazolo[3,4-d]pyrimidin-4-amine;
3-{1-[(3-fluoro-2-methylphenyl)acetyl]-2,3-dihydro-1H-indol-5-yl}-1-methyl-1H-pyrazolo[3,4-d]pyrimidin-4-amine;
5-{1-[(2,5-difluorophenyl)acetyl]-2,3-dihydro-1H-indol-5-yl}-7-(1-methyl-4-piperidinyl)-7H-pyrrolo[2,3-c]pyrimidin-4-amine;
5-{1-[(3-chloro-4-fluorophenyl)acetyl]-2,3-dihydro-1H-indol-5-yl}-7-methyl-7H-pyrrolo[2,3-d]pyrimidin-4-amine;
5-{1-[(3-chloro-2-fluorophenyl)acetyl]-2,3-dihydro-1H-indol-5-yl}-7-methyl-7H-pyrrolo[2,3-c]pyrimidin-4-amine;

3-{1-[(3-chloro-4-fluorophenyl)acetyl]-2,3-dihydro-1H-indol-5-yl}-1-methyl-1H-pyrazolo[3,4-d]pyrimidin-4-amine;

3-{1-[(3-chloro-2-fluorophenyl)acetyl]-2,3-dihydro-1H-indol-5-yl}-1-methyl-1H-pyrazolo[3,4-c]pyrimidin-4-amine;

5-{1-[(2,3-dimethylphenyl)acetyl]-2,3-dihydro-1H-indol-5-yl}-7-methyl-7H-pyrrolo[2,3-d]pyrimidin-4-amine;

1-(1-methylethyl)-3-{1-[(3-methylphenyl)acetyl]-2,3-dihydro-1H-indol-5-yl}-1H-pyrazolo[3,4-d]pyrimidin-4-amine;

2-(4-amino-3-{1-[(3-methylphenyl)acetyl]-2,3-dihydro-1H-indol-5-yl}-1H-pyrazolo[3,4-d]pyrimidin-1-yl)ethanol;

5-{1-[(3,5-dimethylphenyl)acetyl]-2,3-dihydro-1H-indol-5-yl}-7-methyl-7H-pyrrolo[2,3-d]pyrimidin-4-amine;

5-{1-[(2,5-difluorophenyl)acetyl]-2,3-dihydro-1H-indol-5-yl}-7-(4-piperidinyl)-7H-pyrrolo[2,3-c]pyrimidin-4-amine;

1-ethyl-3-{1-[(3-methylphenyl)acetyl]-2,3-dihydro-1H-indol-5-yl}-1H-pyrazolo[3,4-d]pyrimidin-4-amine;

3-{1-[(2,5-difluorophenyl)acetyl]-2,3-dihydro-1H-indol-5-yl}-7-methylfuro[3,2-c]pyridin-4-amine;

3-{1-[(2,5-difluorophenyl)acetyl]-2,3-dihydro-1H-indol-5-yl}-1-(1-methylethyl)-1H-pyrazolo[3,4-d]pyrimidin-4-amine;

5-{1-[(3,5-difluorophenyl)acetyl]-2,3-dihydro-1H-indol-5-yl}-7-methyl-7H-pyrrolo[2,3-c]pyrimidin-4-amine;

7-methyl-5-{1-[(2,3,5-trifluorophenyl)acetyl]-2,3-dihydro-1H-indol-5-yl}-7H-pyrrolo[2,3-d]pyrimidin-4-amine;

5-{1-[(3,5-dichlorophenyl)acetyl]-2,3-dihydro-1H-indol-5-yl}-7-methyl-7H-pyrrolo[2,3-c]pyrimidin-4-amine;

7-(3-azetidinyl)-5-{1-[(3-methylphenyl)acetyl]-2,3-dihydro-1H-indol-5-yl}-7H-pyrrolo[2,3-d]pyrimidin-4-amine;

5-{1-[(4-fluorophenyl)acetyl]-2,3-dihydro-1H-indol-5-yl}-7-methyl-7H-pyrrolo[2,3-d]pyrimidin-4-amine;

7-methyl-5-{1-[(4-methylphenyl)acetyl]-2,3-dihydro-1H-indol-5-yl}-7H-pyrrolo[2,3-d]pyrimidin-4-amine;

5-{1-[(3-chloro-2,4-difluorophenyl)acetyl]-2,3-dihydro-1H-indol-5-yl}-7-methyl-7H-pyrrolo[2,3-d]pyrimidin-4-amine;

5-(1-{[3-fluoro-5-(trifluoromethyl)phenyl]acetyl}-2,3-dihydro-1H-indol-5-yl)-7-methyl-7H-pyrrolo[2,3-d]pyrimidin-4-amine;

7-[(methyloxy)methyl]-5-{1-[(3-methylphenyl)acetyl]-2,3-dihydro-1H-indol-5-yl}-7H-pyrrolo[2,3-d]pyrimidin-4-amine;

7-methyl-5-{1-[(1-methyl-1H-pyrrol-2-yl)acetyl]-2,3-dihydro-1H-indol-5-yl}-7H-pyrrolo[2,3-d]pyrimidin-4-amine;

5-{1-[(2,5-difluorophenyl)acetyl]-2,3-dihydro-1H-indol-5-yl}-7-(1-methylethyl)-7H-pyrrolo[2,3-d]pyrimidin-4-amine;

5-{1-[(5-chloro-2-fluorophenyl)acetyl]-2,3-dihydro-1H-indol-5-yl}-7-methyl-7H-pyrrolo[2,3-d]pyrimidin-4-amine;

5-{1-[(2,5-difluorophenyl)acetyl]-2,3-dihydro-1H-indol-5-yl}-7-[2-(4-morpholinyl)ethyl]-7H-pyrrolo[2,3-d]pyrimidin-4-amine;

5-{1-[(2,4-difluorophenyl)acetyl]-2,3-dihydro-1H-indol-5-yl}-7-methyl-7H-pyrrolo[2,3-d]pyrimidin-4-amine;

5-{1-[(3,4-difluorophenyl)acetyl]-2,3-dihydro-1H-indol-5-yl}-7-methyl-7H-pyrrolo[2,3-d]pyrimidin-4-amine;

phenylmethyl[2-(4-amino-3-{1-[(2,5-difluorophenyl)acetyl]-2,3-dihydro-1H-indol-5-yl}furo[3,2-c]pyridin-7-yl)ethyl]carbamate;

5-{1-[(2,5-difluorophenyl)acetyl]-2,3-dihydro-1H-indol-5-yl}-7-(3-methylbutyl)-7H-pyrrolo[2,3-d]pyrimidin-4-amine;

5-{1-[(2,5-difluorophenyl)acetyl]-2,3-dihydro-1H-indol-5-yl}-7-[2-(dimethylamino)ethyl]-7H-pyrrolo[2,3-d]pyrimidin-4-amine;

5-{1-[(6-chloro-2-pyridinyl)acetyl]-2,3-dihydro-1H-indol-5-yl}-7-methyl-7H-pyrrolo[2,3-d]pyrimidin-4-amine;

3-{1-[(3-chloro-2,4-difluorophenyl)acetyl]-2,3-dihydro-1H-indol-5-yl}-1-methyl-1H-pyrazolo[3,4-d]pyrimidin-4-amine;

7-(2-aminoethyl)-3-{1-[(2,5-difluorophenyl)acetyl]-2,3-dihydro-1H-indol-5-yl}furo[3,2-c]pyridin-4-amine;

4-amino-3-{1-[(2,5-difluorophenyl)acetyl]-2,3-dihydro-1H-indol-5-yl}furo[3,2-c]pyridine-7-carbonitrile;

5-{1-[(3,5-dimethyl-1H-pyrazol-1-yl)acetyl]-2,3-dihydro-1H-indol-5-yl}-7-methyl-7H-pyrrolo[2,3-d]pyrimidin-4-amine;

5-[4-fluoro-1-(phenylacetyl)-2,3-dihydro-1H-indol-5-yl]-7-methyl-7H-pyrrolo[2,3-d]pyrimidin-4-amine;

5-{4-fluoro-1-[(1-methyl-1H-pyrrol-2-ypacetyl]-2,3-dihydro-1H-indol-5-yl}-7-methyl-7H-pyrrolo[2,3-d]pyrimidin-4-amine;

5-{1-[(2,5-difluorophenyl)acetyl]-4-fluoro-2,3-dihydro-1H-indol-5-yl}-7-methyl-7H-pyrrolo[2,3-d]pyrimidin-4-amine;

5-{1-[(2,5-difluorophenyl)acetyl]-2,3-dihydro-1H-indol-5-yl}furo[2,3-d]pyrimidin-4-amine;

5-(1-{[3-(trifluoromethyl)phenyl]acetyl}-2,3-dihydro-1H-indol-5-yl)furo[2,3-d]pyrimidin-4-amine;

5-{1-[(3-chloro-5-fluorophenyl)acetyl]-2,3-dihydro-1H-indol-5-yl}furo[2,3-d]pyrimidin-4-amine;

5-{1-[(3-methylphenyl)acetyl]-2,3-dihydro-1H-indol-5-yl}furo[2,3-d]pyrimidin-4-amine;

5-(1-{[3-fluoro-5-(trifluoromethyl)phenyl]acetyl}-2,3-dihydro-1H-indol-5-yl)furo[2,3-d]pyrimidin-4-amine;

5-{1-[(2,5-difluorophenyl)acetyl]-2,3-dihydro-1H-indol-5-yl}-7-[2-(4-piperidinyl)ethyl]-7H-pyrrolo[2,3-d]pyrimidin-4-amine;

7-methyl-5-{1-[(6-methyl-2-pyridinyl)acetyl]-2,3-dihydro-1H-indol-5-yl}-7H-pyrrolo[2,3-d]pyrimidin-4-amine;

5-(1-{[4-fluoro-3-(trifluoromethyl)phenyl]acetyl}-2,3-dihydro-1H-indol-5-yl)-7-methyl-7H-pyrrolo[2,3-d]pyrimidin-4-amine;

5-{1-[(2,5-difluorophenyl)acetyl]-2,3-dihydro-1H-indol-5-yl}-7-(3-oxetanyl)-7H-pyrrolo[2,3-d]pyrimidin-4-amine;

3-{1-[(2,5-difluorophenyl)acetyl]-2,3-dihydro-1H-indol-5-yl}-7-[2-(dimethylamino)ethyl]furo[3,2-c]pyridin-4-amine;

7-methyl-5-(1-{[6-(trifluoromethyl)-2-pyridinyl]acetyl}-2,3-dihydro-1H-indol-5-yl)-7H-pyrrolo[2,3-d]pyrimidin-4-amine;

7-(3-oxetanyl)-5-(1-{[3-(trifluoromethyl)phenyl]acetyl}-2,3-dihydro-1H-indol-5-yl)-7H-pyrrolo[2,3-d]pyrimidin-4-amine;

7-[2-(4-morpholinyl)ethyl]-5-(1-{[3-(trifluoromethyl)phenyl]acetyl}-2,3-dihydro-1H-indol-5-yl)-7H-pyrrolo[2,3-d]pyrimidin-4-amine;

7-(1-methylethyl)-5-(1-{[3-(trifluoromethyl)phenyl]acetyl}-2,3-dihydro-1H-indol-5-yl)-7H-pyrrolo[2,3-d]pyrimidin-4-amine;

7-(3-methylbutyl)-5-(1-{[3-(trifluoromethyl)phenyl]acetyl}-2,3-dihydro-1H-indol-5-yl)-7H-pyrrolo[2,3-d]pyrimidin-4-amine;

4-{1-[(3-methylphenyl)acetyl]-2,3-dihydro-1H-indol-5-yl}-1H-pyrazolo[3,4-c]pyridin-3-amine;

7-chloro-3-{1-[(2,5-difluorophenyl)acetyl]-2,3-dihydro-1H-indol-5-yl}furo[3,2-c]pyridin-4-amine;

7-(3-azetidinyl)-5-(1-{[3-(trifluoromethyl)phenyl]acetyl}-2,3-dihydro-1H-indol-5-yl)-7H-pyrrolo[2,3-d]pyrimidin-4-amine;

7-(1-methyl-3-azetidinyl)-5-(1-{[3-(trifluoromethyl)phenyl]
acetyl}-2,3-dihydro-1H-indol-5-yl)-7H-pyrrolo[2,3-d]py-
rimidin-4-amine;

7-[2-(dimethylamino)ethyl]-5-(1-{[3-(trifluoromethyl)phe-
nyl]acetyl}-2,3-dihydro-1H-indol-5-yl)-7H-pyrrolo[2,3-
d]pyrimidin-4-amine;

5-(4-fluoro-1-{[3-(trifluoromethyl)phenyl]acetyl}-2,3-dihy-
dro-1H-indol-5-yl)-7-methyl-7H-pyrrolo[2,3-d]pyrimi-
din-4-amine;

5-{4-fluoro-1-[(6-methyl-2-pyridinyl)acetyl]-2,3-dihydro-
1H-indol-5-yl}-7-methyl-7H-pyrrolo[2,3-d]pyrimidin-4-
amine;

5-(4-fluoro-1-{[6-(trifluoromethyl)-2-pyridinyl]acetyl}-2,3-
dihydro-1H-indol-5-yl)-7-methyl-7H-pyrrolo[2,3-d]pyri-
midin-4-amine;

5-{1-[(3,5-dimethyl-1H-pyrazol-1-yl)acetyl]-4-fluoro-2,3-
dihydro-1H-indol-5-yl}-7-methyl-7H-pyrrolo[2,3-d]pyri-
midin-4-amine;

5-(4-fluoro-1-{[4-fluoro-3-(trifluoromethyl)phenyl]acetyl}-
2,3-dihydro-1H-indol-5-yl)-7-methyl-7H-pyrrolo[2,3-d]
pyrimidin-4-amine;

3-{1-[(2,5-difluorophenyl)acetyl]-4-fluoro-2,3-dihydro-1H-
indol-5-yl}furo[3,2-c]pyridin-4-amine;

5-{4-fluoro-1-[(4-fluorophenyl)acetyl]-2,3-dihydro-1H-in-
dol-5-yl}-7-methyl-7H-pyrrolo[2,3-d]pyrimidin-4-
amine;

4-(1-{[3-(trifluoromethyl)phenyl]acetyl}-2,3-dihydro-1H-
indol-5-yl)-1H-pyrazolo[3,4-c]pyridin-3-amine;

1-methyl-4-(1-{[3-(trifluoromethyl)phenyl]acetyl}-2,3-di-
hydro-1H-indol-5-yl)-1H-pyrazolo[3,4-c]pyridin-3-
amine;

7-(3-azetidinyl)-5-{1-[(2,5-difluorophenyl)acetyl]-2,3-dihy-
dro-1H-indol-5-yl}-7H-pyrrolo[2,3-d]pyrimidin-4-
amine;

7-[2-(4-piperidinyl)ethyl]-5-(1-{[3-(trifluoromethyl)phenyl]
acetyl}-2,3-dihydro-1H-indol-5-yl)-7H-pyrrolo[2,3-d]py-
rimidin-4-amine;

7-(2-aminoethyl)-3-{1-[(2,5-difluorophenyl)acetyl]-4-
fluoro-2,3-dihydro-1H-indol-5-yl}furo[3,2-c]pyridin-4-
amine;

3-{1-[(3,5-dimethyl-1H-pyrazol-1-yl)acetyl]-2,3-dihydro-
1H-indol-5-yl}-1-methyl-1H-pyrazolo[3,4-d]pyrimidin-
4-amine;

5-(1-{[3-(trifluoromethyl)phenyl]acetyl}-2,3-dihydro-1H-
indol-5-yl)-1H-pyrrolo[2,3-d]pyrimidin-4-amine;

5-{4-chloro-1-[(6-methyl-2-pyridinyl)acetyl]-2,3-dihydro-
1H-indol-5-yl}-7-methyl-7H-pyrrolo[2,3-d]pyrimidin-4-
amine; and 5-(4-chloro-1-{[6-(trifluoromethyl)-2-pyridinyl]acetyl}-2,
3-dihydro-1H-indol-5-yl)-7-methyl-7H-pyrrolo[2,3-d]py-
rimidin-4-amine;

and salts thereof including pharmaceutically acceptable salts thereof.

The skilled artisan will appreciate that salts, including pharmaceutically acceptable salts, of the compounds according to Formula I may be prepared. Indeed, in certain embodiments of the invention, salts including pharmaceutically-acceptable salts of the compounds according to Formula I may be preferred over the respective free base. Accordingly, the invention is further directed to salts, including pharmaceutically-acceptable salts, of the compounds according to Formula I.

The salts of the compounds of the invention are readily prepared by those of skill in the art.

The pharmaceutically acceptable salts of the compounds of the invention are readily prepared by those of skill in the art.

The compounds according to Formula I may contain one or more asymmetric centers (also referred to as a chiral center) and may, therefore, exist as individual enantiomers, diastereomers, or other stereoisomeric forms, or as mixtures thereof.

Chiral centers, such as chiral carbon atoms, may be present in a substituent such as an alkyl group. Where the stereochemistry of a chiral center present in a compound of Formula I, or in any chemical structure illustrated herein, if not specified the structure is intended to encompass all individual stereoisomers and all mixtures thereof. Thus, compounds according to Formula I containing one or more chiral centers may be used as racemic mixtures, enantiomerically enriched mixtures, or as enantiomerically pure individual stereoisomers.

The compounds according to Formula I may also contain double bonds or other centers of geometric asymmetry. Where the stereochemistry of a center of geometric asymmetry present in Formula I, or in any chemical structure illustrated herein, is not specified, the structure is intended to encompass the trans (E) geometric isomer, the cis (Z) geometric isomer, and all mixtures thereof. Likewise, all tautomeric forms are also included in Formula I whether such tautomers exist in equilibrium or predominately in one form.

The compounds of Formula I or salts, including pharmaceutically acceptable salts, thereof may exist in solid or liquid form. In the solid state, the compounds of the invention may exist in crystalline or noncrystalline form, or as a mixture thereof. For compounds of the invention that are in crystalline form, the skilled artisan will appreciate that pharmaceutically acceptable solvates may be formed wherein solvent molecules are incorporated into the crystalline lattice during crystallization. Solvates wherein water is the solvent that is incorporated into the crystalline lattice are typically referred to as "hydrates." Hydrates include stoichiometric hydrates as well as compositions containing variable amounts of water. The invention includes all such solvates.

The skilled artisan will further appreciate that certain compounds of Formula I or salts, including pharmaceutically acceptable salts thereof that exist in crystalline form, including the various solvates thereof, may exhibit polymorphism (i.e. the capacity to occur in different crystalline structures). These different crystalline forms are typically known as "polymorphs." Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions. The invention includes all such polymorphs.

DEFINITIONS

"Alkyl" refers to a hydrocarbon chain having the specified number of member atoms. For example, $C_1$-$C_4$ alkyl refers to an alkyl group having from 1 to 4 member atoms. Alkyl groups may be saturated, unsaturated, straight or branched. Representative branched alkyl groups have one, two, or three branches. Alkyl includes methyl, ethyl, ethylene, propyl (n-propyl and isopropyl), butene, and butyl (n-butyl, isobutyl, and t-butyl).

"Alkoxy" refers to an —O-alkyl group wherein "alkyl" is as defined herein. For example, $C_1$-$C_4$alkoxy refers to an alkoxy group having from 1 to 4 member atoms. Representative branched alkoxy groups have one, two, or three branches. Examples of such groups include methoxy, ethoxy, propoxy, and butoxy.

"Aryl" refers to an aromatic hydrocarbon ring. Aryl groups are monocyclic ring systems or bicyclic ring systems. Examples of such monocyclic aryl rings include phenyl and biphenyl. Examples of such bicyclic aryl rings include naphthalene, biphenyl and rings wherein phenyl is fused to a cycloalkyl or cycloalkenyl ring having 5, 6, or 7 member atoms, for example tetrahydronaphthalene.

"Cycloalkyl" refers to a saturated or unsaturated non aromatic hydrocarbon ring having the specified number of member atoms. Cycloalkyl groups are monocyclic ring systems. For example, $C_3$-$C_7$ cycloalkyl refers to a cycloalkyl group having from 3 to 7 member atoms. Examples of cycloalkyl as used herein includes cyclopropyl, cyclobutyl, cyclopentyl, cyclohexyl, cyclobutenyl, cyclopentenyl and cyclohexenyl.

"Halo" refers to the halogen radicals fluoro, chloro, bromo, and iodo.

"Heteroaryl" refers to an aromatic ring containing from 1 to 4 heteroatoms as member atoms in the ring. Heteroaryl groups containing more than one heteroatom may contain different heteroatoms. Heteroaryl groups are monocyclic ring systems. Monocyclic heteroaryl rings have 5 or 6 member atoms. Heteroaryl includes pyrrolyl, pyrazolyl, imidazolyl, oxazolyl, isoxazolyl, thiazolyl, isothiazolyl, furanyl, furazanyl, thienyl, triazolyl, pyridinyl, pyrimidinyl, pyridazinyl, pyrazinyl, triazinyl, tetrazinyl.

"Heterocycloalkyl" refers to a saturated or unsaturated ring containing from 1 to 4 heteroatoms as member atoms in the ring. However, heterocycloalkyl rings are not aromatic. Heterocycloalkyl groups containing more than one heteroatom may contain different heteroatoms. Heterocycloalkyl groups are monocyclic ring systems or a monocyclic ring fused with an aryl ring or to a heteroaryl ring having from 4 to 11 member atoms. In certain embodiments, heterocycloalkyl is saturated. In other embodiments, heterocycloalkyl is unsaturated but not aromatic. Heterocycloalkyl includes pyrrolidinyl, tetrahydrofuranyl, dihydrofuranyl, pyranyl, tetrahydropyranyl, dihydropyranyl, tetrahydrothienyl, pyrazolidinyl, oxazolidinyl, thiazolidinyl, piperidinyl, homopiperidinyl, piperazinyl, morpholinyl, thiamorpholinyl, 1,3-dioxolanyl, 1,3-dioxanyl, 1,4-dioxanyl, 1,3-oxathiolanyl, 1,3-oxathianyl, 1,3-dithianyl, 1,3oxazolidin-2-one, hexahydro-1H-azepin, 4,5,6,7,tetrahydro-1H-benzimidazol, piperidinyl, 1,2,3,6-tetrahydro-pyridinyl and azetidinyl.

Suitably "Heterocycloalkyl" includes: oxetanyl.

"Bicycloheteroaryl" refers to two fused aromatic rings containing from 1 to 6 heteroatoms as member atoms. Bicycloheteroaryl groups containing more than one heteroatom may contain different heteroatoms. Bicycloheteroaryl rings have from 6 to 11 member atoms. Bicycloheteroaryl includes: 1H-pyrrolo[3,2-c]pyridine, 1H-pyrazolo[4,3-c]pyridine, 1H-pyrazolo[3,4-d]pyrimidine, 1H-pyrrolo[2,3-d]pyrimidine, 7H-pyrrolo[2,3-d]pyrimidine, thieno[3,2-c]pyridine, thieno[2,3-d]pyrimidine, furo[2,3-c]pyridine, furo[2,3-d]pyrimidine, indolyl, isoindolyl, indolizinyl, indazolyl, purinyl, quinolinyl, isoquinolinyl, quinoxalinyl, quinazolinyl, pteridinyl, cinnolinyl, azabenzimidazolyl, tetrahydrobenzimidazolyl, benzimidazolyl, benopyranyl, benzoxazolyl, benzofuranyl, isobenzofuranyl, benzothiazolyl, benzothienyl, imidazo[4.5-c]pyridine, imidazo[4.5-b]pyridine, furopyridinyl and napthyridinyl.

Suitably "Bicycloheteroaryl" refers to two fused aromatic rings containing from 1 to 6 heteroatoms as member atoms. Bicycloheteroaryl groups containing more than one heteroatom may contain different heteroatoms. Bicycloheteroaryl rings have from 6 to 11 member atoms. Bicycloheteroaryl includes: 1H-pyrazolo[3,4-d]pyrimidine, 1H-pyrrolo[2,3-d]pyrimidine, 7H-pyrrolo[2,3-d]pyrimidine, thieno[3,2-c]pyridine, thieno[2,3-d]pyrimidine, furo[2,3-c]pyridine, indolyl, isoindolyl, indolizinyl, indazolyl, purinyl, quinolinyl, isoquinolinyl, quinoxalinyl, quinazolinyl, pteridinyl, cinnolinyl, azabenzimidazolyl, tetrahydrobenzimidazolyl, benzimidazolyl, benopyranyl, benzoxazolyl, benzofuranyl, isobenzofuranyl, benzothiazolyl, benzothienyl, imidazo[4.5-c]pyridine, imidazo[4.5-b]pyridine, furopyridinyl and napthyridinyl.

Suitably "Bicycloheteroaryl" includes: 1H-pyrazolo[3,4-d]pyrimidine, 1H-pyrrolo[2,3-d]pyrimidine, 7H-pyrrolo[2,3-d]pyrimidine, thieno[3,2-c]pyridine, indolyl, isoindolyl, indolizinyl, indazolyl, purinyl, quinolinyl, isoquinolinyl, quinoxalinyl, quinazolinyl, pteridinyl, cinnolinyl, azabenzimidazolyl, tetrahydrobenzimidazolyl, benzimidazolyl, benopyranyl, benzoxazolyl, benzofuranyl, isobenzofuranyl, benzothiazolyl, benzothienyl, imidazo[4.5-c]pyridine, imidazo[4.5-b]pyridine, furopyridinyl and napthyridinyl.

"Heteroatom" refers to a nitrogen, sulphur or oxygen atom.

"Pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

As used herein the symbols and conventions used in these processes, schemes and examples are consistent with those used in the contemporary scientific literature, for example, the *Journal of the American Chemical Society* or the *Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

Ac (acetyl);
$Ac_2O$ (acetic anhydride);
ACN (acetonitrile);
AIBN (azobis(isobutyronitrile));
ATP (adenosine triphosphate);
Bis-pinacolatodiboron (4,4,4',4',5,5,5',5'-Octamethyl-2,2'-bi-1,3,2-dioxaborolane);
BSA (bovine serum albumin);
BINAP (2,2'-bis(diphenylphosphino)-1,1'-binaphthyl);
BMS (borane-dimethyl sulphide complex);
Bn (benzyl);
Boc (tert-Butoxycarbonyl);
$Boc_2O$ (di-tert-butyl dicarbonate);
BOP (Benzotriazole-1-yl-oxy-tris-(dimethylamino)-phosphonium hexafluorophosphate);
C18 (refers to 18-carbon alkyl groups on silicon in HPLC stationary phase);
CH3CN (acetonitrile);
Cy (cyclohexyl);
CAN (cerric ammonium nitrate);
Cbz (benzyloxycarbonyl);
CSI (chlorosulfonyl isocyanate);
DABCO (1,4-Diazabicyclo[2.2.2]octane);
DAST ((Diethylamino)sulfur trifluoride);
DBU (1,8-Diazabicyclo[5.4.0]undec-7-ene);
DCC (Dicyclohexyl Carbodiimide);
DCE (1,2-dichloroethane);
DDQ (2,3-Dichloro-5,6-dicyano-1,4-benzoquinone);
DCM (dichloromethane);
DIEA (Hünig's base, diisopropylethyl amine, N-ethyl-N-(1-methylethyl)-2-propanamine);
DIPEA (Hünig's base, diisopropylethyl amine, N-ethyl-N-(1-methylethyl)-2-propanamine);
DMAP (4-dimethylaminopyridine);
DME (1,2-dimethoxyethane);
DMF (N,N-dimethylformamide);
DMSO (dimethylsulfoxide);

DPPA (diphenyl phosphoryl azide);
EDC (N-(3-dimethylaminopropyl)-N' ethylcarbodiimide);
EDTA (ethylenediaminetetraacetic acid);
EtOAc (ethyl acetate);
EtOH (ethanol);
Et$_2$O (diethyl ether);
HEPES (4-(2-hydroxyethyl)-1-piperazine ethane sulfonic acid);
HATU (O-(7-Azabenzotriazol-1-yl)-N,N,N',N'-tetramethyluronium hexafluorophosphate);
HOAt (1-hydroxy-7-azabenzotriazole);
HOBt (1-hydroxybenzotriazole);
HOAc (acetic acid);
HPLC (high pressure liquid chromatography);
HMDS (hexamethyldisilazide);
Hunig's Base (N,N-Diisopropylethylamine);
IPA (isopropyl alcohol);
Indoline (2,3-dihydro-1H-indole);
KHMDS (potassium hexamethyldisilazide);
LAH (lithium aluminum hydride);
LDA (lithium diisopropylamide);
LHMDS (lithium hexamethyldisilazide)
MeOH (methanol);
MTBE (methyl tert-butyl ether);
mCPBA (m-chloroperbezoic acid);
NaHMDS (sodium hexamethyldisilazide);
NBS (N-bromosuccinimide);
PE (petroleum ether);
Pd$_2$(dba)$_3$ (Tris(dibenzylideneacetone)dipalladium(0));
Pd(dppf)Cl$_2$ ([1,1'-Bis(diphenylphosphino)ferrocene]dichloropalladium(II));
PyBOP (benzotriazol-1-yl-oxytripyrrolidinophosphonium hexafluorophosphate);
PyBrOP (bromotripyrrolidinophosphonium hexafluorophosphate);
RPHPLC (reverse phase high pressure liquid chromatography);
RuPhos (2-Dicyclohexylphosphino-2',6'-diisopropoxybiphenyl);
SFC (supercritical fluid chromatography);
SGC (silica gel chromatography);
T3P® (propane phosphonic acid anhydride);
TEA (triethylamine);
TEMPO (2,2,6,6-Tetramethylpiperidine 1-oxyl, free radical);
TFA (trifluoroacetic acid); and
THF (tetrahydrofuran)
All references to ether are to diethyl ether and brine refers to a saturated aqueous solution of NaCl.

Compound Preparation

The compounds according to Formula I are prepared using conventional organic synthetic methods. A suitable synthetic route is depicted below in the following general reaction schemes.

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

As shown in Scheme 1, commercially available 5-bromoindoline 1 is acylated with a carboxylic acid using a coupling reagent (e.g. EDC, DCC or HATU) to form the amide bond in 2. Conversion of 2 to the boronate ester and subsequent Suzuki-Miyaura coupling affords the product 3. The boronate ester (represented by 4) may be purified and isolated if desired and subjected to the Suzuki-Miyaura coupling in a separate synthetic procedure. Bicycloheteroaryl halides A and B are known compounds or are readily prepared by established methods.

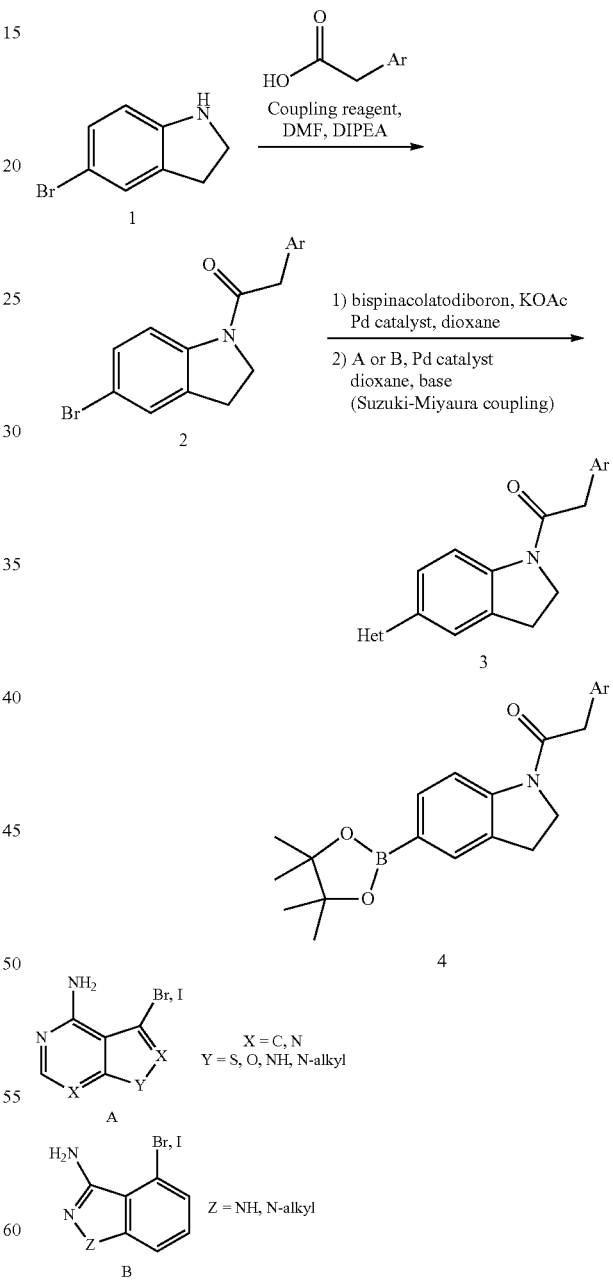

Alternatively, the compounds of the invention can be prepared as shown in Scheme 2. The nitrogen of 5-bromoindoline 1 can be protected with the tert-butylcarbamate (Boc) group. Transformation to the heteroaryl substituted indoline 6 is accomplished as in Scheme 1, with or without isolation of the intermediate boronate ester. Deprotection of the Boc group with HCl affords the indoline 7, which can be converted to 3 using a coupling reagent (e.g. EDC, DCC or HATU) to form the amide bond.

then be further manipulated by convention methods such as a transition metal mediated coupling reaction to give 10 which can have a variety of R substituents such as aryl or alkyl groups.

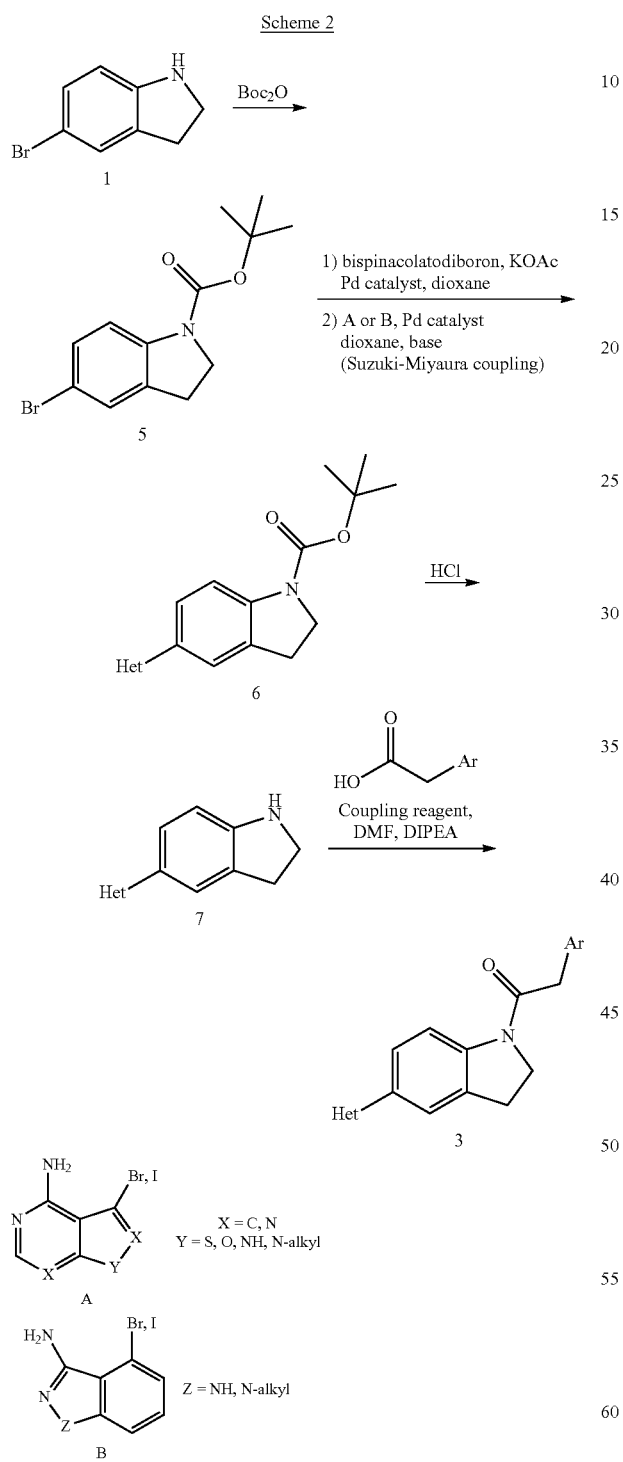

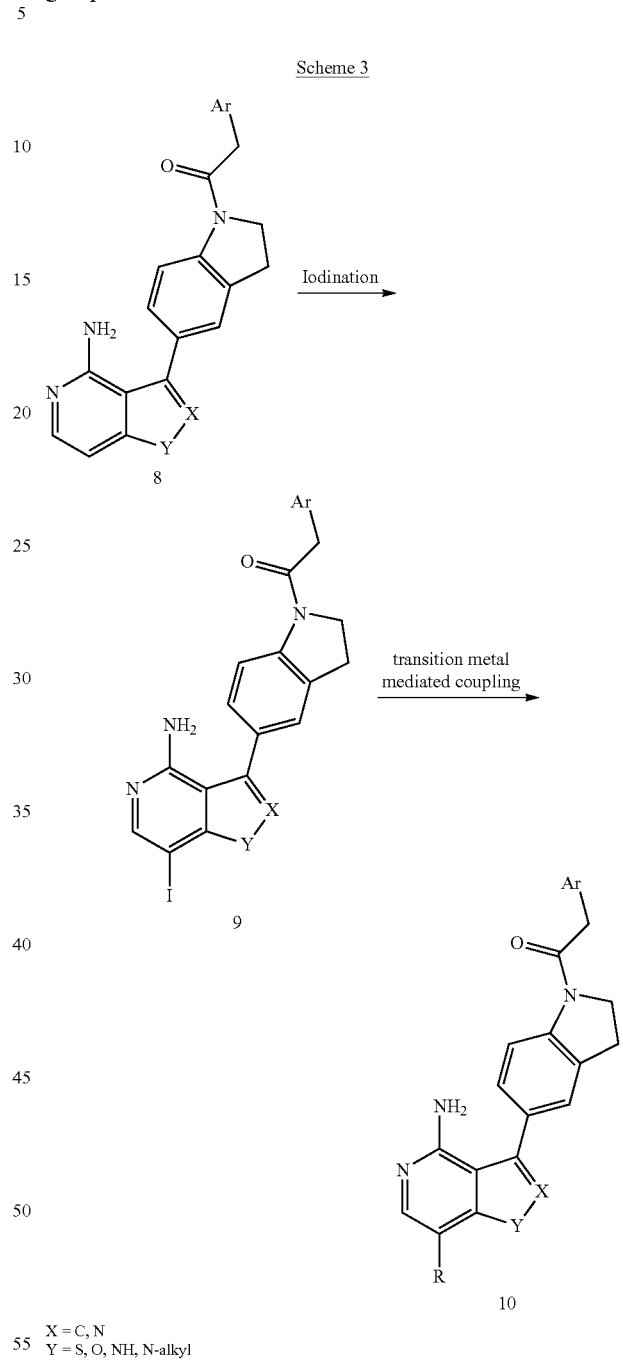

Examples of the invention containing a 2-aminopyridine ring as part of the bicylic heteroaryl group may be further substituted as shown in Scheme 3. The aminopyridine ring in a compound such as 8 may be iodonitated to give 9, which can Examples of the invention with indazole and 1H-pyrazolo[3,4-c]pyridin-3-amine groups as R1, represented by 15 may be prepared according to Scheme 4. The boroate ester 4 can be coupled using Suzuki-Miyaura conditions with 11 or 13, to afford compounds 12 and 14, respectively. The fluoronitrile 12 or chloronitrile of the pyridine 14 can be reacted with hydrazine or an alkyl hydrazine to effect cyclization and formation of the bicycloheteroaryl indazole or 1H-pyrazolo[3,4-c]pyridin-3-amine groups in 15.

Scheme 4

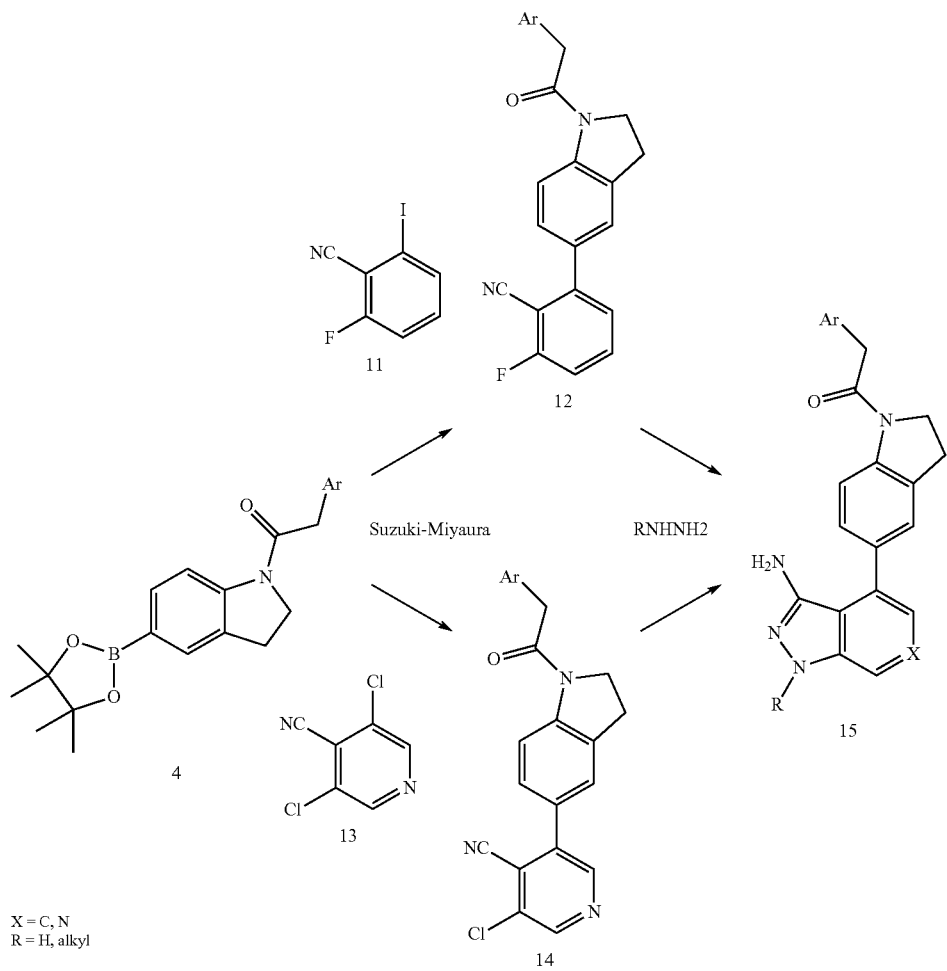

X = C, N
R = H, alkyl

Compounds of the invention containing a furo[2,3-d]pyrimidin-4-amine bicycloheteroaryl R1 group can be synthesized as shown in Scheme 5. Starting with 1,5-diacetyl indoline 16, bromination followed by displacement with sodium acetate and then base hydrolysis affords the hydroxylketone 17, which when reacted with malononitrile in the presence of diethylamine provdes the furan 18. Reaction of 18 with bis(ethyloxy)methyl acetate to prepare 19, followed by treatment of 19 with ammonia in methanol affords the intermediate 20. The acetamide can be hydrolyzed with base to afford the indoline 21, which when reacted under suitable condition with an aryl or heteroaryl acetic acid derivative afford the compounds of the invention with general structure 22.

Scheme 5

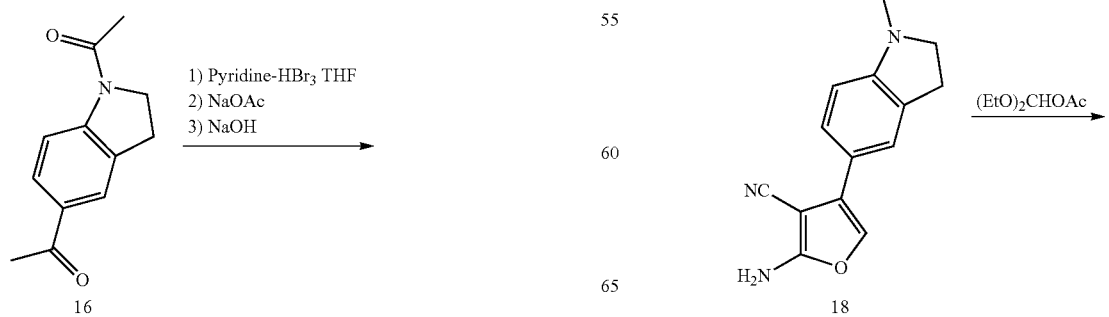

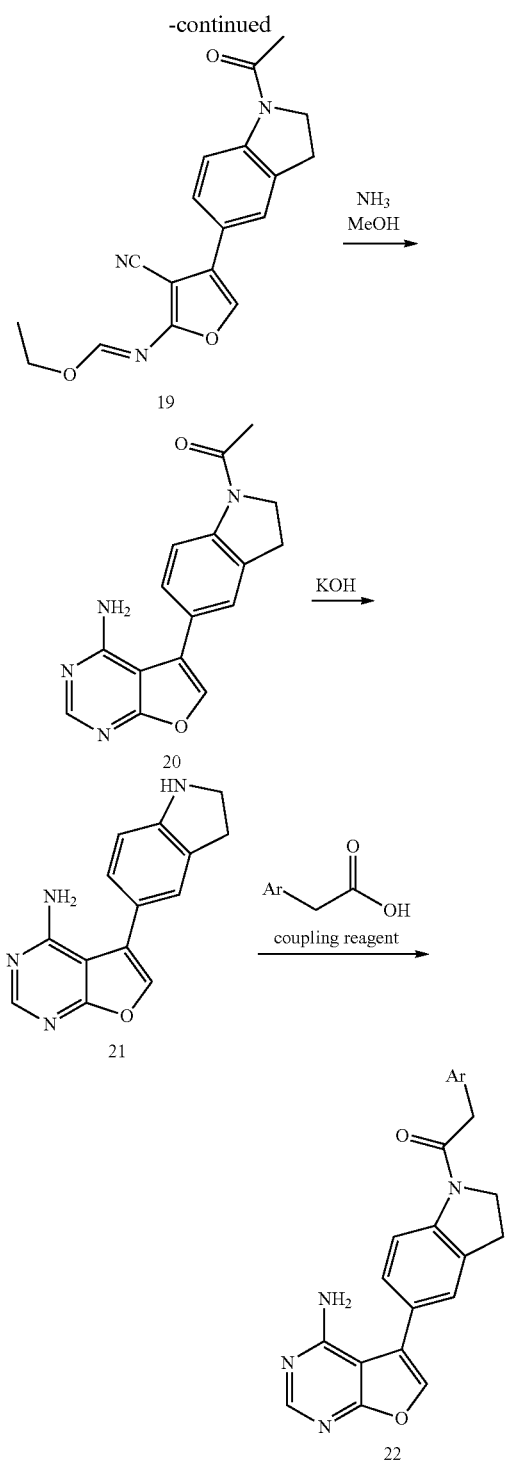

Methods of Use

The compounds according to Formula I and pharmaceutically acceptable salts thereof are inhibitors of PERK. These compounds are potentially useful in the treatment of conditions wherein the underlying pathology is attributable to (but not limited to) activation of the UPR pathway, for example, cancer and more specifically cancers of the breast, colon, and lung, pancreas and skin. Accordingly, another aspect the invention is directed to methods of treating such conditions.

Suitably, the present invention relates to a method for treating or lessening the severity of breast cancer, including inflammatory breast cancer, ductal carcinoma, and lobular carcinoma.

Suitably the present invention relates to a method for treating or lessening the severity of colon cancer.

Suitably the present invention relates to a method for treating or lessening the severity of pancreatic cancer, including insulinomas, adenocarcinoma, ductal adenocarcinoma, adenosquamous carcinoma, acinar cell carcinoma, and glucagonoma.

Suitably the present invention relates to a method for treating or lessening the severity of skin cancer, including melanoma and metastatic melanoma.

Suitably the present invention relates to a method for treating or lessening the severity of lung cancer including small cell lung cancer, non-small cell lung cancer, squamous cell carcinoma, adenocarcinoma, and large cell carcinoma.

Suitably the present invention relates to a method for treating or lessening the severity of cancers selected from the group consisting of brain (gliomas), glioblastomas, astrocytomas, glioblastoma multiforme, Bannayan-Zonana syndrome, Cowden disease, Lhermitte-Duclos disease, Wilm's tumor, Ewing's sarcoma, Rhabdomyosarcoma, ependymoma, medulloblastoma, head and neck, kidney, liver, melanoma, ovarian, pancreatic, adenocarcinoma, ductal adenocarcinoma, adenosquamous carcinoma, acinar cell carcinoma, glucagonoma, insulinoma, prostate, sarcoma, osteosarcoma, giant cell tumor of bone, thyroid, lymphoblastic T cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, plasmacytoma, Immunoblastic large cell leukemia, mantle cell leukemia, multiple myeloma, megakaryoblastic leukemia, multiple myeloma, acute megakaryocytic leukemia, promyelocytic leukemia, erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer.

Suitably the present invention relates to a method for treating or lessening the severity of pre-cancerous syndromes in a mammal, including a human, wherein the pre-cancerous syndrome is selected from: cervical intraepithelial neoplasia, monoclonal gammapathy of unknown significance (MGUS), myelodysplastic syndrome, aplastic anemia, cervical lesions, skin nevi (pre-melanoma), prostatic intraepithleial (intraductal) neoplasia (PIN), Ductal Carcinoma in situ (DCIS), colon polyps and severe hepatitis or cirrhosis.

Suitably the present invention relates to a method for treating or lessening the severity of additional diseases associated with UPR activation including: Type 1 diabetes, Alzheimer's disease, stroke, Parkinson disease, Huntington's disease, amyotrophic lateral sclerosis, myocardial infarction, cardiovascular disease, atherosclerosis, and arrhythmias.

The compounds of this invention inhibit angiogenesis which is implicated in the treatment of ocular diseases. *Nature Reviews Drug Discovery* 4, 711-712 (September 2005). Suitably the present invention relates to a method for treating or lessening the severity of ocular diseases/angiogenesis. In embodiments of methods according to the invention, the disorder of ocular diseases, including vascular leakage can be: edema or neovascularization for any occlusive or inflammatory retinal vascular disease, such as rubeosis irides, neovascular glaucoma, pterygium, vascularized glaucoma filtering blebs, conjunctival papilloma; choroidal neovascularization, such as neovascular age-related macular degeneration (AMD), myopia, prior uveitis, trauma, or idiopathic; macular edema, such as post surgical macular edema, macular edema secondary to uveitis including retinal and/or choroidal inflammation, macular edema secondary to diabetes, and macular edema secondary to retinovascular occlusive disease (i.e. branch and central retinal vein occlusion); retinal neovascularization due to diabetes, such as retinal vein occlusion, uveitis, ocular ischemic syndrome from carotid artery disease, ophthalmic or retinal artery occlusion, sickle cell retinopathy, other ischemic or occlusive neovascular retinopathies, retinopathy of prematurity, or Eale's Disease; and genetic disorders, such as VonHippel-Lindau syndrome.

In some embodiments, the neovascular age-related macular degeneration is wet age-related macular degeneration. In other embodiments, the neovascular age-related macular degeneration is dry age-related macular degeneration and the patient is characterized as being at increased risk of developing wet age-related macular degeneration.

The methods of treatment of the invention comprise administering an effective amount of a compound according to Formula I or a pharmaceutically acceptable salt, thereof to a patient in need thereof.

The invention also provides a compound according to Formula I or a pharmaceutically-acceptable salt thereof for use in medical therapy, and particularly in cancer therapy. Thus, in further aspect, the invention is directed to the use of a compound according to Formula I or a pharmaceutically acceptable salt thereof in the preparation of a medicament for the treatment of a disorder characterized by activation of the UPR, such as cancer.

By the term "treating" and derivatives thereof as used herein, is meant prophylactic and therapeutic therapy. Prophylactic therapy is appropriate, for example, when a subject is considered at high risk for developing cancer, or when a subject has been exposed to a carcinogen.

As used herein, the term "effective amount" and derivatives thereof means that amount of a drug or pharmaceutical agent that will elicit the biological or medical response of a tissue, system, animal or human that is being sought, for instance, by a researcher or clinician. Furthermore, the term "therapeutically effective amount" and derivatives thereof means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, "patient" or "subject" refers to a human or other animal. Suitably the patient or subject is a human.

The compounds of Formula I or pharmaceutically acceptable salts thereof may be administered by any suitable route of administration, including systemic administration. Systemic administration includes oral administration, and parenteral administration. Parenteral administration refers to routes of administration other than enteral, transdermal, or by inhalation, and is typically by injection or infusion. Parenteral administration includes intravenous, intramuscular, intraperitoneal injection, and subcutaneous injection or infusion.

The compounds of Formula I or pharmaceutically acceptable salts thereof may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the condition being treated, the severity of the condition being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Additionally, the compounds of Formula I or pharmaceutically-acceptable salts thereof may be administered as prodrugs. As used herein, a "prodrug" of a compound of the invention is a functional derivative of the compound which, upon administration to a patient, eventually liberates the compound of the invention in vivo. Administration of a compound of the invention as a prodrug may enable the skilled artisan to do one or more of the following: (a) modify the onset of the compound in vivo; (b) modify the duration of action of the compound in vivo; (c) modify the transportation or distribution of the compound in vivo; (d) modify the solubility of the compound in vivo; and (e) overcome or overcome a side effect or other difficulty encountered with the compound. Where a —COOH or —OH group is present, pharmaceutically acceptable esters can be employed, for example methyl, ethyl, and the like for —COOH, and acetate maleate and the like for —OH, and those esters known in the art for modifying solubility or hydrolysis characteristics.

The compounds of Formula I and pharmaceutically acceptable salts thereof may be co-administered with at least one other active agent known to be useful in the treatment of cancer.

By the term "co-administration" as used herein is meant either simultaneous administration or any manner of separate sequential administration of a PERK inhibiting compound, as described herein, and a further active agent or agents, known to be useful in the treatment of cancer, including chemotherapy and radiation treatment. The term further active agent or agents, as used herein, includes any compound or therapeutic agent known to or that demonstrates advantageous properties when administered to a patient in need of treatment for cancer. Preferably, if the administration is not simultaneous, the compounds are administered in a close time proximity to each other. Furthermore, it does not matter if the compounds are administered in the same dosage form, e.g. one compound may be administered by injection and another compound may be administered orally.

Typically, any anti-neoplastic agent that has activity versus a susceptible tumor being treated may be co-administered in the treatment of cancer in the present invention. Examples of such agents can be found in Cancer Principles and Practice of Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved.

Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; cell cycle signaling inhibitors; proteasome inhibitors; and inhibitors of cancer metabolism.

Examples of a further active ingredient or ingredients (anti-neoplastic agent) for use in combination or co-administered with the presently invented PERK inhibiting compounds are chemotherapeutic agents.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the $G_2/M$ phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)—N-benzoyl-3-phenylisoserine; is a natural diterpene product isolated from the Pacific yew tree *Taxus brevifolia* and is commercially available as an injectable solution TAXOL®. It is a member of the taxane family of terpenes. It was first isolated in 1971 by Wani et al. J. Am. Chem., Soc., 93:2325. 1971), who characterized its structure by chemical and X-ray crystallographic methods. One mechanism for its activity relates to paclitaxel's capacity to bind tubulin, thereby inhibiting cancer cell growth. Schiff et al., Proc. Natl, Acad, Sci. USA, 77:1561-1565 (1980); Schiff et al., Nature, 277:665-667 (1979); Kumar, J. Biol, Chem, 256: 10435-10441 (1981). For a review of synthesis and anticancer activity of some paclitaxel derivatives see: D. G. I. Kingston et al., Studies in Organic Chemistry vol. 26, entitled "New trends in Natural Products Chemistry 1986", Attaur-Rahman, P. W. Le Quesne, Eds. (Elsevier, Amsterdam, 1986) pp 219-235.

Paclitaxel has been approved for clinical use in the treatment of refractory ovarian cancer in the United States (Markman et al., Yale Journal of Biology and Medicine, 64:583, 1991; McGuire et al., Ann. Intern, Med., 111:273, 1989) and for the treatment of breast cancer (Holmes et al., J. Nat. Cancer Inst., 83:1797, 1991.) It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p. 16-23, 1995).

Docetaxel, (2R,3S)—N-carboxy-3-phenylisoserine, N-tert-butyl ester, 13-ester with 5β-20-epoxy-1,2α,4,7β,10β, 13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree. The dose limiting toxicity of docetaxel is neutropenia.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleukoblastine[R—(R*,R*)-2,3-dihydroxybutanedioate (1:2) (salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer. The primary dose limiting side effects of cisplatin are nephrotoxicity, which may be controlled by hydration and diuresis, and ototoxicity.

Carboplatin, platinum, diammine [1,1-cyclobutane-dicarboxylate(2-)-O,O'], is commercially available as PARAPLATIN® as an injectable solution. Carboplatin is primarily indicated in the first and second line treatment of advanced ovarian carcinoma. Bone marrow suppression is the dose limiting toxicity of carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil.

Busulfan, 1,4-butanediol dimethanesulfonate, is commercially available as MYLERAN® TABLETS. Busulfan is indicated for the palliative treatment of chronic myelogenous leukemia. Bone marrow suppression is the most common dose limiting side effects of busulfan.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics are non-phase specific agents, which bind or intercalate with DNA. Typically, such action results in stable DNA complexes or strand breakage, which disrupts ordinary function of the nucleic acids, leading to cell death. Examples of antibiotic anti-neoplastic agents include, but are not limited to, actinomycins such as dactinomycin, anthrocyclins such as daunorubicin and doxorubicin; and bleomycins.

Dactinomycin, also know as Actinomycin D, is commercially available in injectable form as COSMEGEN®. Dactinomycin is indicated for the treatment of Wilm's tumor and rhabdomyosarcoma. Nausea, vomiting, and anorexia are the most common dose limiting side effects of dactinomycin.

Daunorubicin, (8S-cis-)-8-acetyl-10-[(3-amino-2,3,6-trideoxy-α-L-Iyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Myelosuppression is the most common dose limiting side effect of daunorubicin.

Doxorubicin, (8S,10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas. Myelosuppression is the most common dose limiting side effect of doxorubicin.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas. Pulmonary and cutaneous toxicities are the most common dose limiting side effects of bleomycin.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers. Myelosuppression is the most common side effect of etoposide. The incidence of leucopenia tends to be more severe than thrombocytopenia.

Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leucopenia and thrombocytopenia.

Antimetabolite neoplastic agents are phase specific anti-neoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mercaptopurine, thioguanine, and gemcitabine.

5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate.

Cytarabine, 4-amino-1-β-D-arabinofuranosyl-2 (1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Cytarabine induces leucopenia, thrombocytopenia, and mucositis.

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Myelosuppression, including leucopenia, thrombocytopenia, and anemia, is the most common dose limiting side effect of thioguanine administration. However, gastrointestinal side effects occur and can be dose limiting. Other purine analogs include pentostatin, erythrohydroxynonyladenine, fludarabine phosphate, and cladribine.

Gemcitabine, 2'-deoxy-2',2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Myelosuppression, including leucopenia, thrombocytopenia, and anemia, is the most common dose limiting side effect of gemcitabine administration.

Methotrexate, N-[4[[(2,4-diamino-6-pteridinyl)methyl]methylamino]benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leucopenia, thrombocytopenia, and anemia) and mucositis are expected side effect of methotrexate administration.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino) carbonyloxy]-1H-pyrano[3',4',6,7]indolizino[1,2-b]quinoline-3,14(4H,12H)-dione hydrochloride, is commercially available as the injectable solution CAMPTOSAR®.

Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I:DNA: irintecan or SN-38 ternary complex with replication enzymes.

Irinotecan is indicated for treatment of metastatic cancer of the colon or rectum. The dose limiting side effects of irinotecan HCl are myelosuppression, including neutropenia, and GI effects, including diarrhea.

Topotecan HCl, (S)-10-[(dimethylamino)methyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN®. Topotecan is a derivative of camptothecin which binds to the topoisomerase I DNA complex and prevents religation of singles strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

Also of interest, is the camptothecin derivative of Formula A following, including the racemic mixture (R,S) form as well as the R and S enantiomers:

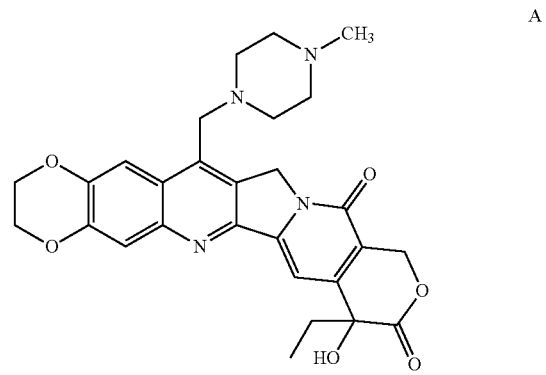 [SMILES: CCC1(O)C(=O)OCc2c1cc1n(c2=O)Cc2c-1nc1cc3c(cc1c2CN1CCN(C)CC1)OCCO3]

known by the chemical name "7-(4-methylpiperazino-methylene)-10,11-ethylenedioxy-20(R,S)-camptothecin (racemic mixture) or "7-(4-methylpiperazino-methylene)-10,11-ethylenedioxy-20(R)-camptothecin (R enantiomer) or "7-(4-methylpiperazino-methylene)-10,11-ethylenedioxy-20(S)-camptothecin (S enantiomer). Such compound as well as related compounds are described, including methods of making, in U.S. Pat. Nos. 6,063,923; 5,342,947; 5,559,235; 5,491,237 and pending U.S. patent application Ser. No. 08/977,217 filed Nov. 24, 1997.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, androgens, and anti-androgens such as flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) such those described in U.S. Pat. Nos. 5,681,835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagagonists such as goserelin acetate and luprolide.

Signal transduction pathway inhibitors are those inhibitors, which block or inhibit a chemical process which evokes an intracellular change. As used herein this change is cell proliferation or differentiation. Signal tranduction inhibitors useful in the present invention include inhibitors of receptor tyrosine kinases, non-receptor tyrosine kinases, SH2/SH3 domain blockers, serine/threonine kinases, phosphotidylinositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain.

Receptor tyrosine kinases are involved in the regulation of cell growth and are generally termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath, John C., Exp. Opin. Ther. Patents (2000) 10(6):803-818; Shawver et al DDT Vol 2, No. 2 Feb. 1997; and Lofts, F. J. et al, "Growth factor receptors as targets", New Molecular Targets for Cancer Chemotherapy, ed. Workman, Paul and Kerr, David, CRC press 1994, London.

Suitably, the pharmaceutically active compounds of the invention are used in combination with a VEGFR inhibitor, suitably 5-[[4-[(2,3-dimethyl-2H-indazol-6-yl)methylamino]-2-pyrimidinyl]amino]-2-methylbenzenesulfonamide, or a pharmaceutically acceptable salt, suitably the monohydrochloride salt thereof, which is disclosed and claimed n International Application No. PCT/US01/49367, having an International filing date of Dec. 19, 2001, International Publication Number WO02/059110 and an International Publication date of Aug. 1, 2002, the entire disclosure of which is hereby incorporated by reference, and which is the compound of Example 69. 5-[[4-[(2,3-dimethyl-2H-indazol-6-yl)methylamino]-2-pyrimidinyl]amino]-2-methylbenzenesulfonamide can be prepared as described in International Application No. PCT/US01/49367.

Suitably, 5-[[4-[(2,3-dimethyl-2H-indazol-6-yl)methylamino]-2-pyrimidinyl]amino]-2-methylbenzenesulfonamide is in the form of a monohydrochloride salt. This salt form can be prepared by one of skill in the art from the description in International Application No. PCT/US01/49367, having an International filing date of Dec. 19, 2001.

5-[[4-[(2,3-dimethyl-2H-indazol-6-yl)methylamino]-2-pyrimidinyl]amino]-2-methylbenzenesulfonamide is sold commercially as the monohydrochloride salt and is known by the generic name pazopanib and the trade name Votrient®.

Pazopanib is implicated in the treatment of cancer and ocular diseases/angiogenesis. Suitably the present invention relates to the treatment of cancer and ocular diseases/angiogenesis, suitably age-related macular degeneration, which method comprises the administration of a compound of Formula (I) alone or in combination with pazopanib.

Tyrosine kinases, which are not growth factor receptor kinases are termed non-receptor tyrosine kinases. Non-receptor tyrosine kinases for use in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S, and Corey, S. J., (1999) Journal of Hematotherapy and Stem Cell Research 8 (5): 465-80; and Bolen, J. B., Brugge, J. S., (1997) Annual review of Immunology. 15: 371-404.

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, akt kinase family members, PDK1 and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; U.S. Pat. No. 6,268,391; Pearce, L. R et al. Nature Reviews Molecular Cell Biology (2010) 11, 9-22. and Martinez-lacaci, L., et al, Int. J. Cancer (2000), 88(1), 44-52.

Suitably, the pharmaceutically active compounds of the invention are used in combination with a MEK inhibitor. Suitably, N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]phenyl}acetamide, or a pharmaceutically acceptable salt or solvate, suitably the dimethyl sulfoxide solvate, thereof, which is disclosed and claimed in International Application No. PCT/JP2005/011082, having an International filing date of Jun. 10, 2005; International Publication Number WO 2005/121142 and an International Publication date of Dec. 22, 2005, the entire disclosure of which is hereby incorporated by reference. N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]phenyl}acetamide, can be prepared as described in United States Patent Publication No. US 2006/0014768, Published Jan. 19, 2006, the entire disclosure of which is hereby incorporated by reference.

Suitably, the pharmaceutically active compounds of the invention are used in combination with a B-Raf inhibitor. Suitably, N-{3-[5-(2-Amino-4-pyrimidinyl)-2-(1,1-dimethylethyl)-1,3-thiazol-4-yl]-2-fluorophenyl}-2,6-difluorobenzenesulfonamide, or a pharmaceutically acceptable salt thereof, which is disclosed and claimed in International Application No. PCT/US2009/042682, having an International filing date of May 4, 2009, the entire disclosure of which is hereby incorporated by reference. N-{3-[5-(2-Amino-4-pyrimidinyl)-2-(1,1-dimethylethyl)-1,3-thiazol-4-yl]-2-fluorophenyl}-2,6-difluorobenzenesulfonamide can be prepared as described in International Application No. PCT/US2009/042682.

Suitably, the pharmaceutically active compounds of the invention are used in combination with an Akt inhibitor. Suitably, N-{(1S)-2-amino-1-[(3,4-difluorophenyl)methyl]ethyl}-5-chloro-4-(4-chloro-1-methyl-1H-pyrazol-5-yl)-2-furancarboxamide or a pharmaceutically acceptable salt thereof, which is disclosed and claimed in International Application No. PCT/US2008/053269, having an International filing date of Feb. 7, 2008; International Publication Number WO 2008/098104 and an International Publication date of Aug. 14, 2008, the entire disclosure of which is hereby incorporated by reference. N-{(1S)-2-amino-1-[(3,4-difluorophenyl)methyl]ethyl}-5-chloro-4-(4-chloro-1-methyl-1H-pyrazol-5-yl)-2-furancarboxamide is the compound of example 224 and can be prepared as described in International Application No. PCT/US2008/053269.

Suitably, the pharmaceutically active compounds of the invention are used in combination with an Akt inhibitor. Suitably, N-{(1S)-2-amino-1-[(3-fluorophenyl)methyl]ethyl}-5-chloro-4-(4-chloro-1-methyl-1H-pyrazol-5-yl)-2-thiophenecarboxamide or a pharmaceutically acceptable salt thereof, which is disclosed and claimed in International Application No. PCT/US2008/053269, having an International filing date of Feb. 7, 2008; International Publication Number WO 2008/098104 and an International Publication date of Aug. 14, 2008, the entire disclosure of which is hereby incorporated by reference. N-{(1S)-2-amino-1-[(3-fluorophenyl)methyl]ethyl}-5-chloro-4-(4-chloro-1-methyl-1H-pyrazol-5-yl)-2-thiophenecarboxamide is the compound of example and can be prepared as described in International Application No. PCT/US2008/053269. Suitably, N-{(1S)-2-amino-1-[(3-fluorophenyl)methyl]ethyl}-5-chloro-4-(4-chloro-1-methyl-1H-pyrazol-5-yl)-2-thiophenecarboxamide is in the form of a hydrochloride salt. The salt form can be prepared by one of skill in the art from the description in International Application No. PCT/US2010/022323, having an International filing date of Jan. 28, 2010.

Inhibitors of Phosphotidylinositol-3 Kinase family members including blockers of PI3-kinase, ATM, DNA-PK, and Ku may also be useful in the present invention. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer res, (2000) 60(6), 1541-1545.

Also of interest in the present invention are Myo-inositol signaling inhibitors such as phospholipase C blockers and Myoinositol analogues. Such signal inhibitors are described in Powis, G., and Kozikowski A., (1994) New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9 (2) 99-102; and BioChim. Biophys. Acta, (19899) 1423(3):19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example lmclone C225 EGFR specific antibody (see Green, M. C. et al, Monoclonal Antibody Therapy for Solid Tumors, Cancer Treat. Rev., (2000), 26(4), 269-286); Herceptin® erbB2 antibody (see Tyrosine Kinase Signalling in Breast cancer:erbB Family Receptor Tyrosine Kniases, Breast cancer Res., 2000, 2(3), 176-183); and 2CB VEGFR2 specific antibody (see Brekken, R. A. et al, Selective Inhibition of VEGFR2Activity by a monoclonal Anti-VEGF antibody blocks tumor growth in mice, Cancer Res. (2000) 60, 5117-5124).

Non-receptor kinase angiogenesis inhibitors may also be useful in the present invention. Inhibitors of angiogenesis related VEGFR and TIE2 are discussed above in regard to signal transduction inhibitors (both receptors are receptor tyrosine kinases). Angiogenesis in general is linked to erbB2/EGFR signaling since inhibitors of erbB2 and EGFR have been shown to inhibit angiogenesis, primarily VEGF expression. Accordingly, non-receptor tyrosine kinase inhibitors may be used in combination with the compounds of the present invention. For example, anti-VEGF antibodies, which do not recognize VEGFR (the receptor tyrosine kinase), but bind to the ligand; small molecule inhibitors of integrin (alpha beta$_3$) that will inhibit angiogenesis; endostatin and angiostatin (non-RTK) may also prove useful in combination with the disclosed compounds. (See Bruns C J et al (2000), Cancer Res., 60: 2926-2935; Schreiber A B, Winkler M E, and Derynck R. (1986), Science, 232: 1250-1253; Yen L et al. (2000), Oncogene 19: 3460-3469).

Agents used in immunotherapeutic regimens may also be useful in combination with the compounds of Formula (I). There are a number of immunologic strategies to generate an immune response. These strategies are generally in the realm of tumor vaccinations. The efficacy of immunologic approaches may be greatly enhanced through combined inhibition of signaling pathways using a small molecule inhibitor. Discussion of the immunologic/tumor vaccine approach against erbB2/EGFR are found in Reilly R T et al. (2000), Cancer Res. 60: 3569-3576; and Chen Y, Hu D, Eling D J, Robbins J, and Kipps T J. (1998), Cancer Res. 58: 1965-1971.

Agents used in proapoptotic regimens (e.g., bcl-2 antisense oligonucleotides) may also be used in the combination of the present invention. Members of the Bcl-2 family of proteins block apoptosis. Upregulation of bcl-2 has therefore been linked to chemoresistance. Studies have shown that the epidermal growth factor (EGF) stimulates anti-apoptotic members of the bcl-2 family (i.e., mcl-1). Therefore, strategies designed to downregulate the expression of bcl-2 in tumors have demonstrated clinical benefit and are now in Phase II/III trials, namely Genta's G3139 bcl-2 antisense oligonucleotide. Such proapoptotic strategies using the antisense oligonucleotide strategy for bcl-2 are discussed in Water J S et al. (2000), J. Clin. Oncol. 18: 1812-1823; and Kitada S et al. (1994), Antisense Res. Dev. 4: 71-79.

Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania et al, Exp. Opin. Ther. Patents (2000) 10(2):215-230. Further, p21WAF1/CIP1 has been described as a potent and universal inhibitor of cyclin-dependent kinases (Cdks) (Ball et al., *Progress in Cell Cycle Res.*, 3: 125 (1997)). Compounds that are known to induce expression of p21WAF1/CIP1 have been implicated in the suppression of cell proliferation and as having tumor suppressing activity (Richon et al., *Proc. Nat. Acad. Sci. U.S.A.* 97(18): 10014-10019 (2000)), and are included as cell cycle signaling inhibitors. Histone deacetylase (HDAC) inhibitors are implicated in the transcriptional activation of p21WAF1/CIP1 (Vigushin et al., *Anticancer Drugs*, 13(1): 1-13 (January 2002)), and are suitable cell cycle signaling inhibitors for use in combination herein. Examples of such HDAC inhibitors include 1. Vorinostat, including pharmaceutically acceptable salts thereof. Marks et al., *Nature Biotechnology* 25, 84 to 90 (2007); Stenger, *Community Oncology* 4, 384-386 (2007). Vorinostat has the following chemical structure and name:

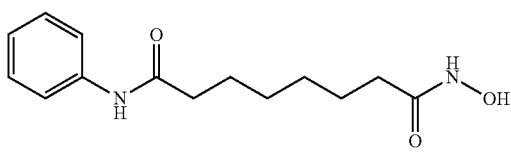

N-hydroxy-N'-phenyl-octanediamide

2. Romidepsin, including pharmaceutically acceptable salts thereof. Vinodhkumar et al., *Biomedicine & Pharmacotherapy* 62 (2008) 85-93. Romidepsin, has the following chemical structure and name:

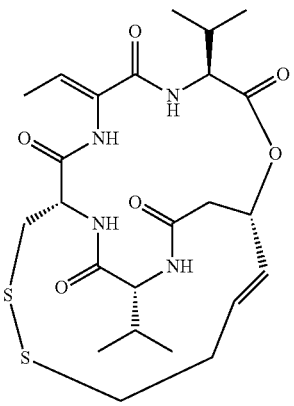 [SMILES: C/C=C1\NC(=O)[C@H]2CSSCC/C=C/[C@H](CC(=O)N[C@H](C(C)C)C(=O)N2)OC(=O)[C@H](C(C)C)NC1=O]

(1S,4S,7Z,10S,16E,21R)-7-ethylidene-4,21-di(propan-2-yl)-2-oxa-12,13-dithia-5,8,20,23-tetrazabicyclo[8.7.6]tricos-16-ene-3,6,9,19,22-pentone 3. Panobinostat, including pharmaceutically acceptable salts thereof. *Drugs of the Future* 32(4): 315-322 (2007).

Panobinostat, has the following chemical structure and name:

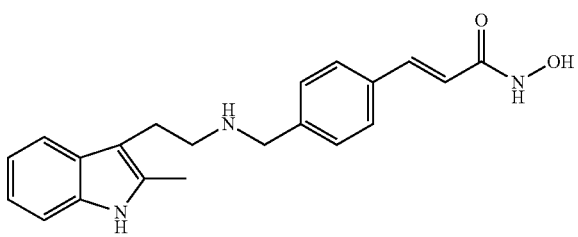 [SMILES: Cc1[nH]c2ccccc2c1CCNCc1ccc(/C=C/C(=O)NO)cc1]

(2E)-N-hydroxy-3-[4-({[2-(2-methyl-1H-indol-3-yl)ethyl]amino}methyl)phenyl]acrylamide 4. Valproic acid, including pharmaceutically acceptable salts thereof. Gottlicher, et al., EMBO J. 20(24): 6969-6978 (2001).

Valproic acid, has the following chemical structure and name:

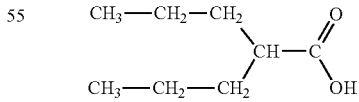

2-propylpentanoic acid

5. Mocetinostat (MGCD0103), including pharmaceutically acceptable salts thereof. Balasubramanian et al., Cancer Letters 280: 211-221 (2009).

Mocetinostat, has the following chemical structure and name:

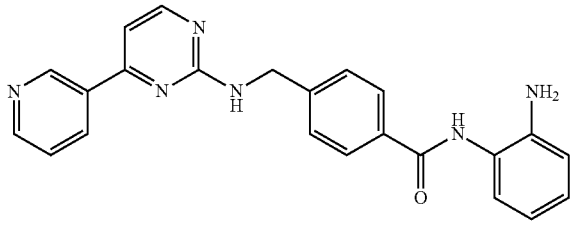 [SMILES: Nc1ccccc1NC(=O)c1ccc(CNc2nccc(-c3cccnc3)n2)cc1]

N-(2-Aminophenyl)-4-[[(4-pyridin-3-ylpyrimidin-2-yl)amino]methyl]benzamide

Further examples of such HDAC inhibitors are included in Bertrand European Journal of Medicinal Chemistry 45, (2010) 2095-2116, particularly the compounds of table 3 therein as indicated below.

Hydroxamic acids

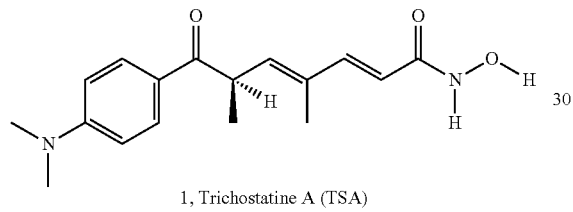

1, Trichostatine A (TSA)

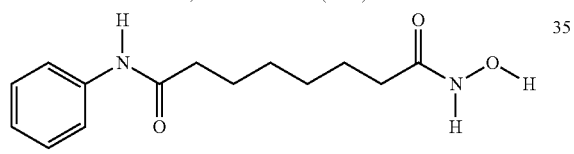

2, SAHA

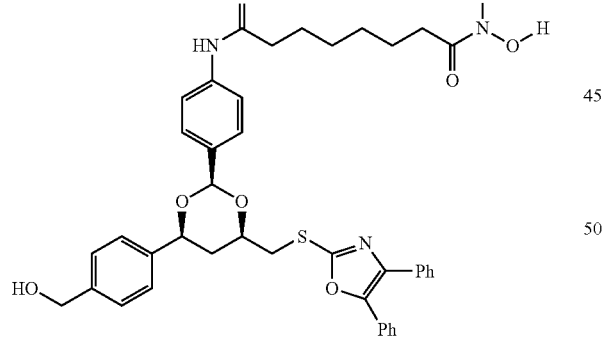

3, Tubacin

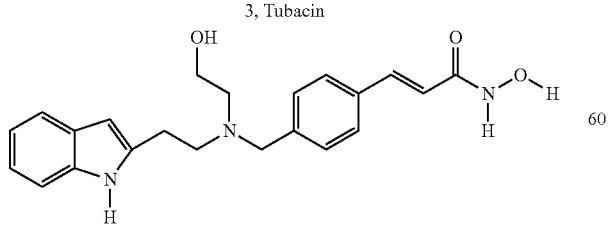

4, LAQ824

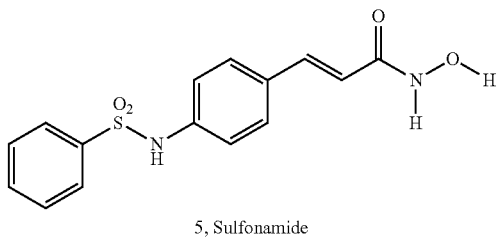

5, Sulfonamide

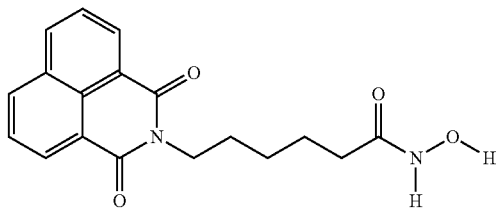

6, Scriptaid

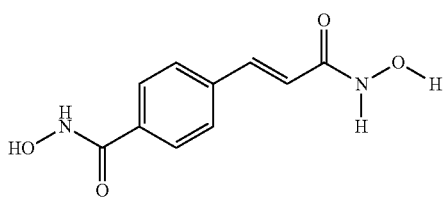

7, CBHA

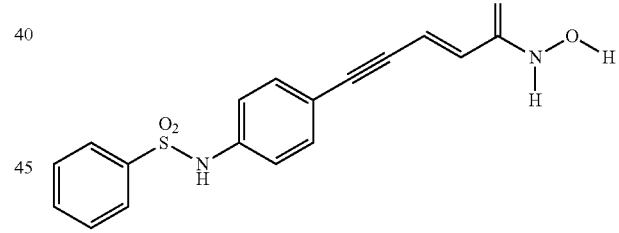

8, Oxamflatin

Cyclic tetrapeptides

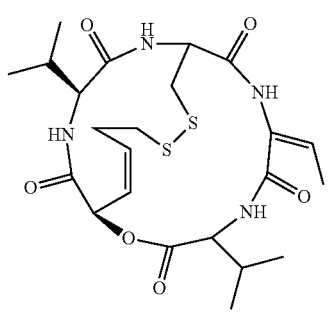

9, FK226

-continued

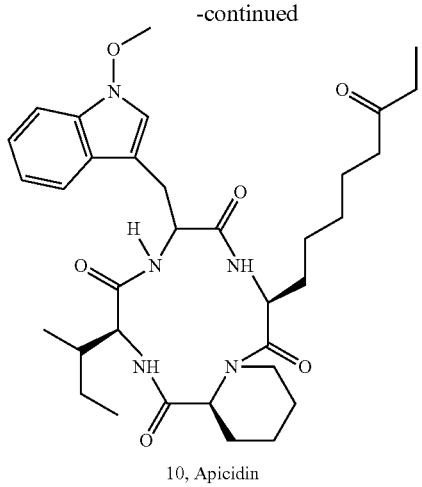
10, Apicidin

Short chain carboxylic acids

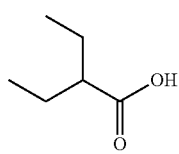
11, Valproic acid

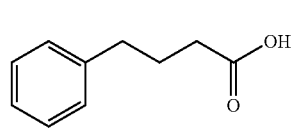
12, Phenylbutyric acid

Benzamides

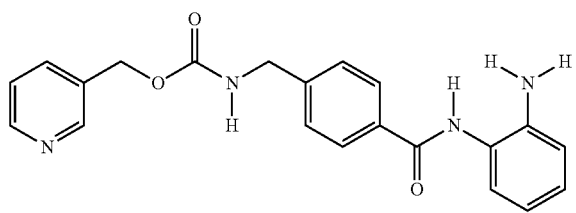
13, MS-275

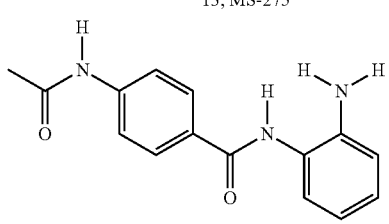
14, Cl-994

Keto derivatives

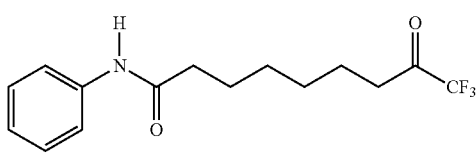
15, Trifluorométhyl cétone

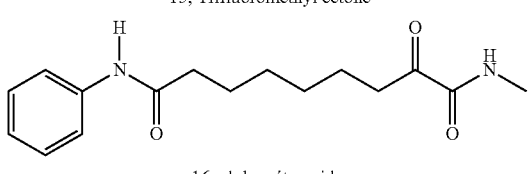
16, alpha-cétoamide

Proteasome inhibitors are drugs that block the action of proteasomes, cellular complexes that break down proteins, like the p53 protein. Several proteasome inhibitors are marketed or are being studied in the treatment of cancer. Suitable proteasome inhibitors for use in combination herein include:

1. Bortezomib (Velcade®), including pharmaceutically acceptable salts thereof. Adams J, Kauffman M (2004), *Cancer Invest* 22 (2): 304-11.

Bortezomib has the following chemical structure and name.

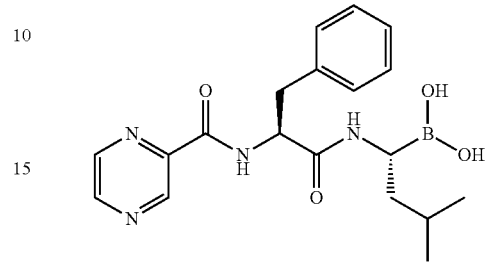

[(1R)-3-methyl-1-({(2S)-3-phenyl-2-[(pyrazin-2-ylcarbonyl)amino]propanoyl}amino)butyl]boronic acid 2. Disulfuram, including pharmaceutically acceptable salts thereof. Bouma et al. (1998). *J. Antimicrob. Chemother.* 42 (6): 817-20.

Disulfuram has the following chemical structure and name.

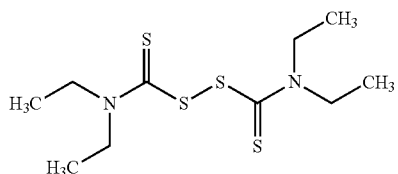

1,1',1'',1'''-[disulfanediylbis(carbonothioylnitrilo)] tetraethane

3. Epigallocatechin gallate (EGCG), including pharmaceutically acceptable salts thereof. Williamson et al., (December 2006), *The Journal of Allergy and Clinical Immunology* 118 (6): 1369-74.

Epigallocatechin gallate has the following chemical structure and name.

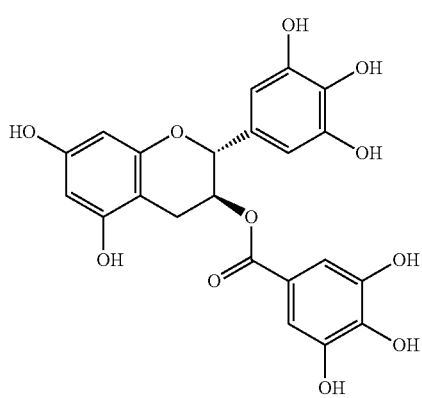 [SMILES: O=C(O[C@H]1Cc2c(O)cc(O)cc2O[C@@H]1c1cc(O)c(O)c(O)c1)c1cc(O)c(O)c(O)c1]

R2R,3R)-5,7-dihydroxy-2-(3,4,5-trihydroxyphenyl)chroman-3-A3,4,5-trihydroxybenzoate 4. Salinosporamide A, including pharmaceutically acceptable salts thereof. Feling et al., (2003), *Angew. Chem. Int. Ed. Engl.* 42 (3): 355-7.

Salinosporamide A has the following chemical structure and name.

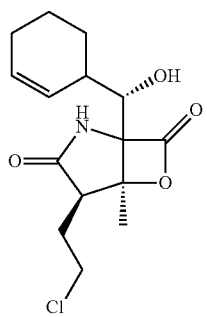 [SMILES: C[C@@]12OC(=O)C1([C@@H](O)C1C=CCCC1)NC(=O)[C@@H]2CCCl]

(4R,5S)-4-(2-chloroethyl)-1-((1S)-cyclohex-2-enyl(hydroxy)methyl)-5-methyl-6-oxa-2-azabicyclo3.2.0heptane-3,7-dione 5. Carfilzomib, including pharmaceutically acceptable salts thereof. Kuhn D J, et al, Blood, 2007, 110:3281-3290.

Carfilzomib has the following chemical structure and name.

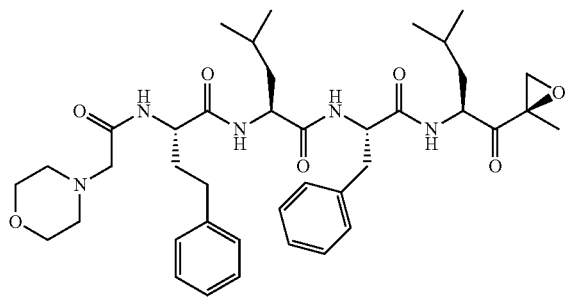 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)[C@@]1(C)CO1]

(S)-4-methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide The 70 kilodalton heat shock proteins (Hsp70s) and 90 kilodalton heat shock proteins (Hsp90s) are a families of ubiquitously expressed heat shock proteins. Hsp70s and Hsp90s are over expressed certain cancer types. Several Hsp70s and Hsp90s inhibitors are being studied in the treatment of cancer. Suitable Hsp70s and Hsp90s inhibitors for use in combination herein include:

1. 17-AAG (Geldanamycin), including pharmaceutically acceptable salts thereof. Jia W et al. Blood. 2003 Sep. 1; 102(5):1824-32.

17-AAG (Geldanamycin) has the following chemical structure and name.

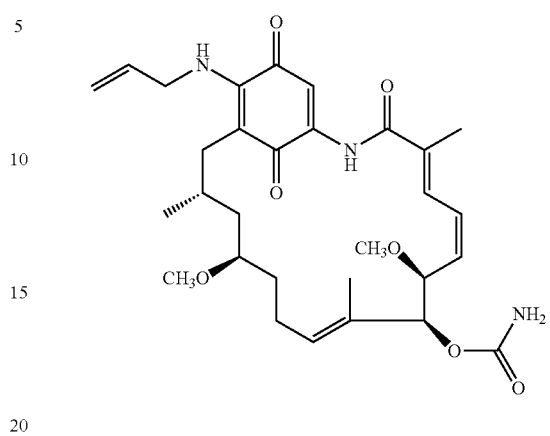

17-(Allylamino)-17-demethoxygeldanamycin

2. Radicicol, including pharmaceutically acceptable salts thereof. (Lee et al., Mol Cell Endocrinol. 2002, 188, 47-54)

Radicicol has the following chemical structure and name.

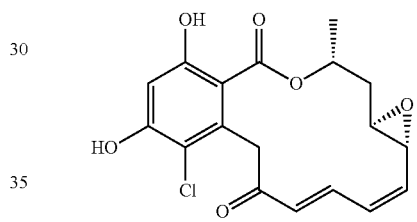

(1aR,2Z,4E,14R,15aR)-8-chloro-9,11-dihydroxy-14-methyl-15,15a-dihydro-1aH-benzo[c]oxireno[2,3-k][1]oxacyclotetradecine-6,12(7H,14H)-dione Inhibitors of cancer metabolism—Many tumor cells show a markedly different metabolism from that of normal tissues. For example, the rate of glycolysis, the metabolic process that converts glucose to pyruvate, is increased, and the pyruvate generated is reduced to lactate, rather than being further oxidized in the mitochondria via the tricarboxylic acid (TCA) cycle. This effect is often seen even under aerobic conditions and is known as the Warburg Effect.

Lactate dehydrogenase A (LDH-A), an isoform of lactate dehydrogenase expressed in muscle cells, plays a pivotal role in tumor cell metabolism by performing the reduction of pyruvate to lactate, which can then be exported out of the cell. The enzyme has been shown to be upregulated in many tumor types. The alteration of glucose metabolism described in the Warburg effect is critical for growth and proliferation of cancer cells and knocking down LDH-A using RNA-i has been shown to lead to a reduction in cell proliferation and tumor growth in xenograft models.

D. A. Tennant et. al., Nature Reviews, 2010, 267.
P. Leder, et. al., Cancer Cell, 2006, 9, 425.

High levels of fatty acid synthase (FAS) have been found in cancer precursor lesions. Pharmacological inhibition of FAS affects the expression of key oncogenes involved in both cancer development and maintenance.

Alli et al. *Oncogene* (2005) 24, 39-46. doi:10.1038

Inhibitors of cancer metabolism, including inhibitors of LDH-A and inhibitors of fatty acid biosynthesis (or FAS inhibitors), are suitable for use in combination with the compounds of this invention.

In one embodiment, the cancer treatment method of the claimed invention includes the co-administration a compound of Formula (I) and/or a pharmaceutically acceptable salt thereof and at least one anti-neoplastic agent, such as one selected from the group consisting of anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, cell cycle signaling inhibitors; proteasome inhibitors; and inhibitors of cancer metabolism.

Compositions

The pharmaceutically active compounds within the scope of this invention are useful as PERK inhibitors in mammals, particularly humans, in need thereof.

The present invention therefore provides a method of treating cancer, arthritis and other conditions requiring PERK inhibition, which comprises administering an effective amount of a compound of Formula (I) or a pharmaceutically acceptable salt thereof. The compounds of Formula (I) also provide for a method of treating the above indicated disease states because of their demonstrated ability to act as PERK inhibitors. The drug may be administered to a patient in need thereof by any conventional route of administration, including, but not limited to, intravenous, intramuscular, oral, subcutaneous, intradermal, and parenteral.

The pharmaceutically active compounds of the present invention are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical compositions are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the presently invented pharmaceutically active compounds in a pharmaceutical dosage unit as described above will be an efficacious quantity preferably selected from the range of 0.001-100 mg/kg of active compound, preferably 0.001-50 mg/kg. When treating a human patient in need of a PERK inhibitor, the selected dose is administered preferably from 1-6 times daily, orally or parenterally. Preferred forms of parenteral administration include topically, rectally, transdermally, by injection and continuously by infusion. Oral dosage units for human administration preferably contain from 0.05 to 3500 mg of active compound. Oral administration, which uses lower dosages, is preferred. Parenteral administration, at high dosages, however, also can be used when safe and convenient for the patient.

Optimal dosages to be administered may be readily determined by those skilled in the art, and will vary with the particular PERK inhibitor in use, the strength of the preparation, the mode of administration, and the advancement of the disease condition. Additional factors depending on the particular patient being treated will result in a need to adjust dosages, including patient age, weight, diet, and time of administration.

The method of this invention of inducing PERK inhibitory activity in mammals, including humans, comprises administering to a subject in need of such activity an effective PERK inhibiting amount of a pharmaceutically active compound of the present invention.

The invention also provides for the use of a compound of Formula (I) or a pharmaceutically acceptable salt thereof in the manufacture of a medicament for use as a PERK inhibitor.

The invention also provides for the use of a compound of Formula (I) or a pharmaceutically acceptable salt thereof in the manufacture of a medicament for use in therapy.

The invention also provides for the use of a compound of Formula (I) or a pharmaceutically acceptable salt thereof in the manufacture of a medicament for use in treating cancer.

The invention also provides for a pharmaceutical composition for use as a PERK inhibitor which comprises a compound of Formula (I) or a pharmaceutically acceptable salt thereof and a pharmaceutically acceptable carrier.

The invention also provides for a pharmaceutical composition for use in the treatment of cancer which comprises a compound of Formula (I) or a pharmaceutically acceptable salt thereof and a pharmaceutically acceptable carrier.

In addition, the pharmaceutically active compounds of the present invention can be co-administered with further active ingredients, such as other compounds known to treat cancer, or compounds known to have utility when used in combination with a PERK inhibitor.

Without further elaboration, it is believed that one skilled in the art can, using the preceding description, utilize the present invention to its fullest extent. The following Examples are, therefore, to be construed as merely illustrative and not a limitation of the scope of the present invention in any way.

EXAMPLES

While particular embodiments of the present invention are described, the skilled artisan will appreciate that various changes and modifications can be made without departing from the spirit and scope of the invention.

Bicycloheteroaryl halides used in the invention as chemical intermediates are listed below in the table. When available, the corresponding references to the synthetic preparation are given. For intermediates without a cited literature reference, details of the synthetic preparation are included in the examples below.

| Intermediate | Name | Reference |
|---|---|---|
| | 3-bromo-1-methyl-1H-pyrazolo[3,4-d]pyrimidin-4-amine | Leonova and Yashunskii, Chemistry of Heterocyclic Compounds Volume 18, Number 7, July, 1982, 753-755 |
| | 3-bromo-1H-pyrazolo[3,4-d]pyrimidin-4-amine | Leonova and Yashunskii, Chemistry of Heterocyclic Compounds Volume 18, Number 7, July, 1982, 753-755 |
| | 5-bromo-7H-pyrrolo[2,3-d]pyrimidin-4-amine | Commercially available. Also see Gerster, J. F et. al, J. Het. Chem. 1969, 6, 207-213. |
| | 5-bromo-7-methyl-7H-pyrrolo[2,3-d]pyrimidin-4-amine | Details below (in Example 4) |
| | 3-bromothieno[3,2-c]pyridin-4-amine | Miyazaki, Y et. al. Bioorganic and Medicinal Chemistry Letters, 2007, 17, 250-254 |
| | 3-bromofuro[3,2-c]pyridin-4-amine | Miyazaki, Y et. al. Bioorganic and Medicinal Chemistry Letters, 2007, 17, 250-254 |
| | 5-bromothieno[2,3-d]pyrimidin-4-amine | Details below (in Example 31) |

Example 1

1-methyl-3-[1-(phenylacetyl)-2,3-dihydro-1H-indol-5-yl]-1H-pyrazolo[3,4-d]pyrimidin-4-amine

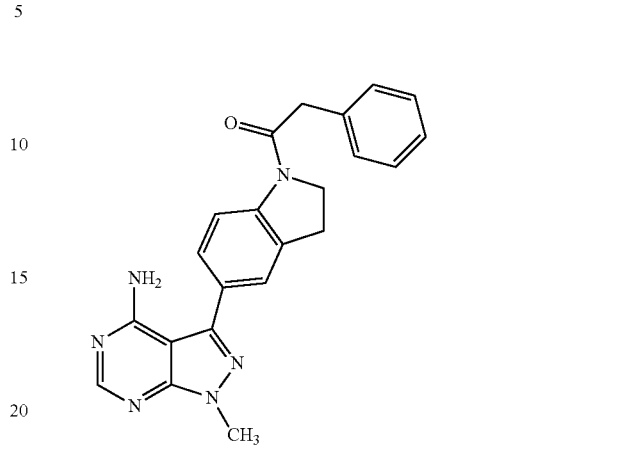

5-bromo-1-(phenylacetyl)-2,3-dihydro-1H-indole

To a mixture of phenylacetic acid (0.687 g, 5.05 mmol) and HATU (2.112 g, 5.55 mmol) in N,N-Dimethylformamide (DMF) (5 mL) was added Hunig's base (0.882 mL, 5.05 mmol), and the resulting mixture was stirred for 15 minutes at room temperature. 5-bromo-2,3-dihydro-1H-indole (1 g, 5.05 mmol) was added, and the reaction mixture was stirred at room temperature overnight. The reaction was poured onto water, and the resulting precipitate was filtered and air dried to afford the 5-bromo-1-(phenylacetyl)-2,3-dihydro-1H-indole (1.24 g) as a tan solid.

1-methyl-3-[1-(phenylacetyl)-2,3-dihydro-1H-indol-5-yl]-1H-pyrazolo[3,4-d]pyrimidin-4-amine To 5-bromo-1-(phenylacetyl)-2,3-dihydro-1H-indole (122 mg, 0.386 mmol), bis(pinacolato)diboron (125 mg, 0.491 mmol), PdCl2(dppf)-CH2Cl2 adduct (28.6 mg, 0.035 mmol) were added 1,4-Dioxane (2 mL) and ammonium acetate (81 mg, 1.052 mmol) into a 5 mL microwave vial. The mixture was then bubble N2 gas for 5 minutes then capped and heated in oil bath at 80° C. After 1 hr the reaction was cooled then 3-bromo-1-methyl-1H-pyrazolo[3,4-d]pyrimidin-4-amine (80 mg, 0.351 mmol), 2M K2CO3 (1 mL) and an additional 10 mg of PdCl2(dppf) catalyst were added. The vial was then capped and heated in a microwave reactor for 15 minutes at 110° C. The reaction was then concentrated then dissolved in 2 mL of DMSO and the solid was filtered off using a syringe filter and the filtrated was purified on HPLC: (HPLC condition: Gilson System using Trilution software with a Sunfire 5u C18(2) 100A. 50×30.00 mm 5 micron. 7.3-minute run (47 ml/min, 20% ACN/H2O, 0.1% TFA to 40% ACN/H2O, 0.1% TFA) with UV detection at 254 nm). Product fractions were combined and the volume was reduced to remove most of the MeCN. The water left behind was transferred into a 40 mL vial and freeze-dried to isolated 1-methyl-3-[1-(phenylacetyl)-2,3-dihydro-1H-indol-5-yl]-1H-pyrazolo[3,4-d]pyrimidin-4-amine trifluoroacetate salt (42 mg, 0.084 mmol, 24.02% yield) as a white solid. LC-MS (ES) m/z=385 [M+H]+. $^1$H NMR (400 MHz, DMSO-d6) 8.37 (s, 1H), 8.21 (d, J=8.34 Hz, 1H), 7.50 (s, 1H), 7.44 (dd, J=1.52, 8.34 Hz, 1H), 7.24-7.38 (m, 5H), 4.24 (t, J=8.59 Hz, 2H), 3.97 (s, 3H), 3.90 (s, 2H), 3.24 (t, J=8.34 Hz, 2H) the NH2 protons was not observed in spectra.

Example 2

3-{1-[(2,5-difluorophenyl)acetyl]-2,3-dihydro-1H-indol-5-yl}-1-methyl-1H-pyrazolo[3,4-d]pyrimidin-4-amine

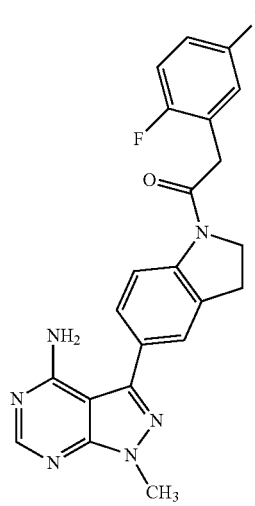

5-bromo-1-[(2,5-difluorophenyl)acetyl]-2,3-dihydro-1H-indole

To a mixture of (2,5-difluorophenyl)acetic acid (0.869 g, 5.05 mmol) and HATU (2.112 g, 5.55 mmol) in N,N-Dimethylformamide (DMF) (10 mL) was added Hunig's base (0.882 mL, 5.05 mmol), and the resulting mixture was stirred for 15 minutes at room temperature. 5-bromo-2,3-dihydro-1H-indole (1 g, 5.05 mmol) was added, and the reaction mixture was stirred at room temperature for 1 hour. The mixture was poured onto water, and the resulting aqueous mixture was filtered to afford 5-bromo-1-[(2,5-difluorophenyl)acetyl]-2,3-dihydro-1H-indole (1.6 g) as a tan solid.

3-{1-[(2,5-difluorophenyl)acetyl]-2,3-dihydro-1H-indol-5-yl}-1-methyl-1H-pyrazolo[3,4-d]pyrimidin-4-amine To a mixture of 5-bromo-1-[(2,5-difluorophenyl)acetyl]-2,3-dihydro-1H-indole (160 mg, 0.454 mmol), bis(pinacolato)diboron (127 mg, 0.500 mmol), and potassium acetate (134 mg, 1.363 mmol) was added 1,4-dioxane (6 mL), and the mixture was degassed with N2 for 10 minutes. PdCl2(dppf)-CH2Cl2 adduct (18.55 mg, 0.023 mmol) was added, and the reaction mixture was stirred for 3 hours at 100 C in a sealed vessel. The reaction was cooled down to room temperature. 3-bromo-1-methyl-1H-pyrazolo[3,4-d]pyrimidin-4-amine (104 mg, 0.454 mmol) and sat. aq. NaHCO3 (2 mL) were added, and N2 gas was bubbled through the mixture for 10 minutes. PdCl2(dppf)-CH2Cl2 adduct (18.55 mg, 0.023 mmol) was added, the vessel was sealed, and the reaction mixture was stirred overnight at 100 C (LCMS:N13207-34suzu). The mixture was allowed to cool to room temperature and poured onto water (~150 mL). The resulting mixture was filtered, and the resulting solid was triturated with Et2O. To the solid in the filter was added a 90:10 mixture of CHCl3:CH3OH (~7 mL), and the resulting mixture was filtered. The filtrate was injected into a 90 g SiO2 columns. Flash chromatography on SiO2 (gradient: 100% CHCl3 to 90:10:1 CHCl3:CH3OH:NH4OH) provided the title compound 3-{1-[(2,5-difluorophenyl)acetyl]-2,3-dihydro-1H-indol-5-yl}-1-methyl-1H-pyrazolo[3,4-d]pyrimidin-4-amine (160 mg) as a brown solid. $^1$H NMR (400 MHz, DMSO-d6) δ 3.29 (t, J=8.34 Hz, 2H), 3.94 (s, 3H), 3.97 (s, 2H), 4.30 (t, J=8.46 Hz, 2H), 7.14-7.31 (m, 3H), 7.44 (d, J=8.34 Hz, 1H), 7.53 (s, 1H), 8.14 (d, J=8.34 Hz, 1H), 8.25 (s, 1H)

Example 3

3-[1-(phenylacetyl)-2,3-dihydro-1H-indol-5-yl]-1H-pyrazolo[3,4-d]pyrimidin-4-amine

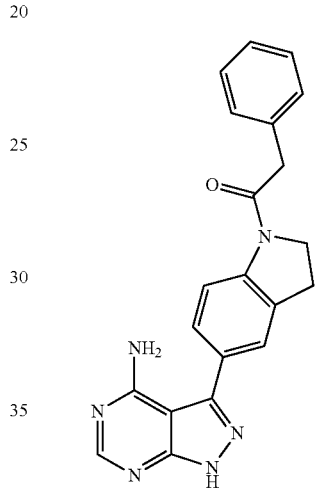

3-[1-(phenylacetyl)-2,3-dihydro-1H-indol-5-yl]-1H-pyrazolo[3,4-d]pyrimidin-4-amine To a mixture of 5-bromo-1-(phenylacetyl)-2,3-dihydro-1H-indole (148 mg, 0.467 mmol),bis(pinacolato)diboron (125 mg, 0.491 mmol), and potassium acetate (138 mg, 1.402 mmol) was added 1,4-dioxane (6 mL), and the mixture was degassed with N2 for 10 minutes. PdCl2(dppf)-CH2Cl2 adduct (19.08 mg, 0.023 mmol) was added, and the reaction mixture was stirred for 3 hours at 100 C into a sealed vessel. The reaction was cooled down to room temperature. 3-bromo-1H-pyrazolo[3,4-d]pyrimidin-4-amine (100 mg, 0.467 mmol) and sat. aq. NaHCO3 (2 mL) were added, and N2 gas was bubbled through the mixture for 10 minutes. PdCl2(dppf)-CH2Cl2 adduct (19.08 mg, 0.023 mmol) was added, the vessel was sealed, and the reaction mixture was stirred for 3 days at 100 C. The mixture was allowed to cool to room temperature and poured onto water (~150 mL). The resulting mixture was filtered, and the resulting solid was triturated with EtOAc. To the dark solid in the filter was added a 80:20 mixture of CHCl3:CH3OH (~7 mL), and the resulting mixture was filtered. The filtrate was injected into a 90 g SiO2 columns. Flash chromatography on SiO2 (gradient: 100% CHCl3 to 90:10:1 CHCl3:CH3OH:NH4OH) provided the title compound. Trituration with Et2O afforded the title compound 3-[1-(phenylacetyl)-2,3-dihydro-1H-indol-5-yl]-1H-pyrazolo[3,4-d]pyrimidin-4-amine (35 mg) as a grey solid.

¹H NMR (400 MHz, DMSO-d₆) 3.24 (t, J=8.34 Hz, 2H), 3.89 (s, 2H), 4.24 (t, J=8.46 Hz, 2H), 7.22-7.40 (m, 6H), 7.44 (d, J=8.34 Hz, 1H), 7.50 (s, 1H), 8.17-8.23 (m, 2H), 13.51 (s, 1H)

Example 4

7-methyl-5-[1-(phenylacetyl)-2,3-dihydro-1H-indol-5-yl]-7H-pyrrolo[2,3-d]pyrimidin-4-amine

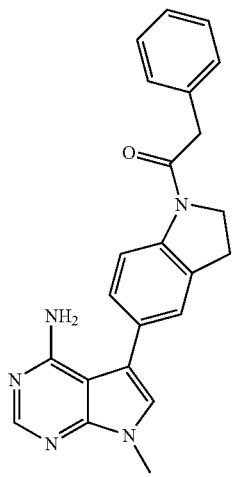 [SMILES: Cn1cc(-c2ccc3c(c2)CCN3C(=O)Cc2ccccc2)c2c(N)ncnc21]

4-chloro-7-methyl-7H-pyrrolo[2,3-d]pyrimidine

To 4-chloro-1H-pyrrolo[2,3-d]pyrimidine (15.2 g, 99 mmol) in N,N-Dimethylformamide (DMF) (100 mL) at 0 C was added 60% NaH (5.15 g, 129 mmol) portionwise. After H2 bubbling stopped, iodomethane (6.81 mL, 109 mmol) was added dropwise, and then the reaction mixture was allowed to warm to room temperature. After 3 hours, the reaction mixture was poured slowly onto water (~800 mL; Caution: H₂ evolution due to quenching excess NaH). The resulting solid was filtered and washed with water followed by hexanes to afford 4-chloro-7-methyl-7H-pyrrolo[2,3-d]pyrimidine (12.2 g) as an off-white solid.

5-bromo-4-chloro-7-methyl-7H-pyrrolo[2,3-d]pyrimidine

To 4-chloro-7-methyl-7H-pyrrolo[2,3-d]pyrimidine (12.15 g, 72.5 mmol) in Dichloromethane (DCM) (200 mL) was added NBS (13.55 g, 76 mmol) portionwise, and the reaction mixture was stirred overnight at room temperature. The solvent was evaporated, and the solid was washed with water and dried to afford 5-bromo-4-chloro-7-methyl-7H-pyrrolo[2,3-d]pyrimidine (17 g) as an off-white solid.

5-bromo-7-methyl-7H-pyrrolo[2,3-d]pyrimidin-4-amine

A suspension of 5-bromo-4-chloro-7-methyl-7H-pyrrolo[2,3-d]pyrimidine (17 g, 69.0 mmol) in ammonium hydroxide (150 mL, 3852 mmol) was stirred for 2 days at 100° C. in a sealed vessel. The reaction was allowed to cool to room temperature and filtered. The collected solid was washed with Et₂O to afford the product 5-bromo-7-methyl-7H-pyrrolo[2,3-d]pyrimidin-4-amine (12.5 g) as a white solid.

7-methyl-5-[1-(phenylacetyl)-2,3-dihydro-1H-indol-5-yl]-7-7H-pyrrolo[2,3-d]pyrimidin-4-amine To a mixture of 5-bromo-1-(phenylacetyl)-2,3-dihydro-1H-indole (139 mg, 0.440 mmol), bis(pinacolato)diboron (117 mg, 0.462 mmol), and potassium acetate (130 mg, 1.321 mmol) was added 1,4-dioxane (6 mL), and the mixture was degassed with N2 for 10 minutes. PdCl₂(dppf)-CH2Cl2 adduct (19.08 mg, 0.023 mmol) was added, and the reaction mixture was stirred for 3 hours at 100 C into a sealed vessel. The reaction was cooled down to room temperature. 5-bromo-7-methyl-7H-pyrrolo[2,3-d]pyrimidin-4-amine (100 mg, 0.440 mmol) and sat. aq. NaHCO₃ (2 mL) were added, and N₂ gas was bubbled through the mixture for 10 minutes. PdCl₂(dppf)-CH2Cl2 adduct (17.98 mg, 0.022 mmol) was added, the vessel was sealed, and the reaction mixture was stirred for 3 days at 100 C). The mixture was allowed to cool to room temperature and poured onto water (~150 mL). The resulting mixture was filtered. The solid in the filter was mixed with a 80:20 mixture of CHCl₃:CH₃OH (~7 mL), and the resulting mixture was filtered. The filtrate was injected into a 90 g SiO2 columns. Flash chromatography on SiO2 (gradient: 100% CHCl₃ to 90:10:1 CHCl₃:CH₃OH: NH₄OH) provided the product. Trituration with Et₂O afforded the title compound 7-methyl-5-[1-(phenylacetyl)-2,3-dihydro-1H-indol-5-yl]-7H-pyrrolo[2,3-d]pyrimidin-4-amine (22 mg) as a tan solid. ¹H NMR (400 MHz, DMSO-d6) δ 3.21 (t, J=8.21 Hz, 2H), 3.73 (s, 3H), 3.87 (s, 2H), 4.21 (t, J=8.46 Hz, 2H), 7.15-7.42 (m, 8H), 8.11-8.15 (m, 2H)

Example 5

3-[1-(phenylacetyl)-2,3-dihydro-1H-indol-5-yl]thieno[3,2-c]pyridin-4-amine

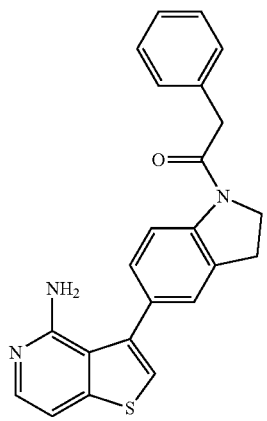 [SMILES: Nc1nccc2scc(-c3ccc4c(c3)CCN4C(=O)Cc3ccccc3)c12]

In a sealed tube, to 5-bromo-1-(phenylacetyl)-2,3-dihydro-1H-indole (0.658 g, 2.081 mmol), bispinacolatodiboron (0.634 g, 2.497 mmol) and potassium acetate (0.613 g, 6.24 mmol) was added 1,4-Dioxane (15 mL) and the mixture was degassed with N2 for 10 minutes. PdCl2(dppf)-CH2Cl2 Adduct (0.085 g, 0.104 mmol) was added and the reaction mixture was stirred for 48 hours at 100° C. The mixture was cooled to room temperature and treated with 5 mL of water, 3-bromothieno[3,2-c]pyridin-4-amine (0.524 g, 2.289 mmol) and NaHCO3 (175 mg). The mixture was degassed with N2 for 10 minutes. PdCl2(dppf)-CH2Cl2 Adduct (0.085 g, 0.104 mmol) was added and the reaction mixture was stirred overnight at 100° C. The mixture was poured onto water and ethyl acetate, then filtered. The filtrate was poured into a separatory funnel. The organic layer was separated and the aqueous layer was further extracted with ethyl acetate. The combined organic layers were washed with brine, dried (MgSO4), filtered and concentrated. Flash chromatography on SiO2 (gradient: 100% CHCl3 to 90:10:1 CHCl3/CH3OH/NH4OH) afforded a few fractions containing the desired product with impurity. The fractions were combined and evaporated. To the resulting residue was dissolved in MeOH/CH2Cl2 (1 mL/5 mL). Then dry loaded and purified by Analogix silica 25/14, gradient 0-100% EtOAc/hexane. The compound came out at 95% EtOAc. The fractions with the pure compound were combined. The solvents were evaporated and the resulting residue was triturated in EtOAc to give off-white solid (280 mg) of the title compound 3-[1-(phenylacetyl)-2,3-dihydro-1H-indol-5-yl]thieno[3,2-c]pyridin-4-amine. LC-MS (ES) m/z=386.0 [M+H]+. 1H NMR (400 MHz, DMSO-d6) δ ppm 8.16 (d, J=8.3 Hz, 1H) 7.82 (d, J=5.6 Hz, 1H) 7.41 (s, 1H) 7.19-7.38 (m, 8H) 5.41 (br. s., 2H) 4.25 (t, J=8.6 Hz, 2H) 3.89 (s, 2H) 3.23 (t, 2H).

Example 6

3-{1-[(2,5-difluorophenyl)acetyl]-2,3-dihydro-1H-indol-5-yl}thieno[3,2-c]pyridin-4-amine

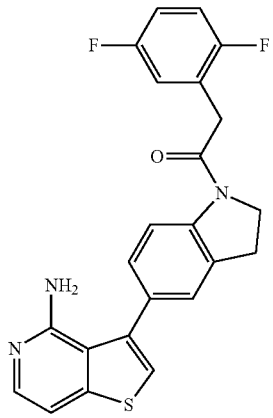 [SMILES: Nc1nccc2scc(-c3ccc4c(c3)CCN4C(=O)Cc3cc(F)ccc3F)c12]

In a sealable tube, to 5-bromo-1-[(2,5-difluorophenyl)acetyl]-2,3-dihydro-1H-indole (0.700 g, 1.988 mmol), bispinacolatodiboron (0.606 g, 2.385 mmol) and potassium acetate (0.585 g, 5.96 mmol) was added 1,4-Dioxane (15 mL) and the mixture was degassed with N2 for 10 minutes. PdCl2(dppf)-CH2Cl2Adduct (0.081 g, 0.99 mmol) was added and the reaction mixture was sealed and stirred for 48 hours at 100° C. The mixture was cooled to room temperature and treated with 5 mL of water, 3-bromothieno[3,2-c]pyridin-4-amine (0.501 g, 2.186 mmol) and sodium bicarbonate (167 mg, 1.988 mmol). The mixture was degassed with N2 for 10 minutes. PdCl2(dppf)-CH2Cl2 adduct (0.085 g, 0.104 mmol) was added and the reaction mixture was stirred overnight at 100° C. The mixture was poured onto water and ethyl acetate, then filtered. The filtrate was poured into a separatory funnel. The organic layer was separated and the aqueous layer was further extracted with ethyl acetate. The combined organic layers were washed with brine, dried (MgSO4) filtered and concentrated. Purified by Analogix silica gel cartridge 25/40, eluting with a gradient of 0-100% EtOAc/hexane. The compound came out at 100% EtOAc in 10 minutes. The pure fractions with the compound were combined. The solvents were evaporated and dried to give an off-white solid (526 mg) of the title compound 3-{1-[(2,5-difluorophenyl)acetyl]-2,3-dihydro-1H-indol-5-yl}thieno[3,2-c]pyridin-4-amine. LC-MS (ES) m/z=422.2 [M+H]+. 1H NMR (400 MHz, DMSO-d6) δ ppm 8.11 (d, J=8.3 Hz, 1H) 7.82 (d, J=5.6 Hz, 1H) 7.42 (s, 1H) 7.35 (s, 1H) 7.12-7.31 (m, 5H) 5.41 (br. s., 2H) 4.31 (t, J=8.3 Hz, 2H) 3.96 (s, 2H) 3.23-3.31 (m, 2H).

Example 7

3-[1-(phenylacetyl)-2,3-dihydro-1H-indol-5-yl]-7-(3-pyridinyl)thieno[3,2-c]pyridin-4-amine

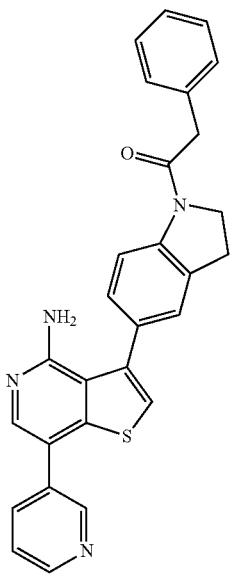 [SMILES: Nc1ncc(-c2cccnc2)c2scc(-c3ccc4c(c3)CCN4C(=O)Cc3ccccc3)c12]

7-iodo-3-[1-(Henylacetyl)-2,3-dihydro-1H-indol-5-yl]thieno[3,2-c]pyridin-4-amine To a solution of 3-[1-(phenylacetyl)-2,3-dihydro-1H-indol-5-yl]thieno[3,2-c]pyridin-4-amine (150 mg, 0.389 mmol) in DMF (3.0 mL) cooled in an ice-bath added NIS (96 mg, 0.428 mmol). The reaction mixture was stirred at rt overnight. Water was poured into the mixture, the formed brown solid was filtered, dried to give 185 mg of the product 7-iodo-3-[1-(phenylacetyl)-2,3-dihydro-1H-indol-5-yl]thieno[3,2-c]pyridin-4-amine.

3-[1-(phenylacetyl)-2,3-dihydro-1H-indol-5-yl]-7-(3-pyridinyl)thieno[3,2-c]pyridin-4-amine To a 25 mL pressure tube was charged 7-iodo-3-[1-(phenylacetyl)-2,3-dihydro-1H-indol-5-yl]thieno[3,2-c]pyridin-4-amine (182 mg, 0.356 mmol), 3-pyridinylboronic acid (43.7 mg, 0.356 mmol), 1,1'-bis(diphenylphosphino)ferrocene-palladium(II)dichloride dichloromethane complex (14.53 mg, 0.018 mmol), and sodium carbonate (75 mg, 0.712 mmol) followed by dioxane (5 mL), and water (1 mL). The reaction was heated at 120° C. for 30 min in microwave reactor. Water (20 mL) and ethyl acetate (20 mL) were added and the layers were separated. The organic layer was washed with brine, concentrated, and the residue purified by silica gel chromatography (0%-100% EtOAc in hexanes) to afford the tittle compound 3-[1-(phenylacetyl)-2,3-dihydro-1H-indol-5-yl]-7-(3-pyridinyl)thieno[3,2-c]pyridin-4-amine (85 mg) as a gray solid. LC-MS (ES) m/z=463.1 [M+H]+. 1H NMR (400 MHz, DMSO-d$_6$) δ ppm 8.88 (d, J=1.8 Hz, 1H) 8.62 (dd, J=4.8, 1.5 Hz, 1H) 8.18 (d, J=8.1 Hz, 1H) 8.10 (dt, J=8.1, 1.9 Hz, 1H) 7.96 (s, 1H) 7.56 (dd, J=8.1, 4.8 Hz, 1H) 7.50 (s, 1H) 7.23-7.40 (m, 7H) 5.63 (br. s., 2H) 4.26 (t, J=8.5 Hz, 2H) 3.90 (s, 2H) 3.24 (t, 2H)

Example 8

1-methyl-4-{1-[(3-methyl phenyl)acetyl]-2,3-dihydro-1H-indol-5-yl}-1H-indazol-3-amine

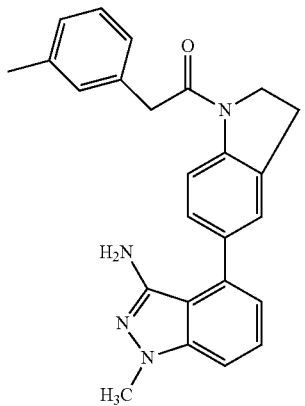 [SMILES: Cc1cccc(CC(=O)N2CCc3cc(-c4cccc5c4c(N)nn5C)ccc32)c1]

1,1-Dimethylethyl 5-bromo-2,3-dihydro-1H-indole-1-carboxylate

To a stirred solution of 5-bromo-2,3-dihydro-1H-indole (30 g, 151 mmol) and DMAP (0.4 g, 3.27 mmol, 0.02 equiv) in 150 mL of MeCN at room temperature was added Boc$_2$O (43 g, 197 mmol, 1.3 equiv) in one portion. The mixture was stirred at rt. After 10 min, the mixture gradually became a suspension. After 3 h, the suspension was filtered. The cake was washed with cold MeCN (60 mL), and sucked under house vacuum for 5 h to give 1,1-Dimethylethyl 5-bromo-2,3-dihydro-1H-indole-1-carboxylate (ca 28.5 g prior to drying). LCMS (ES) m/z=244, 242 as prominent fragments. $^1$H NMR (400 MHz, DMSO-d6) ppm 1.50 (s, 9H), 3.06 (t, J=8.7 Hz, 2H), 3.91 (t, J=8.7 Hz, 2H), 7.31 (dd, J=8.5, 1.9 Hz, 1H), 7.38 (s, 1H), 7.51-7.71 (br s, 0.6H).

1,1-Dimethylethyl 5-(4,4,5,5-tetramethyl-1,3,2-dioxaborolan-2-yl)-2,3-dihydro-1H-indole-1-carboxylate A mixture of 1,1-dimethylethyl 5-bromo-2,3-dihydro-1H-indole-1-carboxylate (32 g, 107 mmol, 1 equiv), bis(pinacolato)diboron (32.7 g, 129 mmol, 1.2 equiv), PdCl2(dppf)-CH2Cl2 adduct (4.38 g, 15.37 mmol, 0.05 equiv) and potassium acetate (26.3 g, 268 mmol, 2.5 equiv) in 350 mL of dioxane in a 1 L flask was evacuated and backflushed with nitrogen, which was repeated 5 times. The mixture was heated at 100° C. for 18 h. LCMS showed conversion complete. The mixture was filtered through Celite and washed with EtOAc (500 mL). The filtrate was concentrated in vacuo. The residue was partitioned between EtOAc (700 mL) and brine (300 mL). The organic was extracted with EtOAc (200 mL). The combined organic was dried over Na2SO4, filtered, and concentrated in vacuo. The residue was dissolved in DCM and split into 7 equal portions. Each was absorbed onto a dryload cartridge right before actual chromatography.

Purification was done on 120 g silica gel cartridges using gradient elution of 1% EtOAc in hexane to 40% EtOAc in hexane. The desired product eluted from 17-24% EtOAc in hexane. The combined fractions were concentrated in vacuo to give a waxy cake in the recovery flask, which was broken up and dried under vacuum at rt for 20 h to give the product (30.54 g, 82% yield) as a light yellow waxy solid. LC-MS (ES) m/z=346 [M+H]+, prominent fragment at 290 [M−55]+. $^1$H NMR (400 MHz, DMSO-d$_6$) δ ppm 1.27 (s, 12H), 1.50 (s, 9H), 3.05 (t, J=8.6 Hz, 2H), 3.91 (t, J=8.7 Hz, 2H), 7.43-7.52 (m, 2H), 7.58-7.80 (br s, 1H).

1,1-dimethylethyl 5-(2-cyano-3-fluorophenyl)-2,3-dihydro-1H-indole-1-carboxylate A mixture of 2-fluoro-6-iodobenzonitrile (2.65 g, 10.73 mmol), 1,1-dimethylethyl 5-(4,4,5,5-tetramethyl-1,3,2-dioxaborolan-2-yl)-2,3-dihydro-1H-indole-1-carboxylate (3.78 g, 10.95 mmol, 1.02 equiv), tricyclohexylphosphine (301 mg, 1.07 mmol, 0.1 equiv), Pd2(dba)3 (491 mg, 0.54 mmol, 0.05 equiv) and K3PO4 (3.87 g, 18.24 mmol, 1.7 equiv) in 40 mL of dioxane and 10 mL of water in a 150 mL pressure vessel was bubbled under argon for 10 min. The mixture was capped and heated in an oil bath at 100° C. for 18 h. LCMS showed conversion complete. The mixture was filtered through Celite. The filtrate was concentrated in vacuo. The residue was partitioned between EtOAc (130 mL) and brine (40 mL). The organic was dried over Na$_2$SO$_4$, filtered, and concentrated in vacuo. The dark brownish oil was stored in the refrigerator for 20 h, which became a cake. Trituration in DCM/hexane (1:4), breaking up of the cake, filtration, and drying under vacuum at room temperature gave 1,1-dimethylethyl 5-(2-cyano-3-fluorophenyl)-2,3-dihydro-1H-indole-1-carboxylate (2.63 g) as a greyish solid. The filtrate was concentrated in vacuo and absorbed onto a dryload cartridge. Purification was done on an RS-120 g silica gel cartridge using gradient elution of 1% EtOAc in hexane to 40% EtOAc in hexane. The product eluted from 29-34% EtOAc in hexane. Concentration in vacuo and drying under vacuum additional 1,1-dimethylethyl 5-(2-cyano-3-fluorophenyl)-2,3-dihydro-1H-indole-1-carboxylate (0.77 g) as a yellow foam.

1,1-dimethylethyl 5-(3-amino-1-methyl-1H-indazol-4-yl)-2,3-dihydro-1H-indole-1-carboxylate To a suspension of 1,1-dimethylethyl 5-(2-cyano-3-fluorophenyl)-2,3-dihydro-1H-indole-1-carboxylate (1.60 g, 4.73 mmol) in 30 mL of EtOH was added 7 mL of methylhydrazine in one portion. The mixture was heated in an oil bath at 100° C. for 24 h. LCMS showed conversion complete. The mixture was cooled and concentrated in vacuo. The residue was partitioned between DCM (60 mL) and water (30 mL). The organic was dried over Na$_2$SO$_4$, filtered, and concentrated in vacuo to give 1,1-dimethylethyl 5-(3-amino-1-methyl-1H-indazol-4-yl)-2,3-dihydro-1H-indole-1-carboxylate as a cream-colored foamy solid (1.70 g).

4-(2,3-dihydro-1H-indol-5-yl)-1-methyl-1H-indazol-3-amine

To a stirred suspension of 1,1-dimethylethyl 5-(3-amino-1-methyl-1H-indazol-4-yl)-2,3-dihydro-1H-indole-1-carboxylate (1.70 g, 4.66 mmol) in 20 mL of EtOH was added 12 mL of 2N HCl. The mixture was heated at 75° C. for 90 min. LCMS showed conversion complete. The mixture was cooled, and concentrated in vacuo. The oily residue was diluted with 40 mL of water, and the pH was adjusted to ~10 by adding 1N NaOH (pH paper). The milky mixture was extracted with 10° A MeOH in DCM (100 mL, then 2×25 mL). The combined organic was dried over Na$_2$SO$_4$, filtered, and concentrated in vacuo to give 4-(2,3-dihydro-1H-indol-5-yl)-1-methyl-1H-indazol-3-amine as a brownish foamy solid (1.13 g). LC-MS (ES) m/z=265 [M+H]+.

1-methyl-4-{1-[(3-methylphenyl)acetyl]-2,3-dihydro-1H-indol-5-yl}-1H-indazol-3-amine To a clear solution of 4-(2,3-dihydro-1H-indol-5-yl)-1-methyl-1H-indazol-3-amine (200 mg, 0.76 mmol, 1 equiv), (3-methylphenyl)acetic acid (114 mg, 0.76 mmol, 1 equiv), and DIEA (145 uL, 0.83 mmol, 1.1 equiv) in 4 mL of DCM was added at rt in one portion solid HATU (316 mg, 0.83 mmol, 1.1 equiv). The mixture as stirred at rt for 20 h. LCMS showed conversion complete. The suspension was filtered. The filtrate was absorbed onto a dryload cartridge. Purification was done on an SF25-24 g silica gel cartridge using gradient elution of 1% EtOAc in hexane to 100% EtOAc. The product eluted in the 100% EtOAc as a broad but well-defined peak. Concentration in vacuo gave a white foam (320 mg). LCMS showed it was only 84% pure with a major impurity at 11%. This material was dissolved in EtOAc (75 mL), and washed with water (25 mL) and brine (15 mL). The organic was dried over $Na_2SO_4$, filtered, and concentrated in vacuo. LCMS showed the impurities still present. The material was dissolved in EtOAc (1 mL) with some material still sticked to the wall of the 100 mL recovery flask, to which was added 3 mL of MTBE. The mixture turned cloudy initially, and was immersed in a water bath at (40° C.). The cloudiness disappeared and then solids began to form on the walls. A spatula was used to scratch the flask. The mixture was then cooled to room temperature and the suspension was filtered. The solids (light tan colored) was washed with MTBE (2 mL). Both LCMS and NMR showed this lot was quite pure. The solid was dried under vacuum at 65° C. for 16 h to give 210 mg as tan-colored solids. LC-MS (ES) m/z=397 [M+H]+. $^1$H NMR (400 MHz, DMSO-$d_6$) δ ppm 2.31 (s, 3H), 3.23 (t, J=8.3 Hz, 2H), 3.78 (s, 3H), 3.83 (s, 2H), 4.23 (t, J=8.6 Hz, 2H), 4.38 (s, 2H), 6.78 (d, J=5.8 Hz, 1H), 7.05-7.15 (m, 13H), 7.20-7.26 (m, 2H), 7.28-7.38 (m, 3H), 8.16 (d, J=8.3 Hz, 1H).

Example 9

3-[1-(phenylacetyl)-2,3-dihydro-1H-indol-5-yl]-7-(4-pyridinyl)thieno[3,2-c]pyridin-4-amine

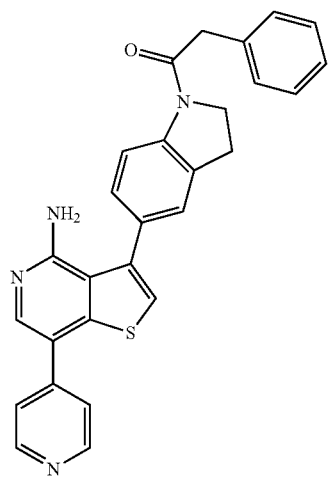 [SMILES: Nc1ncc(-c2ccncc2)c2scc(-c3ccc4c(c3)CCN4C(=O)Cc3ccccc3)c12]

A mixture of 7-iodo-3-[1-(phenylacetyl)-2,3-dihydro-1H-indol-5-yl]thieno[3,2-c]pyridin-4-amine (101 mg, 0.198 mmol), pyridine-4-boronic acid, pinacol ester (53 mg, 0.258 mmol), and PdCl2(dppf)-CH2Cl2 adduct (8 mg, 9.80 μmol) in 1,4-Dioxane (1.5 mL) and saturated aqueous sodium bicarbonate (0.6 mL, 0.600 mmol) was degassed with Nitrogen for 10 minutes in a microwave vial. The vial was then capped and the mixture was stirred at 120° C. in the microwave for 30 min. LCMS showed complete conversion to the desired product, along with a small de-iodo by-product. The mixture was cooled, poured into water (15 mL), and extracted with ethyl acetate (2×15 mL). The extracts were washed with brine (1×15 mL), dried (Na2SO4), filtered, and concentrated in vacuo. The residue was purified by flash chromatography (Analogix, 24 g SiO2, 25%-100% EtOAc in hexanes gradient over 30 minutes, then EtOAc for 10 minutes, then 0-10% MeOH in EtOAc over 20 minutes) to give 3-[1-(phenylacetyl)-2,3-dihydro-1H-indol-5-yl]-7-(4-pyridinyl)thieno[3,2-c]pyridin-4-amine (66 mg, 0.136 mmol, 68.6% yield) as a beige solid. LC/MS (ES) m/z=463 [M+H]+. $^1$H NMR (400 MHz, DMSO-$d_6$) δ 3.24 (t, J=8.46 Hz, 2H), 3.90 (s, 2H), 4.26 (t, J=8.46 Hz, 2H), 5.74 (br. s., 2H), 7.23-7.39 (m, 7H), 7.52 (s, 1H), 7.70-7.75 (m, 2H), 8.09 (s, 1H), 8.18 (d, J=8.34 Hz, 0H), 8.65-8.72 (m, 2H).

Example 10

3-{1-[(2,5-difluorophenyl)acetyl]-2,3-dihydro-1H-indol-5-yl}-7-(3-pyridinyl)thieno[3,2-c]pyridin-4-amine

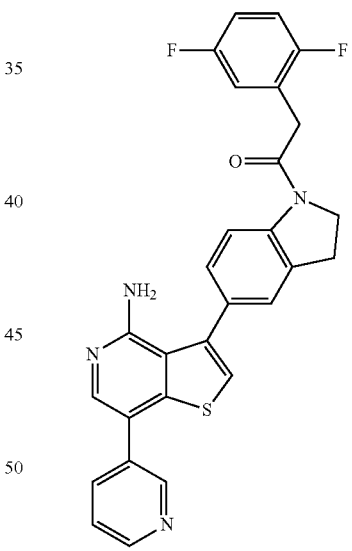

3-{1-[(2,5-difluorophenyl)acetyl]-2,3-dihydro-1H-indol-5-yl}-7-iodothieno[3,2-c]pyridin-4-amine To a solution of 3-{1-[(2,5-difluorophenyl)acetyl]-2,3-dihydro-1H-indol-5-yl}thieno[3,2-c]pyridin-4-amine (150 mg, 0.389 mmol) in DMF (6.0 mL) cooled in an ice-bath was added NIS (264 mg, 1.174 mmol). The reaction mixture was stirred at room temperature overnight. Water was poured into the mixture, the formed brown solid was filtered, dried to give the product 3-{1-[(2,5-difluorophenyl)acetyl]-2,3-dihydro-1H-indol-5-yl}-7-iodothieno[3,2-c]pyridin-4-amine as a brown solid (581 mg). LCMS (ES) m/z=548.2 [M+H]$^+$.

3-{1-[(2,5-difluorophenyl)acetyl]-2,3-dihydro-1H-indol-5-yl}-7-(3-pyridinyl)thieno[3,2-c]pyridin-4-amine To a 25 mL microwave reaction tube was charged 3-{1-[(2,5-difluorophenyl)acetyl]-2,3-dihydro-1H-indol-5-yl}-7-iodothieno[3,2-c]pyridin-4-amine (150 mg, 0.274 mmol), 3-pyridinylboronic acid (33.7 mg, 0.274 mmol), 1,1′-bis(diphenylphosphino)ferrocene-palladium(II)dichloride dichloromethane complex (11.19 mg, 0.014 mmol), and sodium carbonate (58.1 mg, 0.548 mmol) followed by dioxane (5 mL), and water (1 mL). The reaction was heated at 120° C. for 30 min in microwave reactor. Ethyl acetate (20 mL) was added and the layers were separated. The organic layer was washed with brine, concentrated, and the residue purified by silica gel chromatography (0%-100% EtOAc in hexanes). Product came out at 100% EtOAc, the fractions with the product was combined, evaporated to dryness to afford the title compound as a light gray solid (112 mg). $^1$H NMR (400 MHz, DMSO-$d_6$) δ ppm 8.88 (d, J=2.0 Hz, 1H) 8.62 (dd, J=4.8, 1.3 Hz, 1H) 8.04-8.18 (m, 2H) 7.97 (s, 1H) 7.56 (dd, J=7.6, 4.8 Hz, 1H) 7.51 (s, 1H) 7.39 (s, 1H) 7.14-7.32 (m, 4H) 5.64 (br. s., 2H) 4.32 (t, J=8.3 Hz, 2H) 3.97 (s, 2H) 3.29 (t, 2H).

Example 11

3-{1-[(2,5-difluorophenyl)acetyl]-2,3-dihydro-1H-indol-5-yl}-7-(1H-pyrazol-3-yl)thieno[3,2-c]pyridin-4-amine

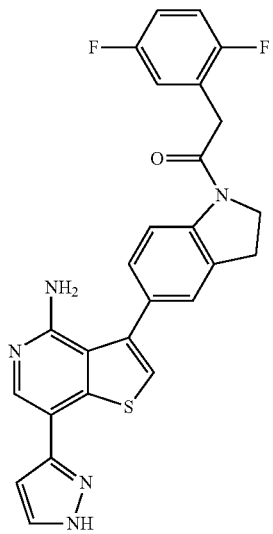 [SMILES: Nc1ncc(-c2cc[nH]n2)c2scc(-c3ccc4c(c3)CCN4C(=O)Cc3cc(F)ccc3F)c12]

To a 25 mL microwave reactor vial was charged 3-{1-[(2,5-difluorophenyl)acetyl]-2,3-dihydro-1H-indol-5-yl}-7-iodothieno[3,2-c]pyridin-4-amine (150 mg, 0.274 mmol), 1H-pyrazol-3-ylboronic acid (30.7 mg, 0.274 mmol), 1,1′-bis(diphenylphosphino)ferrocene-palladium(II)dichloride dichloromethane complex (11.19 mg, 0.014 mmol), and sodium carbonate (58.1 mg, 0.548 mmol) followed by dioxane (5 mL), and water (1 mL). The reaction was heated at 120° C. for 30 min in microwave reactor. Ethyl acetate (20 mL) was added and the layers were separated. The organic layer was washed with brine, concentrated, and the residue purified by silica gel chromatography (0%-100% EtOAc in hexanes). Product came out at 100% EtOAc in 5 minutes, the fractions with the product were combined and evaporated to dryness to afford the title compound as a light gray solid (48 mg). LC/MS (ES) m/z=488.2 [M+H]+. $^1$H NMR (400 MHz, DMSO-$d_6$) δ ppm 12.99 (s, 1H) 8.36 (s, 1H) 8.12 (d, J=8.1 Hz, 1H) 7.85 (s, 1H) 7.48 (s, 1H) 7.38 (s, 1H) 7.14-7.31 (m, 4H) 6.84 (s, 1H) 5.50 (br. s., 2H) 4.32 (t, J=8.5 Hz, 2H) 3.96 (s, 2H) 3.25-3.32 (m, 2H).

Example 12

4-{1-[(2,5-difluorophenyl)acetyl]-2,3-dihydro-1H-indol-5-yl}-1-methyl-1H-indazol-3-amine

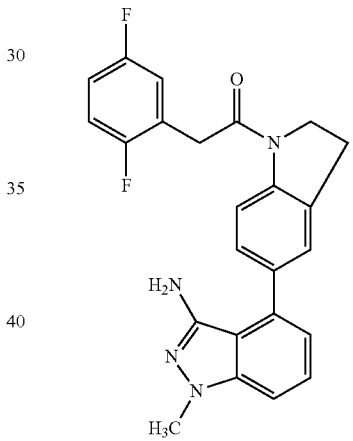

To a clear solution of 4-(2,3-dihydro-1H-indol-5-yl)-1-methyl-1H-indazol-3-amine (300 mg, 1.14 mmol, 1 equiv), (2,5-difluoro)phenylacetic acid (195 mg, 1.14 mmol, 1 equiv), and DIEA (218 uL, 1.25 mmol, 1.1 equiv) in 4 mL of DCM was added at room temperature, in one portion solid HATU was added (475 mg, 1.25 mmol, 1.1 equiv). The mixture as stirred at room temperature for 20 h. LCMS showed conversion complete. The suspension was filtered, and the solid was washed with water (2×3 mL) and with MTBE (2×2 mL), then dried over $P_2O_5$ under vacuum for 20 h to give the title compound.

1H NMR (400 MHz, DMSO-d6 with one drop of TFA) d ppm 3.30 (t, J=8.2 Hz, 2H), 3.96 (s, 2H), 4.04 (s, 3H), 4.31 (t, J=8.5 Hz, 2H), 7.10-7.27 (m, 4H), 7.31 (d, J=8.3 Hz, 1H), 7.43 (s, 1H), 7.54 (t, J=7.8 Hz, 1H), 7.66 (d, J=8.6 Hz, 1H), 8.14 (d, J=8.3 Hz, 1H).

Example 13

3-[1-(phenylacetyl)-2,3-dihydro-1H-indol-5-yl]-7-(1H-pyrazol-4-yl)thieno[3,2-c]pyridin-4-amine

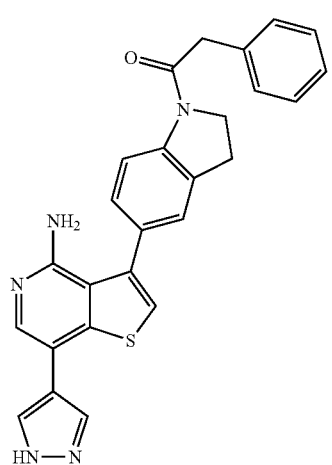 [SMILES: Nc1ncc(-c2cn[nH]c2)c2scc(-c3ccc4c(c3)CCN4C(=O)Cc3ccccc3)c12]

A mixture of 7-iodo-3-[1-(phenylacetyl)-2,3-dihydro-1H-indol-5-yl]thieno[3,2-c]pyridin-4-amine (101 mg, 0.198 mmol), 1-Boc-pyrazol-4-boronic acid pinacol ester (88 mg, 0.299 mmol), and PdCl2(dppf)-CH2Cl2 adduct (9 mg, 0.011 mmol) in 1,4-Dioxane (2.0 mL) and saturated aqueous sodium bicarbonate (0.6 mL, 0.600 mmol) was degassed with Nitrogen for 10 minutes in a microwave vial. The vial was then capped and the mixture was stirred at 120° C. in the microwave for 30 min. LCMS showed complete conversion to the de-Boc product. The mixture was cooled, poured into water (15 mL), and extracted with ethyl acetate (2×15 mL). The extracts were washed with brine (1×15 mL), dried (Na2SO4), filtered, and concentrated in vacuo. The residue was purified by flash chromatography (Analogix, 24 g SiO2, 50%-100% EtOAc in hexanes gradient over 15 minutes, then EtOAc for 5 minutes, then 0-10% MeOH in EtOAc over 20 minutes) to give 3-[1-(phenylacetyl)-2,3-dihydro-1H-indol-5-yl]-7-(1H-pyrazol-4-yl)thieno[3,2-c]pyridin-4-amine (50 mg, 0.105 mmol, 53.3% yield) as a light gray solid. LC/MS (ES) m/z=452 [M+H]+. $^1$H NMR (400 MHz, DMSO-$d_6$) δ 3.24 (t, J=8.34 Hz, 2H), 3.89 (s, 2H), 4.26 (t, J=8.46 Hz, 2H), 5.40 (br. s., 2H), 7.22-7.30 (m, 2H), 7.30-7.40 (m, 5H), 7.48 (s, 1H), 7.95 (br. s., 1H), 8.06 (s, 1H), 8.12-8.21 (m, 2H), 13.10 (br. s., 1H).

Example 14

7-(1-methyl-1H-pyrazol-4-yl)-3-[1-(phenylacetyl)-2,3-dihydro-1H-indol-5-yl]thieno[3,2-c]pyridin-4-amine

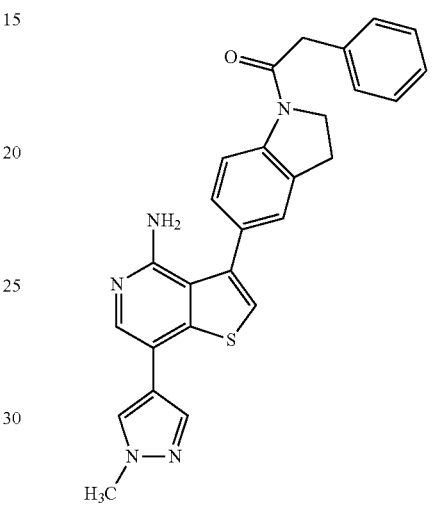

A mixture of 7-iodo-3-[1-(phenylacetyl)-2,3-dihydro-1H-indol-5-yl]thieno[3,2-c]pyridin-4-amine (102 mg, 0.199 mmol), 1-methylpyrazole-4-boronic acid pinacol ester (60 mg, 0.288 mmol), and PdCl2(dppf)-CH2Cl2 adduct (8 mg, 9.80 μmol) in 1,4-Dioxane (2.0 mL) and saturated aqueous sodium bicarbonate (0.6 mL, 0.600 mmol) was degassed with Nitrogen for 10 minutes in a microwave vial. The vial was then capped and the mixture was stirred at 120° C. in the microwave for 30 min. LCMS showed complete conversion. The mixture was cooled, poured into water (15 mL), and extracted with ethyl acetate (2×15 mL). The extracts were washed with brine (1×15 mL), dried (Na2SO4), filtered, and concentrated in vacuo. The residue was purified by flash chromatography (Analogix, 24 g SiO2, 50%-100% EtOAc in hexanes gradient over 10 minutes, then EtOAc for 5 minutes, then 0-10% MeOH in EtOAc over 20 minutes) to give 7-(1-methyl-1H-pyrazol-4-yl)-3-[1-(phenylacetyl)-2,3-dihydro-1H-indol-5-yl]thieno[3,2-c]pyridin-4-amine (69 mg, 0.141 mmol, 70.6% yield) as a light gray solid. LC/MS (ES) m/z=466 [M+H]+. $^1$H NMR (400 MHz, DMSO-$d_6$) δ 3.24 (t, J=8.46 Hz, 2H), 3.89 (s, 2H), 3.93 (s, 3H), 4.26 (t, J=8.46 Hz, 2H), 5.41 (br. s., 2H), 7.22-7.30 (m, 2H), 7.30-7.39 (m, 5H), 7.49 (s, 1H), 7.88 (s, 1H), 8.03 (s, 1H), 8.14 (s, 1H), 8.17 (d, J=8.08 Hz, 1H).

Example 15

3-{1-[(2-fluorophenyl)acetyl]-2,3-dihydro-1H-indol-5-yl}-1-methyl-1H-pyrazolo[3,4-d]pyrimidin-4-amine

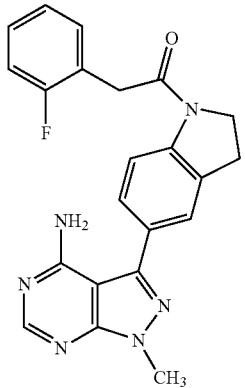 [SMILES: Cn1nc(-c2ccc3c(c2)CCN3C(=O)Cc2ccccc2F)c2c(N)ncnc21]

1,1-dimethylethyl 5-(4-amino-1-methyl-1H-pyrazolo[3,4-d]pyrimidin-3-yl)-2,3-dihydro-1H-indole-1-carboxylate To a 25 mL pressure tube was charged 3-bromo-1-methyl-1H-pyrazolo[3,4-d]pyrimidin-4-amine (670 mg, 2.94 mmol), 1,1-dimethylethyl 5-(4,4,5,5-tetramethyl-1,3,2-dioxaborolan-2-yl)-2,3-dihydro-1H-indole-1-carboxylate (1014 mg, 2.94 mmol), 1,1'-bis(diphenylphosphino)ferrocene-palladium(II)dichloride dichloromethane complex (120 mg, 0.147 mmol), and sodium carbonate (494 mg, 5.88 mmol) followed by dioxane (8 mL), and water (2 mL). The reaction was heated at 120° C. for 40 minutes in a microwave reactor. LCMS showed no more SM. The reaction was cooled to room temperature, the mixture was transferred into a 100 mL Erlenmeyer flask, rinsed by EtOAc, with the water layer and black greasy solid stayed in tube (total 50 mL of EtOAc was added to the mixture). White solid was formed in brown solution. The solid was filtered to give titled product (764 mg).

3-(2,3-dihydro-1H-indol-5-yl)-1-methyl-1H-pyrazolo[3,4-d]pyrimidin-4-amine.2HCl In a 250 mL round bottom flask, 1,1-dimethylethyl 5-(4-amino-1-methyl-1H-pyrazolo[3,4-d]pyrimidin-3-yl)-2,3-dihydro-1H-indole-1-carboxylate (745 mg, 2.033 mmol) was added followed by 4 M HCl in dioxane (12.2 mL). The mixture was stirred overnight at room temperature. LCMS showed no more SM. The light brown colored solid in the reaction mixture was filtered, washed by 20 mL of EtOAc, dried to give the desired product as a off-white solid. LC/MS (ES) m/z=267.1 [M+H]+

3-{1-[(2-fluorophenyl)acetyl]-2,3-dihydro-1H-indol-5-yl}-1-methyl-1H-pyrazolo[3,4-d]pyrimidin-4-amine In a 20 mL vial, to the solution of 3-(2,3-dihydro-1H-indol-5-yl)-1-methyl-1H-pyrazolo[3,4-d]pyrimidin-4-amine.2HCl (70 mg, 0.206 mmol), (2-fluorophenyl)acetic acid (31.8 mg, 0.206 mmol), HATU (78 mg, 0.206 mmol) in DMF (2 mL) was added Hunig's base (0.144 mL, 0.825 mmol). The mixture was stirred at room temperature for overnight. LCMS showed reaction was completed. The reaction was poured into water, white solid formed. The white solid was filtered to give the product. LC/MS (ES) m/z=403.2 [M+H]+. $^1$H NMR (400 MHz, DMSO-$d_6$) δ ppm 3.25-3.32 (m, 2H), 3.91-3.99 (m, 5H), 4.31 (t, J=8.46 Hz, 2H), 7.16-7.24 (m, 2H), 7.32-7.39 (m, 2H), 7.44 (d, J=8.08 Hz, 1H), 7.53 (s, 1H), 8.15 (d, J=8.34 Hz, 1H), 8.25 (s, 1H).

Example 16

3-{1-[(3-fluorophenyl)acetyl]-2,3-dihydro-1H-indol-5-yl}-1-methyl-1H-pyrazolo[3,4-d]pyrimidin-4-amine

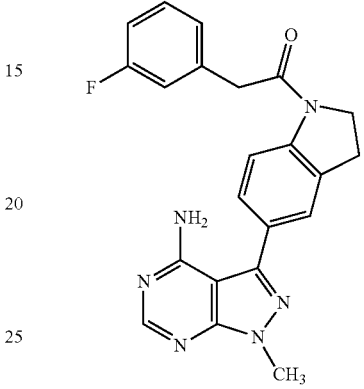

In a 20 mL vial with cap, to the solution of 3-(2,3-dihydro-1H-indol-5-yl)-1-methyl-1H-pyrazolo[3,4-d]pyrimidin-4-amine.2HCl (70 mg, 0.206 mmol), (3-fluorophenyl)acetic acid (31.8 mg, 0.206 mmol), HATU (78 mg, 0.206 mmol) in DMF (2 mL) was added Hunig's base (0.144 mL, 0.825 mmol). The mixture was stirred at rt for overnight. LCMS showed reaction was completed. The reaction was poured into water, white solid formed. The white solid was filtered to give the product. LC/MS (ES) m/z=403.2 [M+H]+. $^1$H NMR (400 MHz, DMSO-$d_6$) δ ppm 3.26 (t, J=8.46 Hz, 2H), 3.93 (s, 5H), 4.25 (t, J=8.46 Hz, 2H), 7.11 (s, 1H), 7.13-7.17 (m, 2H), 7.39 (d, J=6.82 Hz, 1H), 7.44 (d, J=8.34 Hz, 1H), 7.51 (s, 1H), 8.18 (d, J=8.34 Hz, 1H), 8.25 (s, 1H).

Example 17

1-methyl-3-{1-[(2-methylphenyl)acetyl]-2,3-dihydro-1H-indol-5-yl}-1H-pyrazolo[3,4-d]pyrimidin-4-amine

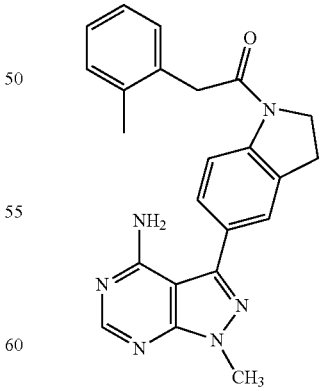

In a 20 mL vial with cap, to the solution of 3-(2,3-dihydro-1H-indol-5-yl)-1-methyl-1H-pyrazolo[3,4-d]pyrimidin-4-amine.2HCl (70 mg, 0.206 mmol), (2-methylphenyl)acetic acid (31.0 mg, 0.206 mmol), HATU (78 mg, 0.206 mmol) in DMF (2 mL) was added Hunig's base (0.144 mL, 0.825 mmol). The mixture was stirred at room temperature for overnight. LCMS showed the reaction was completed. The reaction was poured into water, white solid formed. The white solid was filtered, dried to give the product.

$^1$H NMR (400 MHz, DMSO-d$_6$) δ ppm 2.25 (s, 3H), 3.23-3.31 (m, 2H), 3.90 (s, 2H), 3.94 (s, 3H), 4.28 (t, J=8.59 Hz, 2H), 7.15-7.22 (m, 4H), 7.44 (d, J=8.08 Hz, 1H), 7.52 (s, 1H), 8.18 (d, J=8.34 Hz, 1H), 8.25 (s, 1H).

Example 18

1-methyl-3-{1-[(3-methylphenyl)acetyl]-2,3-dihydro-1H-indol-5-yl}-1H-pyrazolo[3,4-d]pyrimidin-4-amine

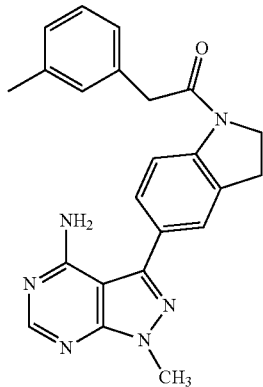 [SMILES: Cc1cccc(CC(=O)N2CCc3cc(-c4nn(C)c5ncnc(N)c45)ccc32)c1]

In a 20 mL vial with cap, to the solution of 3-(2,3-dihydro-1H-indol-5-yl)-1-methyl-1H-pyrazolo[3,4-d]pyrimidin-4-amine.2HCl (70 mg, 0.206 mmol), (3-methylphenyl)acetic acid (31.0 mg, 0.206 mmol), HATU (78 mg, 0.206 mmol) in DMF (2 mL) was added Hunig's base (0.144 mL, 0.825 mmol). The mixture was stirred at room temperaturet for overnight. LCMS showed the reaction was completed. The reaction was poured into water, white solid formed. The white solid was filtered to give the product.

$^1$H NMR (400 MHz, DMSO-d$_6$) δ ppm 2.30 (s, 3H), 3.24 (d, J=8.34 Hz, 2H), 3.84 (s, 2H), 3.93 (s, 3H), 4.19-4.27 (m, 2H), 7.07-7.14 (m, 3H), 7.23 (t, J=7.58 Hz, 1H), 7.44 (d, J=8.34 Hz, 1H), 7.50 (s, 1H), 8.20 (d, J=8.34 Hz, 1H), 8.24 (s, 1H).

Example 19

3-[1-(phenylacetyl)-2,3-dihydro-1H-indol-5-yl]-7-(1,2,3,6-tetrahydro-4-pyridinyl)thieno[3,2-c]pyridin-4-amine

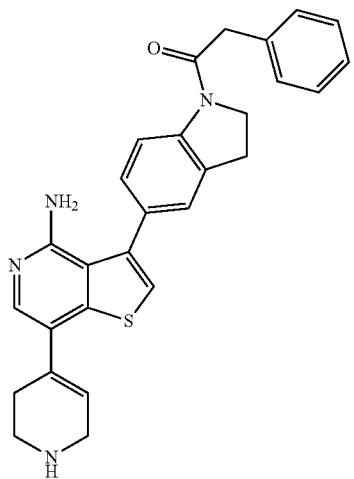 [SMILES: Nc1ncc(C2=CCNCC2)c2scc(-c3ccc4c(c3)CCN4C(=O)Cc3ccccc3)c12]

1,1-dimethylethyl 4-{4-amino-3-[1-(phenylacetyl)-2,3-dihydro-1H-indol-5-yl]thieno[3,2-c]pyridin-7-yl}-3,6-dihydro-1(2H)-pyridinecarboxylate A mixture of 7-iodo-3-[1-(phenylacetyl)-2,3-dihydro-1H-indol-5-yl]thieno[3,2-c]pyridin-4-amine (298 mg, 0.583 mmol), 3,6-dihydro-2H-pyridine-1-N-Boc-4-boronic acid pinacol ester (238 mg, 0.770 mmol), and PdCl2(dppf)-CH2Cl2 adduct (24 mg, 0.029 mmol) in 1,4-Dioxane (6 mL) and saturated aqueous sodium bicarbonate (2 mL, 2.000 mmol) was degassed with Nitrogen for 10 minutes in a microwave vial. The vial was then capped and the mixture was stirred at 120° C. in the microwave reactor for 30 min. LCMS showed complete conversion to the product. The mixture was cooled, poured into water (50 mL), and extracted with ethyl acetate (2×50 mL). The extracts were washed with brine (1×75 mL), dried (Na2SO4), filtered, and concentrated in vacuo. The residue was purified by flash chromatography (Analogix, 40 g SiO2, 25%-100% EtOAc in hexanes gradient over 45 minutes, then EtOAc for 5 minutes) to give 1,1-dimethylethyl 4-{4-amino-3-[1-(phenylacetyl)-2,3-dihydro-1H-indol-5-yl]thieno[3,2-c]pyridin-7-yl}-3,6-dihydro-1(2H)-pyridinecarboxylate (280 mg, 0.494 mmol, 85% yield) as a beige solid. LC/MS (ES) m/z=567 [M+H]$^+$.

3-[1-(phenylacetyl)-2,3-dihydro-1H-indol-5-yl]-7-(1,2,3,6-tetrahydro-4-pyridinyl)thieno[3,2-c]pyridin-4-amine A mixture of 1,1-dimethylethyl 4-{4-amino-3-[1-(phenylacetyl)-2,3-dihydro-1H-indol-5-yl]thieno[3,2-c]pyridin-7-yl}-3,6-dihydro-1(2H)-pyridinecarboxylate (54 mg, 0.095 mmol) and TFA (1.0 mL, 12.98 mmol) in Dichloromethane (DCM) (1 mL) was stirred at room temperature under Nitrogen for 1 hr. The mixture was then concentrated in vacuo, NaHCO3 (5 mL) was added, and it was extracted with methylene chloride (3×5 mL). The extracts were dried (Na$_2$SO$_4$), filtered, and concentrated in vacuo. The residue was purified by flash chromatography (Analogix, 12 g SiO2, DCM to 90/10/1 DCM/MeOH/NH$_4$OH gradient over 20 minutes) to give 3-[1-(phenylacetyl)-2,3-dihydro-1H-indol-5-yl]-7-(1,2,3,6-tetrahydro-4-pyridinyl)thieno[3,2-c]pyridin-4-amine (33 mg, 0.064 mmol, 66.8% yield) as a beige solid. LC/MS (ES) m/z=467 [M+H]+. $^1$H NMR (400 MHz, DMSO-d$_6$) δ 2.42 (d, J=1.77 Hz, 2H), 2.96 (t, J=5.56 Hz, 2H), 3.23 (t, J=8.34 Hz, 2H), 3.43 (d, J=3.03 Hz, 2H), 3.89 (s, 2H), 4.25 (t, J=8.46 Hz, 2H), 5.40 (br. s., 2H), 6.16 (br. s., 1H), 7.19-7.39 (m, 7H), 7.43 (s, 1H), 7.79 (s, 1H), 8.16 (d, J=8.34 Hz, 1H).

Example 20

3-(1-{[3-(trifluoromethyl)phenyl]acetyl}-2,3-dihydro-1H-indol-5-yl)thieno[3,2-c]pyridin-4-amine

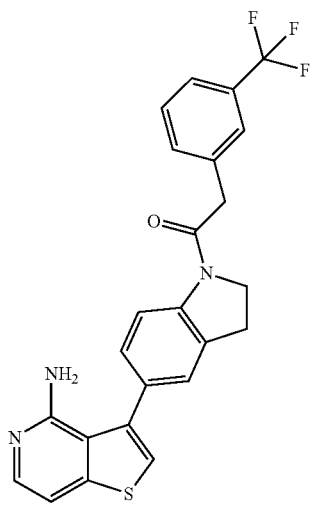 [SMILES: Nc1nccc2scc(-c3ccc4c(c3)CCN4C(=O)Cc3cccc(C(F)(F)F)c3)c12]

1,1-dimethylethyl 5-(4-aminothieno[3,2-c]pyridin-3-yl)-2,3-dihydro-1H-indole-1-carboxylate To a 250 mL round bottom flask was added 3-bromothieno[3,2-c]pyridin-4-amine (2.65 g, 11.59 mmol), 1,1-dimethylethyl 5-(4,4,5,5-tetramethyl-1,3,2-dioxaborolan-2-yl)-2,3-dihydro-1H-indole-1-carboxylate (5 g, 14.48 mmol), 1,4-Dioxane (50 mL) and 2M potassium carbonate (21.72 mL, 43.4 mmol). The reaction was capped and flushed with $N_2$ then $PdCl_2$(dppf)-CH2Cl2 adduct (0.591 g, 0.724 mmol) was added. The reaction was then refluxed overnight under an inert atmosphere. The reaction mixture was cooled to room temperature and then filtered through a silica plug. Then diluted with 150 mL H2O and extracted with ethyl acetate (3×150 mL). The organics were combined and dried over $Na_2SO_4$ and then concentrated to a black residue. This was then purified via normal phase chromatography (50-100% EtOAc/Hexanes). Product fractions were combined and concentrated to afford 1,1-dimethylethyl 5-(4-aminothieno[3,2-c]pyridin-3-yl)-2,3-dihydro-1H-indole-1-carboxylate (5.19 g, 13.42 mmol, 93% yield) as an off white solid. LC/MS (ES) m/z=368.2 [M+H]$^+$

3-(2,3-dihydro-1H-indol-5-yl)thieno[3,2-c]pyridin-4-amine 1,1-dimethylethyl 5-(4-aminothieno[3,2-c]pyridin-3-yl)-2,3-dihydro-1H-indole-1-carboxylate (5.19 g, 14.12 mmol) was taken up in 4 M HCl in dioxane (100 ml, 400 mmol) as a slurry and left to stir at room temperature overnight. The reaction was then filtered and washed with dioxane to afford 3-(2,3-dihydro-1H-indol-5-yl)thieno[3,2-c]pyridin-4-amine (3.44 g) as an off white solid. LC/MS (ES) m/z=268.1 [M+H]$^+$

3-(1-{[3-(trifluoromethyl)phenyl]acetyl}-2,3-dihydro-1H-indol-5-yl)thieno[3,2-c]pyridin-4-amine To a 4 mL screw cap vial was added 3-(2,3-dihydro-1H-indol-5-yl)thieno[3,2-c]pyridin-4-amine (100 mg, 0.374 mmol) followed by HATU (142 mg, 0.374 mmol), 3-trifluoromethylphenyl acetic acid (76 mg, 0.374 mmol) and DIEA (0.261 mL, 1.496 mmol). N,N-Dimethylformamide (DMF) (2 mL) was added and the reaction was sealed and left to stir at room temperature overnight. The reaction mixture was poured into water (4 mL) and extracted with EtOAc (5 mL). The organics were dried over $Na_2SO_4$ and concentrated. The residue was taken up in DCM and purified via normal phase chromatography (0-10% MeOH/DCM). Fractions were collected and concentrated to afford 3-(1-{[3-(trifluoromethyl)phenyl]acetyl}-2,3-dihydro-1H-indol-5-yl)thieno[3,2-c]pyridin-4-amine (106.1 mg) as an orange solid. LC/MS (ES) m/z=454.2 [M+H]$^+$. $^1$H NMR (400 MHz, DMSO-d$_6$) δ ppm 8.15 (d, J=8.3 Hz, 1H) 7.84 (d, J=6.1 Hz, 1H) 7.69 (s, 1H) 7.57-7.67 (m, 3H) 7.52 (s, 1H) 7.36 (d, J=5.8 Hz, 2H) 7.25 (d, J=8.1 Hz, 1H) 5.79 (br. s., 2H) 4.30 (t, J=8.5 Hz, 2H) 4.05 (s, 2H) 3.27 (t, 2H).

Example 21

3-{1-[(2-chlorophenyl)acetyl]-2,3-dihydro-1H-indol-5-yl}thieno[3,2-c]pyridin-4-amine

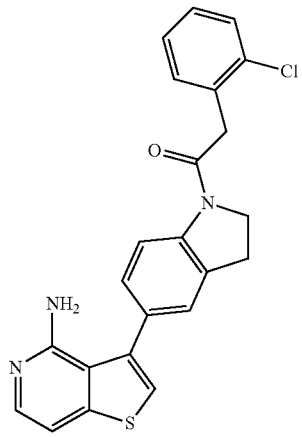 [SMILES: Nc1nccc2scc(-c3ccc4c(c3)CCN4C(=O)Cc3ccccc3Cl)c12]

To a 4 mL screw cap vial was added 3-(2,3-dihydro-1H-indol-5-yl)thieno[3,2-c]pyridin-4-amine (100 mg, 0.374 mmol) followed by HATU (142 mg, 0.374 mmol), 2-chlorophenylacetic acid (63.8 mg, 0.374 mmol) and DIEA (0.261 mL, 1.496 mmol). N,N-Dimethylformamide (DMF) (2 mL) was added and the reaction was sealed and left to stir at room temperature overnight. The reaction mixture was poured into water (4 mL) and extracted with EtOAc (5 mL). The organics were dried over $Na_2SO_4$ and concentrated. The residue was taken up in DCM and purified via normal phase chromatography (0-10% MeOH/DCM). Fractions were collected and concentrated to afford 3-{1-[(2-chlorophenyl)acetyl]-2,3-dihydro-1H-indol-5-yl}thieno[3,2-c]pyridin-4-amine (85.3 mg) as a pink solid. LC/MS (ES) m/z=420.2 [M+H]+ $^1$H NMR (400 MHz, DMSO-d$_6$) δ ppm 3.28 (t, J=8.34 Hz, 2H) 4.02 (s, 2H) 4.32 (t, J=8.46 Hz, 2H) 5.43 (br. s., 2H) 7.23 (d, J=8.08 Hz, 1H) 7.26 (d, J=5.56 Hz, 1H) 7.31-7.37 (m, 3H) 7.39-7.44 (m, 2H) 7.45-7.51 (m, 1H) 7.83 (d, J=5.56 Hz, 1H) 8.11 (d, J=8.08 Hz, 1H).

Example 22

3-{1-[(3-chlorophenyl)acetyl]-2,3-dihydro-1H-indol-5-yl}thieno[3,2-c]pyridin-4-amine

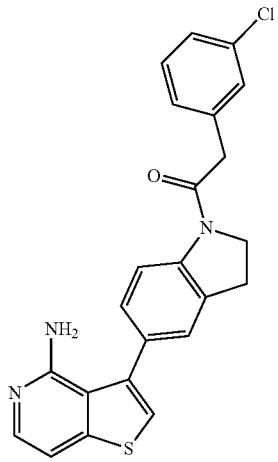 [SMILES: Nc1nccc2scc(-c3ccc4c(c3)CCN4C(=O)Cc3cccc(Cl)c3)c12]

To a 4 mL screw cap vial was added 3-(2,3-dihydro-1H-indol-5-yl)thieno[3,2-c]pyridin-4-amine (100 mg, 0.374 mmol) followed by HATU (142 mg, 0.374 mmol), 3-chlorophenylacetic acid (63.8 mg, 0.374 mmol) and DIEA (0.261 mL, 1.496 mmol). N,N-Dimethylformamide (DMF) (2 mL) was added and the reaction was sealed and left to stir at room temperature overnight. The reaction mixture was poured into water (4 mL) and extracted with EtOAc (5 mL). The organics were dried over Na2SO4 and concentrated. The residue was taken up in DCM and purified via normal phase chromatography (0-10% MeOH/DCM). Fractions were collected and concentrated to afford 3-{1-[(3-chlorophenyl)acetyl]-2,3-dihydro-1H-indol-5-yl}thieno[3,2-c]pyridin-4-amine (42.3 mg) as a yellow solid. LC/MS (ES) m/z=420.2 [M+H]+ $^1$H NMR (400 MHz, DMSO-$d_6$) δ ppm 3.25 (s, 2H) 3.93 (s, 2H) 4.26 (s, 2H) 5.41 (br. s., 2H) 7.20-7.30 (m, 3H) 7.32-7.36 (m, 2H) 7.37-7.40 (m, 2H) 7.42 (s, 1H) 7.82 (d, J=5.56 Hz, 1H) 8.14 (d, J=8.08 Hz, 1H).

Example 23

3-(1-{[3-(methyloxy)phenyl]acetyl}-2,3-dihydro-1H-indol-5-yl)thieno[3,2-c]pyridin-4-amine

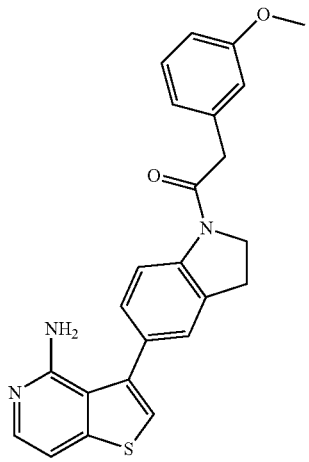 [SMILES: COc1cccc(CC(=O)N2CCc3cc(-c4csc5ccnc(N)c45)ccc32)c1]

To a 4 mL screw cap vial was added 3-(2,3-dihydro-1H-indol-5-yl)thieno[3,2-c]pyridin-4-amine (100 mg, 0.374 mmol) followed by HATU (142 mg, 0.374 mmol), 3-methoxyphenylacetic acid (62.2 mg, 0.374 mmol) and DIEA (0.261 mL, 1.496 mmol). N,N-Dimethylformamide (DMF) (2 mL) was added and the reaction was sealed and left to stir at room temperature overnight. The reaction mixture was poured into water (4 mL) and extracted with EtOAc (5 mL). The organics were dried over Na2SO4 and concentrated. The residue was taken up in DCM and purified via normal phase chromatography (0-10% MeOH/DCM). Fractions were collected and concentrated to afford 3-(1-{[3-(methyloxy)phenyl]acetyl}-2,3-dihydro-1H-indol-5-yl)thieno[3,2-c]pyridin-4-amine (69.4 mg) as a white solid. LC/MS (ES) m/z=416.2 [M+H]+ $^1$H NMR (400 MHz, DMSO-$d_6$) δ ppm 3.22 (t, J=8.34 Hz, 2H) 3.75 (s, 3H) 3.86 (s, 2H) 4.23 (t, J=8.46 Hz, 2H) 5.54 (br. s., 2H) 6.84 (dd, J=8.21, 2.40 Hz, 1H) 6.87-6.91 (m, 2H) 7.21-7.27 (m, 2H) 7.29 (d, J=5.56 Hz, 1H) 7.33 (s, 1H) 7.44 (s, 1H) 7.83 (d, J=5.81 Hz, 1H) 8.17 (d, J=8.34 Hz, 1H).

Example 24

3-(1-{[2-(methyloxy)phenyl]acetyl}-2,3-dihydro-1H-indol-5-yl)thieno[3,2-c]pyridin-4

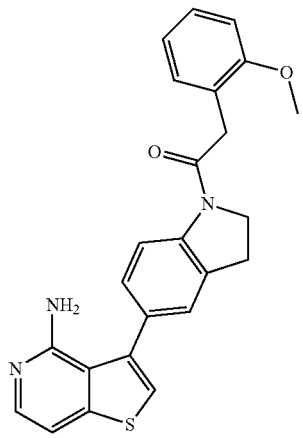 [SMILES: COc1ccccc1CC(=O)N1CCc2cc(-c3csc4ccnc(N)c34)ccc21]

To a 4 mL screw cap vial was added 3-(2,3-dihydro-1H-indol-5-yl)thieno[3,2-c]pyridin-4-amine (100 mg, 0.374 mmol) followed by HATU (142 mg, 0.374 mmol), 2-methoxyphenylacetic acid (62.2 mg, 0.374 mmol) and DIEA (0.261 mL, 1.496 mmol). N,N-Dimethylformamide (DMF) (2 mL) was added and the reaction was sealed and left to stir at room temperature overnight. The reaction mixture was poured into water (4 mL) and extracted with EtOAc (5 mL). The organics were dried over $Na_2SO_4$ and concentrated. The residue was taken up in DCM and purified via normal phase chromatography (0-10% MeOH/DCM). Fractions were collected and concentrated to afford 3-(1-{[2-(methyloxy)phenyl]acetyl}-2,3-dihydro-1H-indol-5-yl)thieno[3,2-c]pyridin-4-amine (40.6 mg) as a white solid. LC/MS (ES) m/z=416.2 [M+H]+ $^1$H NMR (400 MHz, DMSO-$d_6$) δ ppm 3.25 (t, 2H) 3.74-3.84 (m, 5H) 4.27 (t, 2H) 6.01 (br. s., 2H) 6.93 (t, 1H) 7.01 (d, J=7.83 Hz, 1H) 7.20 (dd, J=7.33, 1.52 Hz, 1H) 7.22-7.31 (m, 2H) 7.36 (s, 1H) 7.42 (d, J=6.06 Hz, 1H) 7.57 (s, 1H) 7.84 (d, J=6.06 Hz, 1H) 8.14 (d, J=8.08 Hz, 1H).

Example 25

3-[1-(2-naphthalenylacetyl)-2,3-dihydro-1H-indol-5-yl]thieno[3,2-c]pyridin-4-amine

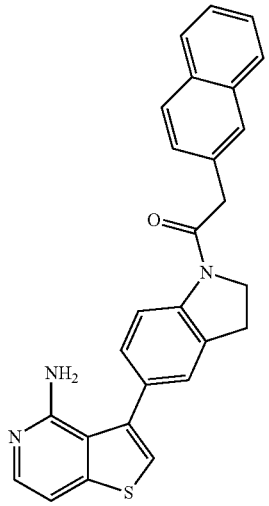 [SMILES: Nc1nccc2scc(-c3ccc4c(c3)CCN4C(=O)Cc3ccc4ccccc4c3)c12]

To a 4 mL screw cap vial was added 3-(2,3-dihydro-1H-indol-5-yl)thieno[3,2-c]pyridin-4-amine (100 mg, 0.374 mmol) followed by HATU (142 mg, 0.374 mmol), 2-napthylacetic acid (69.6 mg, 0.374 mmol) and DIEA (0.261 mL, 1.496 mmol). N,N-Dimethylformamide (DMF) (2 mL) was added and the reaction was sealed and left to stir at room temperature overnight. The reaction mixture was poured into water (4 mL) and extracted with EtOAc (5 mL). The organics were dried over Na2SO4 and concentrated. The residue was taken up in DCM and purified via normal phase chromatography (0-10% MeOH/DCM). Fractions were collected and concentrated to afford 3-[1-(2-naphthalenylacetyl)-2,3-dihydro-1H-indol-5-yl]thieno[3,2-c]pyridin-4-amine (70 mg). LC/MS (ES) m/z=436.2 [M+H]+ $^1$H NMR (400 MHz, DMSO-$d_6$) δ ppm 3.19-3.29 (m, 2H) 4.07 (s, 2H) 4.31 (t, J=8.46 Hz, 2H) 5.45 (br. s., 2H) 7.20-7.29 (m, 2H) 7.33 (s, 1H) 7.42 (s, 1H) 7.46-7.55 (m, 3H) 7.80-7.85 (m, 2H) 7.86-7.95 (m, 3H) 8.18 (d, J=8.08 Hz, 1H).

Example 26

3-[1-(phenylacetyl)-2,3-dihydro-1H-indol-5-yl]-7-(4-piperidinyl)thieno[3,2-c]pyridin-4-amine

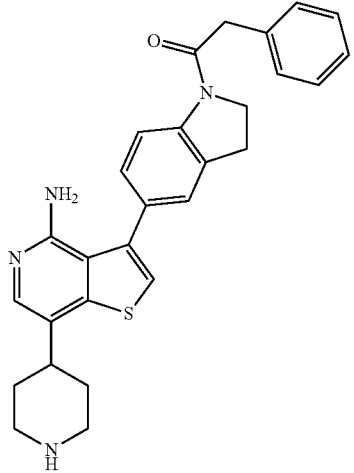 [SMILES: Nc1ncc(C2CCNCC2)c2scc(-c3ccc4c(c3)CCN4C(=O)Cc3ccccc3)c12]

1,1-dimethylethyl 4-{4-amino-3-[1-(phenylacetyl)-2,3-dihydro-1H-indol-5-yl]thieno[3,2-c]pyridin-7-yl}-1-piperidinecarboxylate A suspension of 1,1-dimethylethyl 4-{4-amino-3-[1-(phenylacetyl)-2,3-dihydro-1H-indol-5-yl]thieno[3,2-c]pyridin-7-yl}-3,6-dihydro-1(2H)-pyridinecarboxylate (220 mg, 0.388 mmol) and Pd/C, 10 wt. % (dry basis), wet, Degussa type E101 NE/W, ca. 50% water (25 mg, 0.012 mmol) in Ethanol (10 mL) was stirred under an atmosphere of hydrogen for 2 hours. The starting material never seemed to go into solution (the mixture was a thick gray suspension), so Tetrahydrofuran (THF) (15 mL) was added. It was stirred under hydrogen for another 17 hr, then filtered. LCMS appeared to indicate little or no conversion (based on the mass of the peak). The filtrate was subjected to 10% Pd/C hydrogenation on an H-Cube® reactor at 40° C. and 40 bar for 23 hours (the actual reaction time was less because of an error on the H-cube which stopped the reaction sometime during the night). LCMS appeared to show mostly desired product along with some starting material and a smallish byproduct. It was concentrated in vacuo, and the residue was dry loaded onto silica gel (1 g) and purified by flash chromatography (Analogix, 40 g SiO2, DCM to 95/5/0.5 DCM/MeOH/NH4OH gradient over 42 minutes) to give 1,1-dimethylethyl 4-{4-amino-3-[1-(phenylacetyl)-2,3-dihydro-1H-indol-5-yl]thieno[3,2-c]pyridin-7-yl}-1-piperidinecarboxylate (91 mg) as an off-white solid.

3-[1-(phenylacetyl)-2,3-dihydro-1H-indol-5-yl]-7-(4-piperidinyl)thieno[3,2-c]pyridin-4-amine TFA (0.5 mL, 6.49 mmol) was added to a suspension of 1,1-dimethylethyl 4-{4-amino-3-[1-(phenylacetyl)-2,3-dihydro-1H-indol-5-yl]thieno[3,2-c]pyridin-7-yl}-1-piperidinecarboxylate (90 mg, 0.158 mmol) in Dichloromethane (DCM) (3.5 mL), and the mixture was stirred at room temperature under Nitrogen for 30 min. The reaction mixture was then concentrated in vacuo, taken up in DCM, and passed through a PL-HCO3 MP-resin cartridge, rinsing with more DCM. The filtrate was concentrated in vacuo. The solid (labeled 96-A1) was not quite pure enough for submission (impurities best visible by NMR), so the residue was purified by flash chromatography (Analogix, 24 g SiO2, DCM to 80/20/2 DCM/MeOH/NH4OH gradient over 30 minutes) to give 3-[1-(phenylacetyl)-2,3-dihydro-1H-indol-5-yl]-7-(4-piperidinyl)thieno[3,2-c]pyridin-4-amine (37 mg) as a white solid. LC/MS (ES) m/z=469 [M+H]+. $^1$H NMR (400 MHz, DMSO-d6) δ 1.64-1.77 (m, 2H), 1.77-1.86 (m, 2H), 2.57-2.77 (m, 3H), 3.07 (d, J=12.13 Hz, 2H), 3.22 (t, J=8.34 Hz, 2H), 3.89 (s, 2H), 4.24 (t, J=8.59 Hz, 2H), 5.24 (br. s., 2H), 7.19-7.39 (m, 7H), 7.41 (s, 1H), 7.70 (s, 1H), 8.15 (d, J=8.34 Hz, 1H)

Example 27

7-{3-[(dimethylamino)methyl]phenyl}-3-[1-(phenylacetyl)-2,3-dihydro-1H-indol-5-yl]thieno[3,2-c]pyridin-4-amine

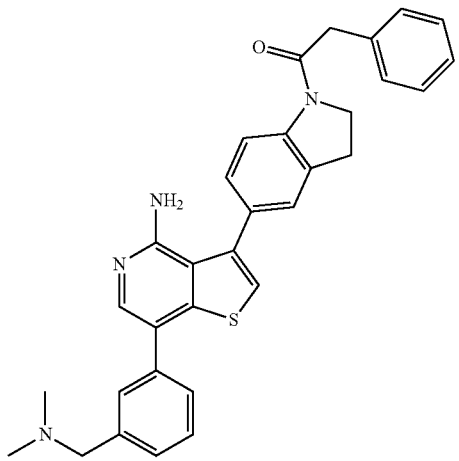 [SMILES: CN(C)Cc1cccc(-c2cnc(N)c3c(-c4ccc5c(c4)CCN5C(=O)Cc4ccccc4)csc23)c1]

3-{4-amino-3-[1-(phenylacetyl)-2,3-dihydro-1H-indol-5-yl]thieno[3,2-c]pyridin-7-yl}benzaldehyde A mixture of 7-iodo-3-[1-(phenylacetyl)-2,3-dihydro-1H-indol-5-yl]thieno[3,2-c]pyridin-4-amine (100 mg, 0.196 mmol), 3-formylphenyl boronic acid (40 mg, 0.267 mmol), and PdCl2(dppf)-CH2Cl2 adduct (9 mg, 0.011 mmol) in 1,4-Dioxane (1.5 mL) and saturated aqueous sodium bicarbonate (0.6 mL, 0.600 mmol) was degassed with Nitrogen for 10 minutes in a microwave vial. The vial was then capped and the mixture was stirred at 120° C. in the microwave for 30 min. LCMS showed complete and relatively clean conversion to the desired product. The mixture was cooled, poured into water (15 mL), and extracted with ethyl acetate (2×15 mL). The extracts were washed with brine (1×15 mL), dried (Na2SO4), filtered, and concentrated in vacuo. The residue was purified by flash chromatography (Analogix, 24 g SiO2, 20%-100% EtOAc in hexanes gradient over 35 minutes) to give 3-{4-amino-3-[1-(phenylacetyl)-2,3-dihydro-1H-indol-5-yl]thieno[3,2-c]pyridin-7-yl}benzaldehyde (66 mg, 0.135 mmol, 68.9% yield) as a tan solid. LC/MS (ES) m/z=490 [M+H]+.

7-{3-[(dimethylamino)methyl]phenyl}-3-[1-(phenylacetyl)-2,3-dihydro-1H-indol-5-yl]thieno[3,2-c]pyridin-4-amine Sodium triacetoxyborohydride (76 mg, 0.359 mmol) was added to a solution of 3-{4-amino-3-[1-(phenylacetyl)-2,3-dihydro-1H-indol-5-yl]thieno[3,2-c]pyridin-7-yl}benzaldehyde (66 mg, 0.135 mmol), dimethylamine, 2.0 M in THF (0.10 mL, 0.200 mmol), and acetic acid (8 μL, 0.140 mmol) in 1,2-Dichloroethane (DCE) (7 mL), and the mixture was stirred at room temperature under Nitrogen for 3 days. LCMS showed only starting material, so another portion each of dimethylamine, 2.0 M in THF (0.20 mL, 0.400 mmol) and sodium triacetoxyborohydride (162 mg, 0.764 mmol) were added. Stirring continued at room temperature for another 3.5 hr, when LCMS showed complete conversion to the desired product. The mixture was poured into saturated aqueous NaHCO3 (15 mL) and extracted with methylene chloride (2×15 mL). The extracts were dried (Na2SO4), filtered, and concentrated in vacuo. The residue was purified by reverse phase HPLC (Gilson, C18, 5% to 45% CH3CN in water with 0.1% TFA, 8 minute gradient). The product fractions were combined and concentrated in vacuo, and the residue was taken up in MeOH and passed through a PL-HCO3 MP-resin cartridge, rinsing with more MeOH. The filtrate was concentrated in vacuo and dried in the vacuum oven overnight to give 7-{3-[(dimethylamino)methyl]phenyl}-3-[1-(phenylacetyl)-2,3-dihydro-1H-indol-5-yl]thieno[3,2-c]pyridin-4-amine (50 mg, 0.092 mmol, 67.9% yield) as a white solid. LC/MS (ES) m/z=519 [M+H]+. $^1$H NMR (400 MHz, DMSO-$d_6$) δ 2.20 (s, 6H), 3.24 (t, J=8.34 Hz, 2H), 3.47 (s, 2H), 3.90 (s, 2H), 4.26 (t, J=8.46 Hz, 2H), 5.53 (br. s., 2H), 7.23-7.30 (m, 2H), 7.30-7.39 (m, 6H), 7.43-7.50 (m, 2H), 7.51-7.56 (m, 1H), 7.60 (s, 1H), 7.90 (s, 1H), 8.18 (d, J=8.34 Hz, 1H).

Example 28

3-{1-[(2,5-dimethylphenyl)acetyl]-2,3-dihydro-1H-indol-5-yl}-1-methyl-1H-pyrazolo[3,4-d]pyrimidin-4-amine

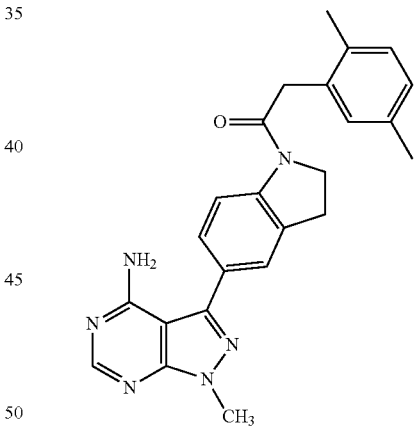

In a 20 mL vial with cap, to the solution of 3-(2,3-dihydro-1H-indol-5-yl)-1-methyl-1H-pyrazolo[3,4-d]pyrimidin-4-amine 2HCl (65.3 mg, 0.192 mmol), (2,5-dimethylphenyl)acetic acid (31.6 mg, 0.192 mmol), HATU (73.2 mg, 0.192 mmol) in DMF (2 mL) was added Hunig's base (0.134 mL, 0.770 mmol). The mixture was stirred at rt for over night. LCMS showed reaction was completed. The reaction was poured into water, white solid formed. It was filtered to give the product as a white solid. LC/MS (ES) m/z=413.3 [M+H]$^+$. $^1$H NMR (400 MHz, DMSO-$d_6$) δ ppm 2.19 (s, 3H), 2.25 (s, 3H), 3.24-3.31 (m, 2H), 3.84 (s, 2H), 3.94 (s, 3H), 4.28 (t, J=8.46 Hz, 2H), 6.99 (s, 2H), 7.08 (d, J=8.34 Hz, 1H), 7.44 (d, J=8.34 Hz, 1H), 7.52 (s, 1H), 8.17 (d, J=8.34 Hz, 1H), 8.25 (s, 1H).

Example 29

3-{1-[(3-fluoro-5-methylphenyl)acetyl]-2,3-dihydro-1H-indol-5-yl}-1-methyl-1H-pyrazolo[3,4-d]pyrimidin-4-amine

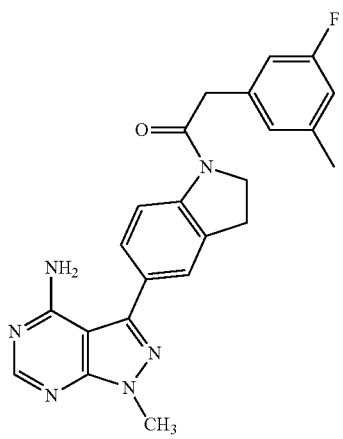 [SMILES: Cc1cc(F)cc(CC(=O)N2CCc3cc(-c4nn(C)c5ncnc(N)c45)ccc32)c1]

In a 20 mL vial with cap, to the solution of 3-(2,3-dihydro-1H-indol-5-yl)-1-methyl-1H-pyrazolo[3,4-d]pyrimidin-4-amine 2HCl (65.3 mg, 0.192 mmol), (3-fluoro-5-methylphenyl)acetic acid (32.4 mg, 0.192 mmol), HATU (73.2 mg, 0.192 mmol) in DMF (2 mL) was added Hunig's base (0.134 mL, 0.77 mmol). The mixture was stirred at room temperature overnight. LCMS showed reaction was completed. The reaction was poured into water, white solid formed. The solid was filtered to give the product as a white solid. The final product has about 0.7 equivalent of DMF. LC/MS (ES) m/z=417.3 [M+H]$^+$ $^1$H NMR (400 MHz, DMSO-d$_6$) δ ppm 2.32 (s, 3H), 3.22-3.29 (m, 2H), 3.88 (s, 2H), 3.93 (s, 3H), 4.24 (t, J=8.59 Hz, 2H), 6.92 (s, 1H), 6.96 (d, J=7.58 Hz, 2H), 7.44 (d, J=8.34 Hz, 1H), 7.51 (s, 1H), 8.19 (d, J=8.34 Hz, 1H), 8.25 (s, 1H).

Example 30

3-{1-[(3,5-dimethylphenyl)acetyl]-2,3-dihydro-1H-indol-5-yl}-1-methyl-1H-pyrazolo[3,4-d]pyrimidin-4-amine

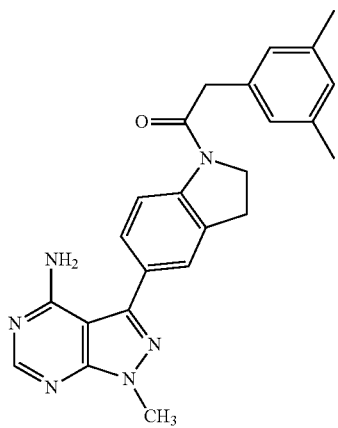 [SMILES: Cc1cc(C)cc(CC(=O)N2CCc3cc(-c4nn(C)c5ncnc(N)c45)ccc32)c1]

In a 20 mL vial with cap, to the solution of 3-(2,3-dihydro-1H-indol-5-yl)-1-methyl-1H-pyrazolo[3,4-d]pyrimidin-4-amine 2HCl (70 mg, 0.206 mmol), (3,5-dimethylphenyl)acetic acid (31.0 mg, 0.206 mmol), HATU (78 mg, 0.206 mmol) in DMF (2 mL) was added Hunig's base (0.144 mL, 0.825 mmol). The mixture was stirred at rt for over night. LCMS showed reaction was completed. The reaction was poured into water, white solid formed. The white solid was filtered to give the product. The final product has about 0.7 equivalent of DMF. LC/MS (ES) m/z=413.3 [M+H]$^+$$^1$H NMR (400 MHz, DMSO-d6) δ ppm 2.26 (s, 6H), 3.23 (s, 2H), 3.79 (s, 2H), 3.93 (s, 3H), 4.21 (s, 2H), 6.88-6.95 (m, 3H), 7.45 (s, 1H), 7.49 (s, 1H), 8.20 (d, J=8.34 Hz, 1H), 8.24 (s, 1H).

Example 31

5-{1-[(2,5-difluorophenyl)acetyl]-2,3-dihydro-1H-indol-5-yl}thieno[2,3-d]pyrimidin-4-amine

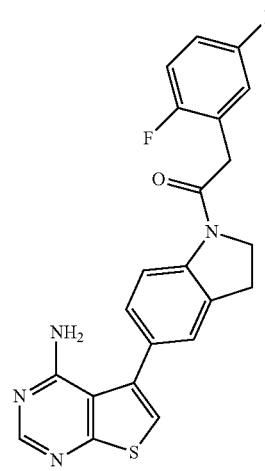

5-bromothieno[2,3-d]pyrimidin-4-amine

A suspension of 5-bromo-4-chlorothieno[2,3-d]pyrimidine (1 g, 4.01 mmol) in concentrated aqueous ammonium hydroxide (150 mL, 3852 mmol) was stirred overnight at 90° C. in a sealed vessel. The reaction was allowed to cool to room temperature and filtered. The white solid in the filter was air dried to afford 5-bromothieno[2,3-d]pyrimidin-4-amine (796 mg). LC/MS (ES) m/z=387.1 [M+H]$^+$.

5-{1-[(2,5-difluorophenyl)acetyl]-2,3-dihydro-1H-indol-5-yl}thieno[2,3-d]pyrimidin-4-amine To a mixture of 5-bromo-1-[(2,5-difluorophenyl)acetyl]-2,3-dihydro-1H-indole (150 mg, 0.426 mmol), bis(pinacolato)diboron (114 mg, 0.447 mmol), and potassium acetate (125 mg, 1.278 mmol) was added 1,4-dioxane (6 mL), and the mixture was degassed with N2 for 10 minutes. PdCl2(dppf)-CH2Cl2 adduct (17.39 mg, 0.021 mmol) was added, and the reaction mixture was stirred for 3 hours at 100 C into a sealed vessel. The reaction was cooled down to room temperature. 5-bromothieno[2,3-d]pyrimidin-4-amine (103 mg, 0.447 mmol) and sat. aq. NaHCO3 (2 mL) were added, and N2 gas was bubbled through the mixture for 10 minutes. PdCl2(dppf)-CH2Cl2 adduct (17.39 mg, 0.021 mmol) was added, the vessel was sealed, and the reaction mixture was stirred overnight at 100 C. The mixture was poured onto water and a precipitate was formed. The mixture was filtered, and the solid was taken up into a mixture of 20% CH$_3$OH/CH2Cl2 mixture, and the resulting mixture was filtered, injected into a 90 g silica gel column, and purified via flash chromatography (gradient: 100% Hexanes to 100% EtOAc). The fractions containing the product were combined and concentrated to afford a solid. Trituration with Et$_2$O afforded 5-{1-[(2,5-difluorophenyl)acetyl]-2,3-dihydro-1H-indol-5-yl}thieno[2, 3-d]pyrimidin-4-amine (120 mg) as a white solid. ¹H NMR (400 MHz, DMSO-d6) δ 3.27 (t, 2H), 3.96 (s, 2H), 4.31 (t, J=8.46 Hz, 2H), 7.13-7.32 (m, 4H), 7.37 (s, 1H), 7.43 (s, 1H), 8.11 (d, J=8.08 Hz, 1H), 8.34 (s, 1H).

Example 32

3-{1-[(2,3-difluorophenyl)acetyl]-2,3-dihydro-1H-indol-5-yl}-1-methyl-1H-pyrazolo[3,4-d]pyrimidin-4-amine

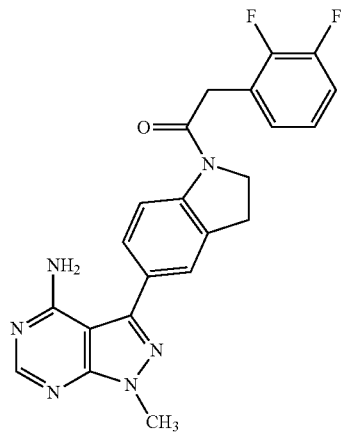 [SMILES: Cn1nc(-c2ccc3c(c2)CCN3C(=O)Cc2cccc(F)c2F)c2c(N)ncnc21]

In a 20 mL vial with cap, to the solution of 3-(2,3-dihydro-1H-indol-5-yl)-1-methyl-1H-pyrazolo[3,4-d]pyrimidin-4-amine 2HCl (68 mg, 0.20 mmol), (2,3-difluorophenyl)acetic acid (34.5 mg, 0.20 mmol), HATU (76 mg, 0.20 mmol) in DMF (2 mL) was added Hunig's base (0.14 mL, 0.802 mmol). The mixture was stirred at room temperature overnight. LCMS showed reaction was completed. The reaction was poured into water, a white solid formed. The solid was filtered to give a white solid as the title compound. The final product has about 0.7 equivalent of DMF.

¹H NMR (400 MHz, DMSO-d6) δ ppm 3.25-3.32 (m, 2H), 3.94 (s, 3H), 4.04 (s, 2H), 4.32 (t, J=8.46 Hz, 2H), 7.16-7.23 (m, 2H), 7.33-7.40 (m, 1H), 7.44 (d, J=8.34 Hz, 1H), 7.53 (s, 1H), 7.96 (s, 1H), 8.14 (d, J=8.08 Hz, 1H), 8.25 (s, 1H).

Example 33

7-methyl-5-{1-[(2-methylphenyl)acetyl]-2,3-dihydro-1H-indol-5-yl}-7H-pyrrolo[2,3-d]pyrimidin-4-amine

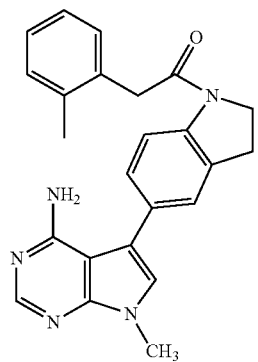 [SMILES: Cc1ccccc1CC(=O)N1CCc2cc(-c3cn(C)c4ncnc(N)c34)ccc21]

In a 20 mL vial with cap, to the solution of 5-(2,3-dihydro-1H-indol-5-yl)-7-methyl-7H-pyrrolo[2,3-d]pyrimidin-4-amine-2HCl (70.6 mg, 0.209 mmol), (2-methylphenyl)acetic acid (31.4 mg, 0.209 mmol), HATU (79 mg, 0.209 mmol) in DMF (2 mL) was added Hunig's base (0.146 mL, 0.836 mmol). The mixture was stirred at room temperature overnight. LCMS showed reaction was completed. The reaction was poured into water (100 mL), white solid formed. EtOAc (100 mL) was used to extract the product. The Organic phase was separated from the water phase, dried by MgSO4, rotavaped to dryness, to give white solid. The solid was sonacated in water (10 mL), then filtered and dried to afford 7-methyl-5-{1-[(2-methylphenyl)acetyl]-2,3-dihydro-1H-indol-5-yl}-7H-pyrrolo[2,3-d]pyrimidin-4-amine (48 mg) as a white solid. ¹H NMR (400 MHz, DMSO-d₆) δ ppm 8.02-8.24 (m, 2H) 7.32 (s, 1H) 7.25 (s, 1H) 7.12-7.24 (m, 5H) 6.07 (br. s., 2H) 4.26 (t, J=8.5 Hz, 2H) 3.87 (s, 2H) 3.73 (s, 3H) 3.24 (t, J=8.5 Hz, 2H) 2.24 (s, 3H).

Example 34

5-{1-[(2-fluorophenyl)acetyl]-2,3-dihydro-1H-indol-5-yl}-7-methyl-7H-pyrrolo[2,3-d]pyrimidin-4-amine

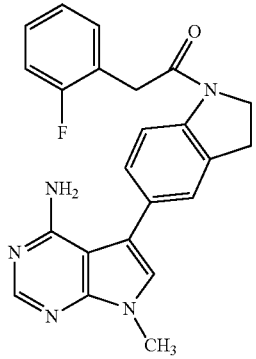 [SMILES: Cn1cc(-c2ccc3c(c2)CCN3C(=O)Cc2ccccc2F)c2c(N)ncnc21]

In a 20 mL vial with cap, to the solution of 5-(2,3-dihydro-1H-indol-5-yl)-7-methyl-7H-pyrrolo[2,3-d]pyrimidin-4-amine-2HCl (70.6 mg, 0.209 mmol), (2-fluorophenyl)acetic acid (32.2 mg, 0.209 mmol), HATU (79 mg, 0.209 mmol) in DMF (2 mL) was added Hunig's base (0.146 mL, 0.836 mmol). The mixture was stirred at room temperature for overnight. LCMS showed reaction was completed. The reaction was poured into water, white solid formed. The solid was filtered and dried to afford 5-{1-[(2-fluorophenyl)acetyl]-2,3-dihydro-1H-indol-5-yl}-7-methyl-7H-pyrrolo[2,3-d]pyrimidin-4-amine (73 mg). ¹H NMR (400 MHz, DMSO-d₆) δ ppm 3.26 (t, J=8.72 Hz, 2H), 3.73 (s, 3H), 3.93 (s, 2H), 4.28 (t, J=8.46 Hz, 2H), 7.19 (d, J=7.58 Hz, 3H), 7.26 (s, 1H), 7.30-7.38 (m, 3H), 8.09 (d, J=8.34 Hz, 1H), 8.14 (s, 1H).

Example 35

5-{1-[(3-fluorophenyl)acetyl]-2,3-dihydro-1H-indol-5-yl}-7-methyl-7H-pyrrolo[2,3-d]pyrimidin-4-amine

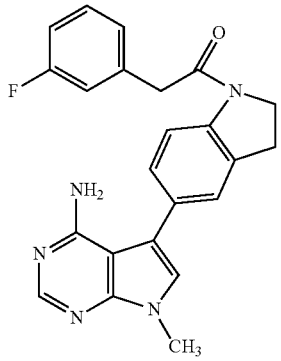 [SMILES: Cn1cc(-c2ccc3c(c2)CCN3C(=O)Cc2cccc(F)c2)c2c(N)ncnc21]

In a 20 mL vial with cap, to the solution of 5-(2,3-dihydro-1H-indol-5-yl)-7-methyl-7H-pyrrolo[2,3-d]pyrimidin-4-amine-2HCl (70.6 mg, 0.209 mmol), (3-fluorophenyl)acetic acid (32.2 mg, 0.209 mmol), HATU (79 mg, 0.209 mmol) in DMF (2 mL) was added Hunig's base (0.146 mL, 0.836 mmol). The mixture was stirred at rt for over night. LCMS showed reaction was completed. The reaction was poured into water, white solid formed. The solid was filtered and dried to afford a white solid as the product. $^1$H NMR (400 MHz, DMSO-$d_6$) δ ppm 3.23 (t, J=8.46 Hz, 2H), 3.73 (s, 3H), 3.92 (s, 2H), 4.19-4.26 (m, 2H), 7.08-7.11 (m, 1H), 7.12-7.17 (m, 2H), 7.23 (d, J=8.34 Hz, 1H), 7.25 (s, 1H), 7.31 (s, 1H), 7.36 (s, 1H), 7.39 (d, J=6.82 Hz, 1H), 8.10-8.17 (m, 2H).

Example 36

3-{1-[(2,3-difluorophenyl)acetyl]-2,3-dihydro-1H-indol-5-yl}thieno[3,2-c]pyridin-4-amine

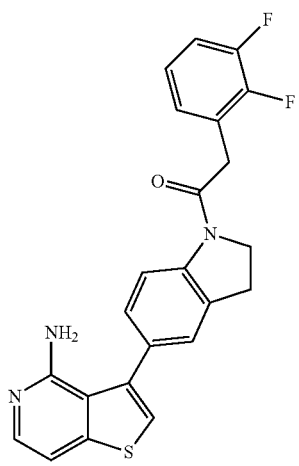 [SMILES: Nc1nccc2scc(-c3ccc4c(c3)CCN4C(=O)Cc3cccc(F)c3F)c12]

To a 4 mL screw cap vial was added 3-(2,3-dihydro-1H-indol-5-yl)thieno[3,2-c]pyridin-4-amine (100 mg, 0.374 mmol) followed by HATU (142 mg, 0.374 mmol), 2,3-difluorophenylacetic acid (56.7 mg, 0.329 mmol) and DIEA (0.261 mL, 1.496 mmol). N,N-Dimethylformamide (DMF) (2 mL) was added and the reaction was sealed and left to stir at room temperature overnight. The reaction mixture was poured into water (4 mL) and extracted with EtOAc (5 mL). The organics were dried over Na$_2$SO$_4$ and concentrated. The residue was taken up in DCM and purified via normal phase chromatography (0-10% MeOH/DCM). Fractions were collected and concentrated to afford 3-{1-[(2,3-difluorophenyl)acetyl]-2,3-dihydro-1H-indol-5-yl}thieno[3,2-c]pyridin-4-amine (31 mg). $^1$H NMR (400 MHz, DMSO-$d_6$) δ ppm 8.12 (d, J=8.1 Hz, 1H) 7.85 (d, J=6.1 Hz, 1H) 7.59 (s, 1H) 7.44 (d, J=6.1 Hz, 1H) 7.32-7.41 (m, 2H) 7.26 (d, J=8.3 Hz, 1H) 7.14-7.24 (m, 2H) 6.06 (d, J=8.8 Hz, 2H) 4.33 (t, J=8.5 Hz, 2H) 4.04 (s, 2H) 3.28 (t, 2H).

Example 37

7-methyl-5-{1-[(3-methylphenyl)acetyl]-2,3-dihydro-1H-indol-5-yl}-7H-pyrrolo[2,3-d]pyrimidin-4-amine

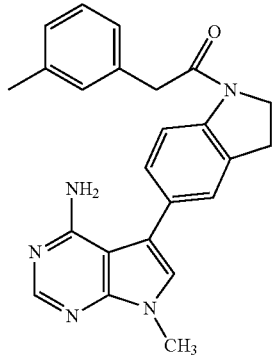 [SMILES: Cc1cccc(CC(=O)N2CCc3cc(-c4cn(C)c5ncnc(N)c45)ccc32)c1]

In a 20 mL vial with cap, to the solution of 5-(2,3-dihydro-1H-indol-5-yl)-7-methyl-7H-pyrrolo[2,3-d]pyrimidin-4-amine-2HCl (70.6 mg, 0.209 mmol), (3-methylphenyl)acetic acid (31.4 mg, 0.209 mmol), HATU (79 mg, 0.209 mmol) in DMF (2 mL) was added Hunig's base (0.146 mL, 0.836 mmol). The mixture was stirred at room temperature for overnight. LCMS showed reaction was completed. The reaction was poured into water, light brown colored solid formed. The solid was filtered and dried to afford 7-methyl-5-{1-[(3-methylphenyl)acetyl]-2,3-dihydro-1H-indol-5-yl}-7H-pyrrolo[2,3-d]pyrimidin-4-amine (57 mg). $^1$H NMR (400 MHz, DMSO-$d_6$) δ ppm 2.30 (s, 3H), 3.16-3.23 (m, 2H), 3.72 (s, 3H), 3.82 (s, 2H), 4.17-4.24 (m, 2H), 7.06-7.14 (m, 3H), 7.20-7.27 (m, 3H), 7.30 (s, 1H), 8.11-8.18 (m, 2H).

Example 38

3-{1-[(3-fluoro-2-methyl phenyl)acetyl]-2,3-dihydro-1H-indol-5-yl}thieno[3,2-c]pyridin-4-amine

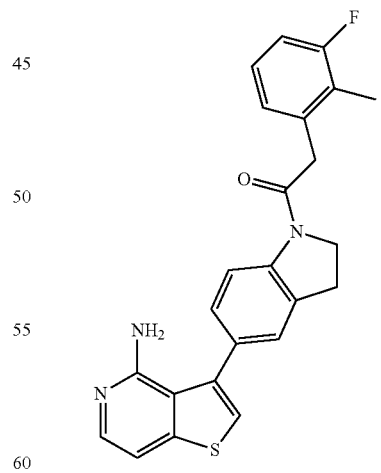

To a 4 mL screw cap vial was added 3-(2,3-dihydro-1H-indol-5-yl)thieno[3,2-c]pyridin-4-amine (100 mg, 0.329 mmol) followed by HATU (125 mg, 0.329 mmol), 3-Fluoro-2-methylphenyl acetic acid (55.4 mg, 0.329 mmol) and DIEA (0.230 mL, 1.317 mmol). N,N-Dimethylformamide (DMF) (2 mL) was added and the reaction was sealed and left to stir at room temperature overnight. The reaction mixture was poured into water (4 mL) and extracted with EtOAc (5 mL). The organics were dried over Na2SO4 and concentrated. The residue was taken up in DCM and purified via normal phase chromatography (0-10% MeOH/DCM). Fractions were collected and concentrated to afford 3-{1-[(3-fluoro-2-methylphenyl)acetyl]-2,3-dihydro-1H-indol-5-yl}thieno[3,2-c]pyridin-4-amine (94.6 mg). $^1$H NMR (400 MHz, DMSO-$d_6$) δ ppm 8.12 (d, J=8.1 Hz, 1H) 7.83 (d, J=5.8 Hz, 1H) 7.41 (s, 1H) 7.35 (s, 1H) 7.26 (d, J=5.6 Hz, 1H) 7.14-7.25 (m, 2H) 7.02-7.11 (m, 2H) 5.42 (br. s., 2H) 4.31 (t, J=8.5 Hz, 2H) 3.97 (s, 2H) 3.27 (t, 2H) 2.15 (m, 3H).

Example 39

3-{2-[5-(4-aminothieno[3,2-c]pyridin-3-yl)-2,3-dihydro-1H-indol-1-yl]-2-oxoethyl}benzonitrile

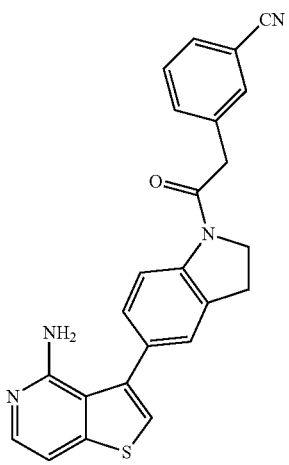 [SMILES: N#Cc1cccc(CC(=O)N2CCc3cc(-c4csc5ccnc(N)c45)ccc32)c1]

To a 4 mL screw cap vial was added 3-(2,3-dihydro-1H-indol-5-yl)thieno[3,2-c]pyridin-4-amine (100 mg, 0.329 mmol) followed by HATU (125 mg, 0.329 mmol), 3-cyanophenylacetic acid (53.0 mg, 0.329 mmol) and DIEA (0.230 mL, 1.317 mmol). N,N-Dimethylformamide (DMF) (2 mL) was added and the reaction was sealed and left to stir at room temperature overnight. The reaction mixture was poured into water (4 mL) and extracted with EtOAc (5 mL). The organics were dried over Na2SO4 and concentrated. The residue was taken up in DCM and purified via normal phase chromatography (0-10% MeOH/DCM). Fractions were collected and concentrated to afford 3-{2-[5-(4-aminothieno[3,2-c]pyridin-3-yl)-2,3-dihydro-1H-indol-1-yl]-2-oxoethyl}benzonitrile (100.8 mg). $^1$H NMR (400 MHz, DMSO-$d_6$) d ppm 8.13 (d, J=8.1 Hz, 1H) 7.83 (d, J=5.8 Hz, 1H) 7.73-7.79 (m, 2H) 7.66 (d, J=7.8 Hz, 1H) 7.52-7.61 (m, 1H) 7.44 (s, 1H) 7.35 (s, 1H) 7.28 (d, J=5.6 Hz, 1H) 7.20-7.26 (m, 1H) 5.48 (br. s., 2H) 4.29 (t, J=8.5 Hz, 2H) 4.00 (s, 2H) 3.27 (t, 2H).

Example 40

3-{1-[(2-fluoro-5-methylphenyl)acetyl]-2,3-dihydro-1H-indol-5-yl}-1-methyl-1H-pyrazolo[3,4-d]pyrimidin-4-amine

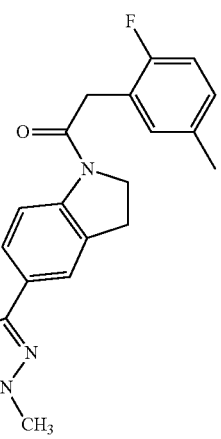

In a 20 mL vial with cap, to the solution of 3-(2,3-dihydro-1H-indol-5-yl)-1-methyl-1H-pyrazolo[3,4-d]pyrimidin-4-amine 2HCl (70 mg, 0.206 mmol), (2-fluoro-5-methylphenyl)acetic acid (34.7 mg, 0.206 mmol), HATU (78 mg, 0.206 mmol) in DMF (2 mL) was added Hunig's base (0.144 mL, 0.825 mmol). The mixture was stirred at room temperature for overnight. LCMS showed reaction was completed. The reaction was poured into water, off-white solid formed. The solid was filtered to give the title compound as an off-white solid. $^1$H NMR (400 MHz, DMSO-$d_6$) δ ppm 2.29 (s, 3H), 3.28 (t, J=8.46 Hz, 2H), 3.89 (s, 2H), 3.93 (s, 3H), 4.29 (t, J=8.46 Hz, 2H), 7.07 (s, 1H), 7.09-7.16 (m, 2H), 7.43 (d, J=8.34 Hz, 1H), 7.52 (s, 1H), 8.15 (d, J=8.34 Hz, 1H), 8.25 (s, 1H).

Example 41

3-{1-[(2,3-dimethyl phenyl)acetyl]-2,3-dihydro-1H-indol-5-yl}-1-methyl-1H-pyrazolo[3,4-d]pyrimidin-4-amine

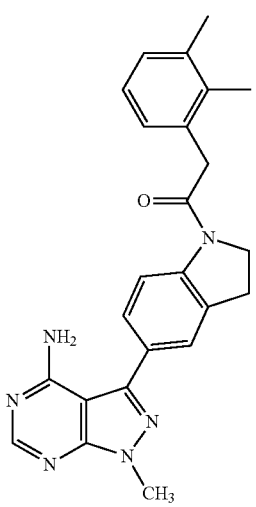 [SMILES: Cc1cccc(CC(=O)N2CCc3cc(-c4nn(C)c5ncnc(N)c45)ccc32)c1C]

In a 20 mL vial with cap, to the solution of 3-(2,3-dihydro-1H-indol-5-yl)-1-methyl-1H-pyrazolo[3,4-d]pyrimidin-4-amine 2HCl (70 mg, 0.206 mmol), (2,3-dimethylphenyl)acetic acid (33.9 mg, 0.206 mmol), HATU (78 mg, 0.206 mmol) in DMF (2 mL) was added Hunig's base (0.144 mL, 0.825 mmol). The mixture was stirred at room temperature for overnight. LCMS showed reaction was completed. The reaction was poured into water, off-white solid formed. The solid was filtered to give the title compound as an off-white solid. $^{1}$H NMR (400 MHz, DMSO-$d_6$) ppm 2.12 (s, 3H), 2.27 (s, 3H), 3.24-3.31 (m, 2H), 3.91 (s, 2H), 3.94 (s, 3H), 4.24-4.32 (m, 2H), 7.03 (d, J=6.82 Hz, 2H), 7.05-7.09 (m, 1H), 7.43 (d, J=8.34 Hz, 1H), 7.52 (s, 1H), 8.17 (d, J=8.34 Hz, 1H), 8.25 (s, 1H).

Example 42

3-{1-[(3-chlorophenyl)acetyl]-2,3-dihydro-1H-indol-5-yl}-1-methyl-1H-pyrazolo[3,4-d]pyrimidin-4-amine

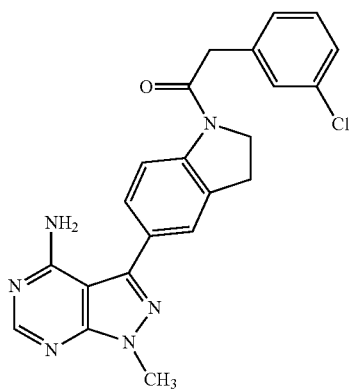 [SMILES: Cn1nc(-c2ccc3c(c2)CCN3C(=O)Cc2cccc(Cl)c2)c2c(N)ncnc21]

In a 20 mL vial with cap, to the solution of 3-(2,3-dihydro-1H-indol-5-yl)-1-methyl-1H-pyrazolo[3,4-d]pyrimidin-4-amine 2HCl (70 mg, 0.206 mmol), (3-chlorophenyl)acetic acid (35.2 mg, 0.206 mmol), HATU (78 mg, 0.206 mmol) in DMF (2 mL) was added Hunig's base (0.144 mL, 0.825 mmol). The mixture was stirred at rt for over night. LCMS showed reaction was completed. The reaction was poured into water, off-white solid formed. The solid was filtered to give the title compound as an off-white solid. The final product has about 0.5 equivalent of DMF. $^{1}$H NMR (400 MHz, DMSO-$d_6$) δ ppm 3.28 (s, 2H), 3.94 (s, 5H), 4.26 (t, J=8.59 Hz, 2H), 7.28 (d, J=7.33 Hz, 1H), 7.35-7.41 (m, 3H), 7.44 (d, J=9.85 Hz, 1H), 7.52 (s, 1H), 8.18 (d, J=8.34 Hz, 1H), 8.25 (s, 1H).

Example 43

1-methyl-3-(1-{[3-(trifluoromethyl)phenyl]acetyl}-2,3-dihydro-1H-indol-5-yl)-1H-pyrazolo[3,4-d]pyrimidin-4-amine

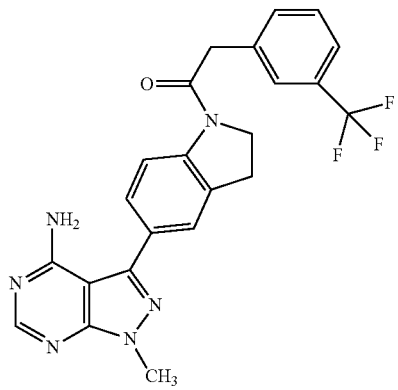 [SMILES: Cn1nc(-c2ccc3c(c2)CCN3C(=O)Cc2cccc(C(F)(F)F)c2)c2c(N)ncnc21]

In a 20 mL vial with cap, to the solution of 3-(2,3-dihydro-1H-indol-5-yl)-1-methyl-1H-pyrazolo[3,4-d]pyrimidin-4-amine 2HCl (70 mg, 0.206 mmol), [3-(trifluoromethyl)phenyl]acetic acid (42.1 mg, 0.206 mmol), HATU (78 mg, 0.206 mmol) in DMF (2 mL) was added Hunig's base (0.144 mL, 0.825 mmol). The mixture was stirred at room temperature for overnight. LCMS showed reaction was completed. The reaction was poured into water, off-white solid formed. The solid was filtered to give t1-methyl-3-(1-{[3-(trifluoromethyl)phenyl]acetyl}-2,3-dihydro-1H-indol-5-yl)-1H-pyrazolo[3,4-d]pyrimidin-4-amine as an off-white solid. The final product has about 0.7 equivalent of DMF. LC/MS (ES) m/z=453.1 [M+H]$^{+1}$H NMR (400 MHz, DMSO-$d_6$) δ ppm 3.25-3.32 (m, 2H), 3.94 (s, 3H), 4.05 (s, 2H), 4.29 (t, J=8.46 Hz, 2H), 7.44 (d, J=8.34 Hz, 1H), 7.52 (s, 1H), 7.59-7.66 (m, 3H), 7.69 (s, 1H), 8.17 (d, J=8.34 Hz, 1H), 8.25 (s, 1H).

Example 44

7-methyl-5-(1-{[3-(trifluoromethyl)phenyl]acetyl}-2,3-dihydro-1H-indol-5-yl)-7H-pyrrolo[2,3-d]pyrimidin-4-amine

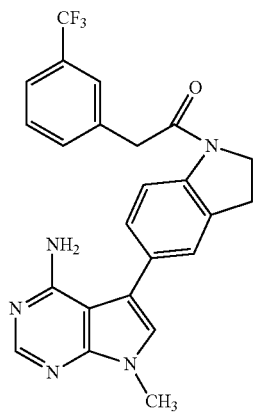

In a 20 mL vial with cap, to the solution of 5-(2,3-dihydro-1H-indol-5-yl)-7-methyl-7H-pyrrolo[2,3-d]pyrimidin-4-amineHCl (70.6 mg, 0.234 mmol), [3-(trifluoromethyl)phenyl]acetic acid (47.8 mg, 0.234 mmol), HATU (89 mg, 0.234 mmol) in DMF (2 mL) was added Hunig's base (0.163 mL, 0.936 mmol). The mixture was stirred at room temperature for overnight. LCMS showed reaction was completed. The reaction was poured into water (100 mL), off-white solid formed. EtOAc (100 mL) was used to extract the product. The Organic phase was separated from the water phase, dried by MgSO$_4$, evaporated to dryness, to give white solid, which still had some starting material. The solid was sonicated in water (10 mL), then filtered and dried to afford 7-methyl-5-(1-{[3-(trifluoromethyl)phenyl]acetyl}-2,3-dihydro-1H-indol-5-yl)-7H-pyrrolo[2,3-d]pyrimidin-4-amine as an off-white solid. LC/MS (ES) m/z=452.1 [M+H]$^+$ $^1$H NMR (400 MHz, DMSO-d6) δ ppm 3.25 (t, J=8.34 Hz, 2H), 3.74 (s, 3H), 4.03 (s, 2H), 4.27 (t, J=8.59 Hz, 2H), 7.22 (m, 1H), 7.28-7.35 (m, 2H), 7.58-7.66 (m, 3H), 7.68 (s, 1H), 8.12 (d, J=8.08 Hz, 1H), 8.17 (s, 1H).

Example 45

5-{1-[(3-fluoro-5-methylphenyl)acetyl]-2,3-dihydro-1H-indol-5-yl}-7-methyl-7H-pyrrolo[2,3-d]pyrimidin-4-amine

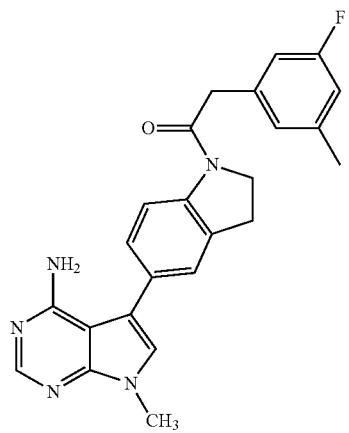 [SMILES: Cc1cc(F)cc(CC(=O)N2CCc3cc(-c4cn(C)c5ncnc(N)c45)ccc32)c1]

To a suspension of 5-(2,3-dihydro-1H-indol-5-yl)-7-methyl-7H-pyrrolo[2,3-d]pyrimidin-4-amine 2HCl salt (200 mg, 0.59 mmol, 1 equiv) and HATU (247 mg, 0.65 mmol, 1.1 equiv) in 2 mL of DMF was added DIEA (0.36 mL, 2.07 mmol, 3.5 equiv) in one portion. The mixture turned into a clear but pitch dark solution, to which was added (3-fluoro-5-methylphenyl)acetic acid (70 mg, 0.42 mmol, 0.7 equiv) as solids. The mixture was stirred at room temperature for 18 hours. To the mixture was added water (15 mL) to give a precipitate, which was filtered. The cake was washed with water and dried under house vacuum for 20 h. The yellowish solids were dissolved in 10% MeOH in DCM, and absorbed onto a dryload cartridge. Purification was done on an SF15-24 g silica gel cartridge using gradient elution of 1% A in EtOAc to 100% A (A was a mixture of 9% MeOH in EtOAc, gradient: 0-5 min, 1% A, 5-15 min, 1-100% A, 15-60 min, 100% A). The combined fractions were concentrated in vacuo to give a suspension (2 mL), which was chilled for 1 h, followed by filtration. the solids were washed with cold MeOH (3 mL), MTBE (2×3 mL) and then hexane (2×3 mL). The solids were dried under vacuum at 65° C. for 20 h to give 5-{1-[(3-fluoro-5-methylphenyl)acetyl]-2,3-dihydro-1H-indol-5-yl}-7-methyl-7H-pyrrolo[2,3-d]pyrimidin-4-amine (97 mg) as light beige solids. LC-MS (ES) m/z=416 [M+H]+. $^1$H NMR (400 MHz, DMSO-d$_6$) δ ppm 2.32 (s, 3H), 3.22 (t, J=8.46 Hz, 2H), 3.73 (s, 3H), 3.86 (s, 2H), 4.21 (t, J=8.46 Hz, 2H), 5.93-6.21 (br s, 1.4H), 6.90-6.99 (m, 3H), 7.23 (d, J=12.0 Hz, 1H), 7.25 (s, 1H), 7.31 (s, 1H), 7.12 (d, J=8.0 hz, 1H), 8.14 (s, 1H).

Example 46

5-{1-[(3-chlorophenyl)acetyl]-2,3-dihydro-1H-indol-5-yl}-7-methyl-7H-pyrrolo[2,3-d]pyrimidin-4-amine

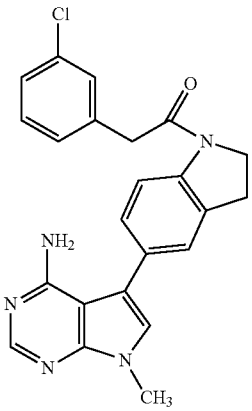 [SMILES: Cn1cc(-c2ccc3c(c2)CCN3C(=O)Cc2cccc(Cl)c2)c2c(N)ncnc21]

In a 20 mL vial with cap, to the solution of 5-(2,3-dihydro-1H-indol-5-yl)-7-methyl-7H-pyrrolo[2,3-d]pyrimidin-4-amine HCl (70.6 mg, 0.234 mmol), (3-chlorophenyl)acetic acid (39.9 mg, 0.234 mmol), HATU (89 mg, 0.234 mmol) in DMF (2 mL) was added Hunig's base (0.163 mL, 0.936 mmol). The mixture was stirred at room temperature for overnight. LCMS showed reaction was completed. The reaction was poured into water (100 mL), purple solid formed. EtOAc (100 mL) was used to extract the product. The Organic phase was separated from the water phase, dried by MgSO$_4$, evaporated to dryness, to give purple solid which still had some starting material. The solid was sonicated in water (10 mL), then filtered and dried to afford 5-{1-[(3-chlorophenyl)acetyl]-2,3-dihydro-1H-indol-5-yl}-7-methyl-7H-pyrrolo[2,3-d]pyrimidin-4-amine as a purple solid.
$^1$H NMR (400 MHz, DMSO-d$_6$) δ ppm 3.24 (t, J=8.59 Hz, 2H), 3.73 (s, 3H), 3.92 (s, 2H), 4.23 (t, J=8.46 Hz, 2H), 6.10 (s, 2H), 7.23 (d, J=8.34 Hz, 1H), 7.26-7.29 (m, 2H), 7.31-7.33 (m, 1H), 7.34-7.39 (m, 3H), 8.12 (d, J=8.34 Hz, 1H), 8.15 (s, 1H).

Example 47

5-{1-[(2-chlorophenyl)acetyl]-2,3-dihydro-1H-indol-5-yl}-7-methyl-7H-pyrrolo[2,3-d]pyrimidin-4-amine

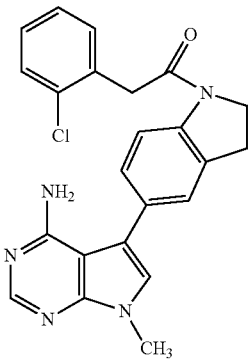 [SMILES: Cn1cc(-c2ccc3c(c2)CCN3C(=O)Cc2ccccc2Cl)c2c(N)ncnc21]

In a 20 mL vial with cap, to the solution of 5-(2,3-dihydro-1H-indol-5-yl)-7-methyl-7H-pyrrolo[2,3-d]pyrimidin-4-amineHCl (70.6 mg, 0.234 mmol), (2-chlorophenyl)acetic acid (39.9 mg, 0.234 mmol), HATU (89 mg, 0.234 mmol) in DMF (2 mL) was added Hunig's base (0.163 mL, 0.936 mmol). The mixture was stirred at room temperature for overnight. LCMS showed reaction was completed. The reaction was poured into water (100 mL), off-white solid formed. The solid was filtered and dried to afford 5-{1-[(2-chlorophenyl)acetyl]-2,3-dihydro-1H-indol-5-yl}-7-methyl-7H-pyrrolo[2,3-d]pyrimidin-4-amine as an off-white solid. NMR showed it has 0.8 eq of DMF. $^1$H NMR (400 MHz, DMSO-$d_6$) δ ppm 3.39 (m, 2H), 3.73 (s, 3H), 4.00 (s, 2H), 4.29 (m, 2H), 7.25 (m, 2H), 7.30-7.36 (m, 3H), 7.40 (d, J=4.55 Hz, 1H), 7.46 (s, 1H), 8.09 (s, 1H), 8.14 (s, 1H).

Example 48

7-methyl-5-(1-{[2-(methyl oxy)phenyl]acetyl}-2,3-dihydro-1H-indol-5-yl)-7H-pyrrolo[2,3-d]pyrimidin-4-amine

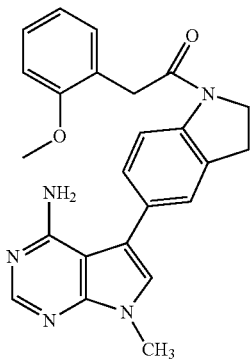 [SMILES: COc1ccccc1CC(=O)N1CCc2cc(-c3cn(C)c4ncnc(N)c34)ccc21]

In a 20 mL vial with cap, to the solution of 5-(2,3-dihydro-1H-indol-5-yl)-7-methyl-7H-pyrrolo[2,3-d]pyrimidin-4-amineHCl (70.6 mg, 0.234 mmol), [2-(methyloxy)phenyl]acetic acid (38.9 mg, 0.234 mmol), HATU (89 mg, 0.234 mmol) in DMF (2 mL) was added Hunig's base (0.163 mL, 0.936 mmol). The mixture was stirred at rt for over night. LCMS showed reaction was completed. The reaction was poured into water (100 mL), purple solid formed. EtOAc (100 mL) was used to extract the product. The Organic phase was seperated from the water phase, dried by MgSO4, evaporated to dryness, to give purple solid, which still had some starting material. The solid was sonicated in water (10 mL), then filtered and dried to afford the title compound 7-methyl-5-(1-{[2-(methyloxy)phenyl]acetyl}-2,3-dihydro-1H-indol-5-yl)-7H-pyrrolo[2,3-d]pyrimidin-4-amine as a light brown solid (22 mg). $^1$H NMR (400 MHz, DMSO-$d_6$) δ ppm 3.23-3.26 (m, 2H), 3.73 (s, 3H), 3.78 (s, 5H), 4.23 (m, 2H), 6.06 (br. s., 2H), 6.89-6.96 (m, 1H), 7.00 (d, J=8.34 Hz, 1H), 7.18-7.25 (m, 4H), 7.31 (s, 1H), 8.10 (d, J=8.08 Hz, 1H), 8.14 (s, 1H).

Example 49

1-methyl-3-(1-{[3-(methyloxy)phenyl]acetyl}-2,3-dihydro-1H-indol-5-yl)-1H-pyrazolo[3,4-d]pyrimidin-4-amine

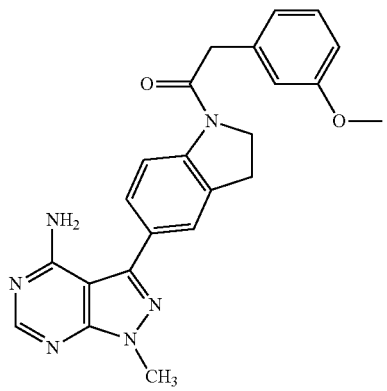 [SMILES: COc1cccc(CC(=O)N2CCc3cc(-c4nn(C)c5ncnc(N)c45)ccc32)c1]

In a 20 mL vial with cap, to the solution of 3-(2,3-dihydro-1H-indol-5-yl)-1-methyl-1H-pyrazolo[3,4-d]pyrimidin-4-amine 2HCl (70 mg, 0.206 mmol), [3-(methyloxy)phenyl]acetic acid (34.3 mg, 0.206 mmol), HATU (78 mg, 0.206 mmol) in DMF (2 mL) was added Hunig's base (0.144 mL, 0.825 mmol). The mixture was stirred at room temperature for overnight. LCMS showed reaction was completed. The reaction was poured into water, off-white solid formed. The solid was filtered to give the product as an off-white solid. The final product has about 0.5 equivalent of DMF. LC-MS (ES) m/z=415.3 [M+H]$^+$. $^1$H NMR (400 MHz, DMSO-$d_6$) δ ppm 3.22 (m., 2H), 3.75 (s, 3H), 3.86 (s, 2H), 3.93 (s, 3H), 4.19-4.26 (m, 2H), 6.84 (d, J=8.34 Hz, 2H), 6.87-6.94 (m, 2H), 7.26 (t, J=8.08 Hz, 1H), 7.44 (d, J=8.08 Hz, 1H), 7.50 (s, 1H), 8.20 (d, J=8.34 Hz, 1H), 8.24 (s, 1H).

Example 50

7-methyl-5-(1-{[3-(methyloxy)phenyl]acetyl}-2,3-dihydro-1H-indol-5-yl)-7H-pyrrolo[2,3-d]pyrimidin-4-amine

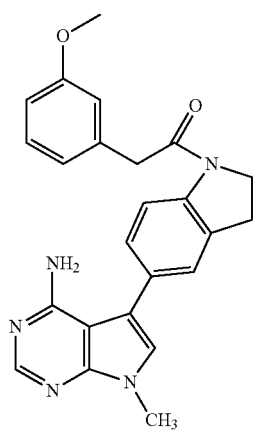 [SMILES: COc1cccc(CC(=O)N2CCc3cc(-c4cn(C)c5ncnc(N)c45)ccc32)c1]

In a 20 mL vial with cap, to the solution of 5-(2,3-dihydro-1H-indol-5-yl)-7-methyl-7H-pyrrolo[2,3-d]pyrimidin-4- amineHCl (70.6 mg, 0.234 mmol), [3-(methyloxy)phenyl] acetic acid (38.9 mg, 0.234 mmol), HATU (89 mg, 0.234 mmol) in DMF (2 mL) was added Hunig's base (0.163 mL, 0.936 mmol). The mixture was stirred at room temperature for overnight. LCMS showed reaction was completed. The reaction was poured into water (100 mL), off-white solid formed. The solid was filtered and dried to afford 7-methyl-5-(1-{[3-(methyloxy)phenyl]acetyl}-2,3-dihydro-1H-indol-5-yl)-7H-pyrrolo[2,3-d]pyrimidin-4-amine as an off-white solid product (91 mg). $^1$H NMR (400 MHz, DMSO-$d_6$) δ ppm 3.21 (t, J=8.46 Hz, 2H), 3.73 (s, 3H), 3.75 (s, 3H), 3.84 (s, 2H), 4.20 (t, J=8.46 Hz, 2H), 6.06 (br. s., 2H), 6.82-6.90 (m, 3H), 7.21-7.26 (m, 3H), 7.28-7.31 (m, 1H), 8.11-8.19 (m, 1H), 8.14 (s, 1H).

Example 51

3-{1-[(2-chlorophenyl)acetyl]-2,3-dihydro-1H-indol-5-yl}-1-methyl-1H-pyrazolo[3,4-d]pyrimidin-4-amine

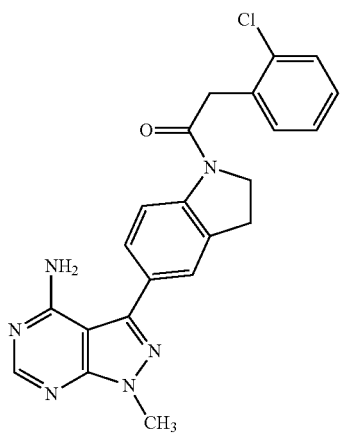 [SMILES: Cn1nc(-c2ccc3c(c2)CCN3C(=O)Cc2ccccc2Cl)c2c(N)ncnc21]

In a 20 mL vial with cap, to the solution of 3-(2,3-dihydro-1H-indol-5-yl)-1-methyl-1H-pyrazolo[3,4-d]pyrimidin-4-amine 2HCl (70 mg, 0.206 mmol), (2-chlorophenyl)acetic acid (35.2 mg, 0.206 mmol), HATU (78 mg, 0.206 mmol) in DMF (2 mL) was added Hunig's base (0.144 mL, 0.825 mmol). The mixture was stirred at room temperature for overnight. LCMS showed reaction was completed. The reaction was poured into water, off-white solid formed. The solid was filtered to give 3-{1-[(2-chlorophenyl)acetyl]-2,3-dihydro-1H-indol-5-yl}-1-methyl-1H-pyrazolo[3,4-d]pyrimidin-4-amine as an off-white solid. $^1$H NMR (400 MHz, DMSO-$d_6$) δ ppm 3.28-3.30 (m, 2H), 3.94 (s, 3H), 4.02 (s, 2H), 4.32 (t, J=8.46 Hz, 2H), 7.31-7.37 (m, 2H), 7.40-7.45 (m, 2H), 7.46-7.49 (m, 1H), 7.53 (s, 1H), 8.15 (d, J=8.34 Hz, 1H), 8.25 (s, 1H).

Example 52

1-methyl-3-(1-{[2-(methyloxy)phenyl]acetyl}-2,3-dihydro-1H-indol-5-yl)-1H-pyrazolo[3,4-d]pyrimidin-4-amine

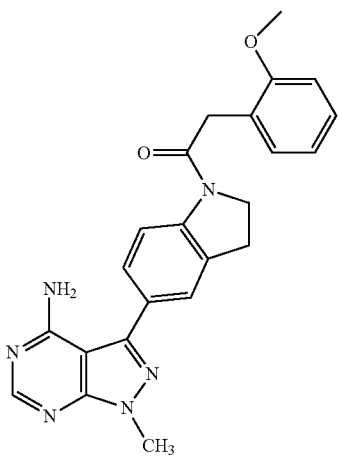 [SMILES: COc1ccccc1CC(=O)N1CCc2cc(-c3nn(C)c4ncnc(N)c34)ccc21]

In a 20 mL vial with cap, to the solution of 3-(2,3-dihydro-1H-indol-5-yl)-1-methyl-1H-pyrazolo[3,4-d]pyrimidin-4-amine 2HCl (70 mg, 0.206 mmol), [2-(methyloxy)phenyl] acetic acid (34.3 mg, 0.206 mmol), HATU (78 mg, 0.206 mmol) in DMF (2 mL) was added Hunig's base (0.144 mL, 0.825 mmol). The mixture was stirred at room temperature for overnight. LCMS showed reaction was completed. The reaction was poured into water, off-white solid formed. The solid was filtered to give the title compound (78 mg) as an off-white solid. $^1$H NMR (400 MHz, DMSO-$d_6$) δ ppm 3.28 (m, 2H), 3.78 (s, 3H), 3.80 (s, 2H), 3.94 (s, 3H), 4.22-4.30 (m, 2H), 6.93 (t, J=7.45 Hz, 1H), 7.01 (d, J=7.83 Hz, 1H), 7.20 (dd, J=7.58, 1.52 Hz, 1H), 7.25-7.32 (m, 1H), 7.43 (d, J=8.34 Hz, 1H), 7.51 (s, 1H), 8.16 (d, J=8.34 Hz, 1H), 8.25 (s, 1H).

Example 53

5-{1-[(3-chloro-5-fluorophenyl)acetyl]-2,3-dihydro-1H-indol-5-yl}-7-methyl-7H-pyrrolo[2,3-d]pyrimidin-4-amine

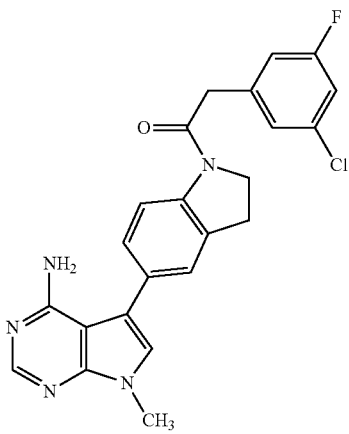 [SMILES: Cn1cc(-c2ccc3c(c2)CCN3C(=O)Cc2cc(F)cc(Cl)c2)c2c(N)ncnc21]

To a suspension of 5-(2,3-dihydro-1H-indol-5-yl)-7-methyl-7H-pyrrolo[2,3-d]pyrimidin-4-amine 2HCl salt (200 mg, 0.59 mmol, 1 equiv) and HATU (247 mg, 0.65 mmol, 1.1 equiv) in 2 mL of DMF was added DIEA (0.36 mL, 2.07 mmol, 3.5 equiv) in one portion. The mixture turned into a clear but pitch dark solution, to which was added (3-Chloro-5-fluorophenyl)acetic acid (60 mg, 0.59 mmol,) as solids. After 1.5 h, added another 30 mg of the acid. After 30 min, the resulting suspension was diluted with 15 mL of water. The aq suspension was filtered, and the cake was washed with water, and dried under house vacuum. This solid was dissolved in 10% MeOH in DCM (not totally dissolved, some was loaded as suspension), and absorbed onto a dryload cartridge. Purification was done on an 24 g silica gel cartridge using gradient elution of 1% A in EtOAc to 100% A (A was a mixture of 9% MeOH in EtOAc, gradient: 0-5 min, 1% A, 5-15 min, 5-100% A, 15-60 min, 100% A). The desired fractions were combined and concentrated in vacuo to give a solid residue, which upon standing for 10 min developed a light tan color. The residue was taken up in CHCl3 (1 mL) and MTBE (6 mL) to give a suspension, which was filtered. The light tan colored cake was washed with MTBE (3 mL) and hexane (2×3 mL), and dried under vacuum at 65° C. for 20 h to give (93 mg) as light tan colored solids. LC-MS (ES) m/z=436 [M+H]+. $^1$H NMR (400 MHz, DMSO-$d_6$+2 drops TFA) δ ppm 3.25 (t, J=8.2 Hz, 2H), 3.84 (s, 3H), 3.96 (s, 2H), 4.25 (t, J=8.5 Hz, 2H), 7.17 (d, J=9.6 Hz, 1H), 7.23-7.29 (m, 2H), 7.30-7.37 (m, 2H), 7.61 (s, 1H), 8.15 (d, J=8.3 Hz, 1H), 8.47 (s, 1H).

Example 54

3-{1-[(2,5-difluorophenyl)acetyl]-2,3-dihydro-1H-indol-5-yl}furo[3,2-c]pyridin-4-amine

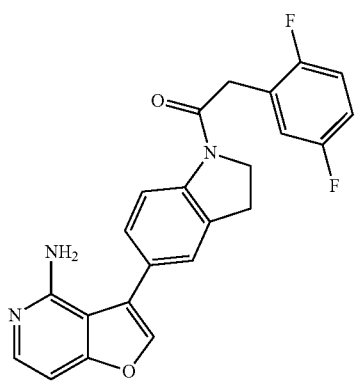 [SMILES: Nc1nccc2occ(-c3ccc4c(c3)CCN4C(=O)Cc3cc(F)ccc3F)c12]

5-(4-aminofuro[3,2-c]pyridin-3-yl)-2,3-dihydro-1H-indole-1-carboxylate

A mixture of 3-bromofuro[3,2-c]pyridin-4-amine (3.002 g, 14.09 mmol), 1,1-dimethylethyl 5-(4,4,5,5-tetramethyl-1,3,2-dioxaborolan-2-yl)-2,3-dihydro-1H-indole-1-carboxylate (5.346 g, 15.48 mmol), and PdCl2(dppf)-CH2Cl2 adduct (0.573 g, 0.702 mmol) in 1,4-Dioxane (120 mL) and saturated aqueous sodium bicarbonate (43 mL, 43.0 mmol) was degassed with Nitrogen for 20 minutes. The mixture was then stirred at reflux under Nitrogen for 16 hours. It was then cooled, poured into half-saturated aqueous NaHCO3 (250 mL), and extracted with ethyl acetate (2×250 mL). The extracts were washed with brine (1×250 mL), dried (Na2SO4), filtered, and concentrated in vacuo. The residue was purified by flash chromatography (Analogix, 400 g SiO2, 20%-100% EtOAc in hexanes gradient over 60 minutes, then 100% EtOAc for 15 more minutes) to give 1,1-dimethylethyl 5-(4-aminofuro[3,2-c]pyridin-3-yl)-2,3-dihydro-1H-indole-1-carboxylate (3.93 g) as an off-white solid. LC/MS (ES) m/z=352 [M+H]+.

3-(2,3-dihydro-1H-indol-5-yl)furo[3,2-c]pyridin-4-amine

A mixture of 1,1-dimethylethyl 5-(4-aminofuro[3,2-c]pyridin-3-yl)-2,3-dihydro-1H-indole-1-carboxylate (1.04 g, 2.96 mmol) and HCl, 4.0 M in dioxane (15 mL, 60.0 mmol) was stirred at room temperature under Nitrogen for 4.5 hr. The reaction mixture was then concentrated in vacuo to give 3-(2,3-dihydro-1H-indol-5-yl)furo[3,2-c]pyridin-4-amine (973 mg, 2.85 mmol, 96% yield) dihydrochloride (2HCl) as an off-white solid. LC/MS (ES) m/z=252 [M+H]+.

3-{1-[(2,5-difluorophenynacetyl]-2,3-dihydro-1H-indol-5-yl}furo[3,2-c]pyridin-4-amine A mixture of 3-(2,3-dihydro-1H-indol-5-yl)furo[3,2-c]pyridin-4-amine 2HCl (688 mg, 2.016 mmol), 2,5-difluorophenylacetic acid (354 mg, 2.057 mmol), HATU (844 mg, 2.220 mmol), and Hunig's base (1.4 mL, 8.02 mmol) in N,N-Dimethylformamide (DMF) (15 mL) was stirred at room temperature for 17 hr. HPLC indicated complete conversion, so the mixture was poured into water (75 mL), the suspension was stirred for about 10 minutes, and the precipitate was collected by vacuum filtration and dried by suction to give 3-{1-[(2,5-difluorophenyl)acetyl]-2,3-dihydro-1H-indol-5-yl}furo[3,2-c]pyridin-4-amine (834 mg, 2.057 mmol, 102% yield) as a tan solid. LC/MS (ES) m/z=406 [M+H]+. $^1$H NMR (400 MHz, DMSO-$d_6$) δ 3.29 (t, J=8.34 Hz, 2H), 3.96 (s, 2H), 4.31 (t, J=8.46 Hz, 2H), 5.52 (s, 2H), 6.93 (d, J=5.81 Hz, 1H), 7.14-7.34 (m, 4H), 7.41 (s, 1H), 7.87 (d, J=5.81 Hz, 1H), 7.92 (s, 1H), 8.13 (d, J=8.08 Hz, 1H).

Example 55

1-methyl-3-{1-[(2,3,5-trifluorophenyl)acetyl]-2,3-dihydro-1H-indol-5-yl}-1H-pyrazolo[3,4-d]pyrimidin-4-amine

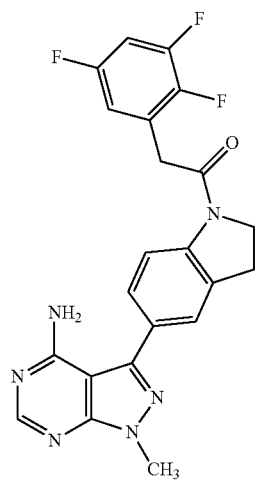 [SMILES: Cn1nc(-c2ccc3c(c2)CCN3C(=O)Cc2cc(F)cc(F)c2F)c2c(N)ncnc21]

A solution of 3-(2,3-dihydro-1H-indol-5-yl)-1-methyl-1H-pyrazolo[3,4-d]pyrimidin-4-amine (100 mg, 0.330 mmol), (2,3,5-trifluorophenyl)acetic acid (69.1 mg, 0.363 mmol), HATU (151 mg, 0.396 mmol), DIEA (0.173 mL, 0.991 mmol) was stirred overnight at room temperature. At this time, LCMS analysis indicated complete conversion, so the reaction mixture was poured into water (10 mL), whereupon a beige precipitate formed. The precipitate was filtered, suspended in DCM-methanol and dry-loaded onto silica, then purified by flash chromatography (0-10% methanol in DCM) to afford 1-methyl-3-{1-[(2,3,5-trifluorophenyl)acetyl]-2,3-dihydro-1H-indol-5-yl}-1H-pyrazolo[3,4-d]pyrimidin-4-amine (72 mg) as a white solid. LC-MS (ES) m/z=439 [M+H]+. $^1$H NMR (400 MHz, DMSO-d$_6$) 3.26-3.32 (m, 2H), 3.94 (s, 3H), 4.06 (s, 2H), 4.28-4.37 (m, 2H), 7.09-7.20 (m, 1H), 7.41-7.52 (m, 2H), 7.53-7.57 (m, 1H), 8.11-8.18 (m, 1H), 8.25 (s, 1H).

Example 56

5-{1-[(2,5-dimethylphenyl)acetyl]-2,3-dihydro-1H-indol-5-yl}-7-methyl-7H-pyrrolo[2,3-d]pyrimidin-4-amine

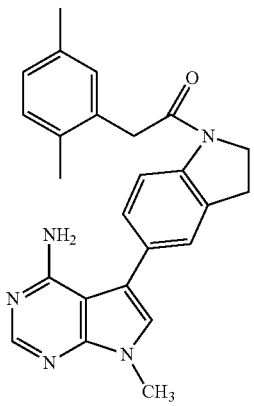 [SMILES: Cc1ccc(C)c(CC(=O)N2CCc3cc(-c4cn(C)c5ncnc(N)c45)ccc32)c1]

In a 20 mL vial with cap, to the solution of 5-(2,3-dihydro-1H-indol-5-yl)-7-methyl-7H-pyrrolo[2,3-d]pyrimidin-4-amineHCl (70.6 mg, 0.234 mmol), (2,5-dimethylphenyl)acetic acid (38.4 mg, 0.234 mmol), HATU (89 mg, 0.234 mmol) in DMF (2 mL) was added Hunig's base (0.163 mL, 0.936 mmol). The mixture was stirred at room temperature for overnight. LCMS showed reaction was completed. The reaction was poured into water (100 mL), purple solid formed. EtOAc (100 mL) was used to extract the product. The Organic phase was separated from the water phase, dried by MgSO4, evaporated to dryness, to give off-white solid, which still had some starting material. The solid was sonicated in water (10 mL) at 50° C., then filtered and dried to afford the title compound as a brown solid. $^1$H NMR (400 MHz, DMSO-d$_6$) ppm 2.19 (s, 3H), 2.25 (s, 3H), 3.24 (m, 2H), 3.73 (s, 3H), 3.82 (s, 2H), 4.25 (t, J=8.21 Hz, 2H), 6.12 (br. s., 2H), 6.94-7.01 (m, 2H), 7.07 (d, J=7.58 Hz, 1H), 7.20-7.28 (m, 2H), 7.32 (s, 1H), 8.11 (d, J=8.34 Hz, 1H), 8.15 (s, 1H).

Example 57

3-{1-[(2,5-difluorophenyl)acetyl]-2,3-dihydro-1H-indol-5-yl}-7-(1H-pyrazol-4-yl)furo[3,2-c]pyridin-4-amine

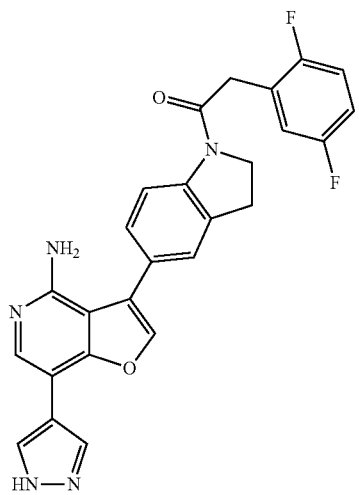 [SMILES: Nc1ncc(-c2cn[nH]c2)c2occ(-c3ccc4c(c3)CCN4C(=O)Cc3cc(F)ccc3F)c12]

3-{1-[(2,5-difluorophenyl)acetyl]-2,3-dihydro-1H-indol-5-yl}-7-iodofuro[3,2-c]pyridin-4-amine A solution of NIS (147 mg, 0.653 mmol) in DMF (3 mL) was added dropwise to a solution of 3-{1-[(2,5-difluorophenyl)acetyl]-2,3-dihydro-1H-indol-5-yl}furo[3,2-c]pyridin-4-amine (257 mg, 0.634 mmol) in DMF (3.5 mL) at −40° C., and the mixture was stirred and allowed to slowly warm to room temperature (temperature was still <−10° C. after 2 hours, and reaction had progressed to about 20% according to HPLC). After 18 hours HPLC indicated complete consumption of starting material, and only a small amount of diiodo byproduct had formed. The reaction mixture was poured into water (35 mL), stirred for about 10 minutes, and the precipitate was collected by vacuum filtration and dried by suction for several hours to give 3-{1-[(2,5-difluorophenyl)acetyl]-2,3-dihydro-1H-indol-5-yl}-7-iodofuro[3,2-c]pyridin-4-amine (253 mg) as a tan solid. LC/MS (ES) m/z=532 [M+H]+.

3-{1-[(2,5-difluorophenyl)acetyl]-2,3-dihydro-1H-indol-5-yl}-7-(1H-pyrazol-4-yl)furo[3,2-c]pyridin-4-amine A mixture of 3-{1-[(2,5-difluorophenyl)acetyl]-2,3-dihydro-1H-indol-5-yl}-7-iodofuro[3,2-c]pyridin-4-amine (142 mg, 0.267 mmol), 1-Boc-pyrazol-4-boronic acid pinacol ester (118 mg, 0.401 mmol), and PdCl2(dppf)-CH2Cl2 adduct (13 mg, 0.016 mmol) in 1,4-Dioxane (3 mL) and saturated aqueous sodium bicarbonate (0.80 mL, 0.800 mmol) was degassed with Nitrogen for 10 minutes in a microwave vial. The vial was then capped and the mixture was stirred at 120° C. in the microwave for 30 min. LCMS showed complete conversion to the de-Boc product. The mixture was cooled, poured into half-saturated aqueous NaHCO3 (25 mL), and extracted with ethyl acetate (2×25 mL). The extracts were washed with brine (1×25 mL), dried (Na2SO4), filtered, and concentrated in vacuo. The residue was purified by flash chromatography (Analogix, 24 g SiO2, 50%-100% EtOAc in hexanes gradient over 10 minutes, then EtOAc for 5 minutes, then 0-10% MeOH in EtOAc over 20 minutes) to give 3-{1-[(2,5-difluorophenyl)acetyl]-2,3-dihydro-1H-indol-5-yl}-7-(1H-pyrazol-4-yl)furo[3,2-c]pyridin-4-amine (121 mg, 0.244 mmol, 91% yield) as a white solid. LC/MS (ES) m/z=472 [M+H]+. 1H NMR (400 MHz, DMSO-$d_6$) δ 3.29 (t, J=8.34 Hz, 2H), 3.97 (s, 2H), 4.31 (t, J=8.46 Hz, 2H), 5.49 (s, 2H), 7.15-7.30 (m, 3H), 7.33 (d, J=8.08 Hz, 1H), 7.44 (s, 1H), 7.99-8.10 (m, 2H), 8.13 (d, J=8.08 Hz, 1H), 8.17-8.29 (m, 2H), 13.01 (br. s., 1H).

Example 58

3-{1-[(3,5-dichlorophenyl)acetyl]-2,3-dihydro-1H-indol-5-yl}-1-methyl-1H-pyrazolo[3,4-d]pyrimidin-4-amine

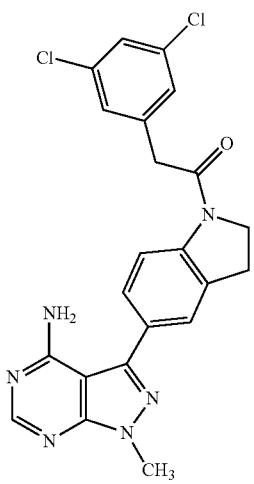 [SMILES: Cn1nc(-c2ccc3c(c2)CCN3C(=O)Cc2cc(Cl)cc(Cl)c2)c2c(N)ncnc21]

A solution of 3-(2,3-dihydro-1H-indol-5-yl)-1-methyl-1H-pyrazolo[3,4-d]pyrimidin-4-amine (89 mg, 0.293 mmol), (3,5-dichlorophenyl)acetic acid (60 mg, 0.293 mmol), HATU (111 mg, 0.293 mmol), DIEA (0.204 mL, 1.171 mmol) was stirred at room temperature overnight. The crude was poured into water and stirred for 30 minutes. The precipitate that formed was collected by filtration, washed with water and dried at the pump for 30 minutes. The crude was adsorbed onto silica and purified by flash chromatography (0-10% methanol in DCM), concentrated and dried overnight in a vacuum oven to afford 3-{1-[(3,5-dichlorophenyl)acetyl]-2,3-dihydro-1H-indol-5-yl}-1-methyl-1H-pyrazolo[3,4-d]pyrimidin-4-amine (80 mg) as a white solid. LCMS (ES) m/z=453, 455 [M+H]+. 1H NMR (400 MHz, DMSO-$d_6$) δ 3.29 (t, J=9.60 Hz, 2H), 3.94 (s, 3H), 3.97 (s, 2H), 4.26 (t, J=8.59 Hz, 2H), 7.40 (d, J=2.02 Hz, 2H), 7.45 (d, J=8.08 Hz, 1H), 7.53 (d, J=1.77 Hz, 2H), 8.17 (d, J=8.34 Hz, 1H), 8.25 (s, 1H).

Example 59

5-{1-[(2,5-difluorophenyl)acetyl]-2,3-dihydro-1H-indol-5-yl}-7-methyl-7H-pyrrolo[2,3-d]pyrimidin-4-amine

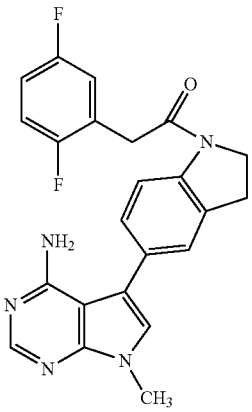 [SMILES: Cn1cc(-c2ccc3c(c2)CCN3C(=O)Cc2cc(F)ccc2F)c2c(N)ncnc21]

In a 20 mL vial with cap, to the solution of 5-(2,3-dihydro-1H-indol-5-yl)-7-methyl-7H-pyrrolo[2,3-d]pyrimidin-4-amine HCl (200 mg, 0.663 mmol), (2,5-difluorophenyl)acetic acid (120 mg, 0.696 mmol), HATU (265 mg, 0.696 mmol) in DMF (5 mL) was added Hunig's base (0.463 mL, 2.65 mmol). The mixture was stirred at room temperature for overnight. LCMS showed reaction was completed. The reaction was poured into water, white solid formed. The solid was filtered and dried to afford 5-{1-[(2,5-difluorophenyl)acetyl]-2,3-dihydro-1H-indol-5-yl}-7-methyl-7H-pyrrolo[2,3-d]pyrimidin-4-amine as a white solid. NMR showed there is 1 eq. of DMF in the compound. LCMS (ES) m/z=420 [M+H]+. 1H NMR (400 MHz, DMSO-$d_6$) d ppm 3.27 (t, J=8.46 Hz, 2H), 3.74 (s, 3H), 3.95 (s, 2H), 4.29 (t, J=8.46 Hz, 2H), 6.05 (br. s., 2H), 7.21-7.27 (m, 5H), 7.34 (s, 1H), 8.09 (d, J=8.34 Hz, 1H), 8.15 (s, 1H).

Example 60

3-{1-[(2,5-difluorophenyl)acetyl]-2,3-dihydro-1H-indol-5-yl}-7-(1H-pyrazol-4-yl)thieno[3,2-c]pyridin-4-amine

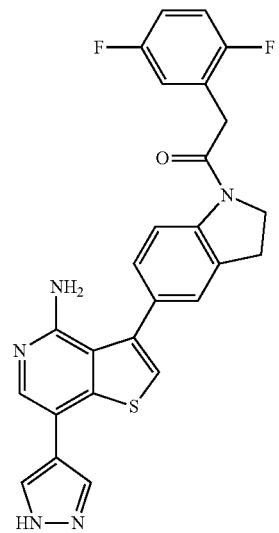 [SMILES: Nc1ncc(-c2cn[nH]c2)c2scc(-c3ccc4c(c3)CCN4C(=O)Cc3cc(F)ccc3F)c12]

To a 25 mL microwave reactor pressure tube was charged 3-{1-[(2,5-difluorophenyl)acetyl]-2,3-dihydro-1H-indol-5-yl}-7-iodothieno[3,2-c]pyridin-4-amine (129 mg, 0.236 mmol), 1,1-dimethylethyl 4-(4,4,5,5-tetramethyl-1,3,2-dioxaborolan-2-yl)-1H-pyrazole-1-carboxylate (69.3 mg, 0.236 mmol), 1,1'-bis(diphenylphosphino)ferrocene-palladium(II) dichloride dichloromethane complex 9.62 mg, 0.012 mmol), and saturated aqueous sodium carbonate (0.707 mL, 0.707 mmol) followed by dioxane (5 mL). The reaction was heated at 120° C. for 40 min in microwave reactor. The reaction was cooled to room temperature, the mixture was transfered into a 100 mL Erlenmeyer flask, rinsed by EtOAc, with the water layer and black greasy solid stayed in tube, total 100 mL of EtOAc was added to the mixture. The EtOAc solution was evaporated to dryness, and re-dissolved with CH2Cl2/MeOH (8 mL/2 mL). It was purified by flash column 25-100% EtOAc/hexane, then 0-10% MeOH/EtOAc, Si SF15-24g, to afford a brown solid. The brown solid was further purified by recrystallizaton in CH3CN to give the title compound 3-{1-[(2,5-difluorophenyl)acetyl]-2,3-dihydro-1H-indol-5-yl}-7-(1H-pyrazol-4-yl)thieno[3,2-c]pyridin-4-amine (40 mg) as a brown solid. $^1$H NMR (400 MHz, DMSO-d$_6$) δ ppm 3.24-3.29 (m, 2H), 3.97 (s, 2H), 4.32 (t, J=8.46 Hz, 2H), 5.40 (s, 2H), 7.18-7.21 (m, 1H), 7.23-7.29 (m, 3H), 7.38 (s, 1H), 7.49 (s, 1H), 7.96 (s, 1H), 8.07 (s, 1H), 8.12 (d, J=8.34 Hz, 2H), 13.09 (s, 1H)

Example 61

3-{1-[(3,5-difluorophenyl)acetyl]-2,3-dihydro-1H-indol-5-yl}-1-methyl-1H-pyrazolo[3,4-d]pyrimidin-4-amine

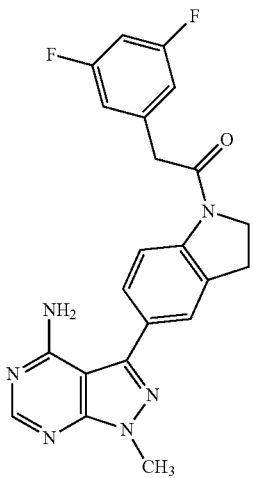 [SMILES: Cn1nc(-c2ccc3c(c2)CCN3C(=O)Cc2cc(F)cc(F)c2)c2c(N)ncnc21]

A solution of 3-(2,3-dihydro-1H-indol-5-yl)-1-methyl-1H-pyrazolo[3,4-d]pyrimidin-4-amine (150 mg, 0.495 mmol), (3,5-difluorophenyl)acetic acid (85 mg, 0.495 mmol), HATU (188 mg, 0.495 mmol), DIEA (0.346 mL, 1.982 mmol) was stirred at room temperature over the weekend. At this time, LCMS analysis indicated complete conversion, so the reaction mixture was poured into water (10 mL), whereupon a beige precipitate formed. The precipitate was filtered, suspended in DCM-methanol and dry-loaded onto silica, then purified by flash chromatography (0-10% methanol in DCM) to afford 3-{1-[(3,5-difluorophenyl)acetyl]-2,3-dihydro-1H-indol-5-yl}-1-methyl-1H-pyrazolo[3,4-d]pyrimidin-4-amine (150 mg, 0.357 mmol, 72.0% yield) as a white solid. LC-MS (ES) m/z=421 [M+H]$^+$. $^1$H NMR (400 MHz, DMSO-d$_6$) δ 3.27 (m, 2H), 3.94 (s, 3H), 3.97 (s, 2H), 4.18-4.32 (m, 2H), 7.02-7.09 (m, 2H), 7.11-7.20 (m, 1H), 7.41-7.47 (m, 1H), 7.50-7.55 (m, 1H), 8.12-8.22 (m, 1H), 8.25 (s, 1H). Note: NH's are not observed as individual peaks.

Example 62

5-{1-[(3-methylphenyl)acetyl]-2,3-dihydro-1H-indol-5-yl}-7-(4-piperidinyl)-7H-pyrrolo[2,3-d]pyrimidin-4-amine

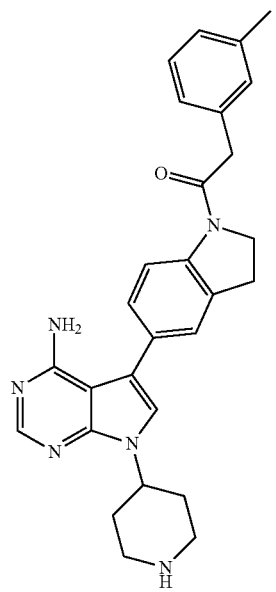 [SMILES: Cc1cccc(CC(=O)N2CCc3cc(-c4cn(C5CCNCC5)c5ncnc(N)c45)ccc32)c1]

In a 350 mL sealed tube, to 5-bromo-1-[(3-methylphenyl)acetyl]-2,3-dihydro-1H-indole (13.57 g, 41.1 mmol), bis(pinacolato)diboron (12.52 g, 49.3 mmol) and potassium acetate (12.10 g, 123 mmol) was added 1,4-Dioxane (200 mL) and the mixture was degassed with N2 for 10 minutes. PdCl2 (dppf)-CH2Cl2Adduct (1.678 g, 2.055 mmol) was added and the reaction mixture was stirred for 48 hours at 100° C. LCMS showed no more SM. The mixture was cooled to room temperature. Ethyl acetate (500 mL) was poured into the mixture, then the mixture was filtered. The filtrate was poured into a separatory funnel. It was washed with brine, dried (MgSO4), filtered and concentrated, and purified by Analogix silica Si90, gradient 0-40% EtOAc/hexane to give 1-[(3-methylphenyl)acetyl]-5-(4,4,5,5-tetramethyl-1,3,2-dioxaborolan-2-yl)-2,3-dihydro-1H-indole (8.35 g) as a white solid. LC-MS (ES) m/z=378.3 [M+H]$^+$.

To 4-chloro-1H-pyrrolo[2,3-d]pyrimidine (5 g, 32.6 mmol) in Chloroform (100 mL) was added NBS (6.08 g, 34.2 mmol), and the reaction mixture was stirred a 70° C. for 3 hours. The reaction was allowed to cool to room temperature, and the mixture was filtered, washing the solid with additional CHCl3 to afford 5-bromo-4-chloro-1H-pyrrolo[2,3-d]pyrimidine as an off-white solid.

To a solution of 5-bromo-4-chloro-1H-pyrrolo[2,3-d]pyrimidine (214 mg, 0.921 mmol), 1,1-dimethylethyl 4-hydroxy-1-piperidinecarboxylate (556 mg, 2.76 mmol) and triphenylphosphine (483 mg, 1.841 mmol) in Tetrahydrofuran (THF) (10 mL) was added dropwise DEAD (0.291 mL, 1.841 mmol). The solution was stirred at room temperature. After 2 hr the reaction was concentrated then loaded on to a 25 g Biotage SNAP column to give 1,1-dimethylethyl 4-(5-bromo-4-chloro-7H-pyrrolo[2,3-d]pyrimidin-7-yl)-1-piperidinecarboxylate (330 mg, 86% yield) as a white solid. $^1$H NMR (400 MHz, DMSO-d$_6$) δ 8.68 (s, 1H), 8.23 (s, 1H), 4.83-4.97 (m, 1H), 4.11 (br. s., 2H), 2.95 (br. s., 2H), 1.84-2.05 (m, 4H), 1.43 (s, 9H)

To 1,1-dimethylethyl 4-(5-bromo-4-chloro-7H-pyrrolo[2,3-d]pyrimidin-7-yl)-1-piperidinecarboxylate (313 mg, 0.753 mmol) was added ammonium hydroxide (2 mL, 51.4 mmol) and 1,4-Dioxane (1 mL) to a 5 mL microwave vial and heated in microwave for 20 min. at 100° C. After total of 35 minutes the reaction was completed. The reaction was concentrated to give 1,1-dimethylethyl 4-(4-amino-5-bromo-7H-pyrrolo[2,3-d]pyrimidin-7-yl)-1-piperidinecarboxylate (336 mg). $^1$H NMR (400 MHz, DMSO-d$_6$) δ 8.09 (s, 1H), 7.60 (s, 1H), 4.71 (tt, J=5.40, 10.64 Hz, 1H), 4.08 (br. s., 2H), 2.91 (br. s., 2H), 1.81-1.94 (m, 4H), 1.43 (s, 9H).

To 1,1-dimethylethyl 4-(4-amino-5-bromo-7H-pyrrolo[2,3-d]pyrimidin-7-yl)-1-piperidinecarboxylate (200 mg, 0.505 mmol), and 1-[(3-methylphenyl)acetyl]-5-(4,4,5,5-tetramethyl-1,3,2-dioxaborolan-2-yl)-2,3-dihydro-1H-indole (228 mg, 0.606 mmol) dissolved in 1,4-Dioxane (4 mL) was added saturated aqueous NaHCO3 (2 mL). The mixture was then bubbled with N2 gas for 10 minutes and then Pd(Ph3P)4 (58.3 mg, 0.050 mmol) was added and then bubbled for 5 additional minutes. Then reaction was then capped and heated at 100° C. overnight. The mixture was allowed to cool then diluted with water (10 mL) then extracted with EtOAc (3×20 ml). The organics were combined, washed with brine, dried over MgSo4, filtered and concentrated to isolate a amber color oil. The oil was then purified on a 25 g Biotage SNAP column conditioned with Hexane and eluting with a gradient of 0 to 10% MeOH in DCM for 30 minutes to afford 1,1-dimethylethyl 4-(4-amino-5-{1-[(3-methylphenyl)acetyl]-2,3-dihydro-1H-indol-5-yl}-7H-pyrrolo[2,3-d]pyrimidin-7-yl)-1-piperidinecarboxylate (230 mg, 80% yield) as a amber color oil. $^1$H NMR (400 MHz, DMSO-d$_6$) δ 8.14 (s, 1H), 8.13 (s, 1H), 7.45 (s, 1H), 7.32 (s, 1H), 7.20-7.26 (m, 2H), 7.12 (s, 1H), 7.09 (t, J=7.58 Hz, 2H), 4.71-4.83 (m, 1H), 4.20 (t, J=8.46 Hz, 2H), 4.08-4.15 (m, 2H), 3.94 (s, 2H), 3.82 (s, 2H), 3.20 (t, J=8.46 Hz, 2H), 2.95 (br. s., 2H), 2.31 (s, 3H), 1.86-1.97 (m, 4H), 1.43 (s, 9H).

To 1,1-dimethylethyl 4-(4-amino-5-{1-[(3-methylphenyl)acetyl]-2,3-dihydro-1H-indol-5-yl}-7H-pyrrolo[2,3-d]pyrimidin-7-yl)-1-piperidinecarboxylate (230 mg, 0.406 mmol) were added 1,4-Dioxane and 4N HCl in dioxane (4 mL, 16.00 mmol). The mixture was allowed to stir overnight at 50° C. The reaction was concentrated. The solid was sonicated with 1:1 Hexane:DCM and the solid was isolated by filtration to isolate 5-{1-[(3-methylphenyl)acetyl]-2,3-dihydro-1H-indol-5-yl}-7-(4-piperidinyl)-7H-pyrrolo[2,3-d]pyrimidin-4-amine (188 mg, 80% yield) as a white solid as the trihydrochloride salt. LC-MS (ES) m/z=467.4 [M+H]$^+$. $^1$H NMR (400 MHz, METHANOL-d$_4$) δ 8.38 (s, 1H), 8.29 (d, J=8.34 Hz, 1H), 7.61 (s, 1H), 7.41 (s, 1H), 7.35 (dd, J=1.77, 8.34 Hz, 1H), 7.22-7.28 (m, 1H), 7.18 (s, 1H), 7.13 (t, J=7.33 Hz, 2H), 5.07-5.18 (m, 1H), 4.25 (t, J=8.46 Hz, 2H), 3.90 (s, 2H), 3.68 (s, 2H), 3.61-3.67 (m, 2H), 3.25-3.31 (m, 3H), 2.41-2.54 (m, 2H), 2.36 (s, 3H), 2.34 (br. s., 2H).

Example 63

5-{1-[(3-methylphenyl)acetyl]-2,3-dihydro-1H-indol-5-yl}-7-(1-methyl-4-piperidinyl)-7H-pyrrolo[2,3-d]pyrimidin-4-amine

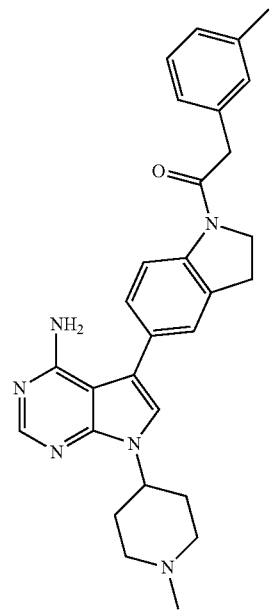 [SMILES: Cc1cccc(CC(=O)N2CCc3cc(-c4cn(C5CCN(C)CC5)c5ncnc(N)c45)ccc32)c1]

To a solution of 5-{1-[(3-methylphenyl)acetyl]-2,3-dihydro-1H-indol-5-yl}-7-(4-piperidinyl)-7H-pyrrolo[2,3-d]pyrimidin-4-amine (97 mg, 0.193 mmol) in DMF (3 mL) was added cesium carbonate (188 mg, 0.578 mmol) then iodomethane (0.013 mL, 0.212 mmol). After 2 hr the reaction was filtered and the filtrate was concentrated and then loaded on to a 10 g SNAP column. Elution with 0 to 10% MeOH in DCM gradient provided 5-{1-[(3-methylphenyl)acetyl]-2,3-dihydro-1H-indol-5-yl}-7-(1-methyl-4-piperidinyl)-7H-pyrrolo[2,3-d]pyrimidin-4-amine (40 mg, 43.2% yield) as a white solid. LC-MS (ES) m/z=481.4 [M+H]$^+$.

Example 64

5-{1-[(3-methylphenyl)acetyl]-2,3-dihydro-1H-indol-5-yl}thieno[2,3-d]pyrimidin-4-amine

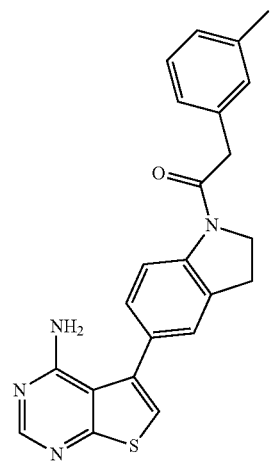 [SMILES: Cc1cccc(CC(=O)N2CCc3cc(-c4csc5ncnc(N)c45)ccc32)c1]

A mixture of 5-bromothieno[2,3-d]pyrimidin-4-amine (90 mg, 0.391 mmol) and 1-[(3-methylphenyl)acetyl]-5-(4,4,5,5-tetramethyl-1,3,2-dioxaborolan-2-yl)-2,3-dihydro-1H-indole (148 mg, 0.391 mmol) in 1,4-Dioxane (6 mL) and sat. aq. NaHCO$_3$ (2 mL) was degassed with N2 for 10 minutes. PdCl2 (dppf)-CH2Cl2 adduct (15.97 mg, 0.020 mmol) was added, and the reaction mixture was stirred overnight at 100° C. in a sealed vessel. The reaction was cooled down to room temperature and poured onto water. The aqueous mixture was filtered, and the solid in the filter was purified via flash chromatography on SiO2 (gradient: 100% Hexanes to 100% EtOAc) to afford the desired product (119 mg) as a white solid. LC-MS (ES) m/z=401.3 [M+H]$^+$. $^1$H NMR (400 MHz, DMSO-d$_6$) δ 2.31 (s, 3H), 3.22 (t, J=8.46 Hz, 2H), 3.84 (s, 2H), 4.23 (t, J=8.46 Hz, 2H), 7.04-7.16 (m, 3H), 7.20-7.29 (m, 2H), 7.34 (s, 1H), 7.42 (s, 1H), 8.17 (d, J=8.34 Hz, 1H), 8.34 (s, 1H).

Example 65

3-{1-[(3-fluoro-5-methyl phenyl)acetyl]-2,3-dihydro-1H-indol-5-yl}furo[3,2-c]pyridin-4-amine

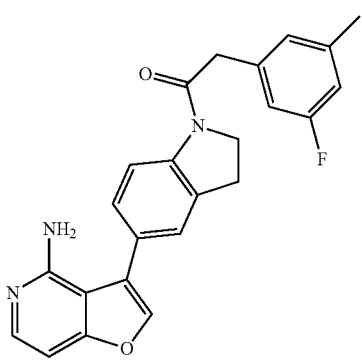 [SMILES: Cc1cc(F)cc(CC(=O)N2CCc3cc(-c4coc5ccnc(N)c45)ccc32)c1]

A mixture of 3-(2,3-dihydro-1H-indol-5-yl)furo[3,2-c]pyridin-4-amine (150 mg, 0.440 mmol), 3-fluoro-5-methylphenylacetic acid (78 mg, 0.464 mmol), HATU (184 mg, 0.484 mmol), and Hunig's base (0.31 mL, 1.775 mmol) in N,N-Dimethylformamide (DMF) (3 mL) was stirred at room temperature for 4 days. Water (10 mL) was added, the mixture was stirred for about 4 hours, and the precipitate was collected by vacuum filtration. The solid was dried in the vacuum oven overnight to give 3-{1-[(3-fluoro-5-methylphenyl)acetyl]-2,3-dihydro-1H-indol-5-yl}furo[3,2-c]pyridin-4-amine (164 mg, 0.388 mmol, 88% yield) as a tan solid. LC/MS (ES) m/z=402 [M+H]$^+$. $^1$H NMR (400 MHz, DMSO-d$_6$) δ 2.32 (s, 3H), 3.24 (t, J=8.46 Hz, 2H), 3.87 (s, 2H), 4.24 (t, J=8.59 Hz, 2H), 5.53 (s, 2H), 6.90-7.00 (m, 4H), 7.30 (d, J=8.34 Hz, 1H), 7.39 (s, 1H), 7.86 (d, J=5.81 Hz, 1H), 7.92 (s, 1H), 8.17 (d, J=8.34 Hz, 1H).

Example 66

3-{1-[(3-chloro-5-fluorophenyl)acetyl]-2,3-dihydro-1H-indol-5-yl}furo[3,2-c]pyridin-4-amine

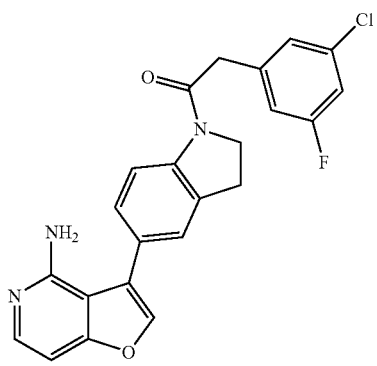 [SMILES: Nc1nccc2occ(-c3ccc4c(c3)CCN4C(=O)Cc3cc(F)cc(Cl)c3)c12]

A mixture of 3-(2,3-dihydro-1H-indol-5-yl)furo[3,2-c]pyridin-4-amine (150 mg, 0.440 mmol), 3-chloro-5-fluorophenylacetic acid (89 mg, 0.472 mmol), HATU (184 mg, 0.484 mmol), and Hunig's base (0.31 mL, 1.775 mmol) in N,N-Dimethylformamide (DMF) (3 mL) was stirred at room temperature for 4 days. Water (10 mL) was added, the mixture was stirred for about an hour, and the precipitate was collected by vacuum filtration. The solid was dried in the vacuum oven overnight to give 3-{1-[(3-chloro-5-fluorophenyl)acetyl]-2,3-dihydro-1H-indol-5-yl}furo[3,2-c]pyridin-4-amine (176 mg, 0.396 mmol, 90% yield) as a beige solid. LC/MS (ES) m/z=422, 424 [M+H]$^+$. $^1$H NMR (400 MHz, DMSO-d$_6$) δ 3.27 (t, 2H), 3.96 (s, 2H), 4.26 (t, J=8.46 Hz, 2H), 5.53 (s, 2H), 6.93 (d, J=5.81 Hz, 1H), 7.14-7.22 (m, 1H), 7.27 (s, 1H), 7.28-7.38 (m, 2H), 7.40 (s, 1H), 7.86 (d, J=5.81 Hz, 1H), 7.92 (s, 1H), 8.15 (d, J=8.34 Hz, 1H).

Example 67

3-{1-[(2-fluoro-5-methylphenyl)acetyl]-2,3-dihydro-1H-indol-5-yl}furo[3,2-c]pyridin-4-amine

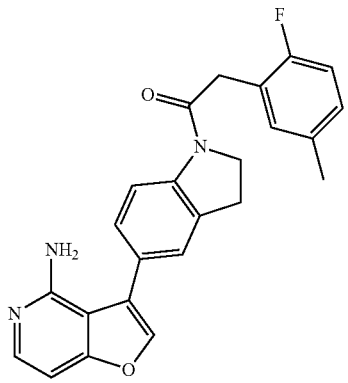 [SMILES: Cc1ccc(F)c(CC(=O)N2CCc3cc(-c4coc5ccnc(N)c45)ccc32)c1]

A mixture of 3-(2,3-dihydro-1H-indol-5-yl)furo[3,2-c]pyridin-4-amine (150 mg, 0.440 mmol), 2-fluoro-5-methylphenylacetic acid (78 mg, 0.464 mmol), HATU (185 mg, 0.487 mmol), and Hunig's base (0.31 mL, 1.775 mmol) in N,N-Dimethylformamide (DMF) (3 mL) was stirred at room temperature for 4 days. Water (10 mL) was added, the mixture was stirred for about an hour, and the precipitate was collected by vacuum filtration. The solid was dried in the vacuum oven overnight to give 3-{1-[(2-fluoro-5-methylphenyl)acetyl]-2,3-dihydro-1H-indol-5-yl}furo[3,2-c]pyridin-4-amine (174 mg, 0.412 mmol, 94% yield) as a beige solid. LC/MS (ES) m/z=402 [M+H]+. $^1$H NMR (400 MHz, DMSO-$d_6$) δ 2.29 (s, 3H), 3.27 (t, J=8.34 Hz, 2H), 3.89 (s, 2H), 4.29 (t, J=8.46 Hz, 2H), 5.53 (s, 2H), 6.93 (d, J=6.06 Hz, 1H), 7.03-7.18 (m, 3H), 7.30 (d, J=8.08 Hz, 1H), 7.40 (s, 1H), 7.86 (d, J=5.81 Hz, 1H), 7.92 (s, 1H), 8.13 (d, J=8.08 Hz, 1H).

Example 68

1-methyl-3-{1-[(1-methyl-1H-pyrrol-2-yl)acetyl]-2,3-dihydro-1H-indol-5-yl}-1H-pyrazolo[3,4-d]pyrimidin-4-amine

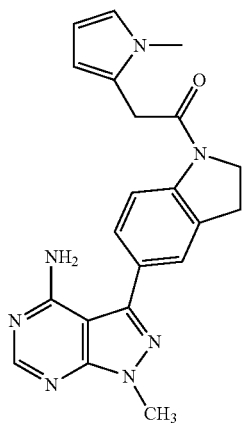 [SMILES: Cn1cccc1CC(=O)N1CCc2cc(-c3nn(C)c4ncnc(N)c34)ccc21]

A solution of 3-(2,3-dihydro-1H-indol-5-yl)-1-methyl-1H-pyrazolo[3,4-d]pyrimidin-4-amine (100 mg, 0.330 mmol), (1-methyl-1H-pyrrol-2-yl)acetic acid (46 mg, 0.33 mmol), HATU (126 mg, 0.330 mmol), and DIEA (0.231 mL, 1.321 mmol) was stirred at room temperature overnight. LCMS indicated good converison, so the crude was poured into water and stirred for 30 minutes. The precipitate that formed was collected by filtration, washed with water and dried at the pump for 30 minutes. The crude was adsorbed onto silica and purified by flash chromatography (0-10% methanol in DCM) to afford 1-methyl-3-{1-[(1-methyl-1H-pyrrol-2-yl)acetyl]-2,3-dihydro-1H-indol-5-yl}-1H-pyrazolo[3,4-d]pyrimidin-4-amine (57.9 mg, 0.149 mmol, 45.2% yield) as a white solid. LC-MS (ES) m/z=388 [M+H]$^+$. $^1$H NMR (400 MHz, DMSO-$d_6$) 3.25 (m, 2H), 3.55 (s, 3H), 3.86-3.90 (m, 2H), 3.94 (s, 3H), 4.21-4.32 (m, 2H), 5.86-5.93 (m, 2H), 6.66-6.71 (m, 1H), 7.41-7.48 (m, 1H), 7.49-7.53 (m, 1H), 8.13-8.22 (m, 1H), 8.23-8.27 (m, 1H). Note: NH's are not observed in the NMR spectrum.

Example 69

3-{1-[(3-chlorophenyl)acetyl]-2,3-dihydro-1H-indol-5-yl}furo[3,2-c]pyridin-4-amine

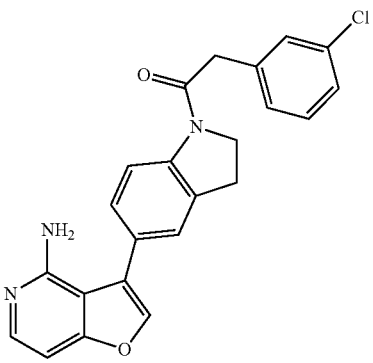 [SMILES: Nc1nccc2occ(-c3ccc4c(c3)CCN4C(=O)Cc3cccc(Cl)c3)c12]

A mixture of 3-(2,3-dihydro-1H-indol-5-yl)furo[3,2-c]pyridin-4-amine (150 mg, 0.440 mmol), 3-chlorophenylacetic acid (79 mg, 0.463 mmol), HATU (185 mg, 0.487 mmol), and Hunig's base (0.31 mL, 1.775 mmol) in N,N-Dimethylformamide (DMF) (3 mL) was stirred at room temperature for 4 days. Water (10 mL) was added, the mixture was stirred for about 4 hours, and the precipitate was collected by vacuum filtration. It was purified by flash chromatography (Analogix, 24 g SiO2, 25%-100% EtOAc in hexanes gradient over 30 minutes, then EtOAc for 10 minutes) to give 3-{1-[(3-chlorophenyl)acetyl]-2,3-dihydro-1H-indol-5-yl}furo[3,2-c]pyridin-4-amine (126 mg, 0.296 mmol, 67.4% yield) as an off-white solid. LC/MS (ES) m/z=404, 406 [M+H]+. $^1$H NMR (400 MHz, DMSO-$d_6$) δ 3.25 (t, J=8.34 Hz, 2H), 3.93 (s, 2H), 4.25 (t, J=8.46 Hz, 2H), 5.54 (br. s., 2H), 6.93 (d, J=5.81 Hz, 1H), 7.24-7.46 (m, 6H), 7.86 (d, J=5.81 Hz, 1H), 7.92 (s, 1H), 8.16 (d, J=8.34 Hz, 1H).

Example 70

5-{1-[(2,3-difluorophenyl)acetyl]-2,3-dihydro-1H-indol-5-yl}-7-methyl-7H-pyrrolo[2,3-d]pyrimidin-4-amine

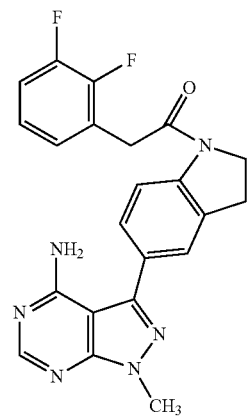

In a 20 mL vial with cap, to the solution of 5-(2,3-dihydro-1H-indol-5-yl)-7-methyl-7H-pyrrolo[2,3-d]pyrimidin-4-amineHCl (70.6 mg, 0.234 mmol), (2,3-difluorophenyl)acetic acid (40.3 mg, 0.234 mmol), HATU (89 mg, 0.234 mmol) in DMF (2 mL) was added Hunig's base (0.163 mL, 0.936 mmol). The mixture was stirred at room temperature over night. The reaction was poured into water (100 mL), white solid formed. EtOAc (100 mL) was used to extract the product. The Organic phase was seperated from the water phase, dried by MgSO$_4$, evaporated to dryness to give a off-white solid. The solid was sonicated in water (10 mL), then filtered and dried to afford a off-white solid as the title compound. It contained 1 eq. of DMF by NMR. $^1$H NMR (400 MHz, DMSO-d$_6$) δ ppm 3.23-3.30 (m, 2H), 3.73 (s, 3H), 4.02 (s, 2H), 4.30 (t, J=8.46 Hz, 2H), 7.17-7.24 (m, 3H), 7.26 (s, 1H), 7.33 (s, 2H), 8.08 (d, J=8.34 Hz, 1H), 8.15 (s, 1H).

Example 71

5-{1-[(2-fluoro-3-methylphenyl)acetyl]-2,3-dihydro-1H-indol-5-yl}-7-methyl-7H-pyrrolo[2,3-d]pyrimidin-4-amine

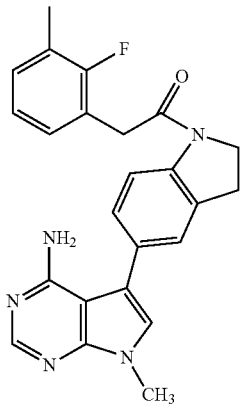 [SMILES: Cc1cccc(CC(=O)N2CCc3cc(-c4cn(C)c5ncnc(N)c45)ccc32)c1F]

In a 20 mL vial with cap, to the solution of 5-(2,3-dihydro-1H-indol-5-yl)-7-methyl-7H-pyrrolo[2,3-d]pyrimidin-4-amineHCl (70.6 mg, 0.234 mmol), (2-fluoro-3-methylphenyl)acetic acid (39.3 mg, 0.234 mmol), HATU (89 mg, 0.234 mmol) in DMF (2 mL) was added Hunig's base (0.163 mL, 0.936 mmol). The mixture was stirred at room temperature overnight. The reaction was poured into water (100 mL), white solid formed. The solid was filtered and dried to afford a off-white solid as the title compound. It had 0.7 eq. of DMF by NMR. $^1$H NMR (400 MHz, DMSO-d$_6$) δ ppm 2.25 (s, 3H), 3.21-3.29 (m, 2H), 3.73 (s, 3H), 3.90 (s, 2H), 4.27 (t, J=8.46 Hz, 2H), 7.07 (d, J=7.58 Hz, 1H), 7.14 (s, 1H), 7.21 (m, 2H), 7.26 (s, 1H), 7.32 (s, 1H), 8.09 (d, J=8.34 Hz, 1H), 8.14 (s, 1H).

Example 72

5-{1-[(3-fluoro-2-methylphenyl)acetyl]-2,3-dihydro-1H-indol-5-yl}-7-methyl-7H-pyrrolo[2,3-d]pyrimidin-4-amine

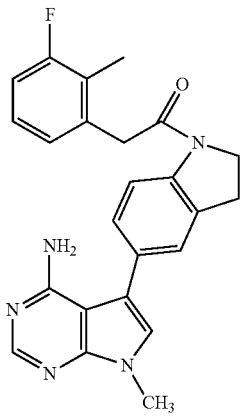 [SMILES: Cc1c(F)cccc1CC(=O)N1CCc2cc(-c3cn(C)c4ncnc(N)c34)ccc21]

In a 20 mL vial with cap, to the solution of 5-(2,3-dihydro-1H-indol-5-yl)-7-methyl-7H-pyrrolo[2,3-d]pyrimidin-4-amineHCl (70.5 mg, 0.234 mmol), (3-fluoro-2-methylphenyl)acetic acid (39.3 mg, 0.234 mmol), HATU (89 mg, 0.234 mmol) in DMF (2 mL) was added Hunig's base (0.163 mL, 0.934 mmol). The mixture was stirred at room temperature overnight. The reaction was poured into water (100 mL), and a white solid formed. The solid was filtered and dried to afford 5-{1-[(3-fluoro-2-methylphenyl)acetyl]-2,3-dihydro-1H-indol-5-yl}-7-methyl-7H-pyrrolo[2,3-d]pyrimidin-4-amine (96 mg) as an off-white solid. $^1$H NMR (400 MHz, DMSO-d$_6$) δ ppm 2.14 (d, J=1.52 Hz, 3H), 3.21-3.29 (m, 2H), 3.73 (s, 3H), 3.95 (s, 2H), 4.28 (t, J=8.46 Hz, 2H), 7.03-7.10 (m, 2H), 7.17-7.22 (m, 1H), 7.24 (s, 1H), 7.25 (s, 1H), 7.32 (s, 1H), 8.10 (d, J=8.34 Hz, 1H), 8.14 (s, 1H).

Example 73

5-{1-[(2-fluoro-5-methylphenyl)acetyl]-2,3-dihydro-1H-indol-5-yl}-7-methyl-7H-pyrrolo[2,3-d]pyrimidin-4-amine

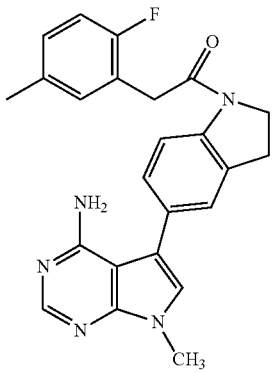 [SMILES: Cc1ccc(F)c(CC(=O)N2CCc3cc(-c4cn(C)c5ncnc(N)c45)ccc32)c1]

In a 20 mL vial with cap, to the solution of 5-(2,3-dihydro-1H-indol-5-yl)-7-methyl-7H-pyrrolo[2,3-d]pyrimidin-4-amineHCl (71.6 mg, 0.237 mmol), (2-fluoro-5-methylphenyl)acetic acid (39.9 mg, 0.237 mmol), HATU (90 mg, 0.237 mmol) in DMF (2 mL) was added Hunig's base (0.166 mL, 0.949 mmol). The mixture was stirred overnight. The reaction was poured into water (100 mL), and a white solid formed. The solid was filtered and dried to afford 5-{1-[(2-fluoro-5-methylphenyl)acetyl]-2,3-dihydro-1H-indol-5-yl}-7-methyl-7H-pyrrolo[2,3-d]pyrimidin-4-amine (85 mg) as an off-white solid. It had 0.8 eq of DMF based on NMR. $^1$H NMR (400 MHz, DMSO-d$_6$) δ ppm 2.29 (s, 3H), 3.25 (t, J=8.46 Hz, 2H), 3.73 (s, 3H), 3.87 (s, 2H), 4.27 (t, J=8.46 Hz, 2H), 7.09-7.16 (m, 3H), 7.22 (d, J=8.08 Hz, 1H), 7.26 (s, 1H), 7.32 (s, 1H), 8.09 (d, J=8.34 Hz, 1H), 8.14 (s, 1H).

Example 74

3-{1-[(2-fluoro-3-methyl phenyl)acetyl]-2,3-dihydro-1H-indol-5-yl}-1-methyl-1H-pyrazolo[3,4-d]pyrimidin-4-amine

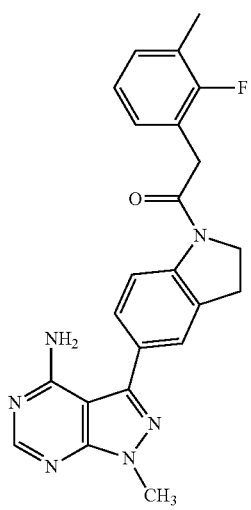 [SMILES: Cc1cccc(CC(=O)N2CCc3cc(-c4nn(C)c5ncnc(N)c45)ccc32)c1F]

In a 20 mL vial with cap, to 3-(2,3-dihydro-1H-indol-5-yl)-1-methyl-1H-pyrazolo[3,4-d]pyrimidin-4-amine 2HCl (70 mg, 0.206 mmol), (2-fluoro-3-methylphenyl)acetic acid (34.7 mg, 0.206 mmol), and HATU (78 mg, 0.206 mmol) in DMF (2 mL) was added Hunig's base (0.144 mL, 0.825 mmol). The mixture was stirred overnight. The reaction was poured into water, off-white solid formed. The solid was filtered to give 3-{1-[(2-fluoro-3-methylphenyl)acetyl]-2,3-dihydro-1H-indol-5-yl}-1-methyl-1H-pyrazolo[3,4-d]pyrimidin-4-amine (71 mg) as an off-white solid. $^1$H NMR (400 MHz, DMSO-d$_6$) δ ppm 2.25 (d, J=1.52 Hz, 3H), 3.24-3.32 (m, 2H), 3.92 (s, 2H), 3.94 (s, 3H), 4.30 (t, J=8.46 Hz, 2H), 7.04-7.11 (m, 1H), 7.16 (s, 1H), 7.21 (s, 1H), 7.44 (d, J=8.34 Hz, 1H), 7.53 (s, 1H), 8.16 (d, J=8.34 Hz, 1H), 8.25 (s, 1H).

Example 75

3-{1-[(3-fluoro-2-methyl phenyl)acetyl]-2,3-dihydro-1H-indol-5-yl}-1-methyl-1H-pyrazolo[3,4-d]pyrimidin-4-amine

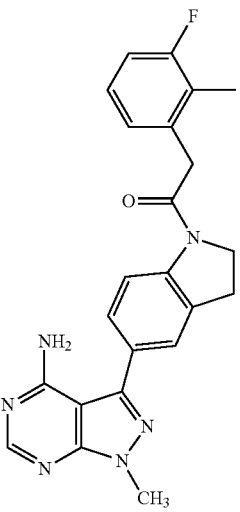 [SMILES: Cc1c(F)cccc1CC(=O)N1CCc2cc(-c3nn(C)c4ncnc(N)c34)ccc21]

In a 20 mL vial with cap, to the solution of 3-(2,3-dihydro-1H-indol-5-yl)-1-methyl-1H-pyrazolo[3,4-d]pyrimidin-4-amine 2HCl (70 mg, 0.206 mmol), (3-fluoro-2-methylphenyl)acetic acid (34.7 mg, 0.206 mmol), HATU (78 mg, 0.206 mmol) in DMF (2 mL) was added Hunig's base (0.144 mL, 0.825 mmol). The mixture was stirred overnight. The reaction was poured into water, and an off-white solid formed. The solid was filtered to give the title compound (73 mg) as an off-white solid. $^1$H NMR (400 MHz, DMSO-d$_6$) δ ppm 2.15 (d, J=1.52 Hz, 3H), 3.24-3.31 (m, 2H), 3.94 (s, 3H), 3.97 (s, 2H), 4.27-4.34 (m, 2H), 7.04-7.11 (m, 2H), 7.19 (d, J=6.32 Hz, 1H), 7.44 (d, J=8.08 Hz, 1H), 7.53 (s, 1H), 8.16 (d, J=8.08 Hz, 1H), 8.25 (s, 1H).

Example 76

5-{1-[(2,5-difluorophenyl)acetyl]-2,3-dihydro-1H-indol-5-yl}-7-(1-methyl-4-piperidinyl)-7H-pyrrolo[2,3-d]pyrimidin-4-amine

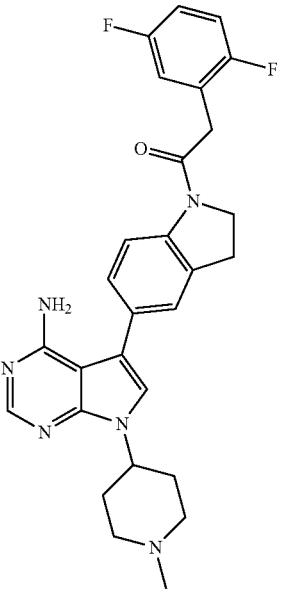 [SMILES: CN1CCC(n2cc(-c3ccc4c(c3)CCN4C(=O)Cc3cc(F)ccc3F)c3c(N)ncnc32)CC1]

To 5-{1-[(2,5-difluorophenyl)acetyl]-2,3-dihydro-1H-indol-5-yl}-7-(4-piperidinyl)-7H-pyrrolo[2,3-d]pyrimidin-4-amine (85 mg, 0.174 mmol) was added N,N-Dimethylformamide (DMF) (2 mL) and cesium carbonate (170 mg, 0.522 mmol). The mixture was then added iodomethane (0.014 mL, 0.226 mmol) and the reaction was let stir at room temp overnight. The reaction was then filtered using the syringe filter and the filtrate was then diluted with water (20 ml) then extracted with EtOAc (3×15 ml). The organics were combined, washed with brine, dried over MgSO4, filtered, concentrated and then loaded on to a 10 g Biotage SNAP column. Elution with 0 to 10% MeOH in DCM over 30 min gradient afforded 5-{1-[(2,5-difluorophenyl)acetyl]-2,3-dihydro-1H-indol-5-yl}-7-(1-methyl-4-piperidinyl)-7H-pyrrolo[2,3-d]pyrimidin-4-amine (16 mg, 0.032 mmol, 18.30% yield) as a white solid. LC/MS (ES) m/z=503.4 [M+H]$^+$. $^1$H NMR (400 MHz, DMSO-d$_6$) δ 8.13 (s, 1H), 8.08 (d, J=8.08 Hz, 1H), 7.40 (s, 1H), 7.36 (s, 1H), 7.15-7.30 (m, 4H), 4.56 (d, J=3.54 Hz, 1H), 4.29 (t, J=8.46 Hz, 2H), 3.95 (s, 2H), 3.27 (t, J=8.46 Hz, 2H), 2.93 (br. s., 2H), 2.27 (s, 3H), 2.04-2.18 (m, 4H), 1.85-1.93 (m, 2H). NHs not observed.

Example 77

5-{1-[(3-chloro-4-fluorophenyl)acetyl]-2,3-dihydro-1H-indol-5-yl}-7-methyl-7H-pyrrolo[2,3-d]pyrimidin-4-amine

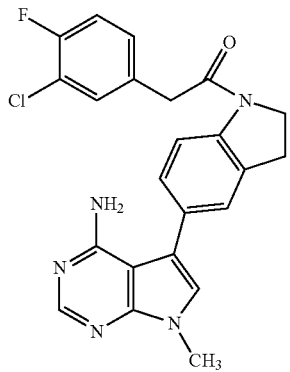 [SMILES: Cn1cc(-c2ccc3c(c2)CCN3C(=O)Cc2ccc(F)c(Cl)c2)c2c(N)ncnc21]

In a 20 mL vial with cap, to the solution of 5-(2,3-dihydro-1H-indol-5-yl)-7-methyl-7H-pyrrolo[2,3-d]pyrimidin-4-amineHCl (66 mg, 0.219 mmol), (3-chloro-4-fluorophenyl) acetic acid (41.2 mg, 0.219 mmol), HATU (83 mg, 0.219 mmol) in DMF (2 mL) was added Hunig's base (0.153 mL, 0.875 mmol). The mixture was stirred at rt for over night. LCMS showed reaction was completed. The reaction was poured into water (100 mL), white solid formed. The solid was filtered and dried to afford a off-white solid as the title compound. $^1$H NMR (400 MHz, DMSO-d$_6$) δ ppm 3.22-3.28 (m, 2H), 3.73 (s, 3H), 3.92 (s, 2H), 4.24 (t, J=8.59 Hz, 2H), 7.23 (d, J=8.34 Hz, 1H), 7.26 (s, 1H), 7.29-7.34 (m, 2H), 7.36-7.42 (m, 1H), 7.53 (dd, J=7.33, 2.02 Hz, 1H), 8.12 (d, J=8.34 Hz, 1H), 8.15 (s, 1H).

Example 78

5-{1-[(3-chloro-2-fluorophenyl)acetyl]-2,3-dihydro-1H-indol-5-yl}-7-methyl-7H-pyrrolo[2,3-d]pyrimidin-4-amine

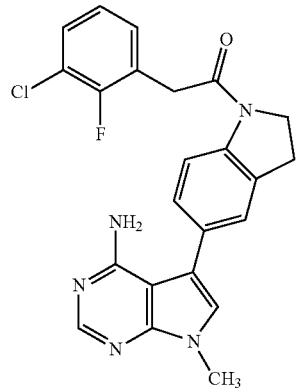 [SMILES: Cn1cc(-c2ccc3c(c2)CCN3C(=O)Cc2cccc(Cl)c2F)c2c(N)ncnc21]

In a 20 mL vial with cap, to the solution of 5-(2,3-dihydro-1H-indol-5-yl)-7-methyl-7H-pyrrolo[2,3-d]pyrimidin-4-amineHCl (66 mg, 0.219 mmol), (3-chloro-2-fluorophenyl) acetic acid (41.2 mg, 0.219 mmol), HATU (83 mg, 0.219 mmol) in DMF (2 mL) was added Hunig's base (0.153 mL, 0.875 mmol). The mixture was stirred overnight. The reaction was poured into water (100 mL), and a white solid formed. The solid was filtered and dried to afford a off-white solid as the title compound. It had 1 eq of DMF based on NMR. $^1$H NMR (400 MHz, DMSO-d$_6$) δ ppm 3.27-3.29 (m, 2H), 3.74 (s, 3H), 4.01 (s, 2H), 4.26-4.33 (m, 2H), 7.20-7.27 (m, 3H), 7.33 (m, 2H), 7.52 (s, 1H), 8.08 (d, J=8.34 Hz, 1H), 8.15 (s, 1H).

Example 79

3-{1-[(3-chloro-4-fluorophenyl)acetyl]-2,3-dihydro-1H-indol-5-yl}-1-methyl-1H-pyrazolo[3,4-d]pyrimidin-4-amine

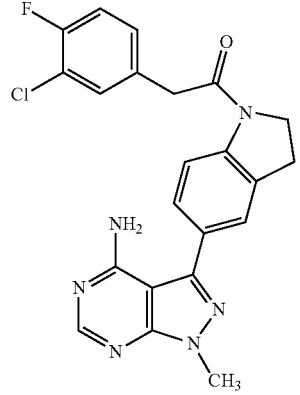 [SMILES: Cn1nc(-c2ccc3c(c2)CCN3C(=O)Cc2ccc(F)c(Cl)c2)c2c(N)ncnc21]

In a 20 mL vial with cap, to the solution of 3-(2,3-dihydro-1H-indol-5-yl)-1-methyl-1H-pyrazolo[3,4-d]pyrimidin-4-amine 2HCl (64.6 mg, 0.190 mmol), (3-chloro-4-fluorophenyl)acetic acid (35.9 mg, 0.190 mmol), HATU (72.4 mg, 0.190 mmol) in DMF (2 mL) was added Hunig's base (0.133 mL, 0.762 mmol). The mixture was stirred overnight. The reaction was poured into water, and an off-white solid formed. The solid was filtered to give the title compound as an off-white solid. $^1$H NMR (400 MHz, DMSO-d$_6$) δ ppm 3.22-3.30 (m, 2H), 3.94 (s, 5H), 4.26 (t, J=8.46 Hz, 2H), 7.33 (dd, J=4.93, 2.15 Hz, 1H), 7.37-7.40 (m, 1H), 7.41-7.47 (m, 1H), 7.51-7.58 (m, 2H), 8.18 (d, J=8.59 Hz, 1H), 8.25 (s, 1H).

Example 80

3-{1-[(3-chloro-2-fluorophenyl)acetyl]-2,3-dihydro-1H-indol-5-yl}-1-methyl-1H-pyrazolo[3,4-d]pyrimidin-4-amine

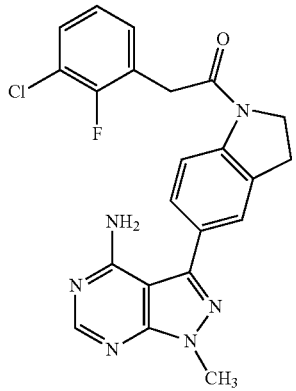 [SMILES: Cn1nc(-c2ccc3c(c2)CCN3C(=O)Cc2cccc(Cl)c2F)c2c(N)ncnc21]

In a 20 mL vial with cap, to the solution of 3-(2,3-dihydro-1H-indol-5-yl)-1-methyl-1H-pyrazolo[3,4-d]pyrimidin-4-amine 2HCl (65.3 mg, 0.192 mmol), (3-chloro-2-fluorophenyl)acetic acid (36.3 mg, 0.192 mmol), HATU (73.2 mg, 0.192 mmol) in DMF (2 mL) was added Hunig's base (0.134 mL, 0.770 mmol). The mixture was stirred overnight. The reaction was poured into water, and off-white solid formed. The solid was filtered to give the title compound as an off-white solid. It has 0.75 eq. of DMF based on NMR. $^1$H NMR (400 MHz, DMSO-d$_6$) δ ppm 3.25-3.31 (m, 2H), 3.94 (s, 3H), 4.04 (s, 2H), 4.32 (t, J=8.46 Hz, 2H), 7.20-7.26 (m, 1H), 7.33 (d, J=1.52 Hz, 1H), 7.35 (s, 1H), 7.44 (d, J=8.08 Hz, 1H), 7.50-7.57 (m, 2H), 8.14 (d, J=8.34 Hz, 1H), 8.25 (s, 1H).

Example 81

5-{1-[(2,3-dimethylphenyl)acetyl]-2,3-dihydro-1H-indol-5-yl}-7-methyl-7H-pyrrolo[2,3-d]pyrimidin-4-amine

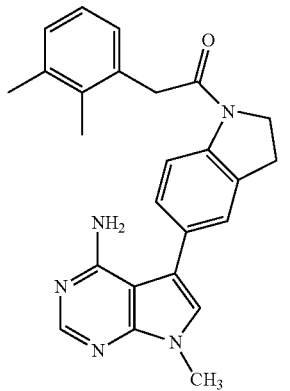 [SMILES: Cc1cccc(CC(=O)N2CCc3cc(-c4cn(C)c5ncnc(N)c45)ccc32)c1C]

In a 20 mL vial with cap, to the solution of 5-(2,3-dihydro-1H-indol-5-yl)-7-methyl-7H-pyrrolo[2,3-d]pyrimidin-4-amineHCl (66 mg, 0.219 mmol), (2,3-dimethylphenyl)acetic acid (35.9 mg, 0.219 mmol), HATU (83 mg, 0.219 mmol) in DMF (2 mL) was added Hunig's base (0.153 mL, 0.875 mmol). The mixture was stirred overnight. The reaction was poured into water (100 mL), and white solid formed. The solid was filtered and dried to afford the title compound (78 mg) as an off-white solid. $^1$H NMR (400 MHz, DMSO-d$_6$) δ ppm 2.12 (s, 3H), 2.27 (s, 3H), 3.20-3.27 (m, 2H), 3.73 (s, 3H), 3.89 (s, 2H), 4.26 (t, J=8.46 Hz, 2H), 7.02 (d, J=6.82 Hz, 2H), 7.05-7.09 (m, 1H), 7.22 (d, J=8.59 Hz, 1H), 7.25 (s, 1H), 7.32 (s, 1H), 8.11 (d, J=8.08 Hz, 1H), 8.14 (s, 1H).

Example 82

1-(1-methylethyl)-3-{1-[(3-methylphenyl)acetyl]-2,3-dihydro-1H-indol-5-yl}-1H-pyrazolo[3,4-d]pyrimidin-4-amine

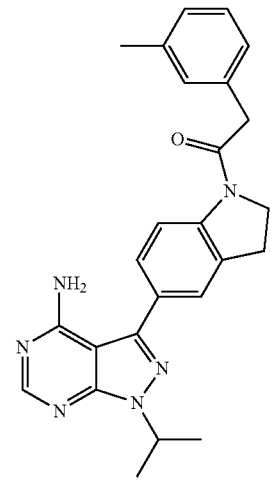 [SMILES: Cc1cccc(CC(=O)N2CCc3cc(-c4nn(C(C)C)c5ncnc(N)c45)ccc32)c1]

3-iodo-1H-pyrazolo[3,4-d]pyrimidin-4-amine

To a solution of 1H-pyrazolo[3,4-d]pyrimidin-4-amine (1000 mg, 7.40 mmol) in N,N-Dimethylformamide (DMF) (30 mL) stirred under nitrogen at room temperature was added NIS (1998 mg, 8.88 mmol). The reaction mixture was stirred at 80° C. for 5 h. The reaction was allowed to cool to room temperature. The mixture was concentrated, and NH4OH solution (20 ml) and EtOH (20 ml) were added. The precipitated white solid was filtered and dried to give 1.24 g of 3-iodo-1H-pyrazolo[3,4-d]pyrimidin-4-amine. LC/MS (ES) m/z=261.9 [M+H]$^+$.

3-iodo-1-(1-methylethyl)-1H-pyrazolo[3,4-d]pyrimidin-4-amine

To 3-iodo-1H-pyrazolo[3,4-d]pyrimidin-4-amine (200 mg, 0.766 mmol) in N,N-Dimethylformamide (DMF) (5 mL) was added cesium carbonate (300 mg, 0.919 mmol) followed by 2-iodopropane (0.080 mL, 0.805 mmol), and the reaction mixture was stirred over the weekend (3 days) at 80° C. in a sealed vessel. The reaction was allowed to cool down to room temperature. The mixture was poured onto water and EtOAc. The organic layer was separated, washed with brine, dried (MgSO4), filtered and concentrated to afford 3-iodo-1-(1- methylethyl)-1H-pyrazolo[3,4-d]pyrimidin-4-amine (160 mg) as a white solid. LC/MS (ES) m/z=3.4.0 [M+H]⁺.

1-(1-methylethyl)-3-{1-[(3-methylohenynacetyl]-2,3-dihydro-1H-indol-5-yl}-1H-pyrazolo[3,4-d]pyrimidin-4-amine To a 25 mL pressure tube was charged 3-iodo-1-(1-methylethyl)-1H-pyrazolo[3,4-d]pyrimidin-4-amine (70.9 mg, 0.234 mmol), 1-[(3-methylphenyl)acetyl]-5-(4,4,5,5-tetramethyl-1,3,2-dioxaborolan-2-yl)-2,3-dihydro-1H-indole (88 mg, 0.234 mmol), 1,1'-bis(diphenylphosphino)ferrocene-palladium(II)dichloride dichloromethane complex (9.55 mg, 0.012 mmol), and sodium bicarbonate (39.3 mg, 0.468 mmol) followed by dioxane (8 mL), and water (2 mL). The reaction was heated at 120° C. for 40 min in microwave reactor. The reaction was cooled to room temperature, the mixture was transferred into a 100 mL erlenmeyer flask, rinsed by EtOAc, the water layer and black greasy solid stayed in tube, total 100 mL of EtOAc was added to the mixture. The EtOAc solution was evaporated to dryness, and re-dissolved with CH2Cl2/MeOH (8 mL/2 mL). It was purified by flash column 25-100% EtOAc/hexane, then 0-10% MeOH/EtOAc, Si SF15-24g, to afford a brown solid. The brown solid was further purified by recrystallization in CH3CN to give a brown solid as the title compound. LC/MS (ES) m/z=427.4 [M+H]⁺. ¹H NMR (400 MHz, DMSO-$d_6$) δ ppm 1.48 (d, J=6.82 Hz, 6H), 2.31 (s, 3H), 3.22-3.27 (m, 2H), 3.85 (s, 2 H), 4.23 (t, J=8.34 Hz, 2H), 5.02-5.09 (m, 1H), 7.07-7.14 (m, 3H), 7.20-7.27 (m, 1H), 7.44 (d, J=8.08 Hz, 1H), 7.51 (s, 1H), 8.20 (d, J=8.08 Hz, 1H), 8.22 (s, 1H).

Example 83

2-(4-amino-3-{1-[(3-methylphenyl)acetyl]-2,3-dihydro-1H-indol-5-yl}-1H-pyrazolo[3,4-d]pyrimidin-1-yl)ethanol

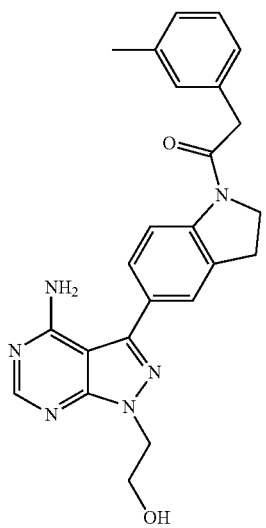 [SMILES: Cc1cccc(CC(=O)N2CCc3cc(-c4nn(CCO)c5ncnc(N)c45)ccc32)c1]

2-(4-amino-3-iodo-1H-pyrazolo[3,4-d]pyrimidin-1-yl)ethanol

To 3-iodo-1H-pyrazolo[3,4-d]pyrimidin-4-amine (200 mg, 0.766 mmol) in N,N-Dimethylformamide (DMF) (5 mL) was added cesium carbonate (300 mg, 0.919 mmol) followed by 2-bromoethanol (0.057 mL, 0.805 mmol), and the reaction mixture was stirred over the weekend (3 days) at 80 C into a sealed vessel. The reaction was allowed to cool down to room temperature. The mixture was concentrated and treated with water (~10 mL). The resulting aqueous mixture was sonicated, and then filtered. The solid in the filter was washed with water (2×10 mL) to afford 2-(4-amino-3-iodo-1H-pyrazolo[3,4-d]pyrimidin-1-yl)ethanol (128 mg) as a white solid after drying. LC/MS (ES) m/z=306.0 [M+H]⁺.

2-(4-amino-3-{1-[(3-methylphenyl)acetyl]-2,3-dihydro-1H-indol-5-yl}-1H-pyrazolo[3,4-d]pyrimidin-1-yl)ethanol To a 25 mL pressure tube was charged 2-(4-amino-3-iodo-1H-pyrazolo[3,4-d]pyrimidin-1-yl)ethanol (63.8 mg, 0.209 mmol), 1-[(3-methylphenyl)acetyl]-5-(4,4,5,5-tetramethyl-1,3,2-dioxaborolan-2-yl)-2,3-dihydro-1H-indole (79 mg, 0.209 mmol), 1,1'-bis(diphenylphosphino)ferrocene-palladium(II)dichloride dichloromethane complex (8.54 mg, 0.011 mmol), and sodium bicarbonate (35.1 mg, 0.418 mmol) followed by dioxane (8 mL), and water (2 mL). The reaction was heated at 120° C. for 40 min in microwave. The reaction was cooled to room temperature, the mixture was transferred into a 100 mL flask, rinsed by EtOAc, with the water layer and black greasy solid stayed in tube (total 100 mL of EtOAc was added to the mixture). The EtOAc solution was concentrated to dryness, and re-dissolved with CH2Cl2/MeOH (8 mL/2 mL). It was purified by flash column 25-100% EtOAc/hexane, then 0-10% MeOH/EtOAc, Si SF15-24g, to afford a brown solid. The brown solid was further purified by recrystallization in CH3CN to give a brown solid as the title compound. LC/MS (ES) m/z=429.4 [M+H]⁺. ¹H NMR (400 MHz, DMSO-$d_6$) δ ppm 2.31 (s, 3H), 3.24 (s, 2H), 3.80-3.88 (m, 4H), 4.19-4.27 (m, 2H), 4.37 (t, J=5.81 Hz, 2H), 4.89 (t, J=5.68 Hz, 1H), 7.07-7.14 (m, 3H), 7.20-7.28 (m, 1H), 7.45 (d, J=8.08 Hz, 1H), 7.51 (s, 1H), 8.21 (d, J=8.34 Hz, 1H), 8.23 (s, 1H).

Example 84

5-{1-[(3,5-dimethylphenyl)acetyl]-2,3-dihydro-1H-indol-5-yl}-7-methyl-7H-pyrrolo[2,3-d]pyrimidin-4-amine

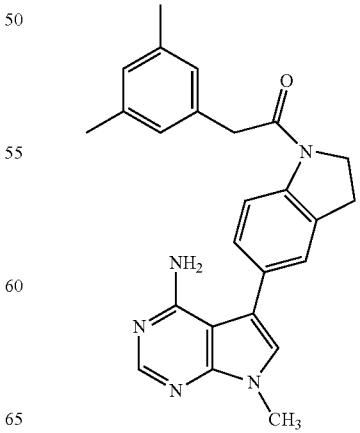

In a 20 mL vial with cap, to the solution of 5-(2,3-dihydro-1H-indol-5-yl)-7-methyl-7H-pyrrolo[2,3-d]pyrimidin-4-amineHCl (66 mg, 0.129 mmol), (3,5-dimethylphenyl)acetic acid (35.9 mg, 0.219 mmol), HATU (83 mg, 0.219 mmol) in DMF (2 mL) was added Hunig's base (0.153 mL, 0.875 mmol). The mixture was stirred overnight. The reaction was poured into water (100 mL), and a white solid formed. The solid was filtered and dried to afford a off-white solid as the title compound. LC/MS (ES) m/z=412.4 [M+H]$^+$. $^1$H NMR (400 MHz, DMSO-d$_6$) δ ppm 2.26 (s, 6H), 3.20 (t, J=8.46 Hz, 2H), 3.73 (s, 3H), 3.77 (s, 2H), 4.19 (t, J=8.46 Hz, 2H), 6.87-6.94 (m, 3H), 7.20-7.27 (m, 1H), 7.25 (s, 1H), 7.29 (s, 1H), 8.14 (d, J=8.34 Hz, 1H), 8.14 (s, 1H).

Example 85

5-{1-[(2,5-difluorophenyl)acetyl]-2,3-dihydro-1H-indol-5-yl}-7-(4-piperidinyl)-7H-pyrrolo[2,3-d]pyrimidin-4-amine

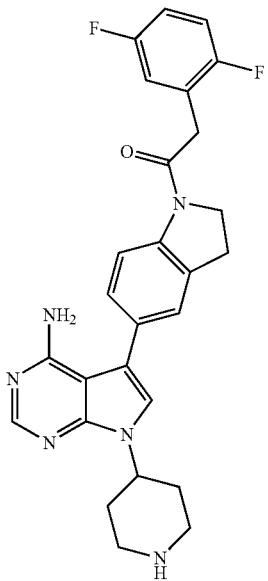 [SMILES: Nc1ncnc2c1c(-c1ccc3c(c1)CCN3C(=O)Cc1cc(F)ccc1F)cn2C1CCNCC1]

1,1-dimethylethyl 4-(5-bromo-4-chloro-7H-pyrrolo[2,3-d]pyrimidin-7-yl)-1-piperidinecarboxylate To a solution of 5-bromo-4-chloro-1H-pyrrolo[2,3-d]pyrimidine (214 mg, 0.921 mmol), 1,1-dimethylethyl 4-hydroxy-1-piperidinecarboxylate (556 mg, 2.76 mmol) and triphenylphosphine (483 mg, 1.841 mmol) in Tetrahydrofuran (THF) (10 mL) was added by drop wise DEAD (0.291 mL, 1.841 mmol). The solution was let stir at room temp. After 2 hr the reaction was concentrated and purified by silica gel chromatography to afford 1,1-dimethylethyl 4-(5-bromo-4-chloro-7H-pyrrolo[2,3-d]pyrimidin-7-yl)-1-piperidinecarboxylate (330 mg, 86% yield) as a white solid 1,1-dimethylethyl 4-(4-amino-5-bromo-7H-pyrrolo[2,3-d]pyrimidin-7-yl)-1-piperidinecarboxylate To 1,1-dimethylethyl 4-(5-bromo-4-chloro-7H-pyrrolo[2,3-d]pyrimidin-7-yl)-1-piperidinecarboxylate (313 mg, 0.753 mmol) was added ammonium hydroxide (2 mL, 51.4 mmol) and 1,4-Dioxane (1 mL) to a 5 mL microwave vial and heated in microwave for 20 min. at 100° C. After total of 35 min. reaction was completed. The reaction was concentrated to give 1,1-dimethylethyl 4-(4-amino-5-bromo-7H-pyrrolo[2,3-d]pyrimidin-7-yl)-1-piperidinecarboxylate (336 mg), which was used without further purification.

1,1-dimethylethyl 4-(4-amino-5-{1-[(2,5-difluorophenyl)acetyl]-2,3-dihydro-1H-indol-5-yl}-7H-pyrrolo[2,3-d]pyrimidin-7-yl)-1-piperidinecarboxylate To 1,1-dimethylethyl 4-(4-amino-5-bromo-7H-pyrrolo[2,3-d]pyrimidin-7-yl)-1-piperidinecarboxylate (138 mg, 0.348 mmol), and 1-[(2,5-difluorophenyl)acetyl]-5-(4,4,5,5-tetramethyl-1,3,2-dioxaborolan-2-yl)-2,3-dihydro-1H-indole (167 mg, 0.418 mmol) were dissolved in 1,4-Dioxane (5. mL) then added saturated NaHCO3 (2 mL). The mixture was then bubbled with N2 gas for 10 min then Pd(Ph3P)4 (40.2 mg, 0.035 mmol) was added, and then the mixture was bubbled for 5 additional minutes. The reaction was then capped and heated at 100° C. for 4 hr. The mixture was allowed to cool then diluted with water (10 mL) then extracted with EtOAc (3×20 ml). The organic were combined, washed with brine, dried over MgSO4, filtered and concentrated to isolated a amber color oil. The oil was then purified on a 25 g Biotage SNAP column conditioned with Hexane eluting with a gradient of 0 to 10% MeOH in DCM for 30 min. to give 1,1-dimethylethyl 4-(4-amino-5-{1-[(2,5-difluorophenyl)acetyl]-2,3-dihydro-1H-indol-5-yl}-7H-pyrrolo[2,3-d]pyrimidin-7-yl)-1-piperidinecarboxylate (160 mg, 0.272 mmol, 78% yield) as a amber color oil. LC/MS (ES) m/z=589.6 [M+H]$^+$.

5-{1-[(2,5-difluorophenyl)acetyl]-2,3-dihydro-1H-indol-5-yl}-7-(4-piperidinyl)-7H-pyrrolo[2,3-d]pyrimidin-4-amine To 1,1-dimethylethyl 4-(4-amino-5-{1-[(2,5-difluorophenyl)acetyl]-2,3-dihydro-1H-indol-5-yl}-7H-pyrrolo[2,3-d]pyrimidin-7-yl)-1-piperidinecarboxylate (180 mg, 0.306 mmol) was added HCl (4 mL, 16.00 mmol) 4M in dioxane. The reaction was let stir at room temp overnight. The reaction was concentrated then diluted with diethyl ether and filtered to isolate 5-{1-[(2,5-difluorophenyl)acetyl]-2,3-dihydro-1H-indol-5-yl}-7-(4-piperidinyl)-7H-pyrrolo[2,3-d]pyrimidin-4-amine (140 mg, 0.249 mmol, 82% yield) as a light yellow solid as the dihydrochloride salt. LC/MS (ES) m/z=489.0 [M+H]$^+$. $^1$H NMR (400 MHz, METHANOL-d$_4$) δ 8.39 (s, 1H), 8.24 (d, J=8.34 Hz, 1H), 7.61 (s, 1H), 7.44 (s, 1H), 7.32-7.37 (m, 1H), 7.04-7.20 (m, 3H), 5.08-5.18 (m, 1H), 4.36 (t, J=8.46 Hz, 2H), 3.99 (s, 2H), 3.68 (s, 3H), 3.65 (d, J=13.89 Hz, 2H), 3.36-3.40 (m, 2H), 2.41-2.53 (m, 2H), 2.37 (d, 2H).

Example 86

1-ethyl-3-{1-[(3-methyl phenyl)acetyl]-2,3-dihydro-1H-indol-5-yl}-1H-pyrazolo[3,4-d]pyrimidin-4-amine

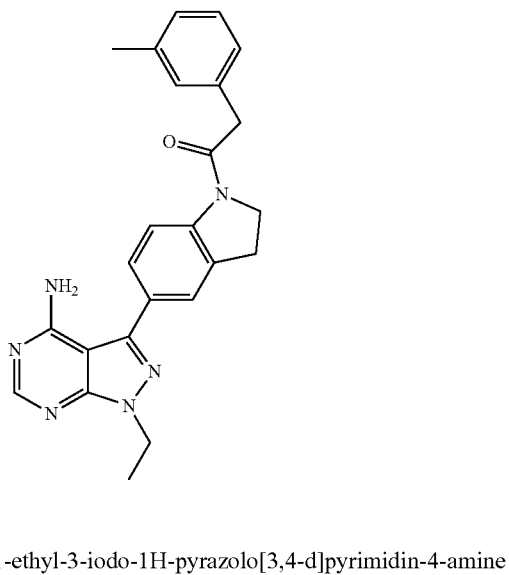

1-ethyl-3-iodo-1H-pyrazolo[3,4-d]pyrimidin-4-amine

To 3-iodo-1H-pyrazolo[3,4-d]pyrimidin-4-amine (200 mg, 0.766 mmol) in N,N-Dimethylformamide (DMF) (5 mL) was added cesium carbonate (300 mg, 0.919 mmol) followed by iodoethane (0.065 mL, 0.805 mmol), and the reaction mixture was stirred over the weekend (3 days) at 80° C. into a sealed vessel. The reaction was allowed to cool down to room temperature. The mixture was poured onto water and EtOAc. The organic layer was separated, washed with brine, dried (MgSO4), filtered and concentrated. Flash chromatography on SiO2 (gradient: 100% CH2Cl2 to 90:10:1 CH2Cl2:CH$_3$OH:NH4OH) afforded 1-ethyl-3-iodo-1H-pyrazolo[3,4-d]pyrimidin-4-amine (115 mg) as a white solid.

1-ethyl-3-{1-[(3-methylphenyl)acetyl]-2,3-dihydro-1H-indol-5-yl}-1H-pyrazolo[3,4-d]pyrimidin-4-amine A 25 mL microwave pressure tube was charged 1-ethyl-3-iodo-1H-pyrazolo[3,4-d]pyrimidin-4-amine (105 mg, 0.363 mmol), 1-[(3-methylphenyl)acetyl]-5-(4,4,5,5-tetramethyl-1,3,2-dioxaborolan-2-yl)-2,3-dihydro-1H-indole (137 mg, 0.363 mmol), 1,1'-bis(diphenylphosphino)ferrocene-palladium(II)dichloride dichloromethane complex (14.83 mg, 0.018 mmol), and sodium bicarbonate (61.0 mg, 0.726 mmol) followed by dioxane (4 mL), and water (1 mL). The reaction was sealed and heated at 120° C. for 40 minutes in a microwave reactor. The reaction was cooled to room temperature, the mixture was transferred into a 100 mL flask, rinsed by EtOAc, with the water layer and black greasy solid stayed in tube (total 50 mL of EtOAc was added to the mixture). The EtOAc solution was evaporated to dryness, and re-dissolved with CH2Cl2/MeOH (4 mL/1 mL). It was purified by flash column 25-100% EtOAc/hexane, then 0-10% MeOH/EtOAc (Analogix Si SF15-24g cartridge), to afford a brown solid. The brown solid was further purified by recrystallization from CH3CN to give the title compound as a brown solid. LC/MS (ES) m/z=413.3 [M+H]$^+$. $^1$H NMR (400 MHz, DMSO-d$_6$) ppm 1.41 (t, J=7.20 Hz, 3H), 2.31 (s, 3H), 3.21-3.29 (m, 2H), 3.85 (s, 2H), 4.23 (t, J=8.46 Hz, 2H), 4.32-4.40 (m, 2H), 7.07-7.14 (m, 3H), 7.21-7.28 (m, 1H), 7.44-7.46 (m, 1H), 7.51 (s, 1H), 8.21 (d, J=8.34 Hz, 1H), 8.24 (s, 1H).

Example 87

3-{1-[(2,5-difluorophenyl)acetyl]-2,3-dihydro-1H-indol-5-yl}-7-methylfuro[3,2-c]pyridin-4-amine

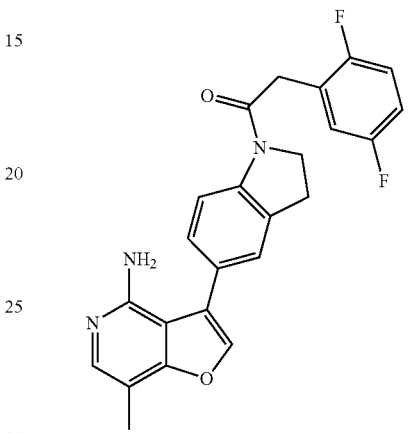

A mixture of 3-{1-[(2,5-difluorophenyl)acetyl]-2,3-dihydro-1H-indol-5-yl}-7-iodofuro[3,2-c]pyridin-4-amine (253 mg, 0.476 mmol), trimethylboroxine (0.07 mL, 0.502 mmol), PdCl2(dppf)-CH2Cl2 adduct (19 mg, 0.023 mmol), and K2CO3 (197 mg, 1.425 mmol) in 1,4-Dioxane (2.5 mL) and Water (0.5 mL) was degassed with Nitrogen for 10 minutes. The vial was then capped and the mixture was stirred at 100° C. for 15 hr. LCMS showed a mixture of starting material (20%), desired product (36%), and the deiodo byproduct (40%). The mixture was filtered, rinsing with EtOAc (about 35 mL). The filtrate was washed with water (1×25 mL) and brine (1×25 mL), dried (Na2SO4), filtered, and concentrated in vacuo. The recovery was fairly low (<200 mg), so the aqueous phases were combined and extracted with methylene chloride (3×25 mL), and the extracts were dried (Na2SO4), filtered, combined with the EtOAc layer from the previous work-up, and concentrated in vacuo (total mass>200 mg). The residue was purified by reverse phase HPLC (Gilson, C18, 25% to 45% CH3CN in water with 0.1% TFA, 8 minute gradient). The product fractions were concentrated, taken up in MeOH, and passed through a PL-HCO3 cartridge. The filtrate was concentrated in vacuo, triturated with ether, and dried in the vacuum oven overnight. NMR indicated that the compound was still a TFA salt, and it showed an impurity The solid was taken up in DCM (5 mL) and poured into saturated aqueous NaHCO3 (5 mL). The organic layer was collected and the aqueous layer was extracted with methylene chloride (2×5 mL). The organic phases were combined, dried (Na2SO4), filtered, and concentrated in vacuo. The residue was repurified by flash chromatography (Analogix, 12 g SiO2, 50%-100% EtOAc in hexanes gradient over 7.5 minutes, EtOAc for 2.5 minutes, then 0-5% MeOH in EtOAc gradient over 10 minutes) to give 3-{1-[(2,5-difluorophenyl)acetyl]-2,3-dihydro-1H-indol-5-yl}-7-methylfuro[3,2-c]pyridin-4-amine (29 mg, 0.066 mmol, 13.79% yield) as a white solid. LC/MS (ES) m/z=420 [M+H]$^+$. $^1$H NMR (400 MHz, DMSO-d$_6$) δ 2.30 (s, 3H), 3.28 (t, J=8.21 Hz, 2H), 3.96 (s, 2H), 4.30 (t, J=8.46 Hz, 2H), 5.31 (s, 2H), 7.14-7.34 (m, 4H), 7.41 (s, 1H), 7.69 (s, 1H), 7.95 (s, 1H), 8.12 (d, J=8.34 Hz, 1H).

Example 88

3-{1-[(2,5-difluorophenyl)acetyl]-2,3-dihydro-1H-indol-5-yl}-1-(1-methylethyl)-1H-pyrazolo[3,4-d]pyrimidin-4-amine

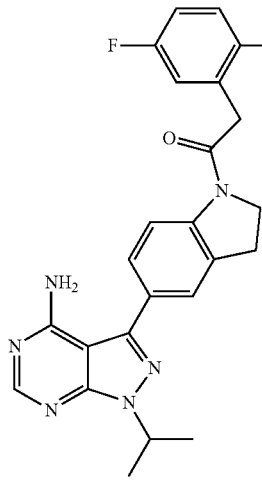

To a 25 mL pressure tube was charged 3-iodo-1-(1-methylethyl)-1H-pyrazolo[3,4-d]pyrimidin-4-amine (70.9 mg, 0.234 mmol), 1-[(2,5-difluorophenyl)acetyl]-5-(4,4,5,5-tetramethyl-1,3,2-dioxaborolan-2-yl)-2,3-dihydro-1H-indole (93 mg, 0.234 mmol), 1,1'-bis(diphenylphosphino)ferrocenepalladium(II)dichloride dichloromethane complex (9.55 mg, 0.012 mmol), and sodium bicarbonate (39.3 mg, 0.468 mmol) followed by dioxane (4 mL), and water (1 mL). The reaction was heated at 120° C. for 40 min in microwave reactor. LCMS showed incomplete conversion. The reaction was heated in microwave at 120° C. for another 1 hour. The reaction was cooled to room temperature, the mixture was transferred into a 100 mL erlenmeyer flask, rinsed by EtOAc, with the water layer and black greasy solid stayed in tube (total 100 mL of EtOAc was added to the mixture). The EtOAc solution was evaporated to dryness, and re-dissolved in CH2Cl2/MeOH (8 mL/2 mL). It was purified by flash column 25-100% EtOAc/hexane, then 0-10% MeOH/EtOAc, Analogix Si SF15-24g, to afford a brown solid. The brown solid was further purified by recrystallization from CH3CN to give the title compound as a brown solid. LC/MS (ES) m/z=449.4 [M+H]$^+$. $^1$H NMR (400 MHz, DMSO-d$_6$) δ ppm 1.49 (d, J=6.82 Hz, 6H), 3.27-3.33 (m, 2H), 3.97 (s, 2H), 4.31 (t, J=8.46 Hz, 2H), 5.06 (t, J=6.82 Hz, 1H), 7.18-7.21 (m, 1H), 7.22-7.27 (m, 2H), 7.44 (d, J=8.08 Hz, 1H), 7.54 (s, 1H), 8.15 (d, J=8.34 Hz, 1H), 8.23 (s, 1H).

Example 89

5-{1-[(3,5-difluorophenyl)acetyl]-2,3-dihydro-1H-indol-5-yl}-7-methyl-7H-pyrrolo[2,3-d]pyrimidin-4-amine

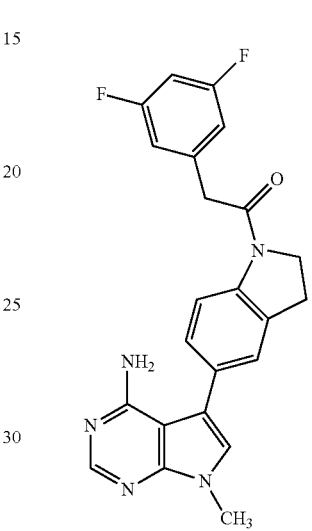

A solution of 5-(2,3-dihydro-1H-indol-5-yl)-7-methyl-7H-pyrrolo[2,3-d]pyrimidin-4-amine 2HCl (150 mg, 0.443 mmol), (3,5-difluorophenyl)acetic acid (76 mg, 0.443 mmol), HATU (169 mg, 0.443 mmol), DIEA (0.310 mL, 1.774 mmol) was stirred at room temperature overnight. LCMS indicated partial conversion, with a mixture of starting material, desired product and bis-acylated material, so the reaction mixture was poured into water (10 mL), and a precipitate formed. The precipitate was collected by filtration, and the residue was washed with water (10 mL), and dried at the pump for an hour. The beige solid was adsorbed onto silica, and purified by flash chromatography (0-10% methanol in DCM, 12-g column) to afford a pale yellow solid which showed presence of bis-acylated material. The product was adsorbed onto silica and purified by flash chromatography (100% EtOAc-10% MeOH in EtOAc, then 10% MeOH in DCM, 24-g column) to afford 5-{1-[(3,5-difluorophenyl)acetyl]-2,3-dihydro-1H-indol-5-yl}-7-methyl-7H-pyrrolo[2,3-d]pyrimidin-4-amine (92 mg, 49.5% yield) as a white solid. LC-MS (ES) m/z=420 [M+H]$^+$. $^1$H NMR (400 MHz, DMSO-d$_6$) δ 3.21-3.28 (m, 2H), 3.74 (s, 3H), 3.95 (s, 2H), 4.24 (t, J=8.34 Hz, 2H), 6.04 (br. s., 2H), 7.06 (d, J=6.57 Hz, 2H), 7.14 (t, J=9.60 Hz, 1H), 7.21-7.29 (m, 2H), 7.33 (s, 1H), 8.07-8.21 (m, 2H).

Example 90

7-methyl-5-{1-[(2,3,5-trifluorophenyl)acetyl]-2,3-dihydro-1H-indol-5-yl}-7H-pyrrolo[2,3-d]pyrimidin-4-amine

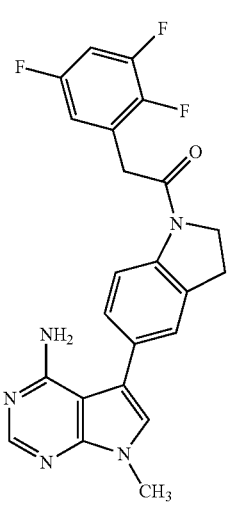 [SMILES: Cn1cc(-c2ccc3c(c2)CCN3C(=O)Cc2cc(F)cc(F)c2F)c2c(N)ncnc21]

A solution of 5-(2,3-dihydro-1H-indol-5-yl)-7-methyl-7H-pyrrolo[2,3-d]pyrimidin-4-amine 2HCl (150 mg, 0.443 mmol), (2,3,5-trifluorophenyl)acetic acid, HATU (169 mg, 0.443 mmol), DIEA (0.310 mL, 1.774 mmol) was stirred at room temperature overnight. LCMS (62-A1-ON) indicated partial conversion, with a mixture of starting material, desired product and bis-acylated material, so the reaction mixture was poured into water (10 mL), and a precipitate formed. The precipitate was collected by filtration, and the residue was washed with water (10 mL), and dried at the pump for an hour. The beige solid was adsorbed onto silica, and purified by flash chromatography (0-10% methanol in DCM, 12-g column) to afford a pale yellow solid which showed presence of bis-acylated material. The product was adsorbed onto silica and purified by flash chromatography (100% EtOAc-10% MeOH in EtOAc, then 10% MeOH in DCM, 12-g column) to afford 7-methyl-5-{1-[(2,3,5-trifluorophenyl)acetyl]-2,3-dihydro-1H-indol-5-yl}-7H-pyrrolo[2,3-d]pyrimidin-4-amine (102 mg, 52.6% yield) as a white solid. LC-MS (ES) m/z=438 [M+H]+. $^1$H NMR (DMSO-$d_6$, 400 MHz): δ 3.28 (t, J=8.3 Hz, 2H), 3.74 (s, 3H), 4.04 (s, 2H), 4.29 (t, J=8.5 Hz, 2H), 6.08 (br. s., 2H), 7.10-7.17 (m, 1H), 7.20-7.28 (m, 2H), 7.34 (s, 1H), 7.42-7.53 (m, 1H), 8.08 (d, J=8.1 Hz, 1H), 8.15 (s, 1H).

Example 91

5-{1-[(3,5-dichlorophenyl)acetyl]-2,3-dihydro-1H-indol-5-yl}-7-methyl-7H-pyrrolo[2,3-d]pyrimidin-4-amine

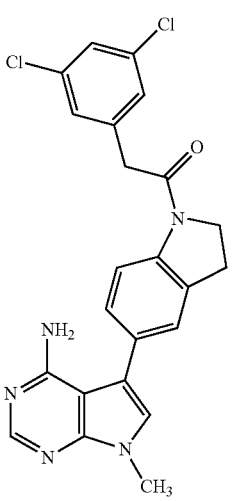 [SMILES: Cn1cc(-c2ccc3c(c2)CCN3C(=O)Cc2cc(Cl)cc(Cl)c2)c2c(N)ncnc21]

A solution of 5-(2,3-dihydro-1H-indol-5-yl)-7-methyl-7H-pyrrolo[2,3-d]pyrimidin-4-amine 2HCl (250 mg, 0.739 mmol), 5-(2,3-dihydro-1H-indol-5-yl)-7-methyl-7H-pyrrolo[2,3-d]pyrimidin-4-amine (250 mg, 0.739 mmol), HATU (281 mg, 0.739 mmol), DIEA (0.516 mL, 2.96 mmol) was stirred at room temperature overnight. LCMS indicated good conversion, so the reaction mixture was poured into water (10 mL), whereupon a precipitate formed. The precipitate was filtered and washed with water (10 ml) and dried at the pump for an hour. The residual pale green solid was adsorbed onto silica and purified by flash chromatography (100% EtOAc to 10% MeOH in EtOAc, 12-g column) to afford 5-{1-[(3,5-dichlorophenyl)acetyl]-2,3-dihydro-1H-indol-5-yl}-7-methyl-7H-pyrrolo[2,3-d]pyrimidin-4-amine (285 mg, 85% yield) as a white solid. LC-MS (ES) m/z=452, 454 [M+H]+. $^1$H NMR (400 MHz, DMSO-$d_6$) δ 3.25 (t, J=8.3 Hz, 2H), 3.74 (s, 3H), 3.95 (s, 2H), 4.24 (t, J=8.5 Hz, 2H), 6.25-5.87 (br. s, 2H), 7.28-7.20 (m, 2H), 7.33 (s, 1H), 7.39 (d, J=1.8 Hz, 2H), 7.52 (d, J=1.8 Hz, 1H), 8.11 (d, J=8.1 Hz, 1H), 8.15 (s, 1H).

Example 92

7-(3-azetidinyl)-5-{1-[(3-methylphenyl)acetyl]-2,3-dihydro-1H-indol-5-yl}-7H-pyrrolo[2,3-d]pyrimidin-4-amine

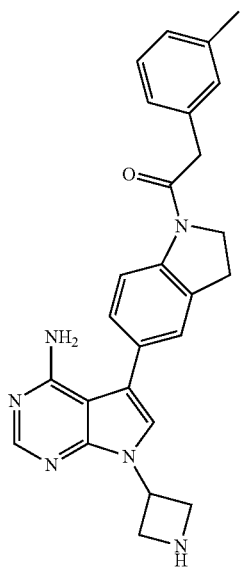 [SMILES: Cc1cccc(CC(=O)N2CCc3cc(-c4cn(C5CNC5)c5ncnc(N)c45)ccc32)c1]

1,1-dimethylethyl 3-(5-bromo-4-chloro-7H-pyrrolo[2,3-d]pyrimidin-7-yl)-1-azetidinecarboxylate To a solution of 5-bromo-4-chloro-1H-pyrrolo[2,3-d]pyrimidine (400 mg, 1.721 mmol), 1,1-dimethylethyl 3-hydroxy-1-azetidinecarboxylate (894 mg, 5.16 mmol) and triphenylphosphine (903 mg, 3.44 mmol) in Tetrahydrofuran (THF) (10 mL) was added dropwise DEAD (545 µl, 3.44 mmol). The solution was let stir at room temp. After 1 hr the reaction observed 10% product and the reaction was heated at 60° C. After 1 hr observed 80% desired product. Additional 100 mg of the 5-bromo-4-chloro-1H-pyrrolo[2,3-d]pyrimidine was added and heating was continued. The reaction was concentrated then loaded on to a 25 g SNAP column with 0 to 35% EtOAc in Hexane gradient over 30 minutes to give 1,1-dimethylethyl 3-(5-bromo-4-chloro-7H-pyrrolo[2,3-d]pyrimidin-7-yl)-1-azetidinecarboxylate (624 mg, 94% yield) as a white solid. LC-MS (ES) m/z=386.9, 389.1 [M+H]+. $^1$H NMR (400 MHz, DMSO-d$_6$) δ 8.69 (s, 1H), 8.38 (s, 1H), 5.53-5.62 (m, 1H), 4.33 (d, J=8.34 Hz, 4H), 1.43 (s, 9H).

1,1-dimethylethyl 3-(4-amino-5-bromo-7H-pyrrolo[2,3-d]pyrimidin-7-yl)-1-azetidinecarboxylate To 1,1-dimethylethyl 3-(5-bromo-4-chloro-7H-pyrrolo[2,3-d]pyrimidin-7-yl)-1-azetidinecarboxylate (690 mg, 1.780 mmol) was added ammonium hydroxide (69.3 µl, 1.780 mmol) in a 20 mL microwave vial. The vial was capped heated at 100° C. for a total of 2 hr in the microwave reactor. The reaction was checked every 0.5 hr. Only 15% desired product was observed. The reaction was filtered. The solid was added NH4OH (4 mL) into a 20 ml microwave vial and the vial was heated in an oil bath at 90° C. for 24 hr. The reaction observed 80% product. Additional 1 ml of NH4OH was added and heating continued overnight. The reaction was filtered and washed to give 1,1-dimethylethyl 3-(4-amino-5-bromo-7H-pyrrolo[2,3-d]pyrimidin-7-yl)-1-azetidinecarboxylate (538 mg) in 78% purity. LC-MS (ES) m/z=368.2, 370.2 [M+H]+.

1,1-dimethylethyl 3-(4-amino-5-{1-[(3-methylphenyl)acetyl]-2,3-dihydro-1H-indol-5-yl}-7H-pyrrolo[2,3-d]pyrimidin-7-yl)-1-azetidinecarboxylate To 1,1-dimethylethyl 3-(4-amino-5-bromo-7H-pyrrolo[2,3-d]pyrimidin-7-yl)-1-azetidinecarboxylate (200 mg, 0.543 mmol), and 1-[(3-methylphenyl)acetyl]-5-(4,4,5,5-tetramethyl-1,3,2-dioxaborolan-2-yl)-2,3-dihydro-1H-indole (246 mg, 0.652 mmol) dissolved in 1,4-Dioxane (4 mL) was added Sat NaHCO3 (2 mL). The mixture was then bubbled N2 gas for 10 minutes then added Pd(Ph3P)4 (62.8 mg, 0.054 mmol) then bubbled for 5 additional minutes. Then reaction was then capped and heated at 100° C. overnight. The mixture was let cool then diluted with water (10 mL) then extracted with EtOAc (3×20 ml). The organics were combined, washed with brine, dried over MgSo4, filtered and concentrated to give an amber color oil. The oil was then purified on a 25 g Biotage SNAP column conditioned with Hexane using a gradient of 0 to 10% MeOH in DCM for 30 minutes to isolate 1,1-dimethylethyl 3-(4-amino-5-{1-[(3-methylphenyl)acetyl]-2,3-dihydro-1H-indol-5-yl}-7H-pyrrolo[2,3-d]pyrimidin-7-yl)-1-azetidinecarboxylate (197 mg, 0.366 mmol, 67.3% yield) as a amber color solid. LC-MS (ES) m/z=539.3 [M+H]+. $^1$H NMR (400 MHz, DMSO-d$_6$) δ 8.11-8.18 (m, 2H), 7.60 (s, 1H), 7.37 (s, 1H), 7.28 (d, J=8.34 Hz, 1H), 7.20-7.26 (m, 1H), 7.06-7.15 (m, 3H), 5.76 (s, 1H), 5.46-5.56 (m, 1H), 4.33 (d, J=8.08 Hz, 4H), 4.21 (t, J=8.46 Hz, 2H), 3.93 (s, 1H), 3.83 (s, 2H), 3.22 (t, J=8.21 Hz, 2H), 2.31 (s, 3H), 1.43 (s, 9H).

7-(3-azetidinyl)-5-{1-[(3-methylphenyl)acetyl]-2,3-dihydro-1H-indol-5-yl}-7H-pyrrolo[2,3-d]pyrimidin-4-amine To 1,1-dimethylethyl 3-(4-amino-5-{1-[(3-methylphenyl)acetyl]-2,3-dihydro-1H-indol-5-yl}-7H-pyrrolo[2,3-d]pyrimidin-7-yl)-1-azetidinecarboxylate (198 mg, 0.368 mmol) was added 4N HCl in dioxane (4 mL, 16.00 mmol). The starting material was oiling out of solution and even heating to 50 degrees C. overnight did not effect conversion. The reaction was then concentrated and DCM (4 mL) and TFA (2 ml) was added. The SM dissolved into solution and after 1 hr the reaction was complete. The reaction was concentrated then diluted with EtOAc (20 mL) and then washed with Sat. Na2CO3. A precipitate cashed out of solution and the mixture was extracted with a mixture of 20% isoproyl alcohol in DCM (3×50 ml). The organics were pooled and dried over Na2SO4, filtered and concentrated to give a yellow oil. The oil was dissolved in 1 ml of DMF and then loaded on to a 10 g Biotage column with 0 to 100% DCM in 95:5:1 mixture of DCM:MeOH:1NH4OH for 15 min then 100% 95:5:1 mixture of DCM:MeOH:1NH4OH for 15 minutes to isolate 7-(3-azetidinyl)-5-{1-[(3-methylphenyl)acetyl]-2,3-dihydro-1H-indol-5-yl}-7H-pyrrolo[2,3-d]pyrimidin-4-amine (103 mg, 0.235 mmol, 63.9% yield) as a clear oil. LC-MS (ES) m/z=439.4 [M+H]+. $^1$H NMR (400 MHz, DMSO-d$_6$) δ 8.15 (d, J=8.34 Hz, 1H), 8.13 (s, 1H), 7.62 (s, 1H), 7.36 (s, 1H), 7.25-7.30 (m, 1H), 7.23 (d, J=7.33 Hz, 1H), 7.06-7.14 (m, 3H), 6.09 (br. s., 2H), 5.50 (t, J=7.45 Hz, 1H), 4.22 (t, J=8.34 Hz, 2H), 3.91-3.96 (m, 2H), 3.78-3.85 (m, 4H), 3.18-3.25 (m, 2H), 2.31 (s, 3H).

Example 93

5-{1-[(4-fluorophenyl)acetyl]-2,3-dihydro-1H-indol-5-yl}-7-methyl-7H-pyrrolo[2,3-d]pyrimidin-4-amine

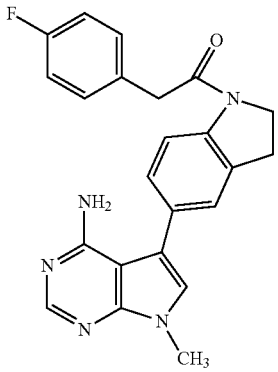 [SMILES: Cn1cc(-c2ccc3c(c2)CCN3C(=O)Cc2ccc(F)cc2)c2c(N)ncnc21]

In a 20 mL vial with cap, to a solution of 5-(2,3-dihydro-1H-indol-5-yl)-7-methyl-7H-pyrrolo[2,3-d]pyrimidin-4-amine HCl (70 mg, 0.232 mmol), (4-fluorophenyl)acetic acid (37.5 mg, 0.244 mmol), and HATU (93 mg, 0.244 mmol) in DMF (2 mL) was added Hunig's base (0.162 mL, 0.928 mmol). The mixture was stirred at overnight. The reaction was poured into water (100 mL), and an off-white solid was formed. The solid was filtered, washed with water (10 mL), and dried to afford the title compound as an off-white solid. LC-MS (ES) m/z=402.3 [M+H]$^+$. $^1$H NMR (400 MHz, DMSO-d$_6$) δ ppm 3.23 (t, J=8.34 Hz, 2H), 3.73 (s, 3H), 3.88 (s, 2H), 4.23 (t, J=8.46 Hz, 2H), 7.15-7.20 (m, 2H), 7.21-7.26 (m, 2H), 7.30-7.37 (m, 3H), 8.13 (d, J=8.34 Hz, 1H), 8.15 (s, 1H).

Example 94

7-methyl-5-{1-[(4-methylphenyl)acetyl]-2,3-dihydro-1H-indol-5-yl}-7H-pyrrolo[2,3-d]pyrimidin-4-amine

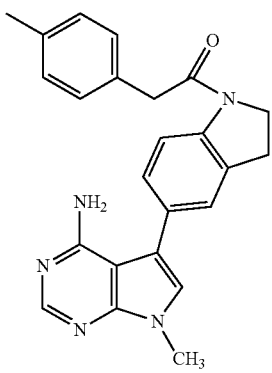 [SMILES: Cc1ccc(CC(=O)N2CCc3cc(-c4cn(C)c5ncnc(N)c45)ccc32)cc1]

In a 20 mL vial with cap, to a solution of 5-(2,3-dihydro-1H-indol-5-yl)-7-methyl-7H-pyrrolo[2,3-d]pyrimidin-4-amineHCl (70 mg, 0.232 mmol), (4-methylphenyl)acetic acid (36.6 mg, 0.244 mmol), and HATU (93 mg, 0.244 mmol) in DMF (2 mL) was added Hunig's base (0.162 mL, 0.928 mmol). The mixture was stirred overnight. The reaction was poured into water (100 mL), and an off-white solid was formed. The solid was filtered, washed with water (10 mL), and dried to afford the title compound as an off-white solid. LC-MS (ES) m/z=598.3 [M+H]$^+$. $^1$H NMR (400 MHz, DMSO-d$_6$) δ ppm 2.30 (s, 3H), 3.20 (t, J=8.34 Hz, 2H), 3.73 (s, 3H), 3.82 (s, 2H), 4.15-4.23 (m, 2H), 7.15 (d, J=8.08 Hz, 2H), 7.20 (d, J=8.08 Hz, 3H), 7.25 (s, 1H), 7.30 (s, 1H), 8.14 (s, 2H).

Example 95

5-{1-[(3-chloro-2,4-difluorophenyl)acetyl]-2,3-dihydro-1H-indol-5-yl}-7-methyl-7H-pyrrolo[2,3-d]pyrimidin-4-amine

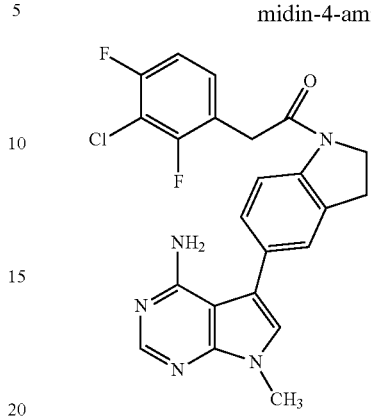

In a 20 mL vial with cap, to a solution of 5-(2,3-dihydro-1H-indol-5-yl)-7-methyl-7H-pyrrolo[2,3-d]pyrimidin-4-amineHCl (70 mg, 0.232 mmol), (3-chloro-2,4-difluorophenyl)acetic acid (47.9 mg 0.232 mmol), and HATU (93 mg, 0.244 mmol) in DMF (2 mL) was added Hunig's base (0.162 mL, 0.928 mmol). The mixture was stirred overnight. The reaction was poured into water (100 mL), and an off-white solid was formed. The solid was filtered, washed with water (10 mL), and dried to afford the title compound as an off-white solid. LC-MS (ES) m/z=454.3 [M+H]+. $^1$H NMR (400 MHz, DMSO-d$_6$) δ ppm 3.22-3.29 (m, 2H), 3.74 (s, 3H), 4.01 (s, 2H), 4.26-4.33 (m, 2H), 7.21-7.28 (m, 1H), 7.26 (s, 1H), 7.29-7.36 (m, 2H), 7.40 (dd, J=8.34, 6.32 Hz, 1H), 8.08 (d, J=8.34 Hz, 1H), 8.15 (s, 1H).

Example 96

5-(1-{[3-fluoro-5-(trifluoromethyl)phenyl]acetyl}-2,3-dihydro-1H-indol-5-yl)-7-methyl-7H-pyrrolo[2,3-d]pyrimidin-4-amine

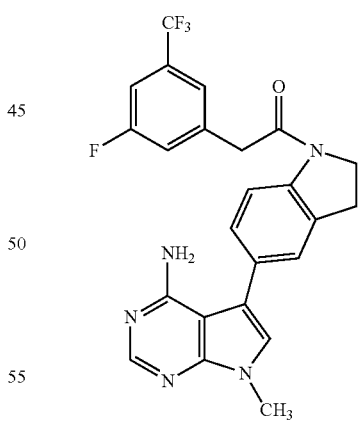

To a suspension of 5-(2,3-dihydro-1H-indol-5-yl)-7-methyl-7H-pyrrolo[2,3-d]pyrimidin-4-amine 2HCl (1.80 g, 5.32 mmol, 1 equiv) and HATU (2.23 g, 5.85 mmol, 1.1 equiv) in 18 mL of DMF was added DIEA (2.97 mL, 17.03 mmol, 3.2 equiv) in one portion. The mixture turned into a light brownish clear solution, and was chilled in an ice bath. To this stirred solution was added [3-fluoro-5-(trifluoromethyl)phenyl]acetic acid portionwise (1.18, 5.32 mmol, 1 equiv) as solids over a period of 1 h. After completion of acid addition, the cooling bath was removed. After 30 min, the mixture became a milky texture. After another 1.5 h, the mixture was poured into to 200 mL of ice water to give a suspension, which was filtered. The cake was washed with water, and ether, and then dried under house vacuum at room temperature for 18 hours. This material was dissolved in 10% MeOH in DCM, and was absorbed onto 3 dryload silica gel cartridges (in about equal portions). Purification was done on Analogix SF40-80 g silica gel cartridge using gradient elution of 1% A to 60% A in CHCl3 (A was a mixture of 3200/800/80 $CHCl_3$/MeOH/NH4OH). The desired product eluted from 23-28% A. The collected fractions were combined and concentrated in vacuo to afford the product as a white residue. The front running impure fractions (21-22% A) were combined and the residue (LCMS showed presence of a non-polar impurity) was dissolved in 10% MeOH in DCM and absorbed onto a dryload cartridge. Purification was done on an Analogix SF25-60 g silica gel cartridge using gradient elution of 1% A in EtOAc 75% A (A was a mixture of 20% MeOH in EtOAc). The desired product eluted from 59-75% A. The combined fractions were conc in vacuo to afford additional product, which was combined with the above pure sample and dissolved in 70 mL of 10% MeOH in DCM, followed by filtration. The filtrate was conc in vacuo. The residue was taken up in 40 mL of 10% MeOH in DCM. The mixture was conc n vacuo to about 10 mL. The suspension was diluted with 20 mL of MTBE, and then concentrated in vacuo to half volume. The mixture was again diluted with 20 mL of MTBE. The resulting suspension was filtered. The cake was washed with MTBE (3×15 mL). The solids were then dried under vacuum at 65° C. for 48 h to afford 5-(1-{[3-fluoro-5-(trifluoromethyl)phenyl]acetyl}-2,3-dihydro-1H-indol-5-yl)-7-methyl-7H-pyrrolo[2,3-d]pyrimidin-4-amine (2.026 g) as white solids. LC-MS (ES) m/z=470 [M+H]+. $^1$H NMR (400 MHz, DMSO-$d_6$) δ ppm 3.26 (t, J=8.3 Hz, 2H), 3.73 (s, 3H), 4.07 (s, 2H), 4.27 (t, J=8.5 Hz, 2H), 5.91-6.26 (br s, 1.4; H), 7.23 (d, J=8.3 Hz, 1H), 7.26 (s, 1H), 7.33 (s, 1H), 7.51 (d, J=9.6 Hz, 1H), 7.56-7.64 (m, 2H), 8.10 (d, J=8.3 Hz, 1H), 8.15 (s, 1H).

Example 97

7-[(methyloxy)methyl]-5-{1-[(3-methylphenyl)acetyl]-2,3-dihydro-1H-indol-5-yl}-7H-pyrrolo[2,3-d]pyrimidin-4-amine

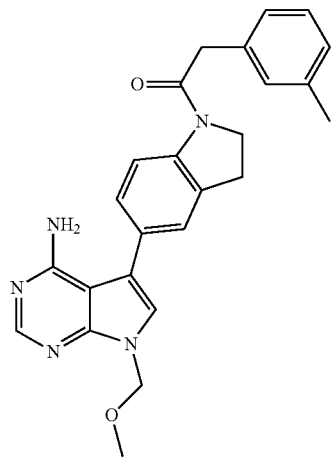 [SMILES: COCn1cc(-c2ccc3c(c2)CCN3C(=O)Cc2cccc(C)c2)c2c(N)ncnc21]

5-bromo-7-[(methyloxy)methyl]-7H-pyrrolo[2,3-d]pyrimidin-4-amine 5-bromo-4-chloro-7-[(methyloxy)methyl]-7H-pyrrolo[2,3-d]pyrimidine (200 mg, 0.723 mmol) was transferred to a 5 mL microwave vial and then ammonium hydroxide (1.5 mL, 38.5 mmol) was added. The mixture was heated in microwave reactor at 100° C. for 30 minutes. The solid was isolated by filtration and dried to give 5-bromo-7-[(methyloxy)methyl]-7H-pyrrolo[2,3-d]pyrimidin-4-amine (132 mg, 71.0% yield) as a white solid. LC-MS (ES) m/z=257.0, 259.0 [M+H]+. $^1$H NMR (400 MHz, DMSO-$d_6$) δ 8.14 (s, 1H), 7.56 (s, 1H), 6.81 (br. s., 2H), 5.43 (s, 2H), 3.21 (s, 3H).

7-[(methyloxy)methyl]-5-{1-[(3-methylphenyl)acetyl]-2,3-dihydro-1H-indol-5-yl}-7H-pyrrolo[2,3-d]pyrimidin-4-amine To 5-bromo-7-[(methyloxy)methyl]-7H-pyrrolo[2,3-d]pyrimidin-4-amine (65 mg, 0.253 mmol), and 1-[(3-methylphenyl)acetyl]-5-(4,4,5,5-tetramethyl-1,3,2-dioxaborolan-2-yl)-2,3-dihydro-1H-indole (114 mg, 0.303 mmol) were dissolved in 1,4-Dioxane (2 mL) was added saturated NaHCO3 (1 mL). The mixture was then bubbled N2 gas for 10 min then added Pd(Ph3P)4 (29.2 mg, 0.025 mmol) then bubbled for 5 additional minutes. The reaction was then capped and heated at 100° C. overnight. The mixture cooled then diluted with water (10 mL) and extracted with EtOAc (3×20 ml). The organics were combined, washed with brine, dried over MgSo4, filtered and concentrated to afford an amber color oil. The oil was then purified on a 10 g Biotage SNAP column conditioned with Hexane using a gradient of 0 to 10% MeOH in DCM for 30 minutes to isolate 7-[(methyloxy)methyl]-5-{1-[(3-methylphenyl)acetyl]-2,3-dihydro-1H-indol-5-yl}-7H-pyrrolo[2,3-d]pyrimidin-4-amine (36 mg) as a white solid. LC-MS (ES) m/z=428.4 [M+H]+. $^1$H NMR (400 MHz, DMSO-$d_6$) δ 8.17 (s, 1H), 8.15 (d, J=8.34 Hz, 1H), 7.37 (s, 1H), 7.32-7.35 (m, 1H), 7.24 (dd, J=7.33, 14.65 Hz, 2H), 7.06-7.15 (m, 3H), 6.15 (br. s., 2H), 5.50 (s, 2H), 4.21 (s, 2H), 3.83 (s, 2H), 3.25 (s, 3H), 3.19-3.25 (m, 2H), 2.31 (s, 3H).

Example 98

7-methyl-5-{1-[(1-methyl-1H-pyrrol-2-yl)acetyl]-2,3-dihydro-1H-indol-5-yl}-7H-pyrrolo[2,3-d]pyrimidin-4-amine

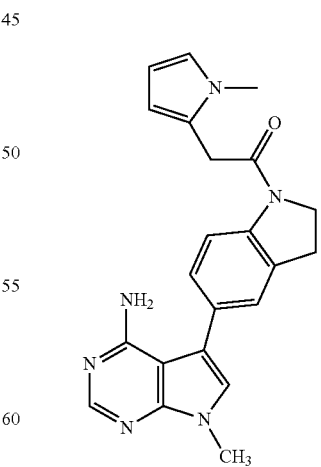

A solution of 5-(2,3-dihydro-1H-indol-5-yl)-7-methyl-7H-pyrrolo[2,3-d]pyrimidin-4-amine 2HCl (250 mg, 0.739 mmol), 5-(2,3-dihydro-1H-indol-5-yl)-7-methyl-7H-pyrrolo[2,3-d]pyrimidin-4-amine.2HCl (250 mg, 0.739 mmol), HATU (281 mg, 0.739 mmol), DIEA (0.516 mL, 2.96 mmol) was stirred at room temperature overnight. The reaction mixture was poured into 20 mL water and stirred for 30 mins. The grey precipitate was filtered, washed with water (10 mL) and dried for an hour at the pump. The residue was adsorbed onto silica and purified by flash chromatography (0-10% MeOH in DCM, 24-g column) to afford 7-methyl-5-{1-[(1-methyl-1H-pyrrol-2-yl)acetyl]-2,3-dihydro-1H-indol-5-yl}-7H-pyrrolo[2,3-d]pyrimidin-4-amine (128 mg, 44.8% yield) as a white solid. LC-MS (ES) m/z=387 [M+H]$^+$. $^1$H NMR (400 MHz, DMSO-$d_6$) δ 3.23 (t, J=8.34 Hz, 2H), 3.54 (s, 3H), 3.73 (s, 3H), 3.86 (s, 2H), 4.25 (t, J=8.59 Hz, 2H), 5.84-5.94 (m, 2H), 5.94-6.32 (m, 2H), 6.68 (t, J=2.15 Hz, 1H), 7.14-7.29 (m, 2H), 7.31 (s, 1H), 8.08-8.20 (m, 2H). An additional crop of material was obtained from crystals observed in the filtrate after standing overnight. The liquid was filtered and the residue washed with water and dried at the pump to yield a second crop of 7-methyl-5-{1-[(1-methyl-1H-pyrrol-2-yl)acetyl]-2,3-dihydro-1H-indol-5-yl}-7H-pyrrolo[2,3-d]pyrimidin-4-amine (65 mg, 22.76% yield) as a beige solid.

Example 99

5-{1-[(2,5-difluorophenyl)acetyl]-2,3-dihydro-1H-indol-5-yl}-7-(1-methylethyl)-7H-pyrrolo[2,3-d]pyrimidin-4-amine

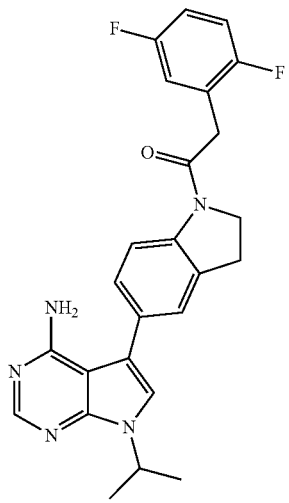 [SMILES: CC(C)n1cc(-c2ccc3c(c2)CCN3C(=O)Cc2cc(F)ccc2F)c2c(N)ncnc21]

To 5-bromo-7-(1-methylethyl)-7H-pyrrolo[2,3-d]pyrimidin-4-amine (100 mg, 0.392 mmol) and 1-[(2,5-difluorophenyl)acetyl]-5-(4,4,5,5-tetramethyl-1,3,2-dioxaborolan-2-yl)-2,3-dihydro-1H-indole (188 mg, 0.470 mmol) was added 1,4-Dioxane (2 mL) and saturated NaHCO3 (1 mL) in a 5 ml sealable vial. The mixture was then bubbled with N2 for 10 minutes then Pd(Ph3P)4 (45.3 mg, 0.039 mmol) was added and bubbled for an additional 5 minutes. It was then capped and heated at 100° C. overnight. The reaction was then checked with LCMS and 10% of the bromide starting material remained. 50 mg of the boronic ester was added, and the reaction was capped and heated at 100° C. for an additional 5 hr. The reaction was diluted with water (5 ml) then extracted with EtOAc (3×10 ml). The organics wer combined, washed with brine and dried over MgSO4, filtered and concentrated. The residual oil was then diluted with DMSO (3 mL) then purified on HPLC: (HPLC condition: Gilson using Trilution software with a Sunfire 5u C18(2) 100A. 50×30.00 mm 5 micron. 7.3-minute run (47 ml/min, 28% ACN/H2O, 0.1% TFA to 53%ACN/H2O, 0.1% TFA) with UV detection at 254 nm). Product fractions were combined and the volume was reduced to remove most of the MeCN. To the water left behind was added saturated NaHCO3 and then the mixture was extracted with EtOAc (3×15 mL). The organics were combined and washed with saturated NaCl solution, dried over MgSO4, filtered and concentrated. The product was transferred into a 40 mL vial with MeCN then added water and freeze-dried to isolate 5-{1-[(2,5-difluorophenyl)acetyl]-2,3-dihydro-1H-indol-5-yl}-7-(1-methylethyl)-7H-pyrrolo[2,3-d]pyrimidin-4-amine (76 mgt, 43.3% yield) as a white solid. LC-MS (ES) m/z=448.4 [M+H]$^+$ $^1$H NMR (400 MHz, DMSO-$d_6$) δ 8.13 (s, 1H), 8.09 (d, J=8.08 Hz, 1H), 7.42 (s, 1H), 7.36 (s, 1H), 7.14-7.30 (m, 4H), 6.08 (br. s., 2H), 4.97 (quin, J=6.76 Hz, 1H), 4.29 (t, J=8.46 Hz, 2H), 3.95 (s, 2H), 3.27 (t, J=8.46 Hz, 2H), 1.46 (d, J=6.82 Hz, 6H).

Example 100

5-{1-[(5-chloro-2-fluorophenyl)acetyl]-2,3-dihydro-1H-indol-5-yl}-7-methyl-7H-pyrrolo[2,3-d]pyrimidin-4-amine

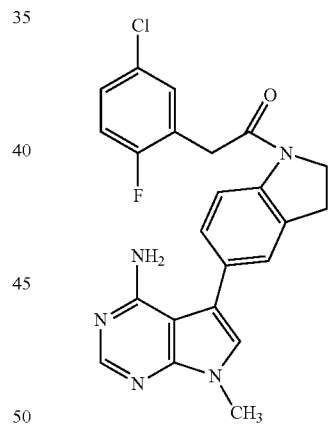

In a 20 mL vial with cap, to the solution of 5-(2,3-dihydro-1H-indol-5-yl)-7-methyl-7H-pyrrolo[2,3-d]pyrimidin-4-amine HCl (70 mg, 0.232 mmol), (5-chloro-2-fluorophenyl) acetic acid (44.2 mg, 0.234 mmol), and HATU (89 mg, 0.234 mmol) in DMF (2 mL) was added Hunig's base (0.162 mL, 0.928 mmol). The mixture was stirred overnight. The reaction was poured into water (100 mL), and an off-white solid was formed. The solid was filtered, washed with water (10 mL), and dried to afford the title compound as an off-white solid. LC-MS (ES) m/z=436.4 [M+H]$^+$ $^1$H NMR (400 MHz, DMSO-$d_6$) δ ppm 3.22-3.30 (m, 2H), 3.74 (s, 3H), 3.96 (s, 2H), 4.25-4.32 (m, 2H), 7.21-7.28 (m, 2H), 7.30 (s, 1H), 7.33 (s, 1H), 7.39-7.44 (m, 1H), 7.47 (dd, J=6.32, 2.78 Hz, 1H), 8.08 (d, J=8.34 Hz, 1H), 8.15 (s, 1H).

Example 101

5-{1-[(2,5-difluorophenyl)acetyl]-2,3-dihydro-1H-indol-5-yl}-7-[2-(4-morpholinyl)ethyl]-7H-pyrrolo[2,3-d]pyrimidin-4-amine

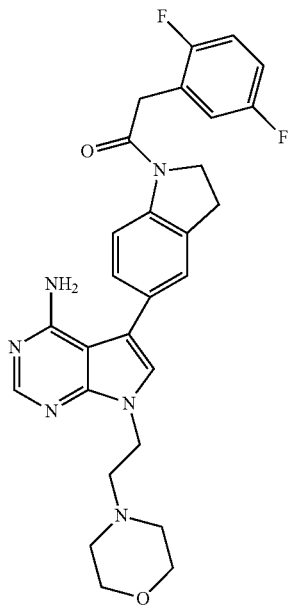 [SMILES: Nc1ncnc2c1c(-c1ccc3c(c1)CCN3C(=O)Cc1cc(F)ccc1F)cn2CCN1CCOCC1]

5-bromo-4-chloro-7-[2-(4-morpholinyl)ethyl]-7H-pyrrolo[2,3-d]pyrimidine

To 5-bromo-4-chloro-1H-pyrrolo[2,3-d]pyrimidine (200 mg, 0.860 mmol), 2-(4-morpholinyl)ethanol (0.316 mL, 2.58 mmol) and triphenylphosphine (451 mg, 1.721 mmol) was added Tetrahydrofuran (THF) (5 mL). To the reaction was then added by dropwise DEAD (0.272 mL, 1.721 mmol). The solution was then let stir overnight at room temperature. The reaction was then concentrated and diluted with water (10 ml) then extracted by EtOAc (3×10 ml). The organics were combined, washed with brine, dried over MgSO4, filtered and concentrated. The yellow crude residue was then loaded onto a 25 g Biotage SNAP column and purified with 0 to 8% MeOH in DCM gradient over 30 minutes to afford 5-bromo-4-chloro-7-[2-(4-morpholinyl)ethyl]-7H-pyrrolo[2,3-d]pyrimidine (245 mg, 82% yield) as a light yellow solid. LC-MS (ES) m/z=347.2 [M+H]$^+$ $^1$H NMR (400 MHz, DMSO-d$_6$) δ 8.67 (s, 1H), 8.05 (s, 1H), 4.39 (t, J=6.19 Hz, 2H), 3.48 (t, J=4.29 Hz, 4H), 2.71 (t, J=6.32 Hz, 2H), 2.42 (br. s., 4H).

5-bromo-7-[2-(4-morpholinyl)ethyl]-7H-pyrrolo[2,3-d]pyrimidin-4-amine

To 5-bromo-4-chloro-7-[2-(4-morpholinyl)ethyl]-7H-pyrrolo[2,3-d]pyrimidine (240 mg, 0.694 mmol) in a 5 mL sealable vial was added ammonium hydroxide (1.5 mL, 38.5 mmol). The reaction vial was capped and heated at 100° C. overnight. The reaction was cooled and solid formed. The solid was isolated by filtration and the solid was washed with NH4OH. The solid was air dried to isolated the desired product 5-bromo-7-[2-(4-morpholinyl)ethyl]-7H-pyrrolo[2,3-d]pyrimidin-4-amine (154 mg, 68.0% yield) as an off white solid. LC-MS (ES) m/z=326.1 [M+H]$^+$ $^1$H NMR (400 MHz, DMSO-d$_6$) 8.10 (s, 1H), 7.47 (s, 1H), 6.69 (br. s., 2H), 4.22 (t, J=6.44 Hz, 2H), 3.52 (t, J=4.42 Hz, 4H), 2.65 (t, J=6.44 Hz, 2H), 2.41 (d, J=4.04 Hz, 4H).

5-{1-[(2,5-difluorophenyl)acetyl]-2,3-dihydro-1H-indol-5-yl}-7-[2-(4-morpholinyl)ethyl]-7H-pyrrolo[2,3-d]pyrimidin-4-amine To 5-bromo-7-[2-(4-morpholinyl)ethyl]-7H-pyrrolo[2,3-d]pyrimidin-4-amine (100 mg, 0.307 mmol), 1-[(2,5-difluorophenyl)acetyl]-5-(4,4,5,5-tetramethyl-1,3,2-dioxaborolan-2-yl)-2,3-dihydro-1H-indole (159 mg, 0.399 mmol) in a 5 ml sealable vial was added 1,4-Dioxane (2 mL) and saturated NaHCO3 (1 mL). The mixture was then bubbled with N2 gas for 10 minutes then Pd(Ph3P)4 (35.4 mg, 0.031 mmol) was added. The mixture was again bubbled N2 gas for 5 minutes then capped and the reaction was heated at 100° C. overnight. The reaction was diluted with water (3 ml) then extracted with EtOAc (3×5 ml). The organics were then combined and washed with brine, dried over MgSO4, filtered and concentrated. The residue was then dissolved in 3 ml of DMSO and purified on HPLC: (HPLC condition: Gilson using Trilution software with a Sunfire 5u C18(2) 100A. 50×30.00 mm 5 micron. 7.3-minute run (47 ml/min, 7% ACN/H2O, 0.1% TFA to 32% ACN/H2O, 0.1% TFA) with UV detection at 254 nm). Product fractions were combined and the volume was reduced to remove most of the MeCN. To the water left behind was added saturated NaHCO3 and then extracted with EtOAc (3×15 mL). The organic was combined wash with saturated NaCl solution, dried over MgSO4, filtered and concentrated. Then it was transferred into a 40 mL vial with MeCN then added water and freeze-dried to isolated 5-{1-[(2,5-difluorophenyl)acetyl]-2,3-dihydro-1H-indol-5-yl}-7-[2-(4-morpholinyl)ethyl]-7H-pyrrolo[2,3-d]pyrimidin-4-amine (76 mg, 47.8% yield) as a white solid. LC-MS (ES) m/z=519.5 [M+H]$^+$.

Example 102

5-{1-[(2,4-difluorophenyl)acetyl]-2,3-dihydro-1H-indol-5-yl}-7-methyl-7H-pyrrolo[2,3-d]pyrimidin-4-amine

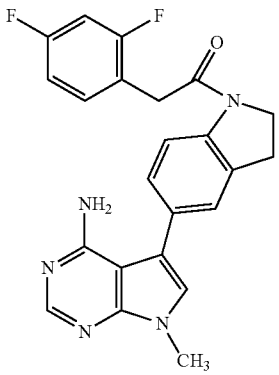 [SMILES: Cn1cc(-c2ccc3c(c2)CCN3C(=O)Cc2ccc(F)cc2F)c2c(N)ncnc21]

In a 20 mL vial with cap, to the solution of 5-(2,3-dihydro-1H-indol-5-yl)-7-methyl-7H-pyrrolo[2,3-d]pyrimidin-4-amineHCl (71 mg, 0.235 mmol), (2,4-difluorophenyl)acetic acid (40.9 mg, 0.238 mmol), and HATU (90 mg, 0.238 mmol) in DMF (2 mL) was added Hunig's base (0.164 mL, 0.941 mmol). The mixture was stirred overnight. The reaction was poured into water (100 mL), and an off-white solid was formed. The solid was filtered, washed with water (10 mL), and dried to afford the title compound as an off-white solid. LC-MS (ES) m/z=420.4 [M+H]$^+$. $^1$H NMR (400 MHz, DMSO-d$_6$) δ ppm 3.26 (t, J=8.34 Hz, 2H), 3.73 (s, 3H), 3.92 (s, 2H), 4.28 (t, J=8.46 Hz, 2H), 7.08-7.09 (m, 1H), 7.20-7.28 (m, 3H), 7.33 (s, 1H), 7.40 (d, J=7.58 Hz, 1H), 8.08 (d, J=8.34 Hz, 1H), 8.15 (s, 1H).

Example 103

5-{1-[(3,4-difluorophenyl)acetyl]-2,3-dihydro-1H-indol-5-yl}-7-methyl-7H-pyrrolo[2,3-d]pyrimidin-4-amine

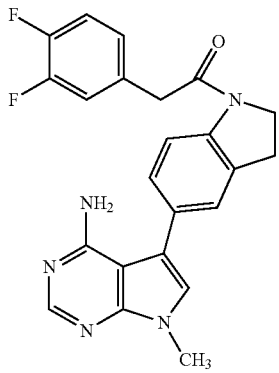 [SMILES: Cn1cc(-c2ccc3c(c2)CCN3C(=O)Cc2ccc(F)c(F)c2)c2c(N)ncnc21]

In a 20 mL vial with cap, to the solution of 5-(2,3-dihydro-1H-indol-5-yl)-7-methyl-7H-pyrrolo[2,3-d]pyrimidin-4-amineHCl (70 mg, 0.232 mmol), (3,4-difluorophenyl)acetic acid (39.9 mg, 0.232 mmol), and HATU (89 mg, 0.234 mmol) in DMF (2 mL) was added Hunig's base (0.162 mL, 0.928 mmol). The mixture was stirred overnight. The reaction was poured into water (100 mL), and an off-white solid was formed. The solid was filtered, washed with water (10 mL), and dried to afford the title compound as an off-white solid. LC-MS (ES) m/z=420.4 [M+H]$^+$. $^1$H NMR (400 MHz, DMSO-d$_6$) δ ppm 3.21-3.28 (m, 2H), 3.73 (s, 3H), 3.91 (s, 2H), 4.24 (t, J=8.21 Hz, 2H), 7.15 (s, 1H), 7.21-7.28 (m, 2H), 7.32 (s, 1H), 7.34-7.42 (m, 2H), 8.12-8.15 (m, 2H).

Example 104 phenylmethyl[2-(4-amino-3-{1-[(2,5-difluorophenyl)acetyl]-2,3-dihydro-1H-indol-5-yl}furo[3,2-c]pyridin-7-yl)ethyl]carbamate

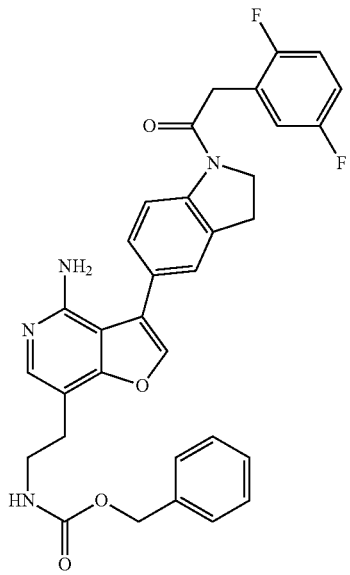 [SMILES: Nc1ncc(CCNC(=O)OCc2ccccc2)c2occ(-c3ccc4c(c3)CCN4C(=O)Cc3cc(F)ccc3F)c12]

bis(1,1-dimethylethyl) (3-{1-[(2,5-difluorophenyl)acetyl]-2,3-dihydro-1H-indol-5-yl}-7-iodofuro[3,2-c]pyridin-4-yl)imidodicarbonate A mixture of 3-{1-[(2,5-difluorophenyl)acetyl]-2,3-dihydro-1H-indol-5-yl}-7-iodofuro[3,2-c]pyridin-4-amine (1.652 g, 2.488 mmol), Boc2O (4.06 mL, 17.48 mmol), triethylamine (2.42 mL, 17.46 mmol), and DMAP (0.017 g, 0.139 mmol) in Dichloromethane (DCM) (25 mL) was stirred at room temperature under Nitrogen for 17 hours. LCMS indicated only about 50% conversion, so another portion of Boc2O (4.06 mL, 17.48 mmol) was added, and stirring continued for 3 days (weekend). The reaction mixture was then concentrated in vacuo and the residue was purified by flash chromatography (Analogix, 90 g SiO2, 5%-30% EtOAc in hexanes gradient over 50 minutes) to give bis(1,1-dimethylethyl) (3-{1-[(2,5-difluorophenyl)acetyl]-2,3-dihydro-1H-indol-5-yl}-7-iodofuro[3,2-c]pyridin-4-yl)imidodicarbonate (749 mg, 1.024 mmol, 41.2% yield) as a yellow foam. LC/MS (ES) m/z=732 [M+H]+.

bis(1,1-dimethylethyl) {3-{1-[(2,5-difluorophenyl)acetyl]-2,3-dihydro-1H-indol-5-yl}-7-[2-({[(phenylmethyl)oxy]carbonyl}amino)ethyl]furo[3,2-c]pyridin-4-yl}imidodicarbonate A mixture of bis(1,1-dimethylethyl) (3-{1-[(2,5-difluorophenyl)acetyl]-2,3-dihydro-1H-indol-5-yl}-7-iodofuro[3,2-c]pyridin-4-yl)imidodicarbonate (302 mg, 0.413 mmol), potassium benzyl-N-[2-(trifluoroboranuidyl)ethyl]carbamate (90 mg, 0.316 mmol), palladium(II) acetate (9 mg, 0.040 mmol), RuPhos (38 mg, 0.081 mmol), and cesium carbonate (403 mg, 1.237 mmol) in Toluene (3 mL) and Water (1 mL) was degassed with Nitrogen for 10 minutes. The 25 mL vial was then capped and it was stirred vigorously at 95° C. for 16 hours. LCMS showed complete consumption of starting material and good conversion to the desired product, along with a 23% peak corresponding to the de-iodo byproduct. It was cooled, diluted with ethyl acetate (15 mL), and washed with a mixture of water (5 mL) and saturated aqueous NaHCO3 (10 mL). The aqueous phase was back-extracted with EtOAc (15 mL), and the combined organic phases were washed with brine (1×15 mL), dried (Na2SO4), filtered, and concentrated in vacuo. The residue was purified by flash chromatography (Analogix, 40 g SiO2, 5%-70% EtOAc in hexanes gradient over 55 minutes) to give bis(1,1-dimethylethyl) {3-{1-[(2,5-difluorophenyl)acetyl]-2,3-dihydro-1H-indol-5-yl}-7-[2-({[(phenylmethyl)oxy]carbonyl}amino)ethyl]furo[3,2-c]pyridin-4-yl}imidodicarbonate (149 mg, 0.190 mmol, 46.1% yield) as an off-white foam. LC/MS (ES) m/z=783.9 [M+H]$^+$.

phenylmethyl[2-(4-amino-3-{1-[(2,5-difluorophenyl)acetyl]-2,3-dihydro-1H-indol-5-yl}furo[3,2-c]pyridin-7-yl)ethyl]carbamate A mixture of bis(1,1-dimethylethyl) {3-{1-[(2,5-difluorophenyl)acetyl]-2,3-dihydro-1H-indol-5-yl}-7-[2-({[(phenylmethyl)oxy]carbonyl}amino)ethyl]furo[3,2-c]pyridin-4-yl}imidodicarbonate (149 mg, 0.190 mmol) and 4.0 M HCl in dioxane (2.0 mL, 8.00 mmol) was stirred at room temperature under Nitrogen for 4 hr. The crude reaction mixture was then concentrated in vacuo and azeotroped once with acetonitrile. The residue was taken up in DCM and passed through a PL-HCO3 MP-resin cartridge, rinsing with more DCM. The filtrate was then concentrated in vacuo to give the free base of phenylmethyl[2-(4-amino-3-{1-[(2,5-difluorophenyl)

acetyl]-2,3-dihydro-1H-indol-5-yl}furo[3,2-c]pyridin-7-yl) ethyl]carbamate (105 mg, 0.162 mmol, 85% yield) as an off-white foam (purity estimated at 90%). LC/MS (ES) m/z=583.6 [M+H]+. $^1$H NMR (400 MHz, DMSO-d$_6$) d 2.86 (t, J=7.07 Hz, 2H), 3.22-3.34 (m, 4H), 3.96 (s, 2H), 4.31 (t, J=8.34 Hz, 2H), 5.02 (s, 2H), 5.38 (s, 2H), 7.14-7.44 (m, 12H), 7.68 (s, 1H), 7.93 (s, 1H), 8.12 (d, J=8.34 Hz, 1H).

Example 105

5-{1-[(2,5-difluorophenyl)acetyl]-2,3-dihydro-1H-indol-5-yl}-7-(3-methylbutyl)-7H-pyrrolo[2,3-d]pyrimidin-4-amine

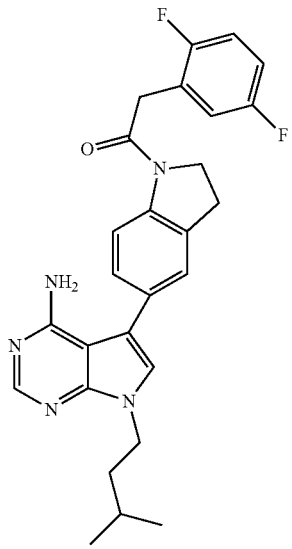 [SMILES: CC(C)CCn1cc(-c2ccc3c(c2)CCN3C(=O)Cc2cc(F)ccc2F)c2c(N)ncnc21]

5-bromo-7-(3-methylbutyl)-7H-pyrrolo[2,3-d]pyrimidin-4-amine

To 5-bromo-4-chloro-7-(3-methylbutyl)-7H-pyrrolo[2,3-d]pyrimidine (210 mg, 0.694 mmol) in a 5 mL sealable vial was added ammonium hydroxide (1.5 mL, 38.5 mmol). The mixture was then capped and heated at room temp overnight. The reaction was cooled and a precipitate formed. The solid was isolated by filtration and air dried to isolated 5-bromo-7-(3-methylbutyl)-7H-pyrrolo[2,3-d]pyrimidin-4-amine (191 mg, 0.675 mmol, 97% yield) as a light brown solid. For 50-A1: LC/MS (ES) m/z=283.2, 285.2 [M+H]+. $^1$H NMR (400 MHz, DMSO-d$_6$) 8.10 (s, 1H), 7.48 (s, 1H), 6.70 (br. s., 2H), 4.12 (t, J=7.20 Hz, 2H), 1.64 (q, J=6.99 Hz, 2H), 1.44 (ddd, J=6.69, 6.82, 13.26 Hz, 1H), 0.90 (d, J=6.57 Hz, 6H).

1-[(2,5-difluorophenyl)acetyl]5-(4,4,5,5-tetramethyl-1,3,2-dioxaborolan-2-yl)-2,3-dihydro-1H-indole In a sealed tube, to 5-bromo-1-[(2,5-difluorophenyl) acetyl]-2,3-dihydro-1H-indole (3.5 g, 9.94 mmol), bis(pinacolato)diboron (3.03 g, 11.93 mmol) and potassium acetate (2.93 g, 29.8 mmol) was added 1,4-Dioxane (15 mL) and the mixture was degassed with N2 for 10 minutes. PdCl2(dppf)-CH2Cl2Adduct (0.406 g, 0.497 mmol) was added and the reaction mixture was stirred for 48 hours at 100° C. The mixture was cooled to room temperature. Ethyl acetate (300 mL) was poured onto the mixture, stirred, then filtered. The filtrate was poured into a separatory funnel. It was washed with brine, dried (MgSO4), filtered and concentrated. Puri-fied by Analogix silica Si90, gradient 0-40% EtOAc/hexane afforded 1-[(2,5-difluorophenyl)acetyl]-5-(4,4,5,5-tetramethyl-1,3,2-dioxaborolan-2-yl)-2,3-dihydro-1H-indole as a white solid (2.01 g). LC-MS (ES) m/z=400.3 [M+H]+.

5-{1-[(2,5-difluorophenyl)acetyl]-2,3-dihydro-1H-indol-5-yl}-7-(3-methylbutyl)-7H-pyrrolo[2,3-d]pyrimidin-4-amine To 5-bromo-7-(3-methylbutyl)-7H-pyrrolo[2,3-d]pyrimidin-4-amine (113 mg, 0.399 mmol), 1-[(2,5-difluorophenyl)acetyl]-5-(4,4,5,5-tetramethyl-1,3,2-dioxaborolan-2-yl)-2,3-dihydro-1H-indole (207 mg, 0.519 mmol) in a 5 ml sealable vial was added 1,4-Dioxane (2 mL) and saturated NaHCO3 (1 mL). The mixture was then bubbled with N2 gas for 10 min then Pd(Ph3P)4 (46.1 mg, 0.040 mmol) was added. The mixture was again bubbled N2 gas for 5 minutes then capped and the reaction was heated at 100° C. overnight. The reaction was diluted with water (3 ml) then extracted with EtOAc (3×mL). The organic swere combined and washed with brine, dried over Mg2SO4, filtered and concentrated. The resulting amber color oil was dissolved in 3 ml DMSO and purified by HPLC: (HPLC condition: Gilson using Trilution software with a Sunfire 5u C18(2) 100A. 50×30.00 mm 5 micron. 7.3-minute run (47 ml/min, 30% ACN/H2O, 0.1% TFA to 55% ACN/H2O, 0.1% TFA) with UV detection at 254 nm). Product fractions were combined and the volume was reduced to remove most of the MeCN. The water left behind was added to saturated NaHCO3 and then extracted with EtOAc (3×15 mL). The organic was combined wash with saturated NaCl solution, dried over MgSO4, filtered and concentrated. Then it was transferred into a 40 mL vial with MeCN then added water and freeze-dried to give 5-{1-[(2,5-difluorophenyl)acetyl]-2,3-dihydro-1H-indol-5-yl}-7-(3-methylbutyl)-7H-pyrrolo[2,3-d]pyrimidin-4-amine (58 mg, 30.6% yield) as a white solid. For 50-A1: LC/MS (ES) m/z=476.5 [M+H]+. $^1$H NMR (400 MHz, DMSO-d$_6$) δ 8.14 (s, 1H), 8.08 (d, J=8.34 Hz, 1H), 7.35 (s, 1H), 7.33 (s, 1H), 7.15-7.30 (m, 4H), 6.06 (br. s., 2H), 4.29 (t, J=8.34 Hz, 2H), 4.18 (t, J=7.20 Hz, 2H), 3.95 (s, 2H), 3.27 (t, J=8.46 Hz, 2H), 1.69 (q, J=7.07 Hz, 2H), 1.44-1.56 (m, 1H), 0.93 (d, J=6.57 Hz, 6H).

Example 106

5-{1-[(2,5-difluorophenyl)acetyl]-2,3-dihydro-1H-indol-5-yl}-7-[2-(dimethylamino)ethyl]-7H-pyrrolo[2,3-d]pyrimidin-4-amine

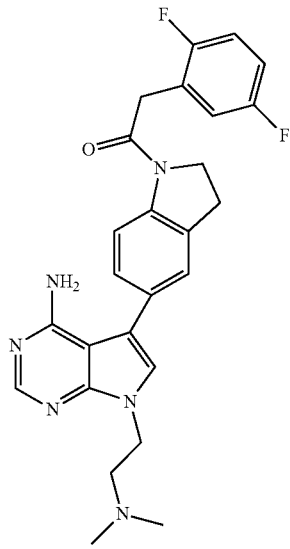 [SMILES: CN(C)CCn1cc(-c2ccc3c(c2)CCN3C(=O)Cc2cc(F)ccc2F)c2c(N)ncnc21]

[2-(5-bromo-4-chloro-7H-pyrrolo[2,3-d]pyrimidin-7-yl)ethyl]dimethylamine

To a solution of 5-bromo-4-chloro-1H-pyrrolo[2,3-d]pyrimidine (200 mg, 0.860 mmol), 2-(dimethylamino)ethanol (230 mg, 2.58 mmol) and triphenylphosphine (451 mg, 1.721 mmol) in Tetrahydrofuran (THF) (10 mL) was added dropwise DEAD (0.272 mL, 1.721 mmol). The solution was allowed to stir at room temperature. After 2 hr the reaction was concentrated then loaded on to a 25 g Biotage SNAP column and eluted with 0 to 8% MeOH in DCM gradient over 30 minutes to give [2-(5-bromo-4-chloro-7H-pyrrolo[2,3-d]pyrimidin-7-yl)ethyl]dimethylamine (175 mg, 67.0% yield) as a white solid. LC/MS (ES) m/z=303.1, 305.1 [M+H]+. 1H NMR (400 MHz, DMSO-d6) δ 8.67 (s, 1H), 8.04 (s, 1H), 4.36 (t, J=6.19 Hz, 2H), 2.67 (t, J=6.19 Hz, 2H), 2.16 (s, 6H).

5-bromo-7-[2-(dimethylamino)ethyl]-7H-pyrrolo[2,3-d]pyrimidin-4-amine

To [2-(5-bromo-4-chloro-7H-pyrrolo[2,3-d]pyrimidin-7-yl)ethyl]dimethylamine (175 mg, 0.576 mmol) was added ammonium hydroxide (22.45 µl, 0.576 mmol) in to a 5 ml sealable vial. The vial was then capped and heated at 100° C. overnight. The reaction was cooled to room temperature and concentrated to a light brown oil of 5-bromo-7-[2-(dimethylamino)ethyl]-7H-pyrrolo[2,3-d]pyrimidin-4-amine (190 mg, 0.669 mmol, 116% yield), which was used without further purification. LC/MS (ES) m/z=284.1 [M+H]+. 1H NMR (400 MHz, DMSO-d6) δ 8.14 (s, 1H), 7.53 (s, 1H), 6.82 (br. s., 2H), 4.48 (t, J=6.32 Hz, 2H), 3.41 (br. s., 2H), 2.71 (s, 6H).

5-{1-[(2,5-difluorophenyl)acetyl]-2,3-dihydro-1H-indol-5-yl}-7-[2-(dimethylamino)ethyl]-7H-pyrrolo[2,3-d]pyrimidin-4-amine To 5-bromo-7-[2-(dimethylamino)ethyl]-7H-pyrrolo[2,3-d]pyrimidin-4-amine (100 mg, 0.352 mmol), 1-[(2,5-difluorophenyl)acetyl]-5-(4,4,5,5-tetramethyl-1,3,2-dioxaborolan-2-yl)-2,3-dihydro-1H-indole (183 mg, 0.457 mmol) in a 5 ml sealable vial was added 1,4-Dioxane (2 mL) and saturated NaHCO3 (1 mL). The mixture was then bubbled N2 gas for 10 minutes then Pd(Ph3P)4 (40.7 mg, 0.035 mmol) was added. The mixture was again bubbled N2 gas for 5 minutes then capped and the reaction was heated at 100° C. overnight. The reaction was diluted with water (3 ml) then extracted with EtOAc (3×mL). The organics were combined and washed with brine, dried over Mg2SO4, filtered and concentrated. The resulting amber color oil was dissolved in 3 mL of DMSO and purified by HPLC: (HPLC condition: Gilson using Trilution software with a Sunfire 5u C18(2) 100A. 50×30.00 mm 5 micron. 7.3-minute run (47 ml/min, 7% ACN/H2O, 0.1% TFA to 37% ACN/H2O, 0.1% TFA) with UV detection at 254 nm). Product fractions were combined and the volume was reduced to remove most of the MeCN. The water left behind was added to saturated NaHCO3 and then extracted with EtOAc (3×15 mL). The organic was combined wash with saturated NaCl solution, dried over MgSO4, filtered and concentrated. Then it was transferred into a 40 mL vial with MeCN then added water and freeze-dried to give 5-{1-[(2,5-difluorophenyl)acetyl]-2,3-dihydro-1H-indol-5-yl}-7-[2-(dimethylamino)ethyl]-7H-pyrrolo[2,3-d]pyrimidin-4-amine (35 mg). LC/MS (ES) m/z=477.5 [M+H]+. 1H NMR (400 MHz, DMSO-d6) δ 8.14 (s, 1H), 8.09 (d, J=8.08 Hz, 1H), 7.33 (s, 2H), 7.15-7.30 (m, 4H), 6.06 (br. s., 2H), 4.24-4.33 (m, 4H), 3.95 (s, 2H), 3.24-3.30 (m, 2H), 2.72 (br. s., 2H), 2.24 (br. s., 6H).

Example 107

5-{1-[(6-chloro-2-pyridinyl)acetyl]-2,3-dihydro-1H-indol-5-yl}-7-methyl-7H-pyrrolo[2,3-d]pyrimidin-4-amine

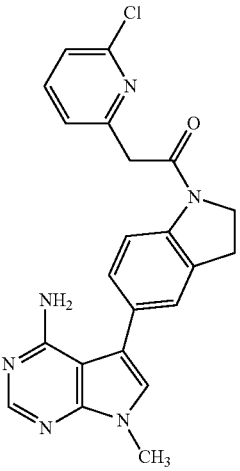 [SMILES: Cn1cc(-c2ccc3c(c2)CCN3C(=O)Cc2cccc(Cl)n2)c2c(N)ncnc21]

A solution of 5-(2,3-dihydro-1H-indol-5-yl)-7-methyl-7H-pyrrolo[2,3-d]pyrimidin-4-amine 2HCl (150 mg, 0.443 mmol), (6-chloro-2-pyridinyl)acetic acid (76 mg, 0.443 mmol), HATU (169 mg, 0.443 mmol), DIEA (0.310 mL, 1.774 mmol) was stirred at room temperature overnight. The resulting suspension was poured into water (10 mL) and stirred for 30 min. The resulting precipitate was collected by filtration, and the residue was washed with water (10 mL), dried at the pump for ca. 1 hour. The solid residue was dissolved in acetone and adsorbed onto silica and purified by flash chromatography (0-10% MeOH in EtOAc) to afford 5-{1-[(6-chloro-2-pyridinyl)acetyl]-2,3-dihydro-1H-indol-5-yl}-7-methyl-7H-pyrrolo[2,3-d]pyrimidin-4-amine (99.8 mg, 53.7% yield) as a beige solid. LC-MS (ES) m/z=419 [M+H]+. 1H NMR (400 MHz, DMSO-d6) δ 3.25 (t, J=8.34 Hz, 2H), 3.74 (s, 3H), 4.08 (s, 2H), 4.27 (t, J=8.46 Hz, 2H), 5.92-6.22 (m, 2H), 7.20-7.28 (m, 2H), 7.33 (s, 1H), 7.38-7.46 (m, 2H), 7.87 (t, J=7.83 Hz, 1H), 8.10 (d, J=8.34 Hz, 1H), 8.15 (s, 1H).

Example 108

3-{1-[(3-chloro-2,4-difluorophenyl)acetyl]-2,3-dihydro-1H-indol-5-yl}-1-methyl-1H-pyrazolo[3,4-d]pyrimidin-4-amine

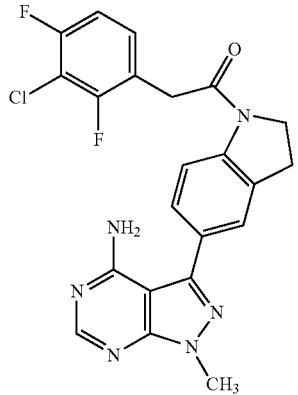 [SMILES: Cn1nc(-c2ccc3c(c2)CCN3C(=O)Cc2ccc(F)c(Cl)c2F)c2c(N)ncnc21]

In a 20 mL vial with cap, to a solution of 3-(2,3-dihydro-1H-indol-5-yl)-1-methyl-1H-pyrazolo[3,4-d]pyrimidin-4-amine HCl (70 mg, 0.231 mmol), (3-chloro-2,4-difluorophenyl)acetic acid (47.8 mg 0.231 mmol), and HATU (88 mg, 0.231 mmol) in DMF (2 mL) was added Hunig's base (0.162 mL, 0.925 mmol). The mixture was stirred overnight. The reaction was poured into water (100 mL), and an off-white solid was formed. The solid was filtered, washed with water (10 mL), and dried to afford the title compound as an off-white solid. LC-MS (ES) m/z=455.4 [M+H]$^+$. $^1$H NMR (400 MHz, DMSO-$d_6$) δ ppm 3.24-3.31 (m, 2H), 3.94 (s, 3H), 4.03 (s, 2H), 4.32 (t, J=8.46 Hz, 2H), 7.30-7.36 (m, 1H), 7.39-7.46 (m, 2H), 7.54 (s, 1H), 8.14 (d, J=8.34 Hz, 1H), 8.25 (s, 1H).

Example 109

7-(2-aminoethyl)-3-{1-[(2,5-difluorophenyl)acetyl]-2,3-dihydro-1H-indol-5-yl}furo[3,2-c]pyridin-4-amine

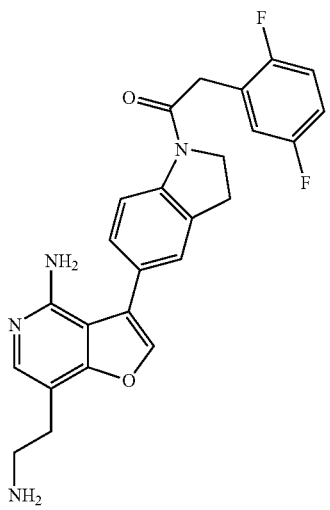 [SMILES: NCCc1cnc(N)c2c(-c3ccc4c(c3)CCN4C(=O)Cc3cc(F)ccc3F)coc12]

A suspension of phenylmethyl[2-(4-amino-3-{1-[(2,5-difluorophenyl)acetyl]-2,3-dihydro-1H-indol-5-yl}furo[3,2-c]pyridin-7-yl)ethyl]carbamate (91 mg, 0.156 mmol) and Pd/C (10 wt. % dry basis), wet (ca. 50% water), Degussa type E101 NE/W (27 mg, 0.013 mmol) in Ethanol (1 mL) and Tetrahydrofuran (THF) (5 mL) was stirred under an atmosphere of hydrogen for 3 hours. LCMS showed no conversion, and it appeared that the starting material was not very soluble in the reaction mixture. Some N,N-Dimethylformamide (DMF) (2 mL) was added along with another portion of Pd/C (10 wt. % dry basis), wet (ca. 50% water), Degussa type E101 NE/W (65 mg, 0.031 mmol), and the mixture was stirred under an atmosphere of hydrogen for another 19 hours. LCMS showed a mixture of product and a byproduct. The mixture was filtered and the filtrate was concentrated in vacuo. An attempt was made to convert the byproduct to the desired product by taking the mixture up in MeOH (ca. 10 mL), adding 2 M HCl (ca. 1 mL), and stirring at room temperature for 5 hours. No reaction was observed, so it was heated to 50° C. for another 16 hours. HPLC still showed no conversion, so the mixture was concentrated in vacuo. The residue was taken up in MeOH (1.5 mL) and purified by reverse phase HPLC (Gilson, C18, 20% to 27% CH3CN in water with 0.1% TFA, 8 minute gradient). The product fractions were concentrated in vacuo and azeotroped with acetonitrile three times. The residue was then taken up in DCM and passed through a Varian PL-HCO3 MP-resin cartridge, rinsing with more DCM. The filtrate was then concentrated in vacuo and dried in the vacuum oven overnight to give the free base of 7-(2-aminoethyl)-3-{1-[(2,5-difluorophenyl)acetyl]-2,3-dihydro-1H-indol-5-yl}furo[3,2-c]pyridin-4-amine (18 mg, 24.41% yield) as a white solid. LC/MS (ES) m/z=449 [M+H]+. $^1$H NMR (400 MHz, DMSO-$d_6$) d 1.53 (br. s., 2H), 2.72-2.79 (m, 2H), 2.79-2.86 (m, 2H), 3.28 (t, J=8.34 Hz, 2H), 3.96 (s, 2H), 4.30 (t, J=8.59 Hz, 2H), 5.33 (s, 2H), 7.14-7.33 (m, 4H), 7.41 (s, 1H), 7.69 (s, 1H), 7.93 (s, 1H), 8.12 (d, J=8.34 Hz, 1H).

Example 110

4-amino-3-{1-[(2,5-difluorophenyl)acetyl]-2,3-dihydro-1H-indol-5-yl}furo[3,2-c]pyridine-7-carbonitrile

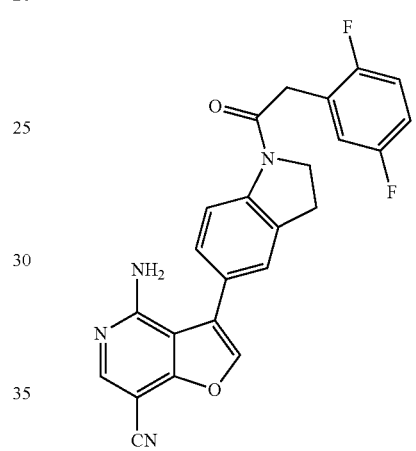

bis(1,1-dimethylethyl) (7-cyano-3-{1-[(2,5-difluorophenyl)acetyl]-2,3-dihydro-1H-indol-5-yl}furo[3,2-c]pyridin-4-yl)imidodicarbonate A mixture of bis(1,1-dimethylethyl) (3-{1-[(2,5-difluorophenyl)acetyl]-2,3-dihydro-1H-indol-5-yl}-7-iodofuro[3,2-c]pyridin-4-yl)imidodicarbonate (391 mg, 0.534 mmol), zinc (II) cyanide (83 mg, 0.707 mmol), and tetrakis(triphenylphosphine)palladium(0) (30 mg, 0.026 mmol) in N,N-Dimethylformamide (DMF) (4 mL) was degassed with Nitrogen for 10 minutes. The vial was then capped and it was stirred at 120° C. in the microwave reactor for 30 minutes. The crude reaction mixture was combined with the crude reaction mixture from an identical small-scale test reaction, diluted with EtOAc (25 mL), washed with half-saturated aqueous NaHCO3 (2×25 mL), dried (Na2SO4), filtered, and concentrated in vacuo to give an orange oil (331 mg). LCMS indicated a mixture of the bis(1,1-dimethylethyl) (7-cyano-3-{1-[(2,5-difluorophenyl)acetyl]-2,3-dihydro-1H-indol-5-yl}furo[3,2-c]pyridin-4-yl)imidodicarbonate and the non-Boc product (ca. 3:2). The mixture was used without further purification.

4-amino-3-{1-[(2,5-difluorophenyl)acetyl]-2,3-dihydro-1H-indol-5-yl}furo[3,2-c]pyridine-7-carbonitrile A mixture of bis(1,1-dimethylethyl) (7-cyano-3-{1-[(2,5-difluorophenyl)acetyl]-2,3-dihydro-1H-indol-5-yl}furo[3,2- c]pyridin-4-yl)imidodicarbonate (359 mg, 3:2 mixture with non-Boc as described above) and 4.0 M HCl in dioxane (3.0 mL, 12.00 mmol) was stirred at room temperature under Nitrogen for 14 hr. The mixture was concentrated in vacuo and taken up in EtOAc (50 mL) and saturated aqueous sodium bicarbonate (50 mL). The layers were separated and the aqueous layer was extracted with EtOAc (50 mL). The combined organic layers were washed with brine (1×50 mL), dried (Na2SO4), filtered, and concentrated in vacuo. The residue was purified by flash chromatography (Analogix, 40 g SiO2, 15%-85% EtOAc in hexanes gradient over 52 minutes) to give 4-amino-3-{1-[(2,5-difluorophenyl)acetyl]-2,3-dihydro-1H-indol-5-yl}furo[3,2-c]pyridine-7-carbonitrile (118 mg, 45.7% yield) as a white solid. LC/MS (ES) m/z=431 [M+H]$^+$. $^1$H NMR (400 MHz, DMSO-d$_6$) δ 3.28 (t, 2H), 3.97 (s, 2H), 4.30 (t, J=8.46 Hz, 2H), 6.57 (br. s., 2H), 7.14-7.33 (m, 4H), 7.40 (s, 1H), 8.09-8.17 (m, 2H), 8.38 (s, 1H).

Example 111

5-{1-[(3,5-dimethyl-1H-pyrazol-1-yl)acetyl]-2,3-dihydro-1H-indol-5-yl}-7-methyl-7H-pyrrolo[2,3-d]pyrimidin-4-amine

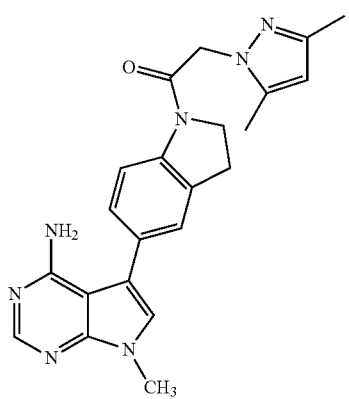 [SMILES: Cc1cc(C)n(CC(=O)N2CCc3cc(-c4cn(C)c5ncnc(N)c45)ccc32)n1]

To a mixture of 5-(2,3-dihydro-1H-indol-5-yl)-7-methyl-7H-pyrrolo[2,3-d]pyrimidin-4-amine dihydrochloride (175 mg, 0.517 mmol) and (3,5-dimethyl-1H-pyrazol-1-yl)acetic acid (80 mg, 0.517 mmol) in N,N-Dimethylformamide (DMF) (3 mL) was added DIPEA (0.271 mL, 1.552 mmol) dropwise. The mixture was cooled in an ice bath, and T3P (1-propanephosphonic acid cyclic anhydride), 50% in ethylacetate (~1.68M) (0.370 mL, 0.621 mmol) was then added dropwise. After stirring 30 minutes, the ice bath was removed and the mixture was allowed to warm to room temperature and stir 2 hours. The mixture was diluted with water (~5 mL) and basified to pH 7-8 with 0.5M NaOH. Methanol was added to give a clear solution. This solution was loaded onto a reversed phase C18 SF25-55g Analogix cartridge and the product purified by eluting with a gradient of 30-95% methanol-water. The combined pure fractions containing the product was evaporated and azeotroped with acetonitrile and then benzene to give a solid that was triturated with acetonitrile (~4 mL), filtered and washed with acetonitrile to afford 5-{1-[(3,5-dimethyl-1H-pyrazol-1-yl)acetyl]-2,3-dihydro-1H-indol-5-yl}-7-methyl-7H-pyrrolo[2,3-d]pyrimidin-4-amine (90 mg, 41.2% yield) as a white solid after drying under vacuum. LCMS (ES) m/z=402.4 [M+H]$^+$. $^1$H NMR (400 MHz, DMSO-d$_6$) δ ppm 8.15 (s, 1H) 8.07 (d, J=8.1 Hz, 1H) 7.34 (s, 1H) 7.20-7.29 (m, 2H) 6.08 (br. s, 2H) 5.86 (s, 1H) 5.09 (s, 2H) 4.26 (t, J=8.3 Hz, 2H) 3.74 (s, 3H) 3.27 (t, J=8.3 Hz, 2H) 2.17 (s, 3H) 2.10 (s, 3H).

Example 112

5-[4-fluoro-1-(phenylacetyl)-2,3-dihydro-1H-indol-5-yl]-7-methyl-7H-pyrrolo[2,3-d]pyrimidin-4-amine

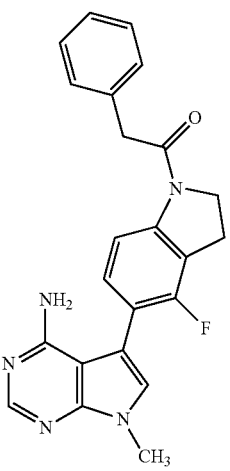 [SMILES: Cn1cc(-c2ccc3c(c2F)CCN3C(=O)Cc2ccccc2)c2c(N)ncnc21]

4-fluoro-2,3-dihydro-1H-indole

To a stirred solution of 4-fluoro-1H-indole (950 mg, 7.03 mmol) in Acetic Acid (20 mL) at 12° C. under nitrogen was added sodium cyanoborohydride (1458 mg, 23.20 mmol) portionwise. The reaction was stirred at 12° C. for 2 hours, and at room temperature overnight. The reaction was worked up by pouring into sodium hydroxide (10 N). The aqueous was extracted with diethyl ether (3×100 mL), and the combined organics dried over sodium sulfate. LCMS analysis at this point indicated presence of product and some acylated product, along with some acylated starting material. The crude was dissolved in THF (10 mL) and treated with NaOH (6 N, 2 mL), then stirred at r.t. for 2 h. The reaction was stirred overnight, but no change in LCMS was observed, so the organic layer was removed, and the aqueous extracted with diethyl ether (2×10 mL), the combined organics were dried over sodium sulfate. The dried solution was filtered and concentrated, and the residue was purified by flash chromatography (0-25% EtOAc in hexanes, 24-g silica gel column) to afford 4-fluoro-2,3-dihydro-1H-indole (510 mg, 3.72 mmol, 52.9% yield) as a colorless oil. LC-MS (ES) m/z=138 [M+H]$^+$. $^1$H NMR (400 MHz, DMSO-d$_6$) δ 2.94 (t, J=8.59 Hz, 2H), 3.48 (t, J=8.59 Hz, 2H), 5.79 (br. s., 1H), 6.23-6.35 (m, 2H), 6.87-6.99 (m, 1H).

1,1-dimethylethyl 4-fluoro-2,3-dihydro-1H-indole-1-carboxylate

A solution of 4-fluoro-2,3-dihydro-1H-indole (500 mg, 3.65 mmol), Boc2O (0.846 mL, 3.65 mmol), DIEA (1.273 mL, 7.29 mmol), DMAP (44.5 mg, 0.365 mmol) was stirred at room temperature overnight. The reaction mixture was poured into 0.1 N HCl (10 mL) and extracted with ethyl acetate (3×20 mL). The combined organics were dried over sodium sulfate, filtered and concentrated to afford 1,1-dimethylethyl 4-fluoro-2,3-dihydro-1H-indole-1-carboxylate (0.866 g, 100% yield) as a colorless oil. LC-MS (ES) m/z=182 [M+H-tBu]+. $^1$H NMR (400 MHz, DMSO-d$_6$) δ 1.51 (s, 9H), 3.08 (t, J=8.72 Hz, 2H), 3.97 (t, J=8.72 Hz, 2H), 6.77 (t, J=8.72 Hz, 1H), 7.11-7.26 (m, 1H), 7.27-7.66 (m, 1H).

1,1-dimethylethyl 5-bromo-4-fluoro-2,3-dihydro-1H-indole-1-carboxylate

To a solution of 1,1-dimethylethyl 4-fluoro-2,3-dihydro-1H-indole-1-carboxylate (0.866 g, 3.65 mmol) in Dichloromethane (DCM) (10 mL) was added a solution of NBS (0.650 g, 3.65 mmol) in Dichloromethane (DCM) (10 mL). The reaction was stirred overnight. The reaction mixture was poured into sodium bicarbonate (aq., sat., 50 mL) and extracted with ethyl acetate (3×100 mL). The combined organic layers were dried over sodium sulfate, filtered and concentrated. The residue was purified by flash chromatography (0-30% EtOAc in hexanes, 24-g silica gel column) to afford 1,1-dimethylethyl 5-bromo-4-fluoro-2,3-dihydro-1H-indole-1-carboxylate (1 g, 87% yield) as a (4:1 LCMS, 10:1 by 1H NMR) mixture with the starting material. The mixture was used without further purification. LC-MS (ES) m/z=260, 262 [M+H-t-Bu]+. $^1$H NMR (400 MHz, DMSO-d$_6$) δ 1.51 (s, 9H), 3.13 (t, J=8.72 Hz, 2H), 3.94-4.08 (m, 2H), 7.26-7.63 (m, 2H).

1,1-dimethylethyl 4-fluoro-5-(4,4,5,5-tetramethyl-1,3,2-dioxaborolan-2-yl)-2,3-dihydro-1H-indole-1-carboxylate A mixture of 1,1-dimethylethyl 5-bromo-4-fluoro-2,3-dihydro-1H-indole-1-carboxylate (1 g, 3.16 mmol), PdCl2(dppf)-CH2Cl2 adduct (0.129 g, 0.158 mmol), potassium acetate (0.776 g, 7.91 mmol) and bis(pinacolato)diboron (0.803 g, 3.16 mmol) in 1,4-Dioxane (20 mL) was stirred at 100° C. overnight on a stirrer hot-plate. LCMS indicated complete conversion to the desired product. The reaction mixture was poured into 1:1 NaCl (aq. sat.): H2O, (100 mL) and ethyl acetate (100 mL), shaken, and filtered through celite. The resulting mixture was separated and the aqueous layer was extracted with two additional portions of ethyl acetate (2×50 mL). The combined organics were dried over sodium sulfate, filtered, and concentrated. The residue was purified by flash chromatography (0-25% EtOAc in hexanes, 40 g silica gel column) to afford 1,1-dimethylethyl 4-fluoro-5-(4,4,5,5-tetramethyl-1,3,2-dioxaborolan-2-yl)-2,3-dihydro-1H-indole-1-carboxylate (660 mg, 57.4% yield) as a pale yellow oil. LC-MS (ES) m/z=308 [M+H-tBu]+. $^1$H NMR (400 MHz, DMSO-d$_6$) δ 1.29 (s, 12H), 1.51 (s, 9H), 3.05 (t, J=8.72 Hz, 2H), 3.98 (t, J=8.72 Hz, 2H), 7.22-7.61 (m, 2H).

1,1-dimethylethyl 5-(4-amino-7-methyl-7H-pyrrolo[2,3-d]pyrimidin-5-yl)-4-fluoro-2,3-dihydro-1H-indole-1-carboxylate A mixture of 5-bromo-7-methyl-7H-pyrrolo[2,3-d]pyrimidin-4-amine (413 mg, 1.817 mmol), 1,1-dimethylethyl 4-fluoro-5-(4,4,5,5-tetramethyl-1,3,2-dioxaborolan-2-yl)-2,3-dihydro-1H-indole-1-carboxylate (660 mg, 1.817 mmol), Pd2(dba)3 (83 mg, 0.091 mmol) and Potassium Phosphate (K3PO4) (771 mg, 3.63 mmol) and (t-Bu)3PHBF4 (52.7 mg, 0.182 mmol) in 1,4-Dioxane (7.5 mL) and Water (2.5 mL) was stirred at 100° C. overnight on a stirrer hot-plate. The reaction mixture was allowed to cool to room temperature, at which point a yellow crystalline precipitate was observed. The organic layer removed, the aqueous was diluted with water (10 mL) and extracted with one portion of ethyl acetate (1×30 mL) and two portions of DCM-MeOH (9:1, x x 30 mL) to solubilize the solids. The combined organics were dried over sodium sulfate, filtered and concentrated. The residue was adsorbed onto silica and purified by flash chromatography (0-100% EtOAc in hexanes→0-10% MeOH in DCM, 40-g silica gel column) to afford 1,1-dimethylethyl 5-(4-amino-7-methyl-7H-pyrrolo[2,3-d]pyrimidin-5-yl)-4-fluoro-2,3-dihydro-1H-indole-1-carboxylate (441 mg, 63.3% yield) as an off-white solid. LC-MS (ES) m/z=384 [M+H]+. $^1$H NMR (400 MHz, DMSO-d$_6$) δ ppm 1.53 (s, 9H), 3.15 (t, J=8.46 Hz, 2H), 3.75 (s, 3H), 4.03 (t, J=8.59 Hz, 2H), 5.88-6.12 (m, 2H), 7.12-7.22 (m, 1H), 7.25 (s, 1H), 7.44-7.72 (m, 1H), 8.15 (s, 1H).

5-(4-fluoro-2,3-dihydro-1H-indol-5-yl)-7-methyl-7H-pyrrolo[2,3-d]pyrimidin-4-amine A suspension of 1,1-dimethylethyl 5-(4-amino-7-methyl-7H-pyrrolo[2,3-d]pyrimidin-5-yl)-4-fluoro-2,3-dihydro-1H-indole-1-carboxylate (430 mg, 1.121 mmol) and HCl (4 M, dioxane) (10 mL, 329 mmol) was stirred at room temperature overnight. LCMS indicated the reaction was complete, so the reaction mixture was filtered and the residue washed with dioxane (10 mL) and dried at the pump for an hour to afford 5-(4-fluoro-2,3-dihydro-1H-indol-5-yl)-7-methyl-7H-pyrrolo[2,3-d]pyrimidin-4-amine 2HCl (314 mg, 79% yield) as an off-white solid. LC-MS (ES) m/z=284 [M+H]+. $^1$H NMR (600 MHz, DMSO-d6) δ ppm 3.14 (t, J=7.93 Hz, 2H), 3.68 (t, J=7.90 Hz, 2H), 3.84 (s, 3H), 6.83 (br. s., 1H), 7.16 (t, J=6.99 Hz, 1H), 7.59 (s, 1H), 8.49 (s, 1H).

5-[4-fluoro-1-(phenylacetyl)-2,3-dihydro-1H-indol-5-yl]-7-methyl-7H-pyrrolo[2,3-d]pyrimidin-4-amine A solution of 5-(4-fluoro-2,3-dihydro-1H-indol-5-yl)-7-methyl-7H-pyrrolo[2,3-d]pyrimidin-4-amine 2HCl (100 mg, 0.281 mmol), Phenylacetic acid (38.2 mg, 0.281 mmol), HATU (107 mg, 0.281 mmol), DIEA (0.196 mL, 1.123 mmol) was stirred at room temperature for 3 days. The resulting suspension was poured into water (10 mL) and stirred for 30 min, and a precipitate formed. The precipitate was collected by filtration, and the residue was washed with water, then dried at the pump for an hour, then adsorbed onto silica and purified by flash chromatography (0-10% MeOH in EtOAc) to afford 5-[4-fluoro-1-(phenylacetyl)-2,3-dihydro-1H-indol-5-yl]-7-methyl-7H-pyrrolo[2,3-d]pyrimidin-4-amine (80.2 mg, 71.2% yield) as a white solid. LC-MS (ES) m/z=402 [M+H]+. $^1$H NMR (400 MHz, DMSO-d$_6$) δ ppm 3.24 (t, J=8.46 Hz, 2H), 3.74 (s, 3H), 3.89 (s, 2H), 4.29 (t, J=8.46 Hz, 2H), 5.79-6.20 (m, 2H), 7.10-7.42 (m, 7H), 7.95 (d, J=8.08 Hz, 1H), 8.15 (s, 1H).

Example 113

5-{4-fluoro-1-[(1-methyl-1H-pyrrol-2-yl)acetyl]-2,3-dihydro-1H-indol-5-yl}-7-methyl-7H-pyrrolo[2,3-d]pyrimidin-4-amine

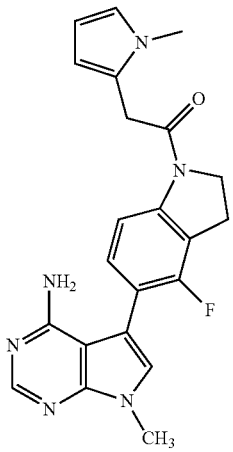 [SMILES: Cn1cccc1CC(=O)N1CCc2c1ccc(-c1cn(C)c3ncnc(N)c13)c2F]

A solution of 5-(4-fluoro-2,3-dihydro-1H-indol-5-yl)-7-methyl-7H-pyrrolo[2,3-d]pyrimidin-4-amine 2HCl (100 mg, 0.281 mmol), (1-methyl-1H-pyrrol-2-yl)acetic acid (39.1 mg, 0.281 mmol), HATU (107 mg, 0.281 mmol), and DIEA (0.245 mL, 1.404 mmol) was stirred at room temperature for 3 days. The resulting suspension was poured into water (10 mL) and stirred for 30 min, and a precipitate formed. The precipitate was collected by filtration, and the residue was washed with water, then dried at the pump for an hour, then adsorbed onto silica and purified by flash chromatography (0-10% MeOH in EtOAc) to afford 5-{4-fluoro-1-[(1-methyl-1H-pyrrol-2-yl)acetyl]-2,3-dihydro-1H-indol-5-yl}-7-methyl-7H-pyrrolo[2,3-d]pyrimidin-4-amine (70 mg, 61.7% yield) as an off-white solid. LC-MS (ES) m/z=405 [M+H]$^+$. $^1$H NMR (400 MHz, DMSO-d$_6$) δ ppm 3.25 (t, J=8.34 Hz, 2H), 3.54 (s, 3H), 3.69-3.79 (m, 3H), 3.87 (s, 2H), 4.33 (t, J=8.34 Hz, 2H), 5.82-5.95 (m, 2H), 5.95-6.19 (m, 2H), 6.69 (t, J=2.27 Hz, 1H), 7.16-7.24 (m, 1H), 7.26 (s, 1H), 7.93 (d, J=8.08 Hz, 1H), 8.15 (s, 1H).

Example 114

5-{1-[(2,5-difluorophenyl)acetyl]-4-fluoro-2,3-dihydro-1H-indol-5-yl}-7-methyl-7H-pyrrolo[2,3-d]pyrimidin-4-amine

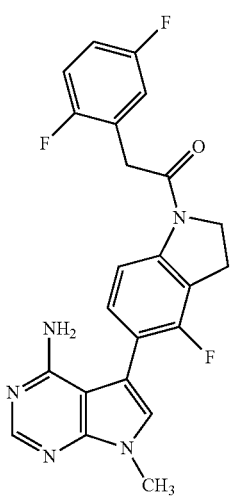 [SMILES: Cn1cc(-c2ccc3c(c2F)CCN3C(=O)Cc2cc(F)ccc2F)c2c(N)ncnc21]

A solution of 5-(4-fluoro-2,3-dihydro-1H-indol-5-yl)-7-methyl-7H-pyrrolo[2,3-d]pyrimidin-4-amine 2HCl (100 mg, 0.281 mmol), 2,5-difluorophenylacetic acid (48.3 mg, 0.281 mmol), HATU (107 mg, 0.281 mmol), and DIEA (0.196 mL, 1.123 mmol) was stirred at room temperature overnight. The reaction mixture was poured into water (10 mL) and a precipitate formed. The precipitate was collected by filtration, and dried at the pump for 1 hour. The residue was adsorbed onto silica and purified by flash chromatography (0-10% MeOH in EtAc) to afford 5-{1-[(2,5-difluorophenyl)acetyl]-4-fluoro-2,3-dihydro-1H-indol-5-yl}-7-methyl-7H-pyrrolo[2,3-d]pyrimidin-4-amine (44.2 mg, 36.0% yield) as a white solid. LC-MS (ES) m/z=438 [M+H]$^+$. $^1$H NMR (400 MHz, DMSO-d$_6$) δ ppm 3.23-3.29 (m, 2H), 3.75 (s, 3H), 3.97 (s, 2H), 4.36 (t, J=8.34 Hz, 2H), 5.78-6.19 (m, 2H), 7.13-7.32 (m, 5H), 7.89 (d, J=8.08 Hz, 1H), 8.15 (s, 1H).

Example 115

5-{1-[(2,5-difluorophenyl)acetyl]-2,3-dihydro-1H-indol-5-yl}furo[2,3-d]pyrimidin-4-amine

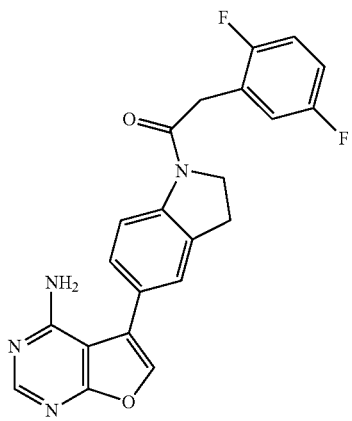 [SMILES: Nc1ncnc2occ(-c3ccc4c(c3)CCN4C(=O)Cc3cc(F)ccc3F)c12]

1-(1-acetyl-2,3-dihydro-1H-indol-5-yl)-2-bromoethanone

To a suspension of 1,5-diacetylindoline (10.0 g, 49.2 mmol) in 90 mL of THF at rt was added pyridinium tribromide (16.52 g, 51.7 mmol, 1 equiv) as solids portionwise over a period of 10 min. When there was still about 1.5 g of pyridinium tribromide left, the mixture solidified. Added another 30 mL of THF to make the mixture stirrable again. The remaining 1.5 g tribromide was added in one portion. The mixture was stirred at rt (no exotherm as checked by a thermometer). After 1.5 h, LCMS showed conversion complete. The suspension was filtered. The cake was washed with THF (2×30 mL), and then water (2×50 mL). The wet cake was sucked under house vacuum at rt for 2 days to give 1-(1-acetyl-2,3-dihydro-1H-indol-5-yl)-2-bromoethanone (12.89 g) as light grey solids. LC-MS (ES) m/z=281.9, 283.9.

1-(1-acetyl-2,3-dihydro-1H-indol-5-yl)-2-hydroxyethanone

To a solid mixture of 1-(1-acetyl-2,3-dihydro-1H-indol-5-yl)-2-bromoethanone (1.0 g, 3.54 mmol) and sodium acetate (1.45 g, 17.71 mmol, 5 equiv) in a 40 mL vial was added EtOH (8 mL) and water (8 mL). The resulting suspension was heated in an oil bath at 70° C. for 3.5 hours. The mixture was cooled in an ice bath, to which was added 0.7 mL of 6 N NaOH. After 2 h, the cold mixture was quenched with 2 ml of 1N HCl, and then concentrated in vacuo. The residue was partitioned between 10% MeOH in DCM and water. The organic was dried over Na2SO4, filtered, and concentrated in vacuo. The residue was taken up between DCM and ether to give a suspension, which was filtered. The yellow solids collected were washed with ether and dried under vacuum to give 1-(1-acetyl-2,3-dihydro-1H-indol-5-yl)-2-hydroxyethanone (534 mg) as a light yellowish solid, which was used without further purification.

4-(1-acetyl-2,3-dihydro-1H-indol-5-yl)-2-amino-3-furancarbonitrile

To a suspension of 1-(1-acetyl-2,3-dihydro-1H-indol-5-yl)-2-hydroxyethanone (0.53 g, 2.41 mmol) and malononitrile (176 mg, 2.66 mmol, 1.1 equiv) in DMF (4 mL) chilled in an ice bath was added diethylamine (380 uL, 3.63 mmol, 1.5 equiv) over a 3 minute period. The resulting mixture was stirred in the ice bath for another 20 minutes, and then the ice bath was removed. The brownish suspension was stirred at ambient temp for 2 hours. LCMS showed product formed in 75%. To the suspension was added 20 mL of water. The warm suspension was filtered. The cake was washed with water, and dried under house vacuum overnight to give 4-(1-acetyl-2,3-dihydro-1H-indol-5-yl)-2-amino-3-furancarbonitrile (360 mg) as beige solids. LC-MS (ES) m/z=268 [M+H]+.

ethyl[4-(1-acetyl-2,3-dihydro-1H-indol-5-yl)-3-cyano-2-furanyl]imidoformate

To a suspension of 4-(1-acetyl-2,3-dihydro-1H-indol-5-yl)-2-amino-3-furancarbonitrile (1.248 g, 4.67 mmol) in 1,4-dioxane (12 mL) was added bis(ethyloxy)methyl acetate (2 mL, 12.29 mmol, 2.63 equiv) in one portion. The resulting suspension was heated in an oil bath at 60° C. After 15 minutes heating, the mixture became a solution. Heating was continued for 4 hours and the mixture was cooled to room temperature. After 10 hours aging at room temperature, the mixture became a suspension. LCMS showed conversion complete. The paste suspension was combined with a previous run (111 mg of starting material 4-(1-acetyl-2,3-dihydro-1H-indol-5-yl)-2-amino-3-furancarbonitrile used), and filtered. The cake was washed with hexane and dried under vacuum (1.20 g) as tan solids. $^1$H NMR (400 MHz, DMSO-d$_6$) δ ppm 1.34 (t, J=7.1 Hz, 3H), 2.18 (s, 3H), 3.19 (t, J=8.6 Hz, 2H), 4.14 (t, J=8.6 Hz, 2H), 4.38 (q, J=6.6 Hz, 2H), 7.38-7.47 (m, 1H), 7.49 (s, 1H), 7.94 (s, 1H), 8.09 (d, J=8.3 Hz, 1H), 8.64 (s, 1H).

5-(1-acetyl-2,3-dihydro-1H-indol-5-yl)furo[2,3-d]pyrimidin-4-amine

To a homogeneous but dark brownish solution of ethyl[4-(1-acetyl-2,3-dihydro-1H-indol-5-yl)-3-cyano-2-furanyl]imidoformate (2.34 g, 7.24 mmol) in 20 mL of DCM was added 6 mL of 7N NH3 in MeOH in one portion. The resulting mixture was stirred at room temperature. After 10 minutes, the mixture became a suspension. After 18 h, LCMS showed conversion complete. The suspension was concentrated in vacuo, and the residue was dried under vacuum to give 5-(1-acetyl-2,3-dihydro-1H-indol-5-yl)furo[2,3-d]pyrimidin-4-amine (1.92 g, 90% yield) as a beige solid. LC-MS (ES) m/z=294.9 [M+H]+.

5-(2,3-dihydro-1H-indol-5-yl)furo[2,3-d]pyrimidin-4-amine

A dark brownish suspension of 5-(1-acetyl-2,3-dihydro-1H-indol-5-yl)furo[2,3-d]pyrimidin-4-amine (1.71 g, 5.81 mmol) and LiOH.H2O (5.50 g, 131 mmol, 22.6 equiv) in 50 mL of EtOH and 10 mL of water and 10 mL of DMSO was degassed and backflushed with nitrogen. This cycle was repeated 4×, and the mixture was heated in an oil bath at 100° C. for 48 h. LCMR showed there was still 22% starting material left. To the mixture was added KOH (FW: 56.11, 3.26 g, 58.1 mmol, 10 equiv) as pellets. The suspension was degassed and heated at 100° C. for another 16 h. LCMS showed there was no starting material left. The mixture was cooled and filtered. The cake was rinsed with 30 mL of EtOH. The filtrate was cooled in an ice bath. The pH was adjusted by adding cold 6N HCl to 7-8. The resulting brownish mixture was concentrated in vacuo. The residue was taken up in water, but gave no solids. This mixture was concentrated in vacuo again to remove as much solvent as possible (water bath temp at 65° C. and vacuum at 3 torr). The solid residue was taken up in water to give a suspension, which was chilled in the refrigerator, followed by filtration. The cake was washed with water (2×8 mL) and dried under house vacuum for 5 h and then vacuum over P2O5 for 15 h to afford 5-(2,3-dihydro-1H-indol-5-yl)furo[2,3-d]pyrimidin-4-amine (0.76 g) as dark tan-colored solids. LC-MS (ES) m/z=252.9 [M+H]$^+$.

5-{1-[(2,5-difluorophenyl)acetyl]-2,3-dihydro-1H-indol-5-yl}furo[2,3-d]pyrimidin-4-amine To a stirred dark brownish solution of 5-(2,3-dihydro-1H-indol-5-yl)furo[2,3-d]pyrimidin-4-amine (360 mg, 1.43 mmol) and HATU (597 mg, 1.57 mmol, 1.1 equiv) in 3 mL of DMF was added DIEA (274 uL, 1.57 mmol, 1.1 equiv). To this mixture was added (2,5-difluorophenyl)acetic acid portionwise (246 mg total, 1.43 mmol, 1 equiv) over a 1 h period. The mixture was stirred for another 2 h and then added to 50 mL of ice water. The resulting suspension was filtered. The brownish cake was washed with water (2×10 mL) and then sucked under house vacuum for 20 h to give crude product (760 mg). This material was dissolved in 10% MeOH in DCM and absorbed onto a dryload cartridge. Purification was done on an SF25-60 g silica gel cartridge using gradient elution of 1% A to 55% A (A was a mixture of 3200 mL DCM, 800 mL of MeOH and 80 mL of conc NH4OH). The desired product eluted from 29-32%. Each fraction was checked by LCMS and the 2 pure fractions were combined with impure product from a previous run and concentrated in vacuo. The residue was dissolved in 10% MeOH in CHCl3, and filtered The filtrate was concentrated in vacuo. The residue was taken up in 1.5 mL of CHCl3, and MTBE (1 mL) and hexane (7 mL) were added to give a suspension. Which was filtered. The cake was washed with hexane (2×4 mL) and then dried under vacuum at 65° C. for 18 h to afford 5-{1-[(2,5-difluorophenyl)acetyl]-2,3-dihydro-1H-indol-5-yl}furo[2, 3-d]pyrimidin-4-amine (295 mg) as an off-white solid. NMR, LCMS and HPLC showed this sample was pure. LC-MS (ES) m/z=407 [M+H]+. $^1$H NMR (400 MHz, DMSO-d$_6$) δ ppm 3.28 (t, J=8.6 Hz, 2H), 3.96 (s, 3H), 4.30 (t, J=8.5 Hz, 2H), 7.13-7.28 (m, 3H), 7.30 (d, J=9.1 Hz, 1H), 7.40 (s, 1H), 7.93 (s, 1H), 8.12 (d, J=8.3 Hz, 1H), 8.25 (s, 1H), NH2 protons are not visible.

Example 116

5-(1-{[3-(trifluoromethyl)phenyl]acetyl}-2,3-dihydro-1H-indol-5-yl)furo[2,3-d]pyrimidin-4-amine

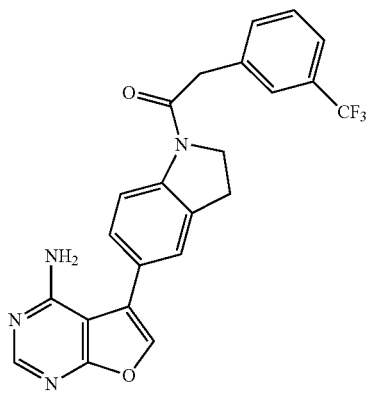 [SMILES: Nc1ncnc2occ(-c3ccc4c(c3)CCN4C(=O)Cc3cccc(C(F)(F)F)c3)c12]

To a stirred dark greenish solution of 5-(2,3-dihydro-1H-indol-5-yl)furo[2,3-d]pyrimidin-4-amine (400 mg, 1.59 mmol) and HATU (663 mg, 1.74 mmol, 1.1 equiv) in 4 mL of DMF was added DIEA (305 uL, 1.74 mmol, 1.1 equiv). To this mixture was added [3-(trifluoromethyl)phenyl]acetic acid portionwise (324 mg total, 1.59 mmol, 1 equiv), about 80 mg at 30 min intervals. After a total of 3 h, LCMS showed there was still 16% starting material left by UV. The mixture was diluted with ice cold water (40 mL) to give a dark greenish suspension, which was filtered. The cake was washed with water (2×8 mL), and sucked under house vacuum for 18 h to afford crude product (900 mg), which was dissolved in 10% DCM in MeOH and absorbed onto a dryload cartridge. Purification was done on an SF25-60 g silica gel cartridge using gradient elution of 1% A to 50% A in DCM (A was a mixture of 3200 mL DCM, 800 mL of MeOH and 80 mL of conc NH4OH). The product eluted around 25-30% A. The fractions with product were combined and concentrated in vacuo. This material contained an impurity, and the residue underwent another silica gel purification on an SF25-80 g silica gel cartridge using gradient elution of 1% B in EtOAc to 50% B (B was a mixture of 10% MeOH in EtOAc). The desired product eluted from 10-13% B. Pure fractions were combined and evaporated. The residue (200 mg) was taken up in CHCl3 (0.45 mL), MTBE (3 mL) and hexane (3 mL) to give a suspension, which was filtered. The solids were washed with hexane (2×3 mL) and dried under vacuum at 65° C. for 18 h to afford 5-(1-{[3-(trifluoromethyl)phenyl]acetyl}-2,3-dihydro-1H-indol-5-yl)furo[2,3-d]pyrimidin-4-amine (170 mg) as light cream-colored solids. LC-MS (ES) m/z=439 [M+H]+. $^1$H NMR (400 MHz, DMSO-$d_6$) δ ppm 3.27 (t, J=8.3 Hz, 2H), 4.05 (s, 2H), 4.28 (t, J=8.6 Hz, 2H), 7.30 (d, J=8.1 Hz, 1H), 7.39 (s, 1H), 7.56-7.66 (m, 3H), 7.68 (s, 1H), 7.93 (s, 1H), 8.15 (d, J=8.3 Hz, 1H), 8.25 (s, 1H), NH2 protons not visible or existed as broad hump.

Example 117

5-{1-[(3-chloro-5-fluorophenyl)acetyl]-2,3-dihydro-1H-indol-5-yl}furo[2,3-d]pyrimidin-4-amine

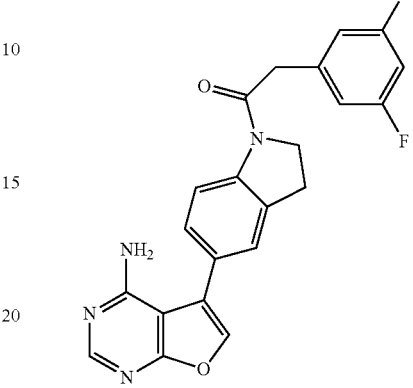

To a stirred dark greenish solution of 5-(2,3-dihydro-1H-indol-5-yl)furo[2,3-d]pyrimidin-4-amine (500 mg, 1.98 mmol) and HATU (829 mg, 2.18 mmol, 1.1 equiv) in 5 mL of DMF was added DIEA (381 uL, 2.18 mmol, 1.1 equiv). To this mixture was added (3-chloro-5-fluorophenyl)acetic acid portionwise (374 mg total, 1.98 mmol, 1 equiv), about 130 mg at 30 min intervals. After 2 h, LCMS showed conversion complete. The mixture was poured into 50 mL of ice cold water to give a suspension, which was filtered. The cake was washed with water (2×10 mL) and dried under house vacuum for 18 h to afford crude product (1.0 g), which was dissolved in 10% MeOH in DCM and absorbed onto a dryload cartridge. Purification was done on an SF25-60 g silica gel cartridge using gradient elution of 1% A in DCM to 50% A in DCM (A was a mixture of 3200/800/80 DCM/MeOH/NH4OH). The desired product eluted impure from 24-30% A. The fractions containing product were combined and concentrated in vacuo and reabsorbed onto a dryload cartridge. Purification was done on an SF25-80 g silica gel cartridge using gradient elution of 1% A to 75% A in EtOAc. (B was a 2.5% MeOH in EtOAc). Two fractions were collected. The first fraction eluted from 15-35% B as a sharp peak, which was conc in vacuo. The residue was taken up in CHCl3 (2 mL) and MTBE (6 mL) as a suspension, which was filtered. The solids were washed with MTBE (2×3 mL) and hexane (2×3 mL). The second fraction eluted from 63-100% B as a broad. The large eluted solvent volume was concentrated in vacuo. This residue was taken up in CHCl3 (2 mL) and MTBE (8 mL) as a suspension, which was filtered. The cake was washed with MTBE (2×3 mL) and hexane (3×4 mL). The solids were combined with the solids above from the first fraction and dried under vacuum at 65° C. for 18 h to afford 5-{1-[(3-chloro-5-fluorophenyl)acetyl]-2,3-dihydro-1H-indol-5-yl}furo[2,3-d]pyrimidin-4-amine (492 mg) as off-white solids. LC-MS (ES) m/z=423 [M+H]+. $^1$H NMR (400 MHz, DMSO-$d_6$) d ppm 3.26 (t, J=8.3 Hz, 2H), 3.97 (s, 2H), 4.25 (t, J=8.5 Hz, 2H), 7.18 (d, J=9.9 Hz, 1H), 7.27 (s, 1H), 7.29-7.38 (m, 2H), 7.39 (s, 1H), 7.93 (s, 1H), 8.15 (d, J=8.1 Hz, 1H), 8.25 (s, 1H), NH2 protons not visible.

Example 118

5-{1-[(3-methylphenyl)acetyl]-2,3-dihydro-1H-indol-5-yl}furo[2,3-c]pyrimidin-4-amine

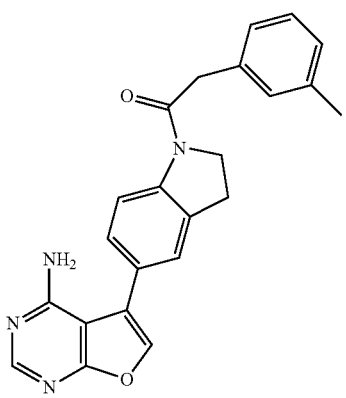 [SMILES: Cc1cccc(CC(=O)N2CCc3cc(-c4coc5ncnc(N)c45)ccc32)c1]

To a stirred dark greenish solution of 5-(2,3-dihydro-1H-indol-5-yl)furo[2,3-d]pyrimidin-4-amine (500 mg, 1.98 mmol) and HATU (829 mg, 2.18 mmol, 1.1 equiv) in 5 mL of DMF was added DIEA (381 uL, 2.18 mmol, 1.1 equiv). To this mixture was added (3-methylphenyl)acetic acid portionwise (298 mg total, 1.98 mmol, 1 equiv), about 100 mg at 30 min intervals. After a total of 2.5 hours, the mixture was poured into 50 mL of ice cold water to give a suspension, which was filtered. The cake was washed with water (2×10 mL) and dried under house vacuum for 18 h to afford crude product (1.0 g), which was dissolved in 10% MeOH in DCM and absorbed onto a dryload cartridge. First pass purification was done on an SF25-60 g silica gel cartridge using gradient elution of 1% A in DCM to 55% A in DCM (A was a mixture of 3200/800/80 DCM/MeOH/NH4OH). The desired product eluted impure from 24-30% A. The fractions were combined and concentrated in vacuo, and reabsorbed onto a dryload cartridge. Second pass purification was done on an SF25-80 g silica gel cartridge using gradient elution of 1% B to 100% B in EtOAc. (B was a 2.5% MeOH in EtOAc). The desired pure product fractions combined, and concentrated in vacuo. The residue was taken up in CHCl3 (1 mL) and MTBE (7 mL) to give a suspension, which was filtered. The cake was washed with MTBE (2×3 mL) and hexane (3×3 mL) and dried under vacuum at 65° C. to afford 5-{1-[(3-methylphenyl)acetyl]-2,3-dihydro-1H-indol-5-yl}furo[2,3-d]pyrimidin-4-amine (431 mg) as beige-colored solids. LC-MS (ES) m/z=385 [M+H]+. 1H NMR (400 MHz, DMSO-d6) δ ppm 2.31 (s, 3H), 3.22 (t, J=8.5 Hz, 2H), 3.84 (s, 2H), 4.22 (t, J=8.6 Hz, 2H), 7.04-7.15 (m, 3H), 7.19-7.26 (m, 1H), 7.30 (d, J=8.3 Hz, 1H), 7.37 (s, 1H), 7.92 (s, 1H), 8.18 (d, J=8.3 Hz, 1H), 8.25 (s, 1H), NH2 protons not visible.

Example 119

5-(1-{[3-fluoro-5-(trifluoromethyl)phenyl]acetyl}-2,3-dihydro-1H-indol-5-yl)furo[2,3-d]pyrimidin-4-amine

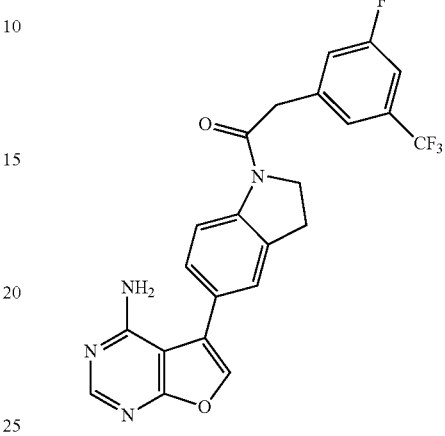

To a stirred dark greenish solution of 5-(2,3-dihydro-1H-indol-5-yl)furo[2,3-d]pyrimidin-4-amine (500 mg, 1.98 mmol) and HATU (829 mg, 2.18 mmol, 1.1 equiv) in 5 mL of DMF was added DIEA (381 uL, 2.18 mmol, 1.1 equiv). To this mixture was added [3-fluoro-5-(trifluoromethyl)phenyl]acetic acid portionwise (440 mg total, 1.98 mmol, 1 equiv), about 110 mg at 30 min intervals. After a total of 2.5 hours, the mixture was poured into 50 mL of ice cold water to give a suspension, which was filtered. The cake was washed with water (2×15 mL) and dried under house vacuum at rt for 18 h to afford crude product (1.10 g), which was dissolved in 10% MeOH in DCM and absorbed onto a dryload cartridge. Purification was done on an SF25-60 g silica gel cartridge using gradient elution of 1% A to 50% A in DCM (A was a mixture of 3200/800/80 DCM/MeOH/NHeOH). The desired product eluted impure from 25-30% A. These fractions were combined and concentrated in vacuo. the residue was re-dissolved in 10% MeOH in DCM and absorbed to dryload cartridge. A second purification was done on an SF25-80 g silica gel cartridge using gradient elution of 1% B to 100% B in EtOAc (B was a mixture of 2.5% MeOH in EtOAc). Note: the product was not very soluble in EtOAc. Two fractions were collected. The first fraction eluted from 8-12% B. The second fraction eluted from 33-100% B. Both were pure by TLC. They were combined and conc in vacuo. The residue was taken up in CHCl3 (3 mL) and MTBE (7 mL) as a suspension, which was filtered. The solids were washed with MTBE (2×3 mL) and hexane (3×4 mL), and dried under vacuum at 65° C. for 18 h to afford 5-(1-{[3-fluoro-5-(trifluoromethyl)phenyl]acetyl}-2,3-dihydro-1H-indol-5-yl)furo[2,3-d]pyrimidin-4-amine (445 mg) as beige solids. LC-MS (ES) m/z=457 [M+H]+. 1H NMR (400 MHz, DMSO-d6) δ ppm 3.28 (t, J=8.5 Hz, 2H), 4.08 (s, 2H), 4.28 (t, J=8.5 Hz, 2H), 7.31 (d, J=8.3 Hz, 1H), 7.40 (s, 1H), 7.51 (d, J=9.9 Hz, 1H), 7.57 (s, 1H), 7.60 (d, J=8.1 Hz), 7.93 (s, 1H), 8.14 (d, J=8.1 Hz, 1H), 8.25 (s, 1H), NH2 protons not visible.

Example 120

5-{1-[(2,5-difluorophenyl)acetyl]-2,3-dihydro-1H-indol-5-yl}-7-[2-(4-piperidinyl)ethyl]-7H-pyrrolo[2,3-d]pyrimidin-4-amine

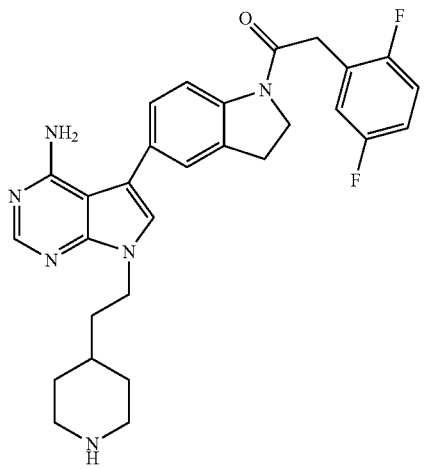 [SMILES: Nc1ncnc2c1c(-c1ccc3c(c1)CCN3C(=O)Cc1cc(F)ccc1F)cn2CCC1CCNCC1]

1,1-dimethylethyl 4-[2-(5-bromo-4-chloro-7H-pyrrolo[2,3-d]pyrimidin-7-yl)ethyl]-1-piperidinecarboxylate To 5-bromo-4-chloro-1H-pyrrolo[2,3-d]pyrimidine (200 mg, 0.860 mmol) in Tetrahydrofuran (THF) (10 mL) was added 1,1-dimethylethyl 4-(2-hydroxyethyl)-1-piperidinecarboxylate (592 mg, 2.58 mmol) and polymer bound triphenylphosphine (574 mg, 1.721 mmol) resin. To the mixture was then added dropwise DEAD (0.272 mL, 1.721 mmol). The stir bar was then removed from the reaction and the reaction was then placed on to a horizontal shaker and the reaction was agitated at room temp overnight. The resin was filtered off and the filtrated was concentrated then loaded on to a 10 g Biotage SNAP column and eluded with 0 to 45% EtOAc in Hexane to give 1,1-dimethylethyl 4-[2-(5-bromo-4-chloro-7H-pyrrolo[2,3-d]pyrimidin-7-yl)ethyl]-1-piperidinecarboxylate (326 mg, 85% yield) as a white solid. LC-MS (ES) m/z=443.4 [M+H]$^+$.

1,1-dimethylethyl 4-[2-(4-amino-5-bromo-7H-pyrrolo[2,3-d]pyrimidin-7-yl)ethyl]-1-piperidinecarboxylate To 1,1-dimethylethyl 4-[2-(5-bromo-4-chloro-7H-pyrrolo[2,3-d]pyrimidin-7-yl)ethyl]-1-piperidinecarboxylate (320 mg, 0.721 mmol) in a 5 ml sealable vial was added ammonium hydroxide (1.5 mL, 38.5 mmol). The vial was then capped and heated at 90° C. overnight. The reaction was then cooled and the solid was isolated filtration and washed with NH4OH. The solid was then air dried to give 1,1-dimethylethyl 4-[2-(4-amino-5-bromo-7H-pyrrolo[2,3-d]pyrimidin-7-yl)ethyl]-1-piperidinecarboxylate (309 mg) as an off white solid that contained a small amount of starting material. It was used without further purification. LC-MS (ES) m/z=424.4 [M+H]$^+$.

1,1-dimethylethyl 4-[2-(4-amino-5-{1-[(2,5-difluorophenyl)acetyl]-2,3-dihydro-1H-indol-5-yl}-7H-pyrrolo[2,3-d]pyrimidin-7-yl)ethyl]-1-piperidinecarboxylate To 1,1-dimethylethyl 4-[2-(4-amino-5-bromo-7H-pyrrolo[2,3-d]pyrimidin-7-yl)ethyl]-1-piperidinecarboxylate (220 mg, 0.518 mmol) and 1-[(2,5-difluorophenyl)acetyl]-5-(4,4,5,5-tetramethyl-1,3,2-dioxaborolan-2-yl)-2,3-dihydro-1H-indole (290 mg, 0.726 mmol) in a 5 ml sealable vial was added 1,4-Dioxane (2 mL) and saturated NaHCO3 (1 mL). The mixture was then bubbled with N2 for 10 minutes then Pd(Ph3P)4 (59.9 mg, 0.052 mmol) was added and N2 was bubbled for 5 minutes. The mixture was then capped and heated at 100° C. After 4 hours the reaction was complete. The reaction was diluted with water (5 ml) then extracted with EtOAc (3×10 ml). The organics were combined, washed with brine, dried over MgSO4, filtered and concentrated. The crude oil was then dissolved in 3 mL of DMSO and then purified on HPLC: (HPLC condition: Gilson using Trilution software with a Sunfire 5u C18(2) 100A. 50×30.00 mm 5 micron. 7.3-minute run (47 ml/min, 2% ACN/H2O, 0.1% TFA to 32% ACN/H2O, 0.1% TFA) with UV detection at 220 nm). Product fractions were combined and the volume was reduced to remove most of the MeCN. The water left behind was added saturated NaHCO3 and then extracted with EtOAc (3×15 mL). The organic was combined wash with saturated NaCl solution, dried over MgSO4, filtered and concentrated. Then the material was transferred to a 40 mL vial with MeCN, then water was added and it was freeze-dried to isolate 1,1-dimethylethyl 4-[2-(4-amino-5-{1-[(2,5-difluorophenyl)acetyl]-2,3-dihydro-1H-indol-5-yl}-7H-pyrrolo[2,3-d]pyrimidin-7-yl)ethyl]-1-piperidinecarboxylate (151 mg, 47.2% yield) as a white powder. LC-MS (ES) m/z=617.6 [M+H]$^+$.

5-{1-[(2,5-difluorophenyl)acetyl]-2,3-dihydro-1H-indol-5-yl}-7-[2-(4-piperidinyl)ethyl]-7H-pyrrolo[2,3-d]pyrimidin-4-amine To 1,1-dimethylethyl 4-[2-(4-amino-5-{1-[(2,5-difluorophenyl)acetyl]-2,3-dihydro-1H-indol-5-yl}-7H-pyrrolo[2,3-d]pyrimidin-7-yl)ethyl]-1-piperidinecarboxylate (157 mg, 0.255 mmol) was added 4N HCl (5 mL, 20.00 mmol) in dioxane and the mixture was allowed to stir at room temperature overnight. The reaction was concentrated and the solid was isolated by filtration and washed with diethyl ether to isolated 115 mg of the desired product as an HCl salt, which was then dissolved in 2 ml of DMSO and purified on HPLC: (HPLC condition: Gilson using Trilution software with a Sunfire 5u C18(2) 100A. 50×30.00 mm 5 micron. 7.3-minute run (47 ml/min, 10% ACN/H2O, 0.1% TFA to 35% ACN/H2O, 0.1% TFA) with UV detection at 254 nm). Product fractions were combined and the volume was reduced to remove most of the MeCN. The water left behind was added saturated NaHCO3 and then extracted with EtOAc (3×15 mL). The organic was combined wash with saturated NaCl solution, dried over MgSO4, filtered and concentrated. The material was then transferred into a 40 mL vial with MeCN. Water was added and then it was freeze-dried to give 5-{1-[(2,5-difluorophenyl)acetyl]-2,3-dihydro-1H-indol-5-yl}-7-[2-(4-piperidinyl)ethyl]-7H-pyrrolo[2,3-d]pyrimidin-4-amine (116 mg, 88% yield) as a white solid. LC-MS (ES) m/z=517.6 [M+H]$^+$. $^1$H NMR (400 MHz, DMSO-d$_6$) δ 8.35 (br. s., 1H), 8.14 (s, 1H), 8.09 (d, J=8.08 Hz, 1H), 7.35 (d, J=4.04 Hz, 2H), 7.15-7.30 (m, 4H), 6.09 (br. s., 2H), 4.29 (t, J=8.34 Hz, 2H), 4.21 (t, J=6.95 Hz, 2H), 3.95 (s, 2H), 3.22-

3.30 (m, 4H), 2.77-2.85 (m, 2H), 1.91 (d, J=12.13 Hz, 2H), 1.77 (q, J=6.65 Hz, 2H), 1.47 (br. s., 1H), 1.26-1.38 (m, 2H).

Example 121

7-methyl-5-{1-[(6-methyl-2-pyridinyl)acetyl]-2,3-dihydro-1H-indol-5-yl}-7H-pyrrolo[2,3-d]pyrimidin-4-amine

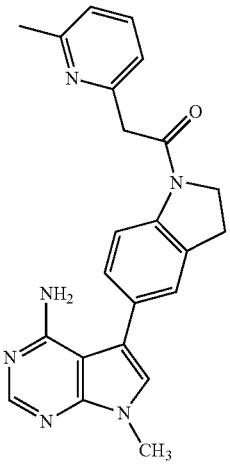 [SMILES: Cc1cccc(CC(=O)N2CCc3cc(-c4cn(C)c5ncnc(N)c45)ccc32)n1]

1,1-dimethylethyl (6-methyl-2-pyridinyl)acetate

To a stirred solution of tert-butyl acetate (1.013 mL, 7.50 mmol), 2-chloro-6-methylpyridine (638 mg, 5 mmol), chloro(2-di-t-butylphosphino-2',4',6'-tri-1-propyl-1,1'-biphenyl)[2-(2-aminoethyl)phenyl]palladium(II) (34.3 mg, 0.050 mmol) in Toluene (10 mL) at 0° C. in a 100-mL round bottom flask under N2 was added a solution of LHMDS (1M in toluene) (15.00 mL, 15.00 mmol) pre-cooled to 0° C. The reaction was stirred for 30 minutes. LCMS indicated the reaction was complete, so it was poured into ammonium chloride (aqueous, saturated) and water (1:1, 40 mL), and extracted with ethyl acetate (3×100 mL). The combined organics were dried over sodium sulfate, filtered and concentrated. The residue was purified by flash chromatography (0-25% EtOAc in hexanes) to afford 1,1-dimethylethyl (6-methyl-2-pyridinyl)acetate (918 mg, 4.43 mmol, 89% yield) as a yellow oil. LC-MS (ES) m/z=208 [M+H]+. $^1$H NMR (400 MHz, DMSO-$d_6$) δ ppm 1.41 (s, 9H), 2.44 (s, 3H), 3.68 (s, 1H), 7.12 (t, J=7.33 Hz, 2H), 7.64 (t, J=7.71 Hz, 1H).

(6-methyl-2-pyridinyl)acetic acid trifluoroacetate salt

To a solution of 1,1-dimethylethyl (6-methyl-2-pyridinyl) acetate (711 mg, 3.43 mmol), triethylsilane (1.370 mL, 8.58 mmol) in Dichloromethane (DCM) (10 mL) was added TFA (3.44 mL, 44.6 mmol) dropwise via syringe. The reaction was stirred for overnight at room temperature. LCMS indicated good conversion, so the reaction was concentrated to a colourless oil, and diethyl ether (6 mL) was added. A white precipitate formed which was collected by filtration, dried at the pump for 10 mins, then under high-vacuum to afford (6-methyl-2-pyridinyl)acetic acid TFA salt (771 mg) as a white solid. LC-MS (ES) m/z=152 [M+H]+. $^1$H NMR (400 MHz, DMSO-$d_6$) δ ppm 2.62 (s, 3H), 3.95 (s, 2H), 7.54 (d, J=7.33 Hz, 2H), 8.11 (br. s., 1H).

7-methyl-5-{1-[(6-methyl-2-pyridinyl)acetyl]-2,3-dihydro-1H-indol-5-yl}-7H-pyrrolo[2,3-d]pyrimidin-4-amine A solution of 5-(2,3-dihydro-1H-indol-5-yl)-7-methyl-7H-pyrrolo[2,3-d]pyrimidin-4-amine 2HCl (150 mg, 0.443 mmol), (6-methyl-2-pyridinyl)acetic acid TFA salt (118 mg, 0.443 mmol), HATU (169 mg, 0.443 mmol), and DIEA (0.387 mL, 2.217 mmol) in N,N-Dimethylformamide (DMF) (3 mL) were stirred overnight at room temperature. At this time, LCMS analysis indicated complete conversion, so water (15 mL) was added to the reaction mixture, and the resulting mixture stirred for 30 minutes at room temperature, forming an emulsion-like mixture. The mixture was extracted with ethyl acetate: methanol (ca. 1% methanol, 3×30 mL) and the combined organics were dried over sodium sulfate, filtered and concentrated. The residue was adsorbed onto silica and purified by flash chromatography (0-10% MeOH in EtOAc, 12-g column) to afford 7-methyl-5-{1-[(6-methyl-2-pyridinyl)acetyl]-2,3-dihydro-1H-indol-5-yl}-7H-pyrrolo[2,3-d]pyrimidin-4-amine (167.3 mg, 0.420 mmol, 95% yield) as an off-white solid. LC-MS (ES) m/z=399 [M+H]+. $^1$H NMR (400 MHz, DMSO-$d_6$) δ ppm 2.46 (s, 3H), 3.23 (t, J=8.34 Hz, 2H), 3.75 (s, 3H), 4.00 (s, 2H), 4.29 (t, J=8.46 Hz, 2H), 6.01-6.41 (m, 2H), 7.17 (t, J=7.33 Hz, 2H), 7.23 (d, J=8.34 Hz, 1H), 7.27-7.34 (m, 2H), 7.68 (t, J=7.58 Hz, 1H), 8.12 (d, J=8.08 Hz, 1H), 8.18 (s, 1H).

Example 122

5-(1-{[4-fluoro-3-(trifluoromethyl)phenyl]acetyl}-2,3-dihydro-1H-indol-5-yl)-7-methyl-7H-pyrrolo[2,3-d]pyrimidin-4-amine

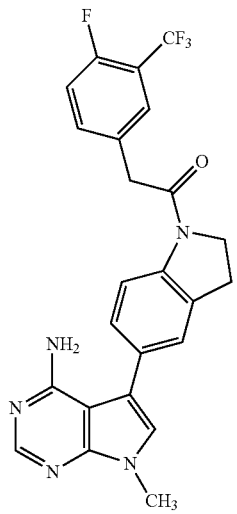 [SMILES: Cn1cc(-c2ccc3c(c2)CCN3C(=O)Cc2ccc(F)c(C(F)(F)F)c2)c2c(N)ncnc21]

A solution of 5-(2,3-dihydro-1H-indol-5-yl)-7-methyl-7H-pyrrolo[2,3-d]pyrimidin-4-amine 2HCl (150 mg, 0.443 mmol), [4-fluoro-3-(trifluoromethyl)phenyl]acetic acid (99 mg, 0.443 mmol), HATU (169 mg, 0.443 mmol), and DIEA (0.310 mL, 1.774 mmol) was stirred at room temperature overnight. LCMS analysis indicated good conversion, so the resulting suspension was poured into water (10 mL) and stirred for 30 min, forming a precipitate. This precipitate was collected by filtration, dried at the pump for an hour, then adsorbed onto silica and purified by flash chromatography (0-8% MeOH in EtOAc, 12-g column) to afford 5-(1-{[4-fluoro-3-(trifluoromethyl)phenyl]acetyl}-2,3-dihydro-1H-indol-5-yl)-7-methyl-7H-pyrrolo[2,3-d]pyrimidin-4-amine (198 mg, 95% yield) as a white solid. LC-MS (ES) m/z=470 [M+H]+. 1H NMR (400 MHz, DMSO-d6) ppm 3.26 (t, J=8.46 Hz, 2H), 3.74 (s, 3H), 4.02 (s, 2H), 4.27 (t, J=8.34 Hz, 2H), 5.91-6.20 (m, 2H), 7.19-7.29 (m, 2H), 7.33 (s, 1H), 7.50 (t, J=9.73 Hz, 1H), 7.64-7.70 (m, 1H), 7.73 (d, J=6.57 Hz, 1H), 8.11 (d, J=8.34 Hz, 1H), 8.15 (s, 1H).

Example 123

5-{1-[(2,5-difluorophenyl)acetyl]-2,3-dihydro-1H-indol-5-yl}-7-(3-oxetanyl)-7H-pyrrolo[2,3-d]pyrimidin-4-amine

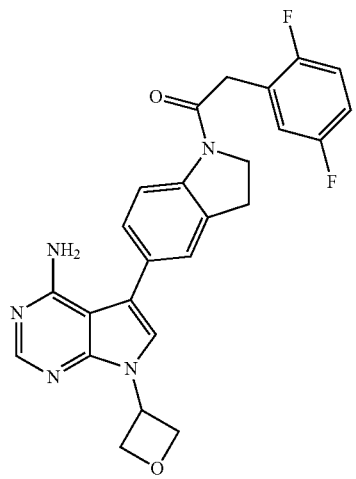 [SMILES: Nc1ncnc2c1c(-c1ccc3c(c1)CCN3C(=O)Cc1cc(F)ccc1F)cn2C1COC1]

5-bromo-4-chloro-7-(3-oxetanyl)-7H-pyrrolo[2,3-d]pyrimidine

To 5-bromo-4-chloro-1H-pyrrolo[2,3-d]pyrimidine (300 mg, 1.291 mmol) were added 3-oxetanol (287 mg, 3.87 mmol), polymer bound triphenylphosphine (860 mg, 2.58 mmol) resin and 1,4-Dioxane (2 mL) into a 5 mL microwave vial then DEAD (0.409 mL, 2.58 mmol) was added. The reaction vial was then capped and heated in microwave reactor for 15 minutes at 85° C. The reaction was not complete so it was heated for a total of 1 hr and the reaction was filtered, concentrated, diluted with EtOAc (10 mL) then washed water (10 ml). The water was back extracted with EtOAc (2×10 ml). The organics were combined then washed with brine, dried over MgSO4, filtered and concentrated. The crude was loaded on to a 10 g Biotage column and purified with 0 to 40% EtOAc in Hexane gradient over 30 minutes to afford 5-bromo-4-chloro-7-(3-oxetanyl)-7H-pyrrolo[2,3-d]pyrimidine (157 mg 42.2% yield) as a white solid. 1H NMR (400 MHz, DMSO-d6) δ 8.70 (s, 1H), 8.45 (s, 1H), 5.95 (t, J=7.07 Hz, 1H), 4.96-5.04 (m, J=7.07, 7.33, 7.45, 7.45 Hz, 4H).

5-bromo-7-(3-oxetanyl)-7H-pyrrolo[2,3-d]pyrimidin-4-amine

To 5-bromo-4-chloro-7-(3-oxetanyl)-7H-pyrrolo[2,3-d]pyrimidine (185 mg, 0.641 mmol) was added ammonium hydroxide (24.97 μl, 0.641 mmol) in a 25 ml sealable vial and heated at 85° C. over 24 hr. The solid was isolated by filtration and washed with water (5 mL) and dried to give 5-bromo-7-(3-oxetanyl)-7H-pyrrolo[2,3-d]pyrimidin-4-amine (106 mg), which was used without further purification.

5-{1-[(2,5-difluorophenyl)acetyl]-2,3-dihydro-1H-indol-5-yl}-7-(3-oxetanyl)-7H-pyrrolo[2,3-d]pyrimidin-4-amine To 5-bromo-7-(3-oxetanyl)-7H-pyrrolo[2,3-d]pyrimidin-4-amine (50 mg, 0.186 mmol) and 1-[(2,5-difluorophenyl)acetyl]-5-(4,4,5,5-tetramethyl-1,3,2-dioxaborolan-2-yl)-2,3-dihydro-1H-indole (104 mg, 0.260 mmol) were added 1,4-Dioxane (2 mL) and sat. NaHCO3 solution (1 mL) in a 5 ml sealable vial. N2 gas was bubbled through the mixture for 10 minutes then Pd(Ph3P)4 (21.47 mg, 0.019 mmol) was added and bubbled N2 for 5 minutes. The mixture was then capped and heated 100° C. overnight. The reaction was diluted with water (3 ml) then extracted with EtOAc (4×5 ml). The organics were then combined, washed with brine, dried over MgSO4, filtered and concentrated. The residual was then diluted with 3 ml of DMSO and purified on HPLC: (HPLC condition: Gilson using Trilution software with a Sunfire 5u C18(2) 100A. 50×30.00 mm 5 micron. 7.3-minute run (47 ml/min, 15% ACN/H2O, 0.1% TFA to 40% ACN/H2O, 0.1% TFA) with UV detection at 254 nm). Product fractions were combined and the volume was reduced to remove most of the MeCN. The water left behind was added saturated NaHCO3 and then extracted with EtOAc (3×15 mL). The organic was combined wash with saturated NaCl solution, dried over MgSO4, filtered and concentrated. The material was then transferred into a 40 mL vial with MeCN then water was added and the solution was freeze-dried to give 5-{1-[(2,5-difluorophenyl)acetyl]-2,3-dihydro-1H-indol-5-yl}-7-(3-oxetanyl)-7H-pyrrolo[2,3-d]pyrimidin-4-amine (53 mg, 61.8% yield) as a white power. LC-MS (ES) m/z=462.4 [M+H]+. 1H NMR (400 MHz, DMSO-d6) δ 8.15 (d, J=3.28 Hz, 1H), 8.08-8.13 (m, 1H), 7.70 (d, J=3.03 Hz, 1H), 7.41 (br. s., 1H), 7.15-7.33 (m, 4H), 6.17 (br. s., 2H), 5.82-5.93 (m, 1H), 4.95-5.07 (m, 4H), 4.30 (br. s., 2H), 3.96 (br. s., 2H), 3.29 (d, J=1.01 Hz, 2H).

Example 124

3-{1-[(2,5-difluorophenyl)acetyl]-2,3-dihydro-1H-indol-5-yl}-7-[2-(dimethylamino)ethyl]furo[3,2-c]pyridin-4-amine

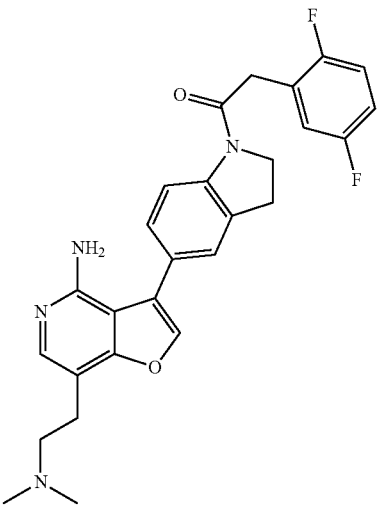 [SMILES: CN(C)CCc1cnc(N)c2c(-c3ccc4c(c3)CCN4C(=O)Cc3cc(F)ccc3F)coc12]

A solution of 7-(2-aminoethyl)-3-{1-[(2,5-difluorophenyl)acetyl]-2,3-dihydro-1H-indol-5-yl}furo[3,2-c]pyridin-4-amine (182 mg, 0.386 mmol) in Tetrahydrofuran (THF) (5 mL) and Methanol (2.5 mL) under Nitrogen was cooled to 0° C. Formaldehyde (37 wt. % in water) (61 µL, 0.812 mmol) was added, and after about 5 minutes sodium triacetoxyborohydride (327 mg, 1.542 mmol) was added in one portion. The mixture was allowed to slowly warm to room temperature and it was stirred for 21 hours. The mixture was then poured into saturated aqueous NaHCO3 (20 mL), diluted with a little water, and extracted with ethyl acetate (2×20 mL). The extracts were washed with brine (1×20 mL), dried (Na2SO4), filtered, and concentrated in vacuo. The residue was purified by flash chromatography (Analogix, 24 g SiO2, DCM to 90/10/1 DCM/MeOH/NH4OH gradient over 40 minutes) to give 3-{1-[(2,5-difluorophenyl)acetyl]-2,3-dihydro-1H-indol-5-yl}-7-[2-(dimethylamino)ethyl]furo[3,2-c]pyridin-4-amine (122 mg, 66.4% yield) as a yellow solid. LC-MS (ES) m/z=477 [M+H]+. 1H NMR (400 MHz, DMSO-d6) δ ppm 2.20 (s, 6H), 2.83 (t, J=7.58 Hz, 2H), 3.28 (t, J=8.34 Hz, 2H), 3.96 (s, 2H), 4.30 (t, J=8.34 Hz, 2H), 5.33 (s, 2H), 7.04-7.36 (m, 4H), 7.41 (s, 1H), 7.72 (s, 1H), 7.93 (s, 1H), 8.12 (d, J=8.34 Hz, 1H). Note: NH's are not observed.

Example 125

7-methyl-5-(1-{[6-(trifluoromethyl)-2-pyridinyl]acetyl}-2,3-dihydro-1H-indol-5-yl)-7H-pyrrolo[2,3-d]pyrimidin-4-amine

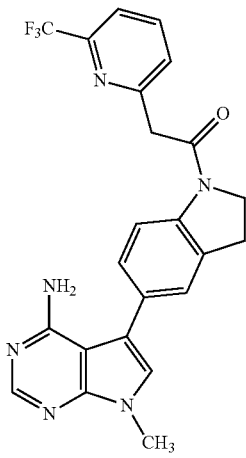 [SMILES: Cn1cc(-c2ccc3c(c2)CCN3C(=O)Cc2cccc(C(F)(F)F)n2)c2c(N)ncnc21]

1,1-dimethylethyl[6-(trifluoromethyl)-2-pyridinyl]acetate

To a stirred solution of tert-butyl acetate (1.013 mL, 7.5 mmol), 2-chloro-6-(trifluoromethyl)pyridine (908 mg, 5.00 mmol), chloro(2-di-t-butylphosphino-2',4',6'-tri-1-propyl-1,1'-biphenyl)[2-(2-aminoethyl)phenyl]palladium(II) (343 mg, 0.500 mmol) in Toluene (10 mL) at 0° C. in a 100-mL RBF under N2 was added a solution of LHMDS (1M in toluene) (15.00 mL, 15.00 mmol) prec-cooled to 0° C. The reaction was stirred for 30 min, but LCMS indicated the reaction was not complete, so the reaction was allowed to warm to room temperature overnight, and LCMS analysis indicated that the reaction was complete, so it was poured into ammonium chloride (aqueous, saturated) and water (1:1, 40 mL), and extracted with ethyl acetate (3×100 mL). The combined organics were dried over sodium sulfate, filtered and concentrated. The residue was purified by flash chromatography (0-25% EtOAC in hexanes, 90-g column) to afford 1,1-dimethylethyl[6-(trifluoromethyl)-2-pyridinyl]acetate (701.3 mg, 53.7% yield) as a pale yellow oil. LC-MS (ES) m/z=206 [M+H-tBu]+. 1H NMR (400 MHz, DMSO-d6) δ ppm 1.41 (s, 9H), 3.88 (s, 2H), 7.61-7.71 (m, 1H), 7.77-7.85 (m, 1H), 8.02-8.11 (m, 1H).

[6-(trifluoromethyl)-2-pyridinyl]acetic acid

To a solution of 1,1-dimethylethyl[6-(trifluoromethyl)-2-pyridinyl]acetate (698 mg, 2.67 mmol), triethylsilane (1.067 mL, 6.68 mmol) in Dichloromethane (DCM) (10 mL) was added TFA (2.68 mL, 34.7 mmol) dropwise via syringe. The reaction was stirred overnight at room temperature. LCMS analysis indicated good conversion, so the reaction was concentrated to a yellow oil. 5 mL of diethyl ether was added but no precipitation occurred, so the solution was concentrated to afford [6-(trifluoromethyl)-2-pyridinyl]acetic acid (535 mg, 2.61 mmol, 98% yield) as a yellow oil which solidified to a yellow solid. LC-MS (ES) m/z=206 [M+H]+. 1H NMR (400 MHz, DMSO-d6) δ ppm 3.89 (s, 2H), 7.70 (d, J=7.83 Hz, 1H), 7.81 (d, J=7.58 Hz, 1H), 7.97-8.16 (m, 1H), 12.26-12.88 (br. s., 1H).

7-methyl-5-(1-{[6-(trifluoromethyl)-2-pyridinyl]acetyl}-2,3-dihydro-1H-indol-5-yl)-7H-pyrrolo[2,3-d]pyrimidin-4-amine A solution of 5-(2,3-dihydro-1H-indol-5-yl)-7-methyl-7H-pyrrolo[2,3-d]pyrimidin-4-amine 2HCl (150 mg, 0.443 mmol), [6-(trifluoromethyl)-2-pyridinyl]acetic acid (91 mg, 0.443 mmol), HATU (169 mg, 0.443 mmol), and DIEA (0.310 mL, 1.774 mmol) in N,N-Dimethylformamide (DMF) (3 mL) were stirred overnight at room temperature. LCMS analysis at this time indicated good conversion, so the reaction mixture was poured into water (10 mL) and stirred for 30 min. The resulting precipitate was collected by filtration, dried at the pump for an hour, adsorbed onto silica and purified by flash chromatography (0-10% MeOH in EtOAc) to afford 7-methyl-5-(1-{[6-(trifluoromethyl)-2-pyridinyl]acetyl}-2,3-dihydro-1H-indol-5-yl)-7H-pyrrolo[2,3-d]pyrimidin-4-amine (80 mg, 39.9% yield) as a beige solid. LC-MS (ES) m/z=453 [M+H]+. 1H NMR (400 MHz, DMSO-d6) δ ppm 3.26 (t, J=8.34 Hz, 2H), 3.74 (s, 3H), 4.21 (s, 2H), 4.31 (t, J=8.46 Hz, 2H), 5.85-6.26 (m, 2H), 7.23 (d, J=8.34 Hz, 1H), 7.26 (s, 1H), 7.34 (s, 1H), 7.71 (d, J=7.83 Hz, 1H), 7.83 (d, J=7.58 Hz, 1H), 8.05-8.13 (m, 2H), 8.15 (s, 1H).

Example 126

7-(3-oxetanyl)-5-(1-{[3-(trifluoromethyl)phenyl]acetyl}-2,3-dihydro-1H-indol-5-yl)-7H-pyrrolo[2,3-d]pyrimidin-4-amine

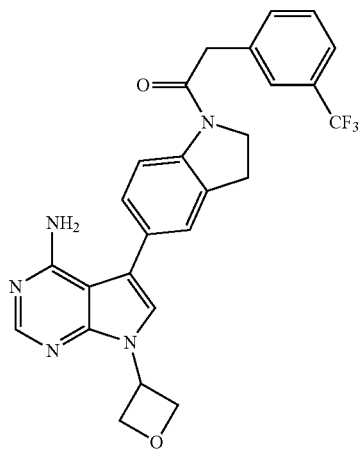 [SMILES: Nc1ncnc2c1c(-c1ccc3c(c1)CCN3C(=O)Cc1cccc(C(F)(F)F)c1)cn2C1COC1]

5-bromo-1-{[3-(trifluoromethyl)phenyl]acetyl}-2,3-dihydro-1H-indole

To 5-bromoindoline (5.0 g, 25.2 mmol, 1 equiv) and [3-(trifluoromethyl)phenyl]acetic acid (6.18 g, 30.3 mmol, 1.2 equiv) in 13 mL of DMF was added propylphosphonic anhydride (36.9 mL of a 1.71 M solution in DMF, 63.1 mmol, 2.5 equiv) followed by DIEA (8.82 mL, 50.5 mmol, 2 equiv). The reddish mixture became warm to touch and was cooled at once in an ice bath. After 30 minutes, the cooling bath was removed and the mixture was stirred at ambient temp. After 18 h, the mixture was diluted with 200 mL of EtOAc and washed with 200 mL of water. The aq was extracted with 150 mL of EtOAc. The combined organic was dried over MgSO4, filtered, and concentrated in vacuo to give a paste residue, which was taken up in ether and hexane to provide a suspension. The suspension was filtered. The solids were washed with hexane and then ether and dried under vacuum to afford crude product (6.17 g) a brownish sticky solids. NMR showed presence of some alkyl impurities, so this lot was redissolved in DCM (150 mL) and washed with water (50 mL). The organic was dried over MgSO4, filtered, and conc in vacuo. The residue was triturated in DCM (5 mL) and ether (75 mL). The suspension was filtered, and the cake was washed with ether. The solids were dried under vacuum to afford 5-bromo-1-{[3-(trifluoromethyl)phenyl]acetyl}-2,3-dihydro-1H-indole (4.73 g) as light cream solids. The filtrate was concentrated in vacuo, and the residue was dissolved in DCM and absorbed onto a dryload cartridge. Purification was done on an SF40-150 g silica gel cartridge using gardient elution of 1% EtOAc in hexane to 45% EtOAc in hexane. The product peak eluted from 24-33% EtOAc. The product fractions were combined and concentrated in vacuo to afford product (2.80 g) as a brownish sticky solid residue. Both NMR and LCMS showed this lot had some impurities. The residue was triturated in DCM and ether. The suspension was filtered, and the cake was washed with ether. The solids were dried under vacuum to afford additional 5-bromo-1-{[3-(trifluoromethyl)phenyl]acetyl}-2,3-dihydro-1H-indole (1.62 g) as off-white solids. Both NMR and LCMS showed this lot was pure. LC-MS (ES) m/z=384 [M+H]+, 386. $^1$H NMR (400 MHz, DMSO-$d_6$) ppm 3.20 (t, J=8.5 Hz, 2H), 4.00 (s, 2H), 4.23 (t, J=8.6 Hz, 2H), 7.32 (dd, J=8.7, 1.9 Hz, 1H), 7.45 (s, 1H), 7.53-7.70 (m, 4H), 7.96 (d, J=8.6 Hz, 1H).

5-(4,4,5,5-tetramethyl-1,3,2-dioxaborolan-2-yl)-1-{[3-(trifluoromethyl)phenyl]acetyl}-2,3-dihydro-1H-indole A mixture of 5-bromo-1-{[3-(trifluoromethyl)phenyl]acetyl}-2,3-dihydro-1H-indole (8.50 g, 22.12 mmol, 1 equiv), bis(pinacolato)diboron (6.74 g, 26.5 mmol, 1.2 equiv), PdCl2(dppf)-CH2Cl2 adduct (1.81 g, 2.21 mmol, 0.1 equiv) and potassium acetate (5.43 g, 55.3 mmol, 2.5 equiv) in 85 mL of dioxane in a 500 mL flask was degassed and backflushed with nitrogen. This process was repeated 4×. The mixture was heated in an oil bath at 100° C. The color of the mixture changed gradually from the initial orange to burgundy over a 30 min period when the temp reached 100° C., and then grew darker as heating progressed. After 20 h, LCMS showed conversion complete. The dark blackish mixture was filtered through celite. The filtrate was conc in vacuo. The residue was partitioned between EtOAc (250 mL) and brine (40 mL). The organic was dried over Na2SO4, filtered, and concentrated in vacuo. The solid residue was dissolved in DCM. About ⅕ was absorbed onto a dryload cartridge. Purification was done on an Analogix SF40-115 g silica gel cartridge using gradient elution of 1% EtOAc in hexane to 45% EtOAc in hexane. However, the dryload cartridge was plugged. The back pressure was too high for the Analogix instrument to function and the pump stalled (the sample was not that soluble in hexane). About a half was injected into the silica gel cartridge, and the desired product eluted from 24-30% EtOAc in hexane. The plugged dryload cartridge was flushed with 100 mL of 100% EtOAc to recover the rest of the injected sample, which was combined with the rest ⅘ of the original DCM sample solution. This mixture was concentrated in vacuo and re-dissolved in DCM (50 mL), and was added to a prepacked gravity column (250 g of coarse grade silica gel packed in 1% DCM in hexane). The column was eluted with 400 mL of 1% DCM in hexane, 400 mL of ⅓ DCM/hexane, 400 mL of 1/1 DCM/hexane, and then 400 mL 1/1 DCM/hexane portions each with 20 mL increment of EtOAc. The desired product eluted from 20 mL to 60 mL EtOAc fractions. The collected fractions (including the one from above Analogix prep) were combined and concentrated in vacuo to about 100 mL volume as a suspension. This suspension was filtered. The cake was washed with hexane (10 mL) and dried under vacuum for 18 h to afford 5-(4,4,5,5-tetramethyl-1,3,2-dioxaborolan-2-yl)-1-{[3-(trifluoromethyl)phenyl]acetyl}-2,3-dihydro-1H-indole (5.98 g) as white solids. LC-MS (ES) m/z=432 [M+H]+. $^1$H NMR (400 MHz, DMSO-$d_6$) δ ppm 1.28 (s, 12H), 3.19 (t, J=8.5 Hz, 2H), 4.02 (s, 2H), 4.23 (t, J=8.6 Hz, 2H), 7.48 (d, J=8.3 Hz, 1H), 7.54 (s, 1H), 7.56-7.69 (m, 14H), 8.03 (d, J=8.1 Hz, 1H).

7-(3-oxetanyl)-5-(1-{[3-(trifluoromethyl)phenyl]acetyl}-2,3-dihydro-1H-indol-5-yl)-7H-pyrrolo[2,3-d]pyrimidin-4-amine To 5-bromo-7-(3-oxetanyl)-7H-pyrrolo[2,3-d]pyrimidin-4-amine (50 mg, 0.186 mmol) and 5-(4,4,5,5-tetramethyl-1,3,2-dioxaborolan-2-yl)-1-{[3-(trifluoromethyl)phenyl]acetyl}-2,3-dihydro-1H-indole (112 mg, 0.260 mmol) were added 1,4-Dioxane (2 mL) and sat. NaHCO3 (1 mL) into a 5 ml sealable. The mixture was then bubbled with N2 gas for 5 minutes. Pd(Ph3P)4 (21.47 mg, 0.019 mmol) was added and the vessel was capped and heated at 100° C. overnight. The reaction was then diluted with water (2 ml) and extracted with EtOAc (3×3 ml). The organics were then combined and washed with brine, dried over MgSO4, filtered, concentrated. The crude was dissolved in 3 mL of DMSO and purified by HPLC: (HPLC condition: Gilson using Trilution software with a Sunfire 5u C18(2) 100A. 50×30.00 mm 5 micron. 7.3-minute run (47 ml/min, 20% ACN/H2O, 0.1% TFA to 45% ACN/H2O, 0.1% TFA) with UV detection at 254 nm). Product fractions were combined and the volume was reduced to remove most of the MeCN. To the water left behind was added saturated NaHCO3 and then the mixture was extracted with EtOAc (3×15 mL). The organics were combined wash with saturated NaCl solution, dried over MgSO4, filtered and concentrated. The material was transferred into a 40 mL vial with MeCN then water was added and the solution was freeze-dried to give 7-(3-oxetanyl)-5-(1-{[3-(trifluoromethyl)phenyl]acetyl}-2,3-dihydro-1H-indol-5-yl)-7H-pyrrolo[2,3-d]pyrimidin-4-amine (46 mg, 50.2% yield) as a white solid. LC-MS (ES) m/z=494.4 [M+H]+. $^1$H NMR (400 MHz, DMSO-$d_6$) δ 8.11-8.17 (m, 2H), 7.67-7.72 (m, 2H), 7.56-7.67 (m, 3H), 7.40 (s, 1H), 7.29 (d, J=8.08 Hz, 1H), 6.16 (br. s., 2H), 5.88 (quin, J=7.14 Hz, 1H), 4.95-5.04 (m, 4H), 4.28 (t, J=8.34 Hz, 2H), 4.04 (s, 2H), 3.27 (t, J=8.34 Hz, 2H).

Example 127

7-[2-(4-morpholinyl)ethyl]-5-(1-{[3-(trifluoromethyl)phenyl]acetyl}-2,3-dihydro-1H-indol-5-yl)-7H-pyrrolo[2,3-d]pyrimidin-4-amine

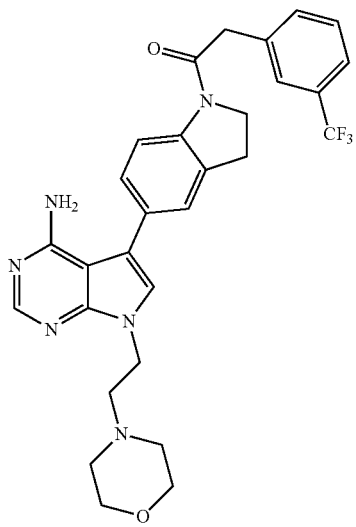 [SMILES: Nc1ncnc2c1c(-c1ccc3c(c1)CCN3C(=O)Cc1cccc(C(F)(F)F)c1)cn2CCN1CCOCC1]

To 5-bromo-7-[2-(4-morpholinyl)ethyl]-7H-pyrrolo[2,3-d]pyrimidin-4-amine (50 mg, 0.153 mmol) and 5-(4,4,5,5-tetramethyl-1,3,2-dioxaborolan-2-yl)-1-{[3-(trifluoromethyl)phenyl]acetyl}-2,3-dihydro-1H-indole (93 mg, 0.215 mmol) were added 1,4-Dioxane (2 mL) and sat. NaHCO3 (1 mL) in a 5 ml sealable vessel. The mixture was then bubbled with N2 gas for 5 minutes then added Pd(Ph3P)4 (17.71 mg, 0.015 mmol) and the reaction was capped and heated at 100° C. overnight. The reaction was then diluted with water (2 ml) then extracted with EtOAc (3×3 ml). The organics were then combined and washed with brine, dried over MgSO4, filtered, and concentrated. The residue was dissolved in 3 mL of DMSO and then purified by HPLC: (HPLC condition: Gilson using Trilution software with a Sunfire 5u C18(2) 100A. 50×30.00 mm 5 micron. 7.3-minute run (47 ml/min, 18% ACN/H2O, 0.1% TFA to 43% ACN/H2O, 0.1% TFA) with UV detection at 220 nm). Product fractions were combined and the volume was reduced to remove most of the MeCN. To the water left behind was added saturated NaHCO3 and then the mixture was extracted with EtOAc (3×15 mL). The organics were combined, washed with saturated NaCl solution, dried over MgSO4, filtered and concentrated. Then the product was transferred into a 40 mL vial with MeCN then added water and freeze-dried to give 7-[2-(4-morpholinyl)ethyl]-5-(1-{[3-(trifluoromethyl)phenyl]acetyl}-2,3-dihydro-1H-indol-5-yl)-7H-pyrrolo[2,3-d]pyrimidin-4-amine (35 mg, 41.5% yield) as a white solid. LC-MS (ES) m/z=551.5 [M+H]+. 1H NMR (400 MHz, DMSO-d6) δ 8.10-8.15 (m, 2H), 7.69 (s, 1H), 7.56-7.66 (m, 3H), 7.33 (s, 2H), 7.24 (d, J=8.34 Hz, 1H), 6.06 (br. s., 2H), 4.24-4.31 (m, 4H), 4.04 (s, 2H), 3.54 (br. s., 4H), 3.22-3.29 (m, J=7.83 Hz, 2H), 2.71 (br. s., 2H), 2.46 (br. s., 4H).

Example 128

7-(1-methylethyl)-5-(1-{[3-(trifluoromethyl)phenyl]acetyl}-2,3-dihydro-1H-indol-5-yl)-7H-pyrrolo[2,3-d]pyrimidin-4-amine

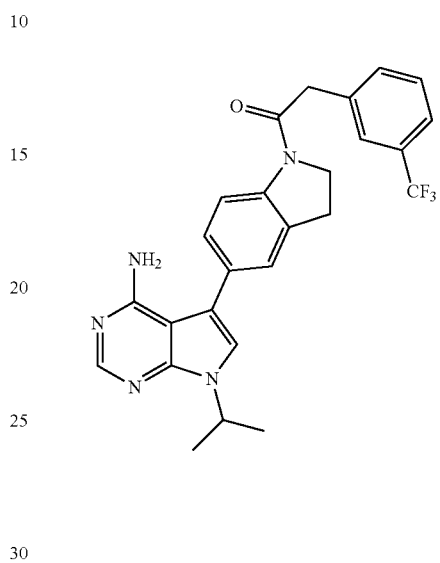

To 5-bromo-7-(1-methylethyl)-7H-pyrrolo[2,3-d]pyrimidin-4-amine (70 mg, 0.274 mmol) and 5-(4,4,5,5-tetramethyl-1,3,2-dioxaborolan-2-yl)-1-{[3-(trifluoromethyl)phenyl]acetyl}-2,3-dihydro-1H-indole (166 mg, 0.384 mmol) were added 1,4-Dioxane (2 mL) and saturated NaHCO3 (1 mL) in a 5 ml sealable vessel. The mixture was then bubbled with N2 gas for 5 minutes then added Pd(Ph3P)4 (317 mg, 0.274 mmol) and the vessel was capped. The reaction was then heated at 100° C. overnight. The reaction was then diluted with water (2 ml) then extracted with EtOAc (3×3 ml). The organics were then combined and washed with brine, dried over MgSO4, filtered and concentrated. The residue was dissolved in 3 mL of DMSO and then purified by HPLC: (HPLC condition: open-access Gilson using Trilution software with a Sunfire 5u C18(2) 100A. 50×30.00 mm 5 micron. 7.3-minute run (47 ml/min, 35% ACN/H2O, 0.1% TFA to 60% ACN/H2O, 0.1% TFA) with UV detection at 220 nm). Product fractions were combined and the volume was reduced to remove most of the MeCN. To the water left behind was added saturated NaHCO3 and the mixture was extracted with EtOAc (3×15 mL). The organics were combined wash with saturated NaCl solution, dried over MgSO4, filtered and concentrated. The product was transferred to a 40 mL vial with MeCN then water was added and the solution was freeze-dried to provide 7-(1-methylethyl)-5-(1-{[3-(trifluoromethyl)phenyl]acetyl}-2,3-dihydro-1H-indol-5-yl)-7H-pyrrolo[2,3-d]pyrimidin-4-amine (62 mg, 47.1% yield) as a white solid. LC-MS (ES) m/z=480.5 [M+H]+. 1H NMR (400 MHz, DMSO-d6) δ 8.23 (s, 1H), 8.13 (d, J=8.34 Hz, 1H), 7.69 (s, 1H), 7.57-7.67 (m, 3H), 7.54 (s, 1H), 7.36 (s, 1H), 7.26 (d, J=8.08 Hz, 1H), 6.57 (br. s., 2H), 4.99 (quin, J=6.76 Hz, 1H), 4.28 (t, J=8.46 Hz, 2H), 4.04 (s, 2H), 3.23-3.28 (m, 2H), 1.47 (d, J=6.82 Hz, 6H).

Example 129

7-(3-methylbutyl)-5-(1-{[3-(trifluoromethyl)phenyl]acetyl}-2,3-dihydro-1H-indol-5-yl)-7H-pyrrolo[2,3-d]pyrimidin-4-amine

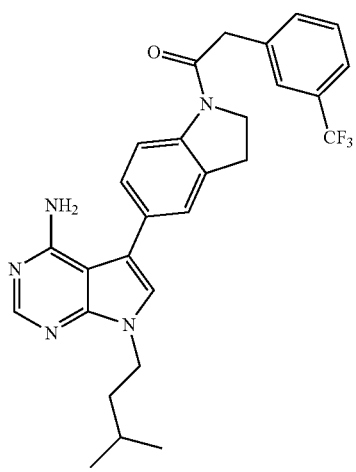 [SMILES: CC(C)CCn1cc(-c2ccc3c(c2)CCN3C(=O)Cc2cccc(C(F)(F)F)c2)c2c(N)ncnc21]

To 5-bromo-7-(3-methylbutyl)-7H-pyrrolo[2,3-d]pyrimidin-4-amine (75 mg, 0.265 mmol) and 5-(4, 4,5,5-tetramethyl-1,3,2-dioxaborolan-2-yl)-1-{[3-(trifluoromethyl)phenyl]acetyl}-2,3-dihydro-1H-indole (160 mg, 0.371 mmol) were added 1,4-Dioxane (2 mL) and saturated NaHCO3 (1 mL) in a 5 ml sealable vessel. The mixture was then bubbled with N2 gas for 5 minutes then Pd(Ph3P)4 (30.6 mg, 0.026 mmol) was added and the vessel was capped. The reaction was then heated at 100° C. overnight. The reaction was then diluted with water (2 ml) then extracted with EtOAc (3×3 ml). The organics were then combined and washed with brine, dried over MgSO4, filtered and concentrated. The crude was dissolved in 3 mL of DMSO and the product purified by HPLC: (HPLC condition: Gilson using Trilution software with a Sunfire 5u C18(2) 100A. 50×30.00 mm 5 micron. 7.3-minute run (47 ml/min, 40% ACN/H2O, 0.1% TFA to 65% ACN/H2O, 0.1% TFA) with UV detection at 254 nm). Product fractions were combined and the volume was reduced to remove most of the MeCN. The water left behind was added saturated NaHCO3 and then extracted with EtOAc (3×15 mL). The organics were combined and washed with saturated NaCl solution, dried over MgSO4, filtered and concentrated. The material was transferred to a 40 mL vial with MeCN then water was added and the solution was freeze-dried. to afford 7-(3-methylbutyl)-5-(1-{[3-(trifluoromethyl)phenyl]acetyl}-2,3-dihydro-1H-indol-5-yl)-7H-pyrrolo[2,3-d]pyrimidin-4-amine (67 mg, 0.132 mmol, 49.8% yield) as a white solid. LC-MS (ES) m/z=508.5 [M+H]$^+$. $^1$H NMR (400 MHz, DMSO-d$_6$) δ 8.15 (s, 1H), 8.11 (d, J=8.34 Hz, 1H), 7.69 (s, 1H), 7.56-7.66 (m, 3H), 7.33 (s, 2H), 7.24 (d, J=8.34 Hz, 1H), 6.10 (br. s., 2H), 4.27 (t, J=8.46 Hz, 2H), 4.18 (t, J=7.33 Hz, 2H), 4.03 (s, 2H), 3.26 (t, J=8.34 Hz, 2H), 1.69 (q, J=6.99 Hz, 2H), 1.50 (dt, J=6.69, 13.39 Hz, 1H), 0.93 (d, J=6.57 Hz, 6H).

Example 130

4-{1-[(3-methyl phenyl)acetyl]-2,3-dihydro-1H-indol-5-yl}-1H-pyrazolo[3,4-c]pyridin-3-amine

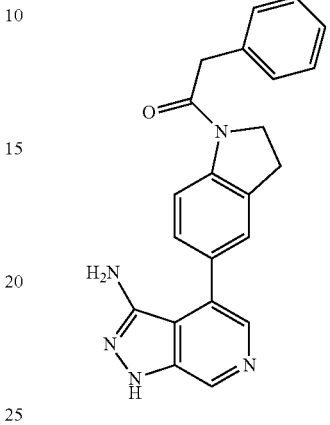

3-chloro-5-{1-[(3-methylphenyl)acetyl]-2,3-dihydro-1H-indol-5-yl}-4-pyridinecarbonitrile A mixture of 3,5-dichloro-4-pyridinecarbonitrile (400 mg, 2.312 mmol), 1-[(3-methylphenyl)acetyl]-5-(4,4,5,5-tetramethyl-1,3,2-dioxaborolan-2-yl)-2,3-dihydro-1H-indole (872 mg, 2.312 mmol), Pd2(dba)$_3$ (42.3 mg, 0.046 mmol) and K3PO4 (982 mg, 4.62 mmol) in 9 mL of dioxane and 3 mL of water in a microwave tube was degassed and backflushed with nitrogen, followed by addition of tri-(t-butyl)phosphonium tetrafluoroborate salt (26.8 mg, 0.092 mmol). The mixture was degassed and backflushed with nitrogen. The mixture was heated in a microwave reactor at 120° C. for 40 minutes. LCMS showed there was no stating material. The mixture was cooled to room temperature, and the mixture was filtered. The filtered solid was purified by silica gel column chromatography on a silica gel cartridge using gradient elution of 100% CH2Cl2 to 90:10:1 CH2Cl2/CH3OH/NH3OH. The combined product fractions were evaporated to dryness to give 3-chloro-5-{1-[(3-methylphenyl)acetyl]-2,3-dihydro-1H-indol-5-yl}-4-pyridinecarbonitrile as a pale yellow solid (255 mg, 26% yield). LCMS [M+1] 388. $^1$H NMR (400 MHz, DMSO-d$_6$) δ 2.31 (s, 3H), 3.24 (t, J=8.34 Hz, 2H), 3.85 (s, 2H), 4.25 (t, J=8.46 Hz, 2H), 7.06-7.14 (m, 3H), 7.20-7.27 (m, 1H), 7.51 (d, J=8.34, 1H), 7.58 (s, 1H), 8.21 (d, J=8.34 Hz, 1H), 8.82 (s, 1H), 8.93 (s, 1H).

4-{1-[(3-methylphenyl)acetyl]-2,3-dihydro-1H-indol-5-yl}-1H-pyrazolo[3,4-c]pyridin-3-amine To 3-chloro-5-{1-[(3-methyl phenyl)acetyl]-2,3-dihydro-1H-indol-5-yl}-4-pyridinecarbonitrile (100 mg, 0.258 mmol) in Ethanol (6 mL) was added hydrazine monohydrate (1 mL, 31.9 mmol), and the reaction mixture was stirred at 80° C. overnight into a sealed vessel. LCMS analysis of the reaction mixture indicated the presence of starting material. Therefore, the reaction mixture was stirred at 100° C. overnight. The mixture was poured onto EtOAc and water. The organic layer was separated, washed with brine, dried (MgSO$_4$), filtered and concentrated. The resulting residue was purified by flash chromatography on SiO2 (gradient: 100% Hexanes to 100% EtOAc to 20% CH3OH/EtOAc). The fractions containing the product were combined, concentrated, and triturated with Et2O to afford 4-{1-[(3-methylphenyl)acetyl]-2,3-dihydro-1H-indol-5-yl}-1H-pyrazolo[3,4-c]pyridin-3-amine (15 mg) as a yellow solid. $^1$H NMR (400 MHz, DMSO-d$_6$) δ 2.32 (s, 3H), 3.25 (t, J=8.34 Hz, 2H), 3.85 (s, 2H), 4.24 (t, J=8.46 Hz, 2H), 4.6 (m, 1.3H(NH2)), 7.05-7.16 (m, 3H), 7.19-7.28 (m, 1H), 7.33 (d, J=8.34 Hz, 1H), 7.42 (s, 1H), 7.93 (s, 1H), 8.21 (d, J=8.34 Hz, 1H), 8.74 (s, 1H), 12.27 (br. s., 1H).

Example 131

7-chloro-3-{1-[(2,5-difluorophenyl)acetyl]-2,3-dihydro-1H-indol-5-yl}furo[3,2-c]pyridin-4-amine

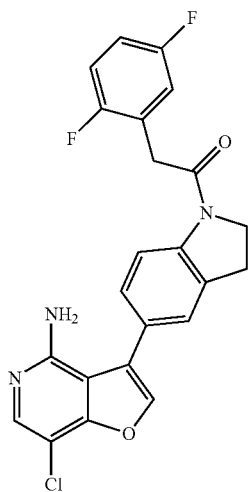 [SMILES: Nc1ncc(Cl)c2occ(-c3ccc4c(c3)CCN4C(=O)Cc3cc(F)ccc3F)c12]

1,1-dimethylethyl 5-(4-aminofuro[3,2-c]pyridin-3-yl)-2,3-dihydro-1H-indole-1-carboxylate 3-Bromofuro[3,2-c]pyridin-4-amine (7.23 g, 33.9 mmol), 1,1-dimethylethyl 5-(4,4,5,5-tetramethyl-1,3,2-dioxaborolan-2-yl)-2,3-dihydro-1H-indole-1-carboxylate (12.90 g, 37.4 mmol), PdCl2(dppf)-CH2Cl2 adduct (1.39 g, 1.702 mmol), 1,4-Dioxane (300 mL), and saturated aqueous sodium bicarbonate (100 mL, 100 mmol) were added to a 3-neck, 1 L flask equipped with a reflux condenser and a heating mantle. The flask was evacuated and filled with nitrogen 4 times, and then the mixture was stirred at reflux under Nitrogen for 2 hr. HPLC showed complete conversion, so it was cooled and allowed to stir at room temperature overnight. The crude mixture was then filtered through celite, rinsing with EtOAc (500 mL). The filtrate was washed with half-saturated aqueous NaHCO3 (500 mL), and the aqueous phase was back-extracted with ethyl acetate (1×500 mL). The combined organic phases was washed with brine (1×500 mL), dried (Na2SO4), filtered, and concentrated in vacuo. The residue was purified by flash chromatography (Analogix, 600 g SiO2, 20%-100% EtOAc in hexanes gradient over 60 minutes, then 100% EtOAc for 30 more minutes). The product fractions were combined and concentrated in vacuo to give 1,1-dimethylethyl 5-(4-aminofuro[3,2-c]pyridin-3-yl)-2,3-dihydro-1H-indole-1-carboxylate (9.23 g, 26.3 mmol, 77% yield) as an off-white solid. LC/MS (ES) m/z=352 [M+H]+.

1,1-dimethylethyl 5-(4-amino-7-iodofuro[3,2-c]pyridin-3-yl)-2,3-dihydro-1H-indole-1-carboxylate A solution of NIS (0.985 g, 4.38 mmol) in DMF (20 mL) was added dropwise to a solution of 1,1-dimethylethyl 5-(4-aminofuro[3,2-c]pyridin-3-yl)-2,3-dihydro-1H-indole-1-carboxylate (1.505 g, 4.28 mmol) in DMF (20 mL) at −40° C. under Nitrogen. The mixture was stirred and allowed to slowly warm to room temperature for 17 hours. LCMS indicated about 85% conversion, so the mixture was cooled to about −30° C. and another portion of NIS (0.193 g, 0.858 mmol) in DMF (3 mL) was added dropwise. It was then allowed to slowly warm to room temperature and stirred for another 24 hours. The reaction mixture was then poured into water (ca. 200 mL) and the precipitate was collected by vacuum filtration and rinsed with Et2O (50 mL) to give 1,1-dimethylethyl 5-(4-amino-7-iodofuro[3,2-c]pyridin-3-yl)-2,3-dihydro-1H-indole-1-carboxylate (2.384 g, 4.00 mmol, 93% yield) as a tan solid. LC/MS (ES) m/z=478 [M+H]+.

1,1-dimethylethyl 5-[4-(bis{[(1,1-dimethylethyl)oxy]carbonyl}amino)-7-iodofuro[3,2-c]pyridin-3-yl]-2,3-dihydro-1H-indole-1-carboxylate A mixture of 1,1-dimethylethyl 5-(4-amino-7-iodofuro[3,2-c]pyridin-3-yl)-2,3-dihydro-1H-indole-1-carboxylate (2.043 g, 4.28 mmol), Boc2O (6.95 mL, 29.9 mmol), triethylamine (4.2 mL, 30.1 mmol), and DMAP (0.028 g, 0.229 mmol) in Dichloromethane (DCM) (40 mL) was stirred at room temperature under Nitrogen for 16 hours. LCMS showed only starting material, and there was water visible in the reaction mixture (starting material must not have been fully dried). The mixture was poured into saturated aqueous NaHCO3 (50 mL) and extracted with methylene chloride (2×50 mL). The extracts were dried (Na2SO4), filtered, and concentrated in vacuo to give a dark oil. The residue was resubjected to the reaction conditions by adding a second portion each of Boc2O (6.95 mL, 29.9 mmol), Dichloromethane (DCM) (40 mL), triethylamine (4.2 mL, 30.1 mmol), and DMAP (0.028 g, 0.229 mmol). The reaction mixture was stirred at room temperature under Nitrogen for 6.5 hr then concentrated in vacuo. The dark residue was purified by flash chromatography (Analogix, 120 g SiO2, 0%-20% EtOAc in hexanes gradient over 60 minutes) to give 1,1-dimethylethyl 5-[4-(bis{[(1,1-dimethylethyl)oxy]carbonyl}amino)-7-iodofuro[3,2-c]pyridin-3-yl]-2,3-dihydro-1H-indole-1-carboxylate (1.44 g). The NMR showed some EtOAc, so the solid was dissolved in dioxane and concentrated in vacuo to give the EtOAc-free product, along with a little dioxane. LC/MS (ES) m/z=678 [M+H]+.

1,1-dimethylethyl 5-[4-(bis{[(1,1-dimethylethyl)oxy]carbonyl}amino)-7-chlorofuro[3,2-c]pyridin-3-yl]-2,3-dihydro-1H-indole-1-carboxylate and 1,1-dimethylethyl 5-[7-chloro-4-({[(1,1-dimethylethyl)oxy]carbonyl}amino)furo[3,2-c]pyridin-3-yl]-2,3-dihydro-1H-indole-1-carboxylate tBuLi (1.7 M in pentane) (0.59 mL, 1.003 mmol) was added dropwise to a solution of 1,1-dimethylethyl 5-[4-(bis{[(1,1-dimethylethyl)oxy]carbonyl}amino)-7-iodofuro[3,2-c]pyridin-3-yl]-2,3-dihydro-1H-indole-1-carboxylate (307 mg, 0.453 mmol) in THF (7 mL) at −78° C. under Nitrogen. The mixture was stirred at that temperature for 15 minutes, then a solution of hexachloroethane (217 mg, 0.917 mmol) in THF (3 mL) was added dropwise. The reaction was stirred and allowed to slowly warm from −78° C. to room temperature for 16 hours. The mixture was then quenched with saturated NH4Cl (25 mL), and extracted with ethyl acetate (2×20 mL). The extracts were washed with brine (1×20 mL), dried (Na2SO4), filtered, and concentrated in vacuo. The residue was purified by flash chromatography (Analogix, 40 g SiO2 [RediSep Gold column], 0%-25% EtOAc in hexanes gradient over 45 minutes). The second peak (1st big one) was collected to give 1,1-dimethylethyl 5-[4-(bis{[(1,1-dimethylethyl)oxy]carbonyl}amino)-7-chlorofuro[3,2-c]pyridin-3-yl]-2,3-dihydro-1H-indole-1-carboxylate (81 mg, 0.138 mmol, 30.5% yield) as a colorless oil. LC/MS (ES) m/z=586, 588 [M+H]+. The third peak to elute was also collected and found to be 1,1-dimethylethyl 5-[7-chloro-4-({[(1,1-dimethylethyl)oxy]carbonyl}amino)furo[3,2-c]pyridin-3-yl]-2,3-dihydro-1H-indole-1-carboxylate (33 mg, 0.068 mmol, 14.99% yield), also as a colorless oil. LC/MS (ES) m/z=486, 488 [M+H]+.

7-chloro-3-(2,3-dihydro-1H-indol-5-yl)furo[3,2-c]pyridin-4-amine

The products 1,1-dimethylethyl 5-[4-(bis{[(1,1-dimethylethyl)oxy]carbonyl}amino)-7-chlorofuro[3,2-c]pyridin-3-yl]-2,3-dihydro-1H-indole-1-carboxylate (81 mg, 0.138 mmol), and 1,1-dimethylethyl 5-[7-chloro-4-({[(1,1-dimethylethyl)oxy]carbonyl}amino)furo[3,2-c]pyridin-3-yl]-2,3-dihydro-1H-indole-1-carboxylate (33 mg, 0.068 mmol) (0.206 mmol total) were combined in DCM and concentrated to a pale yellow oil. To this oil was added 1,4-Dioxane (0.5 mL) and to the resulting solution was added HCl (4 M, dioxane) (2 mL, 8.00 mmol), and the reaction stirred overnight at room temperature. The reaction mixture was concentrated to afford crude 7-chloro-3-(2,3-dihydro-1H-indol-5-yl)furo[3,2-c]pyridin-4-amine (81.5 mg, 0.227 mmol, 164% yield) as a beige solid. LC-MS (ES) m/z=286 [M+H]+. $^1$H NMR (400 MHz, DMSO-$d_6$) δ ppm 2.64 (t, J=7.83 Hz, 2H), 3.09-3.19 (m, 2H), 6.83 (s, 2H), 6.90 (s, 1H), 7.32 (s, 1H), 7.46 (s, 1H). Note, NHs are not observed.

7-chloro-3-{1-[(2,5-difluorophenyl)acetyl]-2,3-dihydro-1H-indol-5-yl}furo[3,2-c]pyridin-4-amine A solution of 7-chloro-3-(2,3-dihydro-1H-indol-5-yl)furo[3,2-c]pyridin-4-amine (58.9 mg, 0.206 mmol), (2,5-difluorophenyl)acetic acid (35.5 mg, 0.206 mmol), HATU (78 mg, 0.206 mmol), and DIEA (0.036 mL, 0.206 mmol) in N,N-Dimethylformamide (DMF) (3 mL) was stirred overnight at room temperature. LCMS analysis at this time indicated good conversion, so the reaction mixture was poured into water (10 mL) and stirred for one hour. The resulting precipitate was collected by filtration, dried at the pump for an hour, adsorbed onto silica and purified by flash chromatography (0-10% MeOH in EtOAc) to afford 7-chloro-3-{1-[(2,5-difluorophenyl)acetyl]-2,3-dihydro-1H-indol-5-yl}furo[3,2-c]pyridin-4-amine (67 mg, 73.9% yield) as a white solid. LC-MS (ES) m/z=440, 442 [M+H]+. $^1$H NMR (400 MHz, DMSO-$d_6$) ppm 3.29 (t, J=8.46 Hz, 2H), 3.96 (s, 2H), 4.31 (t, J=8.34 Hz, 2H), 5.72 (s, 2H), 7.13-7.34 (m, 4H), 7.41 (s, 1H), 7.92 (s, 1H), 8.07 (s, 1H), 8.13 (d, J=8.34 Hz, 1H).

Example 132

7-(3-azetidinyl)-5-(1-{[3-(trifluoromethyl)phenyl]acetyl}-2,3-dihydro-1H-indol-5-yl)-7H-pyrrolo[2,3-d]pyrimidin-4-amine

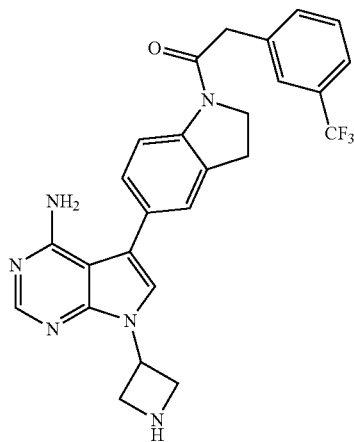 [SMILES: Nc1ncnc2c1c(-c1ccc3c(c1)CCN3C(=O)Cc1cccc(C(F)(F)F)c1)cn2C1CNC1]

To 1,1-dimethylethyl 3-(4-amino-5-bromo-7H-pyrrolo[2,3-d]pyrimidin-7-yl)-1-azetidinecarboxylate (70 mg, 0.190 mmol) and 5-(4,4,5,5-tetramethyl-1,3,2-dioxaborolan-2-yl)-1-{[3-(trifluoromethyl)phenyl]acetyl}-2,3-dihydro-1H-indole (115 mg, 0.266 mmol) were added 1,4-Dioxane (2 mL) and sat. NaHCO3 (1 mL) into a 5 ml sealable. The mixture was then bubbled with N2 gas for 5 minutes, and then Pd(Ph3P)4 (21.97 mg, 0.019 mmol) was added and the vessel was capped. The reaction was then heated at 100° C. overnight. The reaction was then diluted with water (2 ml) then extracted with EtOAc (3×3 ml). The organics were then combined and washed with brine, dried over MgSO4, filtered and concentrated. The crude was dissolved in 3 mL of DMSO and the product was purified by HPLC: (HPLC condition: Gilson using Trilution software with a Sunfire 5u C18(2) 100A. 50×30.00 mm 5 micron. 7.3-minute run (47 ml/min, 35% ACN/H2O, 0.1% TFA to 60% ACN/H2O, 0.1% TFA) with UV detection at 220 nm). Product fractions were combined and the volume was reduced to remove most of the MeCN. The water left behind was added saturated NaHCO3 and then extracted with EtOAc (3×15 mL). The organics were combined wash with saturated NaCl solution, dried over MgSO4, filtered and concentrated. Then the product was transferred to a 40 mL vial with MeCN. Water was added and the solution was freeze-dried. To the white solid obtained was then added a 3 mL of a premixed 2:1 DCM:TFA solution and let stir for 30 min. The reaction was then conc and then. then dissolved in 3 mL of DMSO and then purified on HPLC: (HPLC condition: open-access Gilson using Trilution software with a Sunfire 5u C18(2) 100A. 50×30.00 mm 5 micron. 7.3-minute run (47 ml/min, 5% ACN/H2O, 0.1% TFA to 30% ACN/H2O, 0.1% TFA) with UV detection at 220 nm). Product fractions were combined and the volume was reduced to remove most of the MeCN. The water left behind was then passed though a 0.9 mmol Stratopheres SPE PL-HCO3 MP SPE column and then filtrated was then freeze dried to isolated 7-(3-azetidinyl)-5-(1-{[3-(trifluoromethyl)phenyl]acetyl}-2,3-dihydro-1H-indol-5-yl)-7H-pyrrolo[2,3-d]pyrimidin-4-amine (48 mg, 41.6% yield) as a white solid. LC/MS (ES) m/z=493.5 [M+H]$^+$.

Example 133

7-(1-methyl-3-azetidinyl)-5-(1-{[3-(trifluoromethyl)phenyl]acetyl}-2,3-dihydro-1H-indol-5-yl)-7H-pyrrolo[2,3-d]pyrimidin-4-amine

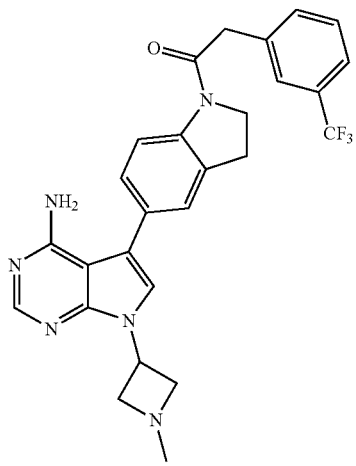 [SMILES: CN1CC(n2cc(-c3ccc4c(c3)CCN4C(=O)Cc3cccc(C(F)(F)F)c3)c3c(N)ncnc32)C1]

To 5-bromo-7-(1-methyl-3-azetidinyl)-7H-pyrrolo[2,3-d]pyrimidin-4-amine (64 mg, 0.227 mmol) and 5-(4,4,5,5-tetramethyl-1,3,2-dioxaborolan-2-yl)-1-{[3-(trifluoromethyl)phenyl]acetyl}-2,3-dihydro-1H-indole (137 mg, 0.318 mmol) were added 1,4-Dioxane (2 mL) and saturated NaHCO3 (1 mL) in a 5 ml sealable vessel. The mixture was then bubbled with N2 gas for 5 minutes and Pd(Ph3P)4 (26.2 mg, 0.023 mmol) was added and the vessel was capped. The reaction was then heated at 100° C. overnight. The reaction was then diluted with water (2 ml) then extracted with EtOAc (3×3 ml). The organics were then combined and washed with brine, dried over MgSO4, filtered and concentrated. The crude product was then dissolved in 3 mL of DMSO and purified by HPLC: (HPLC condition: Gilson using Trilution software with a Sunfire 5u C18(2) 100A. 50×30.00 mm 5 micron. 7.3-minute run (47 ml/min, 20% ACN/H2O, 0.1% TFA to 45% ACN/H2O, 0.1% TFA) with UV detection at 254 nm). Product fractions were combined and the volume was reduced to remove most of the MeCN. To the water left behind was added saturated NaHCO3 and then the mixture was extracted with EtOAc (3×15 mL). The organics were combined and washed with saturated NaCl solution, dried over MgSO4, filtered and concentrated. Then the product was transferred to a 40 mL vial with MeCN then water was added and the solution was freeze-dried to give 7-(1-methyl-3-azetidinyl)-5-(1-{[3-(trifluoromethyl)phenyl]acetyl}-2,3-dihydro-1H-indol-5-yl)-7H-pyrrolo[2,3-d]pyrimidin-4-amine (15 mg, 0.030 mmol, 13.06% yield) as a white solid. LC/MS (ES) m/z=507.5 [M+H]$^+$. $^1$H NMR (400 MHz, DMSO-d$_6$) δ 8.16 (s, 1H), 8.14 (d, J=8.08 Hz, 1H), 7.69 (s, 1H), 7.57-7.67 (m, 4H), 7.38 (s, 1H), 7.27 (d, J=8.08 Hz, 1H), 6.16 (br. s., 2H), 5.41 (quin, J=7.20 Hz, 1H), 4.28 (t, J=8.34 Hz, 2H), 4.06-4.13 (m, 2H), 4.04 (s, 2H), 3.90-3.99 (m, 2H), 3.24-3.29 (m, 2H), 2.65 (br. s., 3H).

Example 134

7-[2-(dimethylamino)ethyl]-5-(1-{[3-(trifluoromethyl)phenyl]acetyl}-2,3-dihydro-1H-indol-5-yl)-7H-pyrrolo[2,3-d]pyrimidin-4-amine

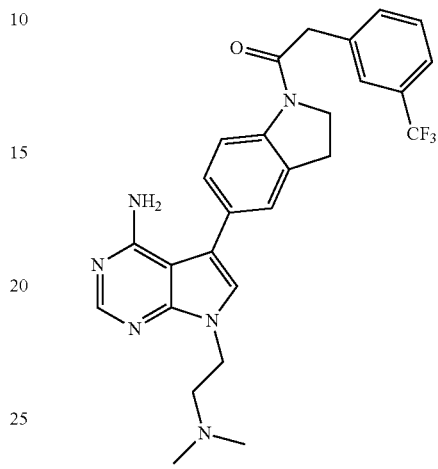

To 5-bromo-7-[2-(dimethylamino)ethyl]-7H-pyrrolo[2,3-d]pyrimidin-4-amine (67 mg, 0.236 mmol) and 5-(4,4,5,5-tetramethyl-1,3,2-dioxaborolan-2-yl)-1-{[3-(trifluoromethyl)phenyl]acetyl}-2,3-dihydro-1H-indole (142 mg, 0.330 mmol) were added 1,4-Dioxane (2 mL) and saturated NaHCO3 (1 mL) in a 5 ml sealable. The mixture was then bubbled with N2 gas for 5 minutes then Pd(Ph3P)4 (27.2 mg, 0.024 mmol) was added and the vessel was capped. The reaction was then heated at 100° C. overnight. The reaction was then diluted with water (2 ml) then extracted with EtOAc (3×3 ml). The organics were then combined and washed with brine, dried over MgSO4, filtered and concentrated. The crude product was dissolved in 3 mL of DMSO and purified by HPLC: (HPLC condition: Gilson using Trilution software with a Sunfire 5u C18(2) 100A. 50×30.00 mm 5 micron. 7.3-minute run (47 ml/min, 15% ACN/H2O, 0.1% TFA to 35% ACN/H2O, 0.1% TFA) with UV detection at 220 nm). Product fractions were combined and the volume was reduced and freeze dried. QC of sample detected some impurities. The freeze dried product was dissolved in DMSO (2.5 mL) and again purified on HPLC: (HPLC condition: Gilson using Trilution software with a Sunfire 5u C18(2) 100A. 50×30.00 mm 5 micron. 7.3-minute run (47 ml/min, 15% ACN/H2O, 0.1% TFA to 35% ACN/H2O, 0.1% TFA) with UV detection at 220 nm). Product fractions were combined and the volume was reduced to remove most of the MeCN. To the water left behind was added saturated NaHCO3 and the mixture was extracted with EtOAc (3×15 mL). The organics were combined washed with saturated NaCl solution, dried over MgSO4, filtered and concentrated. The product was transferred to a 40 mL vial with MeCN, water was added and the solution was freeze-dried to give 7-[2-(dimethylamino)ethyl]-5-(1-{[3-(trifluoromethyl)phenyl]acetyl}-2,3-dihydro-1H-indol-5-yl)-7H-pyrrolo[2,3-c]pyrimidin-4-amine (18 mg). LC/MS (ES) m/z=509.5 [M+H]$^+$. $^1$H NMR (400 MHz, DMSO-d6) δ 8.14 (s, 1H), 8.12 (d, J=8.59 Hz, 1H), 7.69 (s, 1H), 7.58-7.67 (m, 3H), 7.33 (s, 2H), 7.24 (d, J=8.59

Hz, 1H), 6.05 (br. s., 2H), 4.24-4.31 (m, 4H), 4.04 (s, 2H), 3.27 (t, J=8.59 Hz, 2H), 2.70 (br. s., 2H), 2.22 (br. s., 6H).

Example 135

5-(4-fluoro-1-{[3-(trifluoromethyl)phenyl]acetyl}-2,3-dihydro-1H-indol-5-yl)-7-methyl-7H-pyrrolo[2,3-d]pyrimidin-4-amine

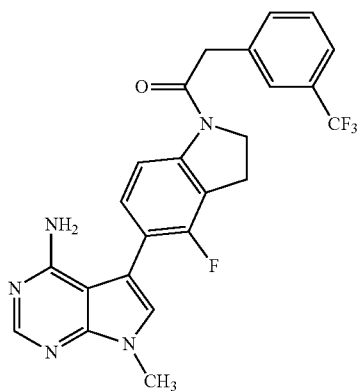 [SMILES: Cn1cc(-c2ccc3c(c2F)CCN3C(=O)Cc2cccc(C(F)(F)F)c2)c2c(N)ncnc21]

To a suspension of 5-(4-fluoro-2,3-dihydro-1H-indol-5-yl)-7-methyl-7H-pyrrolo[2,3-d]pyrimidin-4-amine dihydrochloride (200 mg, 0.56 mmol, 1 equiv) and HATU (235 mg, 0.62 mmol, 1.1 equiv) in DMF (2 mL) at room temperature was added DIEA (314 uL, 1.80 mmol, 3.2 equiv) in one portion. To this mixture was added [3-(trifluoromethyl)phenyl]acetic acid (115 mg, 0.56 mmol, 1 equiv) portionwise over a 1 h period. After a total of 1.5 hours, LCMS showed conversion complete. The mixture was poured into 20 mL of ice cold water to give a suspension, which was filtered. The cake was washed with water and dried under house vacuum. The solid residue was dissolved in 10% MeOH in DCM and absorbed onto a dryload cartridge. Purification was done on an SF25-40 g silica gel cartridge using gradient elution of 1% A in CHCl3 to 60% A in CHCl3 (A was a mixture of 3200/800/80 CHCl3/MeOH/NH4OH, gradient: 0-5 min: 1% A, 5-35 min 5-60% A). The desired product eluted from 27-32% A. The combined fractions were conc in vacuo to give the product, which LCMS showed was only 89% pure. The sample was dissolved in 10% MeOH in DCM and absorbed onto a dryload cartridge. Purification was done on an SF25-60 g silica gel cartridge using gradient elution of 1% A in EtOAc 100% A (A was a mixture of 10% MeOH in EtOAc). The desired product eluted from 67-87% A. The combined fractions were conc in vacuo. The residue was dissolved in 10 mL of 10% MeOH in DCM and concentrated in vacuo to a suspension (about 2 mL). This mixture was diluted with 12 mL of MTBE. The resulting suspension was filtered. The cake was washed with MTBE (3×4 mL) and hexane (3×4 mL), and dried under vacuum at 65° C. for 18 h to afford 5-(4-fluoro-1-{[3-(trifluoromethyl)phenyl]acetyl}-2,3-dihydro-1H-indol-5-yl)-7-methyl-7H-pyrrolo[2,3-d]pyrimidin-4-amine (182 mg) as white solids. LC-MS (ES) m/z=470 [M+H]+. $^1$H NMR (400 MHz, DMSO-d$_6$) δ ppm 3.28 (t, J=8.1 Hz, 2H), 3.74 (s, 3H), 4.04 (s, 2H), 4.34 (t, J=8.3 Hz, 2H), 5.88-6.16 (br s, 1.6H), 7.20 (t, J=8.0 Hz, 1H), 7.27 (s, 1H), 7.54-7.73 (m, 4H), 7.92 (d, J=8.3 Hz, 1H), 8.14 (s, 1H).

Example 136

5-{4-fluoro-1-[(6-methyl-2-pyridinyl)acetyl]-2,3-dihydro-1H-indol-5-yl}-7-methyl-7H-pyrrolo[2,3-d]pyrimidin-4-amine

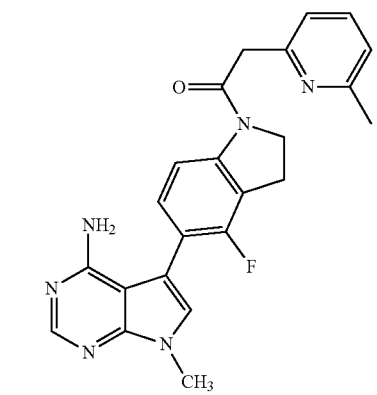 [SMILES: Cc1cccc(CC(=O)N2CCc3c2ccc(-c2cn(C)c4ncnc(N)c24)c3F)n1]

To a suspension of 5-(4-fluoro-2,3-dihydro-1H-indol-5-yl)-7-methyl-7H-pyrrolo[2,3-d]pyrimidin-4-amine dihydrochloride (200 mg, 0.56 mmol, 1 equiv) and HATU (235 mg, 0.62 mmol, 1.1 equiv) in DMF (2 mL) at room temperature was added DIEA (412 uL, 2.36 mmol, 4.2 equiv) in one portion. To this mixture was added (6-methyl-2-pyridinyl)acetic acid TFA salt (148 mg) portionwise over a 1 h period. After a total of 2 h, LCMS showed conversion complete. The mixture was poured into 20 mL of ice cold water to give a suspension, which was filtered. The cake was washed with water and dried under house vacuum to afford crude product, which was dissolved in 10% MeOH in DCM and absorbed onto a dryload cartridge. Purification was done on an Analogix SF25-40 g silica gel cartridge using gradient elution of 1% A in CHCl3 to 60% A in CHCl3 (A was a mixture of 3200/800/80 CHCl3/MeOH/NH4OH, gradient: 0-5 min: 1% A, 5-35 min 5-60% A). The desired product eluted from 27-34% A. The combined fractions were concentrated in vacuo. The residue was dissolved in 10% MeOH in DCM and absorbed onto a dryload cartridge. Purification was done on an Analogix SF25-60 g silica gel cartridge using gradient elution of 1% A in EtOAc 100% A (A was a mixture of 20% MeOH in EtOAc). The desired product eluted from 83-100% A. The combined fractions were concentrated in vacuo. The residue was dissolved in 12 mL of 10% MeOH in DCM and conc in vacuo to a suspension (about 2 mL). This mixture was diluted with 12 mL of MTBE. The resulting suspension was conc in vacuo to reduce to half volume. The mixture was diluted with another 10 mL of MTBE. The suspension was filtered. The cake was washed with MTBE (2×4 mL) and hexane (3×4 mL), and dried under vacuum at 65° C. for 18 h to afford 5-{4-fluoro-1-[(6-methyl-2-pyridinyl)acetyl]-2,3-dihydro-1H-indol-5-yl}-7-methyl-7H-pyrrolo[2,3-d]pyrimidin-4-amine (123 mg) as white solids. LC-MS (ES) m/z=417 [M+H]+. $^1$H NMR (400 MHz, DMSO-d$_6$) δ ppm 2.45 (s, 3H), 3.25 (t, J=8.5 Hz, 2H), 3.74 (s, 3H), 4.00 (s, 2H), 4.35 (t, J=8.5 Hz, 2H), 5.90-6.17 (br. s., 1.6H), 7.12-7.23 (m, 3H), 7.27 (s, 1H), 7.66 (t, J=7.7 Hz, 1H), 7.92 (d, J=8.1 Hz, 1H), 8.14 (s, 1H). (ES) m/z=417 [M+H]+.

Example 137

5-(4-fluoro-1-{[6-(trifluoromethyl)-2-pyridinyl]acetyl}-2,3-dihydro-1H-indol-5-yl)-7-methyl-7H-pyrrolo[2,3-d]pyrimidin-4-amine

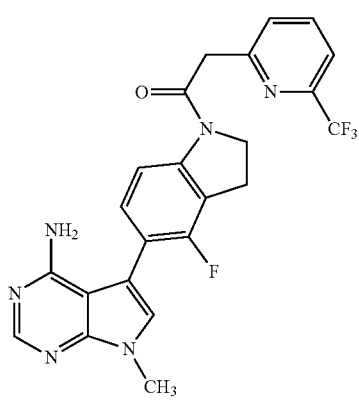 [SMILES: Cn1cc(-c2ccc3c(c2F)CCN3C(=O)Cc2cccc(C(F)(F)F)n2)c2c(N)ncnc21]

To a suspension of 5-(4-fluoro-2,3-dihydro-1H-indol-5-yl)-7-methyl-7H-pyrrolo[2,3-d]pyrimidin-4-amine dihydrochloride (200 mg, 0.56 mmol, 1 equiv) and HATU (235 mg, 0.62 mmol, 1.1 equiv) in DMF (2 mL) at room temperature was added DIEA (412 uL, 2.36 mmol, 4.2 equiv) in one portion. To this mixture was added [6-(trifluoromethyl)-2-pyridinyl]acetic acid (179 mg) portionwise over a 1 hour period. After an additional 30 minutes, LCMS showed conversion complete. The mixture was poured into 20 mL of ice cold water, which gave a suspension that was filtered. The cake was washed with water and dried under house vacuum to give crude product, which was dissolved in 10% MeOH in DCM and absorbed onto a dryload cartridge. Purification was done on an Analogix SF25-40 g silica gel cartridge using gradient elution of 1% A in CHCl3 to 65% A in CHCl3 (A was a mixture of 3200/800/80 CHCl3/MeOH/NH4OH, gradient: 0-5 min: 1% A, 5-35 min 5-60% A). The product eluted from 26-31% A. The combined fractions with product were concentrated in vacuo. The residue was dissolved in 10% MeOH in DCM and absorbed onto a dryload cartridge. Purification was done on an Analogix SF25-60 g silica gel cartridge using gradient elution of 1% A in EtOAc 75% A (A was a mixture of 20% MeOH in EtOAc). The desired product eluted from 51-70% A. The combined fractions were conc in vacuo. The residue was dissolved in 12 mL of 10% MeOH in DCM and concentrated in vacuo to a suspension (about 1 mL). This mixture was diluted with 12 mL of MTBE. The resulting suspension was concentrated in vacuo to reduce to half volume. The mixture was diluted with another 10 mL of MTBE. The suspension was filtered. The cake was washed with MTBE (2×4 mL) and hexane (3×4 mL), and dried under vacuum at 65° C. for 18 h to afford 5-(4-fluoro-1-{[6-(trifluoromethyl)-2-pyridinyl]acetyl}-2,3-dihydro-1H-indol-5-yl)-7-methyl-7H-pyrrolo[2,3-d]pyrimidin-4-amine (205 mg) as white solids. LC-MS (ES) m/z=471 [M+H]+. 1H NMR (400 MHz, DMSO-d6) δ ppm 3.28 (t, J=8.5 Hz, 2H), 3.74 (s, 3H), 4.22 (s, 2H), 4.38 (t, J=8.6 Hz, 2H), 5.90-6.19 (br s, 1.5H), 7.20 (t, J=8.1 Hz, 1H), 7.28 (s, 1H), 7.71 (d, J=7.8 Hz, 1H), 7.83 (d, J=7.6 Hz, 1H), 7.89 (d, J=8.1 Hz, 1H), 8.10 (t, J=7.8 Hz, 1H), 8.14 (s, 1H).

Example 138

5-{1-[(3,5-dimethyl-1H-pyrazol-1-yl)acetyl]-4-fluoro-2,3-dihydro-1H-indol-5-yl}-7-methyl-7H-pyrrolo[2,3-d]pyrimidin-4-amine

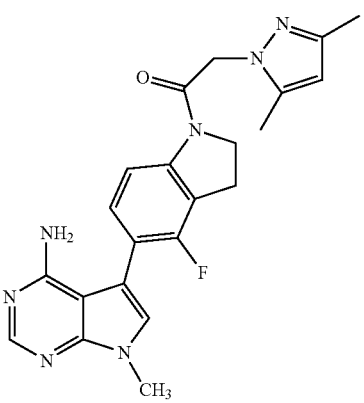 [SMILES: Cc1cc(C)n(CC(=O)N2CCc3c2ccc(-c2cn(C)c4ncnc(N)c24)c3F)n1]

To a suspension of 5-(4-fluoro-2,3-dihydro-1H-indol-5-yl)-7-methyl-7H-pyrrolo[2,3-d]pyrimidin-4-amine dihydrochloride (200 mg, 0.56 mmol, 1 equiv) and HATU (235 mg, 0.62 mmol, 1.1 equiv) in DMF (2 mL) at room temperature was added DIEA (314 uL, 1.80 mmol, 3.2 equiv) in one portion. To this mixture was added (3,5-dimethyl-1H-pyrazol-1-yl)acetic acid (87 mg, 0.56 mmol, 1 equiv) portionwise over a 1 h period. After another 30 min, LCMS showed there was still 27% starting amine left. To the mixture was added 18 mg of (3,5-dimethyl-1H-pyrazol-1-yl)acetic acid. After 1 hour, the mixture was poured into 20 mL of ice cold water to give a suspension, which was filtered. The cake was washed with water and dried under house vacuum to afford crude product, which was dissolved in 10% MeOH in DCM and absorbed onto a dryload cartridge. Purification was done on an Analogix SF25-40 g silica gel cartridge using gradient elution of 1% A in CHCl3 to 65% A in CHCl3 (A was a mixture of 3200/800/80 CHCl3/MeOH/NH4OH, gradient: 0-5 min: 1% A, 5-35 min 5-60% A). There were close-running (front running) impurities with slightly shorter retention time. The desired product eluted from 29-35% A. The combined fractions were concentrated in vacuo. The residue was dissolved in 10% MeOH in DCM and absorbed onto a dryload cartridge. Purification was done on an Analogix SF25-60 g silica gel cartridge using gradient elution of 1% A in EtOAc 100% A (A was a mixture of 20% MeOH in EtOAc). The desired product eluted from 90-100% A. Again, there was a non-polar impurity with slightly shorter retention time. The combined fractions were concentrated in vacuo. The residue was dissolved in 12 mL of 10% MeOH in DCM and concentrated in vacuo. The wet residue was diluted with 12 mL of MTBE. The resulting suspension was concentrated in vacuo to reduce to half volume. The mixture was diluted with another 6 mL of MTBE. The suspension was filtered. The cake was washed with MTBE (2×4 mL) and hexane (3×4 mL), and dried under vacuum at 65° C. for 18 h to afford 5-{1-[(3,5-dimethyl-1H-pyrazol-1-yl)acetyl]-4-fluoro-2,3-dihydro-1H-indol-5-yl}-7-methyl-7H-pyrrolo[2,3-d]pyrimidin-4-amine (98 mg) as white solids. LC-MS (ES) m/z=420 [M+H]+. 1H NMR (400 MHz, DMSO-d6) δ ppm 2.10 (s, 3H), 2.16 (s, 3H), 3.29 (t, J=8.3 Hz, 2H), 3.74 (s, 3H), 4.34 (t, J=8.3 Hz, 2H), 5.11 (s, 2H), 5.86 (s, 1H), 5.93-6.17 (br s, 1.5H), 7.21 (t, J=8.1 Hz, 1H), 7.28 (s, 1H), 7.87 (d, J=8.1 Hz, 1H), 8.14 (s, 1H).

Example 139

5-(4-fluoro-1-{[4-fluoro-3-(trifluoromethyl)phenyl]acetyl}-2,3-dihydro-1H-indol-5-yl)-7-methyl-7H-pyrrolo[2,3-d]pyrimidin-4-amine

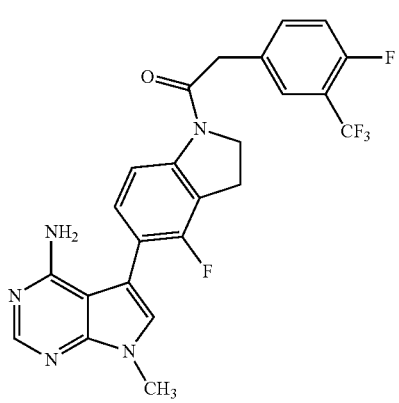 [SMILES: Cn1cc(-c2ccc3c(c2F)CCN3C(=O)Cc2ccc(F)c(C(F)(F)F)c2)c2c(N)ncnc21]

To a suspension of 5-(4-fluoro-2,3-dihydro-1H-indol-5-yl)-7-methyl-7H-pyrrolo[2,3-d]pyrimidin-4-amine dihydrochloride (200 mg, 0.56 mmol, 1 equiv) and HATU (235 mg, 0.62 mmol, 1.1 equiv) in DMF (2 mL) at room temperature was added DIEA (314 uL, 1.80 mmol, 3.2 equiv) in one portion. To this mixture was added [4-fluoro-3-(trifluoromethyl)phenyl]acetic acid (125 mg, 0.56 mmol, 1 equiv) portionwise over a 1 h period. After an additional 1 hour, the mixture was poured into ice cold water to give a suspension, which was filtered. The cake was washed with water and dried under house vacuum to afford crude product, which was dissolved in 10% MeOH in DCM and absorbed onto a dry-load cartridge. Purification was done on an Analogix SF25-40 g silica gel cartridge using gradient elution of 1% A in CHCl3 to 65% A in CHCl3 (A was a mixture of 3200/800/80 CHCl3/MeOH/NH4OH, gradient: 0-5 min: 1% A, 5-35 min 5-60% A). The desired product eluted from 30-36% A. The combined fractions were concentrated in vacuo. The residue was dissolved in 10% MeOH in DCM and absorbed onto a dry-load cartridge. Purification was done on an Analogix SF25-60 g silica gel cartridge using gradient elution of 1% A in EtOAc 75% A (A was a mixture of 20% MeOH in EtOAc). The desired product eluted from 34-64% A. The combined fractions were concentrated in vacuo. The residue was dissolved in 20 mL of 10% MeOH in DCM and concentrated in vacuo. The volume was reduced down to about 4 mL, and the mixture was diluted with 10 mL of MTBE. The resulting suspension was concentrated in vacuo to a wet paste, which was diluted with another 10 mL of MTBE. The suspension was filtered. The cake was washed with MTBE (3×4 mL) and dried under vacuum at 65° C. for 18 h to afford 5-(4-fluoro-1-{[4-fluoro-3-(trifluoromethyl)phenyl]acetyl}-2,3-dihydro-1H-indol-5-yl)-7-methyl-7H-pyrrolo[2,3-d]pyrimidin-4-amine (181 mg) as white solids. LC-MS (ES) m/z=488 [M+H]$^+$. $^1$H NMR (400 MHz, DMSO-$d_6$) δ ppm 3.28 (s, J=8.3 Hz, 2H), 3.74 (s, 3H), 4.03 (s, 2H), 4.34 (t, J=8.3 Hz, 2H), 5.87-6.19 (br s, 1.6H), 7.20 (t, J=8.0 Hz, 1H), 7.27 (s, 1H), 7.45-7.55 (m, 1H), 7.63-7.70 (m, 1H), 7.73 (d, J=7.1 Hz, 1H), 7.91 (d, J=8.1 Hz, 1H), 8.14 (s, 1H).

Example 140

3-{1-[(2,5-difluorophenyl)acetyl]-4-fluoro-2,3-dihydro-1H-indol-5-yl}furo[3,2-c]pyridin-4-amine

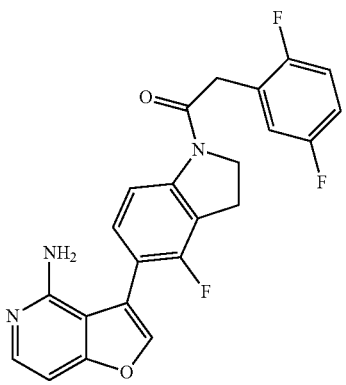 [SMILES: Nc1nccc2occ(-c3ccc4c(c3F)CCN4C(=O)Cc3cc(F)ccc3F)c12]

1,1-dimethylethyl 5-(4-aminofuro[3,2-c]pyridin-3-yl)-4-fluoro-2,3-dihydro-1H-indole-1-carboxylate 3-Bromofuro[3,2-c]pyridin-4-amine (310 mg, 1.455 mmol), 1,1-dimethylethyl 4-fluoro-5-(4,4,5,5-tetramethyl-1,3,2-dioxaborolan-2-yl)-2,3-dihydro-1H-indole-1-carboxylate (577 mg, 1.589 mmol), PdCl2(dppf)-CH2Cl2 adduct (65 mg, 0.080 mmol), 1,4-Dioxane (15 mL), and saturated aqueous sodium bicarbonate (4.5 mL, 4.50 mmol) were added to a 200 mL flask equipped with a reflux condenser. The flask was evacuated and filled with nitrogen 4 times, and then the mixture was stirred at 100° C. under Nitrogen for 15 hours. LCMS showed complete and clean conversion, so it was cooled and filtered through celite, rinsing with EtOAc (50 mL). The filtrate was washed with half-saturated aqueous NaHCO3 (50 mL), and the aqueous phase was back-extracted with ethyl acetate (2×50 mL). The combined organic phases were washed with brine (1×100 mL), dried (Na2SO4), filtered, and concentrated in vacuo. The residue was purified by flash chromatography (Analogix, 60 g SiO2, 10%-75% EtOAc in hexanes gradient over 60 minutes) to give 1,1-dimethylethyl 5-(4-aminofuro[3,2-c]pyridin-3-yl)-4-fluoro-2,3-dihydro-1H-indole-1-carboxylate (205 mg, 0.555 mmol, 38.1% yield) as an off-white solid. LC/MS (ES) m/z=370 [M+H]$^+$ 3-(4-fluoro-2,3-dihydro-1H-indol-5-yl)furo[3,2-c]pyridin-4-amine A mixture of 1,1-dimethylethyl 5-(4-aminofuro[3,2-c]pyridin-3-yl)-4-fluoro-2,3-dihydro-1H-indole-1-carboxylate (205 mg, 0.555 mmol) and HCl, 4.0 M in dioxane (2775 μl, 11.10 mmol) was stirred at room temperature under Nitrogen for 16 hr. The reaction mixture was then concentrated in vacuo to give 3-(4-fluoro-2,3-dihydro-1H-indol-5-yl)furo[3,2-c]pyridin-4-amine (226 mg, 0.555 mmol, 100% yield) as an off-white solid. LC/MS (ES) m/z=270 [M+H]+.

3-{1-[(2,5-difluorophenyl)acetyl]-4-fluoro-2,3-dihydro-1H-indol-5-yl}furo[3,2-c]pyridin-4-amine A mixture of 3-(4-fluoro-2,3-dihydro-1H-indol-5-yl)furo[3,2-c]pyridin-4-amine (190 mg, 0.555 mmol), 2,5-difluorophenylacetic acid (100 mg, 0.583 mmol), HATU (232 mg, 0.611 mmol), and Hunig's base (0.388 mL, 2.221 mmol) in N,N-Dimethylformamide (DMF) (5 mL) was stirred at room temperature for 2 hours. HPLC indicated complete consumption of starting material, so the mixture was poured into water (30 mL), the suspension was stirred for a few minutes, and the precipitate was collected by vacuum filtration and dried in the vacuum oven overnight to give 3-{1-[(2,5-difluorophenyl)acetyl]-4-fluoro-2,3-dihydro-1H-indol-5-yl}furo[3,2-c]pyridin-4-amine (209 mg, 0.469 mmol, 84% yield) as a light tan solid. LC/MS (ES) m/z=424 [M+H]+. $^1$H NMR (400 MHz, DMSO-d$_6$) δ 3.26-3.31 (d, J=8.34 Hz, 2H), 3.97 (s, 3H), 4.38 (t, J=8.46 Hz, 2H), 5.48 (s, 2H), 6.95 (d, J=5.81 Hz, 1H), 7.14-7.35 (m, 4H), 7.87 (d, J=6.06 Hz, 1H), 7.93 (d, J=8.08 Hz, 1H), 7.96 (s, 1H).

Example 141

5-{4-fluoro-1-[(4-fluorophenyl)acetyl]-2,3-dihydro-1H-indol-5-yl}-7-methyl-7H-pyrrolo[2,3-d]pyrimidin-4-amine

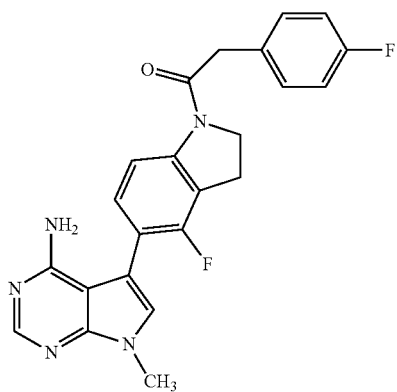 [SMILES: Cn1cc(-c2ccc3c(c2F)CCN3C(=O)Cc2ccc(F)cc2)c2c(N)ncnc21]

To a suspension of 5-(4-fluoro-2,3-dihydro-1H-indol-5-yl)-7-methyl-7H-pyrrolo[2,3-d]pyrimidin-4-amine dihydrochloride (200 mg, 0.56 mmol, 1 equiv) and HATU (235 mg, 0.62 mmol, 1.1 equiv) in DMF (2 mL) at room temperature was added DIEA (314 uL, 1.80 mmol, 3.2 equiv) in one portion. To this mixture was added (4-fluorophenyl)acetic acid (97 mg, 0.56 mmol, 1 equiv) portionwise over a 1 hour period. After an additional 1 hour, the mixture was poured into ice cold water to give a suspension, which was filtered. The cake was washed with water and dried under house vacuum to afford crude product. This material was dissolved in 10% MeOH in DCM and absorbed onto a dryload cartridge. Purification was done on an Analogix SF25-40 g silica gel cartridge using gradient elution of 1% A in CHCl3 to 65% A in CHCl3 (A was a mixture of 3200/800/80 CHCl3/MeOH/NH4OH, gradient: 0-5 min: 1% A, 5-35 min 5-60% A). The desired product eluted from 28-32% A. The combined fractions were concentrated in vacuo. The residue was dissolved in 10% MeOH in DCM and absorbed onto a dryload cartridge. Purification was done on an Analogix SF25-60 g silica gel cartridge using gradient elution of 1% A in EtOAc 75% A (A was a mixture of 20% MeOH in EtOAc). The desired product eluted from 36-60% A (as a broad peak). The combined fractions were concentrated in vacuo. The residue was dissolved in 20 mL of 10% MeOH in DCM and concentrated in vacuo. The volume was reduced down to about 5 mL, and the mixture was diluted with 10 mL of MTBE. The resulting suspension was concentrated in vacuo to a wet paste, which was diluted with another 10 mL of MTBE. The suspension was filtered. The cake was washed with MTBE (3×4 mL) and dried under vacuum at 65° C. for 18 h to afford 5-{4-fluoro-1-[(4-fluorophenyl)acetyl]-2,3-dihydro-1H-indol-5-yl}-7-methyl-7H-pyrrolo[2,3-d]pyrimidin-4-amine (148 mg) as white solids. LC-MS (ES) m/z=420 [M+H]+. $^1$H NMR (400 MHz, DMSO-d$_6$) ppm 3.25 (t, J=8.3 Hz, 2H), 3.74 (s, 3H), 3.89 (s, 2H), 4.30 (t, J=8.3 Hz, 2H), 5.89-6.17 (br s, 1 h), 7.15-7.21 (m, 3H), 7.26 (s, 1H), 7.32-7.35 (m, 2H), 7.93 (d, J=8.3 Hz, 1H), 8.14 (s, 1H).

Example 142

4-(1-{[3-(trifluoromethyl)phenyl]acetyl}-2,3-dihydro-1H-indol-5-yl)-1H-pyrazolo[3,4-c]pyridin-3-amine

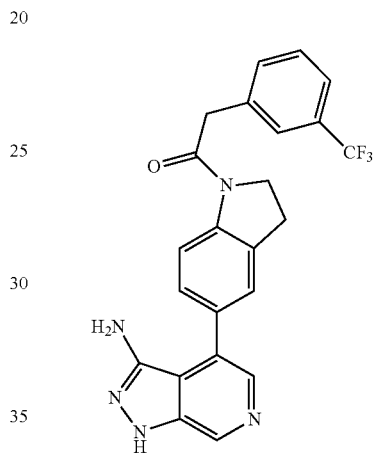

3-chloro-5-(1-{[3-(trifluoromethyl)phenyl]acetyl}-2,3-dihydro-1H-indol-5-yl)-4-pyridinecarbonitrile To 3,5-dichloro-4-pyridinecarbonitrile (300 mg, 1.74 mmol) and 5-(4,4,5,5-tetramethyl-1,3,2-dioxaborolan-2-yl)-1-{[3-(trifluoromethyl)phenyl]acetyl}-2,3-dihydro-1H-indole (823 mg, 1.908 mmol) in a 5 mL sealable vial was added 1,4-Dioxane (5 mL) and saturated NaHCO3 (2.5 mL). The mixture was then bubbled with N2 gas for 5 minutes then Pd(Ph3P)4 (200 mg, 0.173 mmol) was added. The vial was then capped and heated at 100° C. overnight. The reaction was then diluted with water (10 ml) and extracted with EtOAc (3×20 ml). The organic was combined then washed brine, dried over MgSO4, filtered and concentrated. The crude solid was then dissolved in 3 mL of DMF and loaded on to a 50 g Biotage SNAP column conditioned with hexane and purified by silica gel chromatography with 0 to 60% EtOAc in Hexane over a 30 minute gradient. The fractions with the desired product were pool and concentrated. The semi-solid oil was then treated with 20 ml of 5% DCM/Hexane to induce precipitation. The solid was isolated by filtration to give 3-chloro-5-(1-{[3-(trifluoromethyl)phenyl]acetyl}-2,3-dihydro-1H-indol-5-yl)-4-pyridinecarbonitrile (421 mg, 54.9% yield) as a off yellow solid. LC/MS (ES) m/z=442.4 [M+H]+. $^1$H NMR (400 MHz, DMSO-d$_6$) δ 8.94 (s, 1H), 8.83 (s, 1H), 8.18 (d, J=8.34 Hz, 1H), 7.69 (s, 1H), 7.56-7.67 (m, 3H), 7.51 (d, J=8.08 Hz, 1H), 4.31 (t, J=8.59 Hz, 2H), 4.06 (s, 2H), 3.29 (t, 3H).

4-(1-{[3-(trifluoromethyl)phenyl]acetyl}-2,3-dihydro-1H-indol-5-yl)-1H-pyrazolo[3,4-c]pyridin-3-amine To 3-chloro-5-(1-{[3-(trifluoromethyl)phenyl]acetyl}-2,3-dihydro-1H-indol-5-yl)-4-pyridinecarbonitrile (80 mg, 0.181 mmol) was added hydrazine monohydrate (0.266 mL, 5.43 mmol) to a 5 mL sealable vial with Ethanol (3 mL). The reaction was then capped and heated at 100° C. overnight. Observed 80% product and 20% SM. Additional hydrazine monohydrate (0.266 mL, 5.43 mmol) was added and heating was continued overnight. The reaction was concentrated then dissolved in 3 mL of DMSO and purified by HPLC: (HPLC condition: Gilson using Trilution software with a Sunfire 5u C18(2) 100A. 50×30.00 mm 5 micron. 7.3-minute run (47 ml/min, 17% ACN/H2O, 0.1% TFA to 42% ACN/H2O, 0.1% TFA) with UV detection at 220 nm). Product fractions were combined and the volume was reduced to remove most of the MeCN. To the water left behind was added saturated NaHCO3 and it was extracted with EtOAc (3×15 mL). The organics were combined and washed with saturated NaCl solution, dried over MgSO4, filtered and concentrated. The residue was then transferred into a 40 mL vial with MeCN, water was added and the solution was freeze-dried to afford 4-(1-{[3-(trifluoromethyl)phenyl]acetyl}-2,3-dihydro-1H-indol-5-yl)-1H-pyrazolo[3,4-c]pyridin-3-amine (20 mg, 25.3% yield) as a white solid. LC/MS (ES) m/z=438.4 [M+H]$^+$. $^1$H NMR (400 MHz, DMSO-$d_6$) δ 12.29 (s, 1H), 8.74 (s, 1H), 8.18 (d, J=8.34 Hz, 1H), 7.93 (s, 1H), 7.69 (s, 1H), 7.56-7.67 (m, 3H), 7.44 (s, 1H), 7.33 (d, J=8.34 Hz, 1H), 4.61 (br. s., 2H), 4.30 (t, J=8.46 Hz, 2H), 4.05 (s, 2H), 3.26-3.30 (m, 2H).

Example 143

1-methyl-4-(1-{[3-(trifluoromethyl)phenyl]acetyl}-2,3-dihydro-1H-indol-5-yl)-1H-pyrazolo[3,4-c]pyridin-3-amine

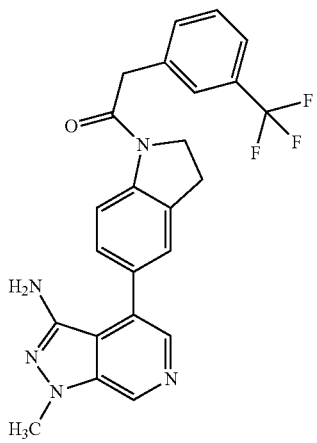 [SMILES: Cn1nc(N)c2c(-c3ccc4c(c3)CCN4C(=O)Cc3cccc(C(F)(F)F)c3)cncc21]

To 3-chloro-5-(1-{[3-(trifluoromethyl)phenyl]acetyl}-2,3-dihydro-1H-indol-5-yl)-4-pyridinecarbonitrile (80 mg, 0.181 mmol) was added Methyl hydrazine (0.286 mL, 5.43 mmol) to a 5 mL sealable vial with Ethanol (3 mL). The reaction was then capped and heated at 100° C. overnight. Observed incomplete conversion. Additional Methyl hydrazine (0.286 mL, 5.43 mmol) was added and heating was continued overnight. The reaction was concentrated, dissolved in 3 mL of DMSO and purified by HPLC: (HPLC condition: Gilson using Trilution software with a Sunfire 5u C18(2) 100A. 50×30.00 mm 5 micron. 7.3-minute run (47 ml/min, 17% ACN/H2O, 0.1% TFA to 42% ACN/H2O, 0.1% TFA) with UV detection at 220 nm). Product fractions were combined and the volume was reduced to remove most of the MeCN. To the water left behind was added saturated NaHCO3 and the mixture was extracted with EtOAc (3×15 mL). The organics were combined, washed with saturated NaCl solution, dried over MgSO4, filtered and concentrated. The product was transferred into a 40 mL vial with MeCN then water was added and the solution was freeze-dried to give 1-methyl-4-(1-{[3-(trifluoromethyl)phenyl]acetyl}-2,3-dihydro-1H-indol-5-yl)-1H-pyrazolo[3,4-c]pyridin-3-amine (34 mg, 41.6% yield) as a light yellow solid. LC/MS (ES) m/z=452.5 [M+H]$^+$. $^1$H NMR (400 MHz, DMSO-d6) δ 8.88 (s, 1H), 8.17 (d, J=8.34 Hz, 1H), 7.94 (s, 1H), 7.69 (s, 1H), 7.56-7.66 (m, 3H), 7.43 (s, 1H), 7.32 (d, J=8.08 Hz, 1H), 4.67 (br. s., 2H), 4.30 (t, J=8.46 Hz, 2H), 4.05 (s, 2H), 3.92 (s, 3H), 3.29 (t, 2H).

Example 144

7-(3-azetidinyl)-5-{1-[(2,5-difluorophenyl)acetyl]-2,3-dihydro-1H-indol-5-yl}-7H-pyrrolo[2,3-d]pyrimidin-4-amine

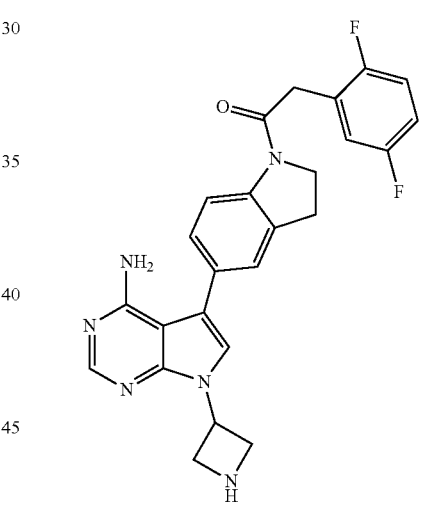

To 1,1-dimethylethyl 3-(4-amino-5-bromo-7H-pyrrolo[2,3-d]pyrimidin-7-yl)-1-azetidinecarboxylate (70 mg, 0.190 mmol) and 1-[(2,5-difluorophenyl)acetyl]-5-(4,4,5,5-tetramethyl-1,3,2-dioxaborolan-2-yl)-2,3-dihydro-1H-indole (106 mg, 0.266 mmol) were added 1,4-dioxane (2 mL) and sat. NaHCO$_3$ (1 mL) into 5 ml sealable vessel. The mixture was then bubbled with N$_2$ gas for 5 min then Pd(Ph3P)4 (21.97 mg, 0.019 mmol) was added and the mixture was sealed and heated at 100° C. overnight.

The reaction was then diluted with water (2 ml) then extracted with EtOAc (3×3 ml). The organics were then combined and washed with brine, dried over MgSO$_4$, filtered and evaporated, then dissolved in 3 mL of DMSO and purified by HPLC: (HPLC condition: Gilson using Trilution software with a Sunfire 5u C18(2) 100A. 50×30.00 mm 5 micron. 7.3-minute run (47 ml/min, 35% ACN/H2O, 0.1% TFA to 60% ACN/H2O, 0.1% TFA) with UV detection at 220 nm). Product fractions were combined and the volume was reduced to remove most of the MeCN. To the water left behind was added saturated NaHCO₃ and the mixture was then extracted with EtOAc (3×15 mL). The organics were combined and washed with saturated NaCl solution, dried over MgSO₄, filtered and concentrated. The residue was transferred to a 40 mL vial with MeCN, then water was added water and the mixture was freeze-dried to give a white solid.

3 mL of a premixed 2:1 DCM:TFA solution was added to the white solid, and the mixture was stirred for 30 minutes. The reaction was then conc and then dissolved in 3 mL of DMSO and then purified on HPLC: (HPLC condition: Gilson using Trilution software with a Sunfire 5u C18(2) 100A. 50×30.00 mm 5 micron. 7.3-minute run (47 ml/min, 5% ACN/H2O, 0.1% TFA to 30% ACN/H2O, 0.1% TFA) with UV detection at 220 nm). Product fractions were combined and the volume was reduced to remove most of the MeCN. The water left behind was then passed though a 0.9 mmol Stratopheres SPE PL-HCO3 MP SPE column and the filtrated was then freeze dried to isolated 7-(3-azetidinyl)-5-{1-[(2,5-difluorophenyl)acetyl]-2,3-dihydro-1H-indol-5-yl}-7H-pyrrolo[2,3-d]pyrimidin-4-amine (47 mg) as a white solid. LC/MS (ES) m/z=461.4 [M+H]⁺. ¹H ¹H NMR (400 MHz, DMSO-d6) δ 9.06 (br. s., 2H), 8.34 (s, 1H), 8.13 (d, J=8.34 Hz, 1H), 7.81 (s, 1H), 7.38 (s, 1H), 7.15-7.31 (m, 4H), 5.70 (qd, J=7.71, 7.96 Hz, 1H), 4.54-4.65 (m, 2H), 4.47 (br. s., 2H), 4.31 (t, J=8.46 Hz, 2H), 3.97 (s, 2H), 3.29 (t, J=8.46 Hz, 2H).

Example 145

7-[2-(4-piperidinyl)ethyl]-5-(1-{[3-(trifluoromethyl)phenyl]acetyl}-2,3-dihydro-1H-indol-5-yl)-7H-pyrrolo[2,3-d]pyrimidin-4-amine

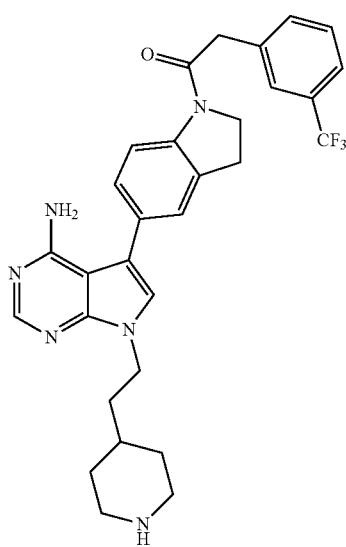 [SMILES: Nc1ncnc2c1c(-c1ccc3c(c1)CCN3C(=O)Cc1cccc(C(F)(F)F)c1)cn2CCC1CCNCC1]

To 1,1-dimethylethyl 4-[2-(4-amino-5-bromo-7H-pyrrolo[2,3-d]pyrimidin-7-yl)ethyl]-1-piperidinecarboxylate (80 mg, 0.189 mmol) and 5-(4,4,5,5-tetramethyl-1,3,2-dioxaborolan-2-yl)-1-{[3-(trifluoromethyl)phenyl]acetyl}-2,3-dihydro-1H-indole (114 mg, 0.264 mmol) were added 1,4-dioxane (2 mL) and sat. NaHCO₃ (1 mL) into a 5 ml sealable vessel. The mixture was then bubbled with N₂ gas for 5 minutes then Pd(Ph3P)4 (21.79 mg, 0.019 mmol) was added and the mixture was sealed and heated at 100° C. overnight. The reaction was then diluted with water (2 ml) then extracted with EtOAc (3×3 ml). The organics were then combined and washed with brine, dried over MgSO₄, filtered and evaporated. The residue was dissolved in 3 mL of DMSO and purified by HPLC: (HPLC condition: Gilson using Trilution software with a Sunfire 5u C18(2) 100A. 50×30.00 mm 5 micron. 7.3-minute run (47 ml/min, 40% ACN/H2O, 0.1% TFA to 65% ACN/H2O, 0.1% TFA) with UV detection at 254 nm). Product fractions were combined and the volume was reduced to remove most of the MeCN. To the water left behind was added saturated NaHCO₃ and the mixture was extracted with EtOAc (3×15 mL). The organics were combined and washed with saturated NaCl solution, dried over MgSO₄, filtered and concentrated. The residue was transferred to a 40 mL vial with MeCN, then water was added water and the mixture was freeze-dried to give a white solid.

To the white solid was added 3 mL of a premixed 2:1 DCM:TFA solution and the mixture was stirred for 30 minutes. The reaction was then concentrated and the residue was dissolved in 3 mL of DMSO and then purified on HPLC: (HPLC condition: Gilson using Trilution software with a Sunfire 5u C18(2) 100A. 50×30.00 mm 5 micron. 7.3-minute run (47 ml/min, 5% ACN/H2O, 0.1% TFA to 30% ACN/H2O, 0.1% TFA) with UV detection at 254 nm). Product fractions were combined and the volume was reduced to remove most of the MeCN. The water left behind was then passed though a 0.9 mmol Stratopheres SPE PL-HCO3 MP SPE column and then filtrated was then freeze dried to isolated 7-[2-(4-piperidinyl)ethyl]-5-(1-{[3-(trifluoromethyl)phenyl]acetyl}-2,3-dihydro-1H-indol-5-yl)-7H-pyrrolo[2,3-d]pyrimidin-4-amine (56 mg) as a white solid. LC/MS (ES) m/z=549.6 [M+H]⁺. ¹H NMR (400 MHz, DMSO-d6) δ 8.52-8.58 (m, 1H), 8.38-8.40 (m, 1H), 8.23-8.30 (m, 1H), 8.15 (d, J=8.34 Hz, 1H), 7.68 (s, 1H), 7.59-7.68 (m, 4H), 7.35 (s, 1H), 7.27 (d, J=7.83 Hz, 1H), 4.24-4.32 (m, 4H), 4.05 (s, 2H), 3.22-3.29 (m, 4H), 2.77-2.87 (m, J=11.87 Hz, 2H), 1.86-1.92 (m, 2H), 1.79 (q, J=7.07 Hz, 2H), 1.48 (br. s., 1H), 1.26-1.38 (m, 2H).

Example 146

7-(2-aminoethyl)-3-{1-[(2,5-difluorophenyl)acetyl]-4-fluoro-2,3-dihydro-1H-indol-5-yl}furo[3,2-c]pyridin-4-amine

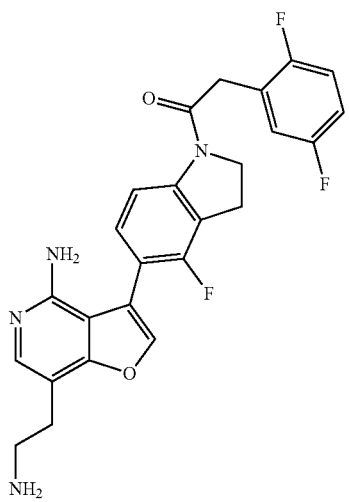 [SMILES: NCCc1cnc(N)c2c(-c3ccc4c(c3F)CCN4C(=O)Cc3cc(F)ccc3F)coc12]

3-{1-[(2,5-difluorophenyl)acetyl]-4-fluoro-2,3-dihydro-1H-indol-5-yl}-7-iodofuro[3,2-c]pyridin-4-amine A solution of NIS (130 mg, 0.578 mmol) in DMF (2 mL) was added dropwise to a solution of 3-{1-[(2,5-difluorophenyl)acetyl]-4-fluoro-2,3-dihydro-1H-indol-5-yl}furo[3,2-c]pyridin-4-amine (190 mg, 0.449 mmol) in DMF (2.5 mL) at −40° C., and the mixture was stirred and allowed to slowly warm to room temperature. It was stirred for 25 hours then poured into water (25 mL) and stirred for a few minutes. The precipitate was collected by vacuum filtration. The damp solid was then rinsed into another filter flask using DCM (50 mL), and the filtrate was dried ($Na_2SO_4$), filtered, and concentrated in vacuo to give 3-{1[(2,5-difluorophenyl)acetyl]-4-fluoro-2,3-dihydro-1H-indol-5-yl}-7-iodofuro[3,2-c]pyridin-4-amine (252 mg) as a dark solid. LC/MS (ES) m/z=550 [M+H]+.

bis(1,1-dimethylethyl) (3-{1-[(2,5-difluorophenyl)acetyl]-4-fluoro-2,3-dihydro-1H-indol-5-yl}-7-iodofuro[3,2-c]pyridin-4-yl)imidodicarbonate and bis(1,1-dimethylethyl) ({5-[4-(bis{[(1,1-dimethylethyl)oxy]carbonyl}amino)-7-iodofuro[3,2-c]pyridin-3-yl]-4-fluoro-2,3-dihydro-1H-indol-1-yl}carbonyl)(2,5-difluorophenyl)propanedioate A mixture of 3-{1-[(2,5-difluorophenyl)acetyl]-4-fluoro-2,3-dihydro-1H-indol-5-yl}-7-iodofuro[3,2-c]pyridin-4-amine (252 mg, 0.459 mmol), $Boc_2O$ (700 mg, 3.21 mmol), triethylamine (0.45 mL, 3.25 mmol), and DMAP (5 mg, 0.041 mmol) in Dichloromethane (DCM) (5 mL) was stirred at room temperature under Nitrogen for 3 hours. LCMS indicated no conversion, so another portion of $Boc_2O$ (770 mg, 3.53 mmol) was added and stirring continued for 16 more hours. LCMS still showed incomplete conversion (about 25% starting material still present), so a third portion of $Boc_2O$ (628 mg, 2.88 mmol) was added, and stirring continued for another 5 hours. LCMS showed close to complete conversion, so the mixture was concentrated in vacuo. The residue was purified by flash chromatography (Analogix, 60 g SiO2, 0%-35% EtOAc in hexanes gradient over 45 minutes) to give bis(1,1-dimethylethyl) (3-{1-[(2,5-difluorophenyl)acetyl]-4-fluoro-2,3-dihydro-1H-indol-5-yl}-7-iodofuro[3,2-c]pyridin-4-yl)imidodicarbonate (63 mg) as a yellow film. Another major peak eluted, and it was also collected to give a tetra-Boc derivative, which was assigned as bis(1,1-dimethylethyl) ({5-[4-(bis{[(1,1-dimethylethyl)oxy]carbonyl}amino)-7-iodofuro[3,2-c]pyridin-3-yl]-4-fluoro-2,3-dihydro-1H-indol-1-yl}carbonyl)(2,5-difluorophenyl)propanedioate (174 mg) by NMR.

7-(2-aminoethyl)-3-{1-[(2,5-difluorophenyl)acetyl]-4-fluoro-2,3-dihydro-1H-indol-5-yl}furo[3,2-c]pyridin-4-amine A mixture of bis(1,1-dimethylethyl) (3-{1-[(2,5-difluorophenyl)acetyl]-4-fluoro-2,3-dihydro-1H-indol-5-yl}-7-iodofuro[3,2-c]pyridin-4-yl)imidodicarbonate (63 mg, 0.084 mmol), bis(1,1-dimethylethyl) ({5-[4-(bis{[(1,1-dimethylethyl)oxy]carbonyl}amino)-7-iodofuro[3,2-c]pyridin-3-yl]-4-fluoro-2,3-dihydro-1H-indol-1-yl}carbonyl)(2,5-difluorophenyl)propanedioate (174 mg, 0.183 mmol), potassium tert-butyl-N-[2-(trifluoroboranuidyl)ethyl]carbamate (136 mg, 0.542 mmol), palladium(II) acetate (6 mg, 0.027 mmol), RuPhos (25 mg, 0.054 mmol), and cesium carbonate (265 mg, 0.813 mmol) in Toluene (3 mL) and Water (1 mL) was degassed with Nitrogen for 10 minutes. The 20 mL vessel was sealed and stirred vigorously at 95° C. for 14 hours. It was cooled, diluted with ethyl acetate (15 mL), and washed with half-saturated aqueous NaHCO3 (15 mL). The aqueous phase was back-extracted with EtOAc (15 mL), and the combined organic phases were washed with brine (1×15 mL), dried ($Na_2SO_4$), filtered, and concentrated in vacuo to give a yellow foam. The residue was stirred with HCl, 4.0 M in dioxane (5 mL, 20.00 mmol) at room temperature for 4 hours, then concentrated in vacuo. The residue was dissolved in a small amount of MeOH and added to 1 M HCl (15 mL). That mixture was extracted with methylene chloride (2×15 mL). The aqueous layer was then made basic with saturated aqueous NaHCO3 (to about pH 9) and extracted with methylene chloride (3×15 mL). The combined organics were dried ($Na_2SO_4$), filtered, and concentrated in vacuo. The residue was dry loaded onto silica gel (0.5 g) and purified by flash chromatography (Analogix, 24 g SiO2, DCM to 75% 90/10/1 DCM/MeOH/$NH_4$OH gradient over 40 minutes) to give 12 mgs of the product. The NMR was not sharp, so the material was taken up in THF, 4 M HCl in dioxane was added, and it was again concentrated in vacuo to give the bis-HCl salt. The material was then purified further by reverse phase HPLC (Gilson, 20 mm×50 mm C18, 5% to 30% CH3CN in water with 0.1% TFA, 8 minute gradient) to give the pure desired product. The product fractions were concentrated in vacuo, azeotroped twice with acetonitrile, taken up in a mixture of DCM and MeOH, and passed through a SratoSpheres SPE PL-HCO3 MP-resin cartridge. The filtrate was then concentrated in vacuo to give the free base of 7-(2-aminoethyl)-3-{1-[(2,5-difluorophenyl)acetyl]-4-fluoro-2,3-dihydro-1H-indol-5-yl}furo[3,2-c]pyridin-4-amine (3 mg) as a white solid. LC/MS (ES) m/z=467 [M+H]+. $^1$H NMR (400 MHz, CHLOROFORM-d) δ 2.93 (t, J=6.82 Hz, 2H), 3.08 (t, J=6.70 Hz, 2H), 3.36 (t, J=8.21 Hz, 2H), 3.84 (s, 2H), 4.31 (t, J=8.59 Hz, 2H), 4.56 (s, 2H), 6.96-7.05 (m, 1H), 7.05-7.16 (m, 2H), 7.33 (t, J=7.96 Hz, 1H), 7.57 (s, 1H), 7.81 (s, 1H), 8.13 (d, J=8.34 Hz, 1H).

Example 147

3-{1-[(3,5-dimethyl-1H-pyrazol-1-yl)acetyl]-2,3-dihydro-1H-indol-5-yl}-1-methyl-1H-pyrazolo[3,4-d]pyrimidin-4-amine

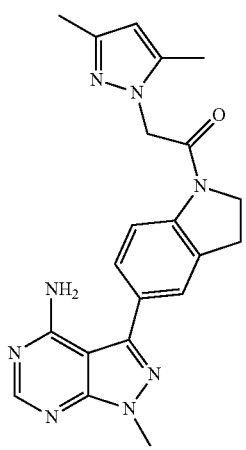 [SMILES: Cc1cc(C)n(CC(=O)N2CCc3cc(-c4nn(C)c5ncnc(N)c45)ccc32)n1]

DIPEA (1.158 mL, 6.63 mmol) was added dropwise to a stirring mixture of 3-(2,3-dihydro-1H-indol-5-yl)-1-methyl- 1H-pyrazolo[3,4-d]pyrimidin-4-amine 2HCl (500 mg, 1.474 mmol) and (3,5-dimethyl-1H-pyrazol-1-yl)acetic acid (239 mg, 1.474 mmol) in N,N-Dimethylformamide (DMF) (10 mL) under nitrogen. The solution was then cooled in an ice bath, and T3P (50 wt % in ethyl acetate) (1.053 mL, 1.769 mmol) was added dropwise slowly over 5 minutes. The mixture was left in the ice bath, and allowed to slowly warm to room temperature and stir overnight. HPLC indicated some starting material remaining, so an additional 0.2 eq (0.175 mL) of T3P solution was added. After stirring 1 hour, HPLC showed no change, so additional DIPEA (1 eq., 0.26 ml) was added, and stirring continued 1 hour, at which time there was no change in conversion. An additional 24 mg of (3,5-dimethyl-1H-pyrazol-1-yl)acetic acid was added and the mixture stirred 1 hour—no change. The Mixture was diluted with water (30 mL) and extracted with 10:1 chloroform:isopropanol (5×25 mL). The combined organics was dried over $Na_2SO_4$ overnight, then filtered and evaporated. Purification by silicagel chromatography (Analogix SF25-60g cartridge) eluting with 0-5% methanol-chloroform afforded the pure product as an off-white powder. Impure fractions were combined and purified by silicagel chromatography (Analogix SF15-24g cartridge) eluting with 0-5% methanol-chloroform to give additional pure product. The combined product was dried under high vacuum to give 3-{1-[(3,5-dimethyl-1H-pyrazol-1-yl)acetyl]-2,3-dihydro-1H-indol-5-yl}-1-methyl-1H-pyrazolo[3,4-d]pyrimidin-4-amine (376 mg) as an off-white powder. LC-MS (ESI) 403.2 [M+H]+. $^1$H NMR (400 MHz, DMSO-d6) δ ppm 8.25 (s, 1H) 8.12 (d, J=8.3 Hz, 1H) 7.54 (s, 1H) 7.46 (d, J=8.3 Hz, 1H) 5.86 (s, 1H) 5.11 (s, 2H) 4.29 (t, J=8.5 Hz, 2H) 3.94 (s, 3H) 3.30 (d, J=8.5 Hz, 2H) 2.17 (s, 3H) 2.10 (s, 3H) ($NH_2$ protons not observed).

Example 148

5-(1-{[3-(trifluoromethyl)phenyl]acetyl}-2,3-dihydro-1H-indol-5-yl)-1H-pyrrolo[2,3-d]pyrimidin-4-amine

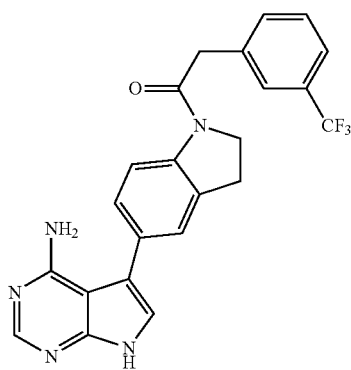 [SMILES: Nc1ncnc2[nH]cc(-c3ccc4c(c3)CCN4C(=O)Cc3cccc(C(F)(F)F)c3)c12]

A mixture of 5-bromo-7H-pyrrolo[2,3-d]pyrimidin-4-amine (101 mg, 0.474 mmol), 5-(4,4,5,5-tetramethyl-1,3,2-dioxaborolan-2-yl)-1-{[3-(trifluoromethyl)phenyl]acetyl}-2,3-dihydro-1H-indole (204 mg, 0.474 mmol), Pd2(dba)3 (8.68 mg, 0.00948 mmol) and K3PO4 (218 mg, 0.948 mmol) in 6 mL of dioxane and 2 mL of water in a microwave tube was degassed and backflushed with nitrogen 3×, followed by addition of tri-(t-butyl)phosphonium tetrafluoroborate (5.50 mg, 0.019 mmol). The mixture was degassed and backflushed with nitrogen 4×. The mixture was heated in an oil bath to 100° C. At 4 h, LCMS showed there was no starting material. The mixture was cooled to rt, EtOAc was added to the mixture. The top EtOAc layer was separated from the bottom layer carefully to avoid disturbance of the Pd residue. The EtOAc layer was rotavaped to dryness to give pale yellow solid. The solid was purified by flash column (Silica SF 15-24g cartridge), eluting with DCM-10% MeOH in DCM. The fractions with the product were combined and evaporated to dryness. The solid was triturated by MeOH, and the residue was filtered and dried to 5-(1-{[3-(trifluoromethyl)phenyl] acetyl}-2,3-dihydro-1H-indol-5-yl)-1H-pyrrolo[2,3-d]pyrimidin-4-amine as an off-white solid. LC/MS [M+1]$^+$438. $^1$H NMR (400 MHz, DMSO-d6) δ 3.25 (t, J=8.34 Hz, 2H), 4.03 (s, 2H), 4.27 (t, J=8.46 Hz, 2H), 5.99 (s, 2H), 7.18 (d, J=2.27 Hz, 1H), 7.21-7.26 (m, 1H), 7.34 (s, 1H), 7.58-7.66 (m, 3H), 7.68 (s, 1H), 8.09-8.12 (m, 2H), 11.74 (s, 1H).

Example 149

5-{4-chloro-1-[(6-methyl-2-pyridinyl)acetyl]-2,3-dihydro-1H-indol-5-yl}-7-methyl-7H-pyrrolo[2,3-d]pyrimidin-4-amine

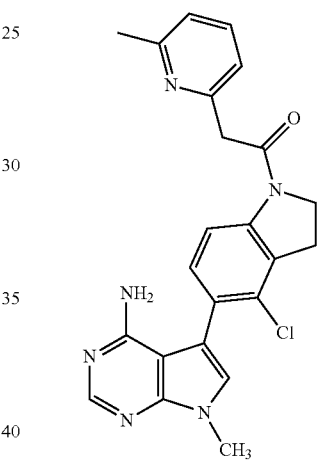

4-chloro-2,3-dihydro-1H-indole

To a stirred solution of 4-chloroindole (5 g, 33.0 mmol) in Acetic Acid (50 mL) at 12° C. under nitrogen was added sodium cyanoborohydride (6.84 g, 109 mmol) portionwise. The reaction was stirred at 12° C. for 2 hours. LCMS indicated complete conversion, so the reaction mixture was diluted with water (300 mL), cooled in an ice-bath and quenched with sodium hydroxide pellets portionwise until the mixture was strongly basic. The mixture was then extracted with diethyl ether (3×200 mL) and the combined organics dried over sodium sulfate, concentrated and the residue purified by flash chromatography (0-30% EtOAc in hexanes) to afford 4-chloro-2,3-dihydro-1H-indole (4.0 g) as a colourless oil. LC-MS (ES) m/z=154 [M+H]$^+$. $^1$H NMR (400 MHz, DMSO-d6) δ ppm 2.94 (t, J=8.59 Hz, 2H), 3.47 (td, J=8.72, 1.77 Hz, 2H), 5.83 (br. s., 1H), 6.40 (d, J=7.83 Hz, 1H), 6.50 (d, J=8.08 Hz, 1H), 6.90 (t, J=7.96 Hz, 1H).

1,1-dimethylethyl
4-chloro-2,3-dihydro-1H-indole-1-carboxylate

A solution of 4-chloro-2,3-dihydro-1H-indole (4.0 g, 26.0 mmol), $Boc_2O$ (6.05 mL, 26.0 mmol), DIEA (9.10 mL, 52.1 mmol), DMAP (0.318 g, 2.60 mmol) was stirred at room temperature overnight. LCMS indicated complete conversion. The reaction mixture was poured into 0.1 N HCl (10 mL) and extracted with ethyl acetate (3×20 mL). The combined organics were dried over sodium sulfate, filtered and concentrated to afford 1,1-dimethylethyl 4-chloro-2,3-dihydro-1H-indole-1-carboxylate (6.36 g) as a yellow oily semi-solid. LC-MS (ES) m/z=198 [M+H-t-Bu]+. $^1$H NMR (400 MHz, DMSO-d6) δ ppm 1.51 (s, 9H), 3.07 (t, J=8.72 Hz, 2H), 3.95 (t, J=8.72 Hz, 2H), 6.98 (d, J=8.84 Hz, 1H), 7.19 (t, J=8.08 Hz, 1H), 7.48-7.70 (m, 1H).

1,1-dimethylethyl 5-bromo-4-chloro-2,3-dihydro-1H-indole-1-carboxylate

To a solution of 1,1-dimethylethyl 4-chloro-2,3-dihydro-1H-indole-1-carboxylate (6.36 g, 25.07 mmol) in Dichloromethane (DCM) (100 mL) was added a solution of NBS (4.91 g, 27.6 mmol) in Dichloromethane (DCM) (200 mL). The reaction was stirred at room temperature for 2 hours. LCMS indicated good conversion, so the reaction mixture was poured into sodium bicarbonate (sat., 300 mL), and separated. The aqueous layer was extracted with ethyl acetate (2×300 mL). The combined organics were dried over sodium sulfate, filtered and concentrated. The residue was purified by flash chromatography (0-30% EtOAc in hexanes, 200 g silica gel column) to afford 1,1-dimethylethyl 5-bromo-4-chloro-2,3-dihydro-1H-indole-1-carboxylate (5.5 g) as an off-white solid. LC-MS (ES) m/z=276, 278 [M+H-t-Bu]+. $^1$H NMR (400 MHz, DMSO-d6) δ ppm 1.50 (s, 9H), 3.01-3.18 (m, 2H), 3.88-4.03 (m, 2H), 7.50-7.58 (m, 2H).

1,1-dimethylethyl 4-chloro-5-(4,4,5,5-tetramethyl-1,3,2-dioxaborolan-2-yl)-2,3-dihydro-1H-indole-1-carboxylate A stirred suspension of 1,1-dimethylethyl 5-bromo-4-chloro-2,3-dihydro-1H-indole-1-carboxylate (5.5 g, 16.54 mmol), bis(pinacolato)diboron (5.04 g, 19.84 mmol), PdCl2(dppf)-CH2Cl2 adduct (0.675 g, 0.827 mmol), potassium acetate (3.25 g, 33.1 mmol) was heated at 100° C. overnight. LCMS indicated good conversion, and the reaction mixture was allowed to cool, then poured into 1:1 NaCl (aq. sat.), H2O, (200 mL) and ethyl acetate (300 mL), shaken, and filtered through celite. The resulting mixture was separated and the aqueous layer was extracted with two additional portions of ethyl acetate (2×300 mL). The combined organics were dried over sodium sulfate, filtered, and concentrated. The residue was purified by flash chromatography (0-25% EtOAc in hexanes, 400 g silica gel column) to afford 1,1-dimethylethyl 4-chloro-5-(4,4,5,5-tetramethyl-1,3,2-dioxaborolan-2-yl)-2,3-dihydro-1H-indole-1-carboxylate (2.6 g) as a white solid. LC-MS (ES) m/z=380 [M+H]+ and 324 [M+H-t-Bu]+. $^1$H NMR (400 MHz, DMSO-d6) δ ppm 1.29 (s, 12H), 1.50 (s, 9H), 3.05 (t, J=8.84 Hz, 2H), 3.96 (t, J=8.72 Hz, 2H), 7.41-7.68 (m, 2H).

1,1-dimethylethyl 5-(4-amino-7-methyl-7H-pyrrolo[2,3-d]pyrimidin-5-yl)-4-chloro-2,3-dihydro-1H-indole-1-carboxylate A mixture of 5-bromo-7-methyl-7H-pyrrolo[2,3-d]pyrimidin-4-amine (510 mg, 2.246 mmol), 1,1-dimethylethyl 4-chloro-5-(4,4,5,5-tetramethyl-1,3,2-dioxaborolan-2-yl)-2,3-dihydro-1H-indole-1-carboxylate (853 mg, 2.246 mmol), Pd2(dba)3 (103 mg, 0.112 mmol) and Potassium Phosphate (K3PO4) (954 mg, 4.49 mmol) and (t-Bu)3PHBF4 (6.52 mg, 0.022 mmol) in 1,4-Dioxane (10 mL) and Water (3.3 mL) in a sealed tube was heated at 100° C. on a stirrer hot plate. At this time, LCMS analysis indicated good conversion, so the reaction mixture was diluted with water (50 mL) and extracted with ethyl acetate (3×100 mL), and the combined organics dried over sodium sulfate and concentrated. The residue was dissolved in DCM (ca. 100 mL), concentrated to minimum volume (ca. 40 mL), then purified by flash chromatography (0-100% EtOAc in hexanes, 40-g silica gel column) to afford 1,1-dimethylethyl 5-(4-amino-7-methyl-7H-pyrrolo[2,3-d]pyrimidin-5-yl)-4-chloro-2,3-dihydro-1H-indole-1-carboxylate (0.716 g) as a yellow solid. LC-MS (ES) m/z=400 [M+H]+. $^1$H NMR (400 MHz, DMSO-d6) δ ppm 1.52 (s, 9H), 3.14 (t, J=8.59 Hz, 2H), 3.74 (s, 3H), 3.96-4.07 (m, 2H), 5.73-6.04 (m, 2H), 7.15-7.26 (m, 2H), 7.57-7.80 (m, 1H), 8.13 (s, 1H).

5-(4-chloro-2,3-dihydro-1H-indol-5-yl)-7-methyl-7H-pyrrolo[2,3-d]pyrimidin-4-amine 2HCl A suspension of 1,1-dimethylethyl 5-(4-amino-7-methyl-7H-pyrrolo[2,3-d]pyrimidin-5-yl)-4-chloro-2,3-dihydro-1H-indole-1-carboxylate (0.716 g, 1.791 mmol) in HCl (4 M, dioxane) (30 mL, 120 mmol) was stirred at room temperature overnight. LCMS indicated good conversion. The reaction mixture was concentrated to afford 5-(4-chloro-2,3-dihydro-1H-indol-5-yl)-7-methyl-7H-pyrrolo[2,3-d]pyrimidin-4-amine 2HCl (667 mg, 1.790 mmol, 100% yield) as an off-white solid. LC-MS (ES) m/z=300 [M+H]+. $^1$H NMR (400 MHz, DMSO-d6) d ppm 3.05 (t, J=8.59 Hz, 2H), 3.56-3.63 (m, 2H), 3.81-3.98 (m, 8H), 6.55-6.62 (m, 1H), 7.01 (d, J=7.58 Hz, 1H), 7.49 (s, 1H), 8.45 (s, 1H).

5-{4-chloro-1-[(6-methyl-2-pyridinyl)acetyl]-2,3-dihydro-1H-indol-5-yl}-7-methyl-7H-pyrrolo[2,3-d]pyrimidin-4-amine To a solution of 5-(4-chloro-2,3-dihydro-1H-indol-5-yl)-7-methyl-7H-pyrrolo[2,3-d]pyrimidin-4-amine 2HCl (300 mg, 0.805 mmol), (6-methyl-2-pyridinyl)acetic acid TFA salt (213 mg, 0.805 mmol), HATU (306 mg, 0.805 mmol), in N,N-Dimethylformamide (DMF) (50 mL) under nitrogen at 0° C. was added DIEA (0.562 mL, 3.22 mmol). The reaction was stirred overnight at room temperature, then poured into water and stirred for one hour. A brown precipitate formed which was collected by filtration and washed with water. The solid was dissolved in ca. 25 mL chloroform, and purified by flash chromatography (0-100% EtOAc in chloroform→0-10% MeOH in EtOAc, 24-g column) to afford 5-{4-chloro-1-[(6-methyl-2-pyridinyl)acetyl]-2,3-dihydro-1H-indol-5-yl}-7-methyl-7H-pyrrolo[2,3-d]pyrimidin-4-amine (144 mg) as a yellow solid. LC-MS (ES) m/z=433 [M+H]+. $^1$H NMR (400 MHz, DMSO-d6) δ ppm 2.45 (s, 3H), 3.24 (t, J=8.46 Hz, 2H), 3.74 (s, 3H), 4.00 (s, 2H), 4.35 (t, J=8.46 Hz, 2H), 5.69-6.08 (m, 2H), 7.16 (t, J=6.82 Hz, 2H), 7.20-7.25 (m, 2H), 7.66 (t, J=7.58 Hz, 1H), 8.03 (d, J=8.34 Hz, 1H), 8.13 (s, 1H).

Example 150

5-(4-chloro-1-{[6-(trifluoromethyl)-2-pyridinyl]acetyl}-2,3-dihydro-1H-indol-5-yl)-7-methyl-7H-pyrrolo[2,3-d]pyrimidin-4-amine

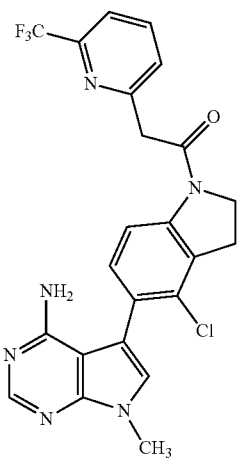 [SMILES: Cn1cc(-c2ccc3c(c2Cl)CCN3C(=O)Cc2cccc(C(F)(F)F)n2)c2c(N)ncnc21]

To a solution of 5-(4-chloro-2,3-dihydro-1H-indol-5-yl)-7-methyl-7H-pyrrolo[2,3-d]pyrimidin-4-amine 2HCl (300 mg, 0.805 mmol), [6-(trifluoromethyl)-2-pyridinyl]acetic acid (90 wt %) (183 mg, 0.805 mmol), HATU (306 mg, 0.805 mmol), in N,N-Dimethylformamide (DMF) (50 mL) under nitrogen at 0° C. was added DIEA (0.562 mL, 3.22 mmol). The reaction was stirred overnight at room temperature, then poured into water and stirred for one hour. A brown precipitate formed which was collected by filtration and washed with water. The solid was dissolved in ca. 25 mL chloroform, and purified by flash chromatography (0-100% EtOAc in chloroform→0-10% MeOH in EtOAc, 24-g column) to afford 5-(4-chloro-1-{[6-(trifluoromethyl)-2-pyridinyl]acetyl}-2,3-dihydro-1H-indol-5-yl)-7-methyl-7H-pyrrolo[2,3-d]pyrimidin-4-amine (161.5 mg) as an off-white solid. LC-MS (ES) m/z=487 [M+H]$^+$. $^1$H NMR (400 MHz, DMSO-d6) δ ppm 3.22-3.30 (m, 2H), 3.74 (s, 3H), 4.22 (s, 2H), 4.37 (t, J=8.34 Hz, 2H), 5.72-6.02 (m, 2H), 7.18-7.25 (m, 2H), 7.71 (d, J=7.83 Hz, 1H), 7.83 (d, J=7.58 Hz, 1H), 8.01 (d, J=8.34 Hz, 1H), 8.10 (t, J=7.96 Hz, 1H), 8.13 (s, 1H).

Example 151

Capsule Composition

An oral dosage form for administering the present invention is produced by filing a standard two piece hard gelatin capsule with the ingredients in the proportions shown in Table I, below.

TABLE I

| INGREDIENTS | AMOUNTS |
| --- | --- |
| 1-methyl-3-[1-(phenylacetyl)-2,3-dihydro-1H-indol-5-yl]-1H-pyrazolo[3,4-d]pyrimidin-4-amine (Compound of Example 1) | 7 mg |
| Lactose | 53 mg |
| Talc | 16 mg |
| Magnesium Stearate | 4 mg |

Example 152

Injectable Parenteral Composition

An injectable form for administering the present invention is produced by stirring 1.7% by weight of 3-{1-[(2,5-difluorophenyl)acetyl]-2,3-dihydro-1H-indol-5-yl}-1-methyl-1H-pyrazolo[3,4-d]pyrimidin-4-amine (Compound of Example 2) in 10% by volume propylene glycol in water.

Example 153

Tablet Composition

The sucrose, calcium sulfate dihydrate and a PERK inhibitor as shown in Table II below, are mixed and granulated in the proportions shown with a 10% gelatin solution. The wet granules are screened, dried, mixed with the starch, talc and stearic acid, screened and compressed into a tablet.

TABLE II

| INGREDIENTS | AMOUNTS |
| --- | --- |
| 3-[1-(phenylacetyl)-2,3-dihydro-1H-indol-5-yl]-1H-pyrazolo[3,4-d]pyrimidin-4-amine (Compound of Example 3) | 12 mg |
| calcium sulfate dihydrate | 30 mg |
| sucrose | 4 mg |
| starch | 2 mg |
| talc | 1 mg |
| stearic acid | 0.5 mg |

Biological Activity

PKR-like Endoplasmic Reticulum Kinase (PERK) Assay (HTRF Format)
Source of the PERK enzyme: GST-PERK (536-1116) cytoplasmic domain was purchased from Invitrogen (www.invitrogen.com) catalogue#PV5106.
Source of substrate: eIF2α: 6-His-Full-length human eIF2a is purified from baculovirus expression in Sf9 insect cells. The eIF2 protein is buffer exchanged by dialysis into PBS, chemically modified by NHS-LC-Biotin and then buffer exchanged by dialysis into 50 mm TRIS pH 7.2/250 mM NaCl/5 mM DTT. Protein is aliquoted and stored at −80° C.
Quench Solution: The quench solution is freshly prepared and when added to the reactions gives final concentrations of 4 nM eIF2αphospho-seryl-Antibody (purchased from Millipore, catalogue #07-760, www.millipore.com), 4 nM Eu-1024 labeled anti-rabbit IgG (purchased from Perkin Elmer, catalogue#AD0083), 40 nM Streptavidin Surelight APC (purchased from Perkin Elmer, catalogue# AD0201) and 15 mM EDTA.
Reactions were performed in black 384-well polystyrene low volume plates (Grenier, #784076) in a final volume of 10 μl. The reaction volume contains, in final concentrations, 10 mM HEPES, 5 mM MgCl$_2$, 5 μM ATP, 1 mM DTT, 2 mM CHAPS, 40 nM biotinylated-6-His-EIF2a, and 0.4 nM GST-PERK (536-1116). Assays were performed by adding GST-PERK solution to assay plates containing compounds and pre-incubated for 30 minutes at room temperature. The reaction is initiated by the addition of ATP and EIF2a substrate solution. Quench solution is added following a one hour incubation at room temperature. The plates are covered for 2 hours at room temperature prior to determination of signal. The resulting signal is quantified on a Viewlux Reader (PerkinElmer). The APC Signal is normalized to the Europium signal by transforming the data through an APC/Eu calculation.

Compounds under analysis were dissolved in DMSO to 1.0 mM and serially diluted 1 to 3 with DMSO through eleven dilutions. 0.1 µl of each concentration was transferred to the corresponding well of an assay plate. This creates a final compound concentration range from 0.00017 to 10 µM.

The data for concentration response curves were plotted as % Inhibition calculated with the data reduction formula 100*(1−(U1−C2)/(C1−C2)) versus concentration of compound where U is the unknown value, C1 is the average control value obtained for 1% DMSO, and C2 is the average control value obtained for 0.1 M EDTA. Data were fitted with a curve described by:

$$y = A + \frac{B - A}{1 + \left(\frac{10x}{10c}\right)D}$$

where A is the minimum y, B is the maximum y concentration [M], D is the slope factor, and x is the $\log_{10}$ of the compound. The results for each compound were recorded as pIC50s, calculated as follows:

pIC50=−Log 10(K).

Abbreviations Used:
APC, Allophycocyanin
ATP, adenosine triphosphate
BSA, bovine serum albumin
CHAPS, 3-[3-Cholamidopropyl)Dimethylammonio]-1-Propanesulfonate
DMSO, dimethyl sulfoxide
DTT, Dithiothreitol
EDTA, ethylenediaminetetraacetic acid
Eu, Europium
HEPES, N-(2-Hydroxyethyl)piperazine-N'-2-ethanesulfonic acid
HPLC, high performance/pressure liquid chromatography
KCl, Potassium chloride
M, molar
mg, milligram
MgCl$_2$, magnesium chloride
ml, milliliter
mM, millimolar
nM, nanomolar
pM, picomolar
MOPS, 3-morpholinopropanesulfonic acid
NaCl, Sodium chloride
NCBI, National Center for Biotechnology Information
PBS, phosphate buffered saline
Tris-HCl, Tris(hydroxymethyl)aminomethane hydrochloride
µM or uM, micromolar Compounds of the invention are tested for activity against PERK in the above assay.

All the compounds of the Examples were tested generally according to the above PERK enzyme assay and in at least one experimental run exhibited a pIC50 value: 7.5 against PERK.

The compound of Example 7 was tested generally according to the above PERK enzyme assay and in at least one set of experimental runs exhibited an average PERK pIC$_{50}$ value of 8.5 against PERK.

The compounds of Examples 4, 6, 14, 19, 22, 23, 42, 55, 82, 93, 102, 119, 121, 138, and 146 were tested generally according to the above PERK enzyme assay and in at least one set of experimental runs exhibited an average pIC50 value: 8.6 against PERK.

The compounds of Examples 9, 13, 18, 30, 31, 44, 59, 62, 64, 73, 74, 81, 89, 92, 111, 125, 131, 133, 134, 136, 137, and 143 were tested generally according to the above PERK assay and in at least one set of experimental runs exhibited an average pIC50 value: ≥9.0.

The compounds of Examples 28, 29, 33, 34, 37, 45, 46, 53, 71, 90, 9196, 100, 112, 114, 127, 130, 141, 144, and 148 were tested generally according to the above PERK assay and in at least one set of experimental runs exhibited an average pIC50 value: ≥9.5.

In the above data, pIC50 is defined as −log(IC50) where the IC50 value is expressed in molar units.

While the preferred embodiments of the invention are illustrated by the above, it is to be understood that the invention is not limited to the precise instructions herein disclosed and that the right to all modifications coming within the scope of the following claims is reserved.

What is claimed is:

1. A compound according to Formula I:

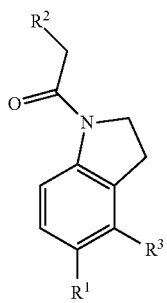

(I)

wherein:
R$^1$ is selected from:
bicycloheteroaryl, and
bicycloheteroaryl substituted with from one to five substituents independently selected from:
halo,
C$_{1-6}$alkyl,
C$_{1-4}$alkyloxy,
—OH,
hydroxyC$_{1-4}$alkyl,
—COOH,
—CONH$_2$,
tetrazole,
—CF$_3$,
—C$_{1-4}$alkylOC$_{1-4}$alkyl,
—CH$_2$CH$_2$N(H)C(O)OCH$_2$aryl
diC$_{1-4}$alkylaminoC$_{1-4}$alkyl,
aminoC$_{1-4}$alkyl,
—NO$_2$,
—NH$_2$,
—CN,
aryl,
aryl substituted with from one to three substituents independently selected from: C$_{1-4}$alkyl, diC$_{1-4}$alkylaminoC$_{1-4}$alkyl, fluoro, chloro, bromo, iodo and —CF$_3$,
heterocycloalkyl,
heterocycloalkyl substituted with from one to three substituents independently selected from:

C$_{1-4}$alkyl, diC$_{1-4}$alkylaminoC$_{1-4}$-alkyl, fluoro, chloro, bromo, iodo and —CF$_3$, _C$_{1-4}$alkylheterocycloalkyl, _C$_{1-4}$alkylheterocycloalkyl substituted with from one to three substituents independently selected from: C$_{1-4}$alkyl, diC$_{1-4}$alkylaminoC$_{1-4}$alkyl, fluoro, chloro, bromo, iodo and —CF$_3$, heteroaryl, and heteroaryl substituted with from one to three substituents independently selected from: C$_{1-4}$alkyl, diC$_{1-4}$alkylaminoC$_{1-4}$alkyl, fluoro, chloro, bromo, iodo and —CF$_3$;

R$^2$ is selected from:
  aryl,
  aryl substituted with from one to five substituents independently selected from: fluoro, chloro, bromo, iodo, C$_{1-4}$alkyl, C$_{1-4}$alkyloxy, —OH, —COOH, —CONH$_2$, —CF$_3$, —C$_{1-4}$alkylOC$_{1-4}$alkyl, —NO$_2$, —NH$_2$ and —CN,
  heteroaryl,
  heteroaryl substituted with from one to five substituents independently selected from: fluoro, chloro, bromo, iodo, C$_{1-4}$alkyl, C$_{1-4}$alkyloxy, —OH, —COOH, —CONH$_2$, —CF$_3$, —C$_{1-4}$alkylOC$_{1-4}$alkyl, —NO$_2$, —NH$_2$ and —CN,
  cycloalkyl, and
  cycloalkyl substituted with from one to five substituents independently selected from: fluoro, chloro, bromo, iodo, C$_{1-4}$alkyl, C$_{1-4}$alkyloxy, —OH, —COOH, —CONH$_2$, —CF$_3$, —C$_{1-4}$alkylOC$_{1-4}$alkyl, —NO$_2$, —NH$_2$ and —CN; and R$^3$ is selected from: hydrogen, fluoro, chloro, bromo and iodo;

or a salt thereof including a pharmaceutically acceptable salt thereof.

2. A compound of Formula (I), as described in claim 1, wherein:

R$^1$ is bicycloheteroaryl substituted with from one to three substituents independently selected from:
  halo,
  C$_{1-6}$alkyl,
  C$_{1-4}$alkyloxy,
  —OH,
  hydroxyC$_{1-4}$alkyl,
  —COOH,
  —CONH$_2$,
  tetrazole,
  —CF$_3$,
  —C$_{1-4}$alkylOC$_{1-4}$alkyl,
  —CH$_2$CH$_2$N(H)C(O)OCH$_2$aryl
  diC$_{1-4}$alkylaminoC$_{1-4}$alkyl,
  aminoC$_{1-4}$alkyl,
  —NO$_2$,
  —NH$_2$,
  —CN,
  aryl,
  aryl substituted with from one to three substituents independently selected from: C$_{1-4}$alkyl, diC$_{1-4}$alkylaminoC$_{1-4}$alkyl, fluoro, chloro, bromo, iodo and —CF$_3$,
  heterocycloalkyl,
  heterocycloalkyl substituted with from one to three substituents independently selected from: C$_{1-4}$alkyl, diC$_{1-4}$alkylaminoC$_{1-4}$alkyl, fluoro, chloro, bromo, iodo and —CF$_3$,
  _C$_{1-4}$alkylheterocycloalkyl,
  _C$_{1-4}$alkylheterocycloalkyl substituted with from one to three substituents independently selected from: C$_{1-4}$alkyl, diC$_{1-4}$alkylaminoC$_{1-4}$alkyl, fluoro, chloro, bromo, iodo and —CF$_3$, heteroaryl, and
  heteroaryl substituted with from one to three substituents independently selected from: C$_{1-4}$alkyl, diC$_{1-4}$alkylaminoC$_{1-4}$alkyl, fluoro, chloro, bromo, iodo and —CF$_3$;

R$^2$ is selected from:
  aryl,
  aryl substituted with from one to five substituents independently selected from: fluoro, chloro, bromo, iodo, C$_{1-4}$alkyl, C$_{1-4}$alkyloxy, —OH, —COOH, —CF$_3$, —C$_{1-4}$alkylOC$_{1-4}$alkyl, —NO$_2$, —NH$_2$ and —CN,
  heteroaryl,
  heteroaryl substituted with from one to five substituents independently selected from: fluoro, chloro, bromo, iodo, C$_{1-4}$alkyl, C$_{1-4}$alkyloxy, —OH, —COOH, —CF$_3$, —C$_{1-4}$alkylOC$_{1-4}$alkyl, —NO$_2$, —NH$_2$ and —CN, cycloalkyl, and
  cycloalkyl substituted with from one to five substituents independently selected from: fluoro, chloro, bromo, iodo, C$_{1-4}$alkyl, C$_{1-4}$alkyloxy, —OH, —COOH, —CF$_3$, —C$_{1-4}$alkylOC$_{1-4}$alkyl, —NO$_2$, —NH$_2$ and —CN; and R$^3$ is selected from: hydrogen, fluoro and chloro;

or a salt thereof including a pharmaceutically acceptable salt thereof.

3. A compound of Formula (I), as described in claim 1, wherein:

R$^1$ is selected from:

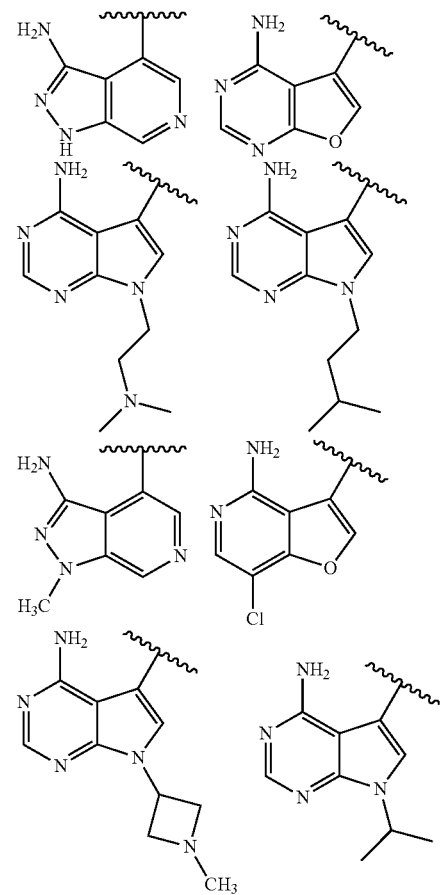

205
-continued
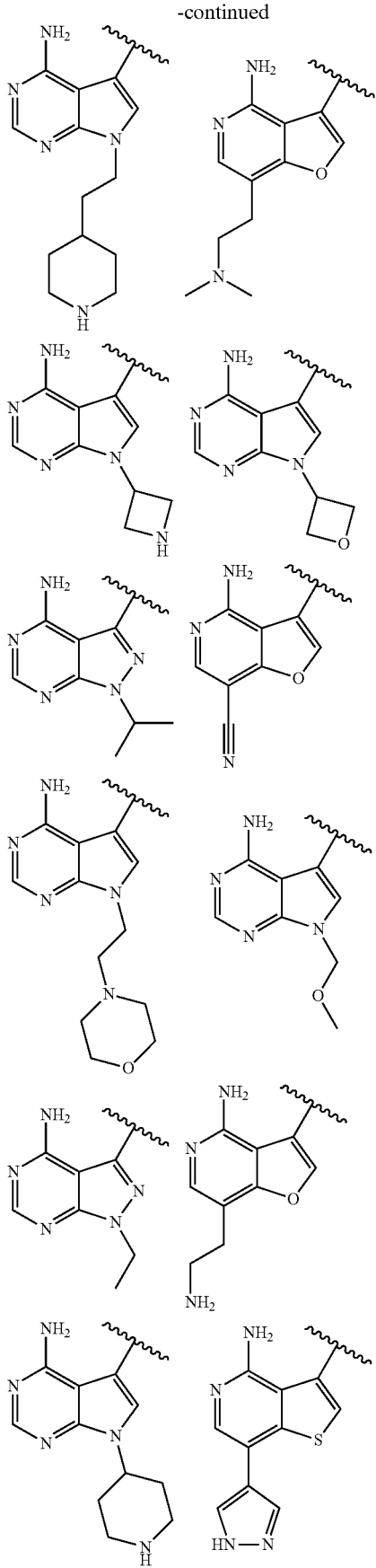
206
-continued
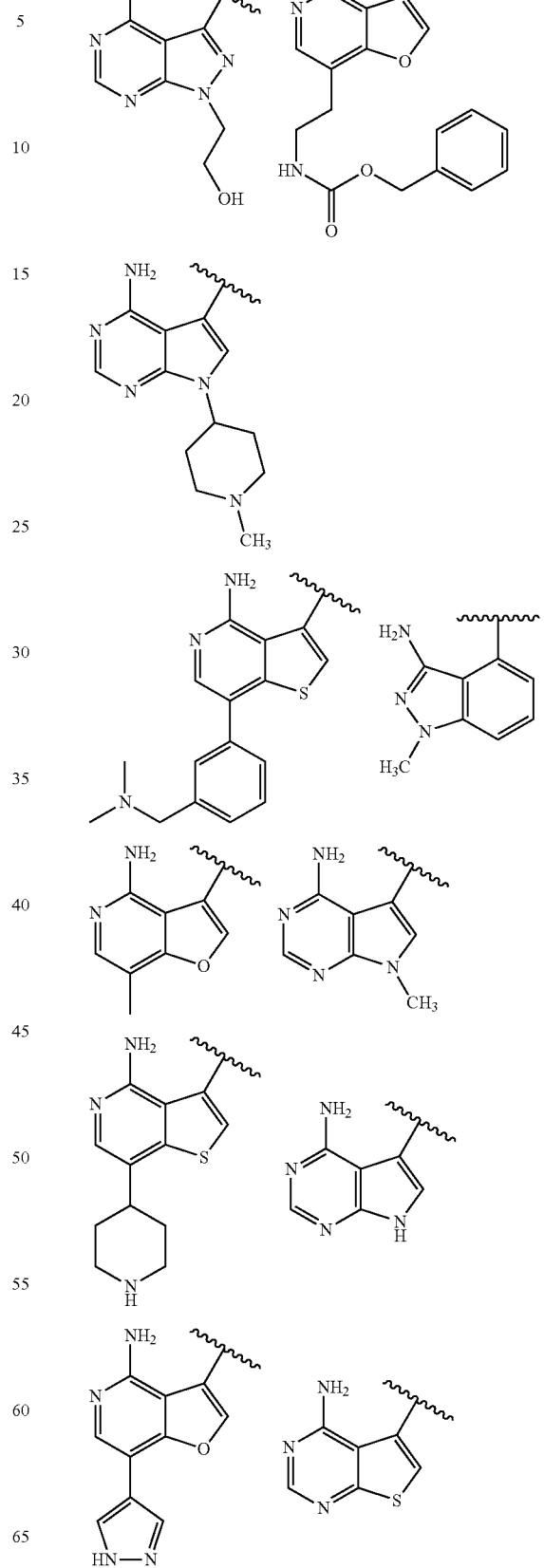

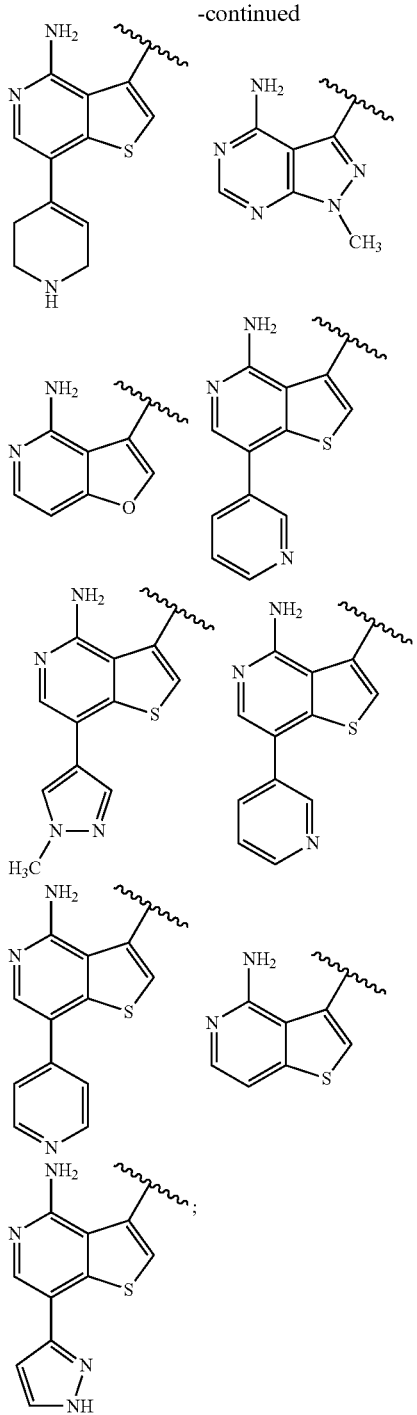

R² is selected from:
  aryl,
  aryl substituted with form one to three substituents independently selected from: halo, $C_{1-4}$alkyl, $C_{1-4}$alkyloxy, —OH, —COOH, —CF₃, —$C_{1-4}$alkylO$C_{1-4}$alkyl, —NO₂, —NH₂ and —CN, heteroaryl,
  heteroaryl substituted with from one to five substituents independently selected from: fluoro, chloro, bromo, iodo, $C_{1-4}$alkyl, $C_{1-4}$alkyloxy, —OH, —COOH, —CF₃, —$C_{1-4}$alkylO$C_{1-4}$alkyl, —NO₂, —NH₂ and —CN; and
R³ is selected from: hydrogen, fluoro and chloro;

or a salt thereof including a pharmaceutically acceptable salt thereof.

4. A compound of claim 1 selected from:
1-methyl-3-[1-(phenylacetyl)-2,3-dihydro-1H-indol-5-yl]-1H-pyrazolo[3,4-d]pyrimidin-4-amine;
3-{1-[(2,5-difluorophenyl)acetyl]-2,3-dihydro-1H-indol-5-yl}-1-methyl-1H-pyrazolo[3,4-d]pyrimidin-4-amine;
3-[1-(phenylacetyl)-2,3-dihydro-1H-indol-5-yl]-1H-pyrazolo[3,4-d]pyrimidin-4-amine;
7-methyl-5-[1-(phenylacetyl)-2,3-dihydro-1H-indol-5-yl]-7H-pyrrolo[2,3-d]pyrimidin-4-amine;
3-[1-(phenylacetyl)-2,3-dihydro-1H-indol-5-yl]thieno[3,2-c]pyridin-4-amine;
3-{1-[(2,5-difluorophenyl)acetyl]-2,3-dihydro-1H-indol-5-yl}thieno[3,2-c]pyridin-4-amine;
3-[1-(phenylacetyl)-2,3-dihydro-1H-indol-5-yl]-7-(3-pyridinyl)thieno[3,2-c]pyridin-4-amine;
1-methyl-4-{1-[(3-methylphenyl)acetyl]-2,3-dihydro-1H-indol-5-yl}-1H-indazol-3-amine;
3-[1-(phenylacetyl)-2,3-dihydro-1H-indol-5-yl]-7-(4-pyridinyl)thieno[3,2-c]pyridin-4-amine;
3-{1-[(2,5-difluorophenyl)acetyl]-2,3-dihydro-1H-indol-5-yl}-7-(3-pyridinyl)thieno[3,2-c]pyridin-4-amine;
3-{1-[(2,5-difluorophenyl)acetyl]-2,3-dihydro-1H-indol-5-yl}-7-(1H-pyrazol-3-yl)thieno[3,2-c]pyridin-4-amine;
4-{1-[(2,5-difluorophenyl)acetyl]-2,3-dihydro-1H-indol-5-yl}-1-methyl-1H-indazol-3-amine;
3-[1-(phenylacetyl)-2,3-dihydro-1H-indol-5-yl]-7-(1H-pyrazol-4-yl)thieno[3,2-c]pyridin-4-amine;
7-(1-methyl-1H-pyrazol-4-yl)-3-[1-(phenylacetyl)-2,3-dihydro-1H-indol-5-yl]thieno[3,2-c]pyridin-4-amine;
3-{1-[(2-fluorophenyl)acetyl]-2,3-dihydro-1H-indol-5-yl}-1-methyl-1H-pyrazolo[3,4-d]pyrimidin-4-amine;
3-{1-[(3-fluorophenyl)acetyl]-2,3-dihydro-1H-indol-5-yl}-1-methyl-1H-pyrazolo[3,4-d]pyrimidin-4-amine;
1-methyl-3-{1-[(2-methylphenyl)acetyl]-2,3-dihydro-1H-indol-5-yl}-1H-pyrazolo[3,4-d]pyrimidin-4-amine;
1-methyl-3-{1-[(3-methylphenyl)acetyl]-2,3-dihydro-1H-indol-5-yl}-1H-pyrazolo[3,4-d]pyrimidin-4-amine;
3-[1-(phenylacetyl)-2,3-dihydro-1H-indol-5-yl]-7-(1,2,3,6-tetrahydro-4-pyridinyl)thieno[3,2-c]pyridin-4-amine;
3-(1-{[3-(trifluoromethyl)phenyl]acetyl}-2,3-dihydro-1H-indol-5-yl)thieno[3,2-c]pyridin-4-amine;
3-{1-[(2-chlorophenyl)acetyl]-2,3-dihydro-1H-indol-5-yl}thieno[3,2-c]pyridin-4-amine;
3-{1-[(3-chlorophenyl)acetyl]-2,3-dihydro-1H-indol-5-yl}thieno[3,2-c]pyridin-4-amine;
3-(1-{[3-(methyloxy)phenyl]acetyl}-2,3-dihydro-1H-indol-5-yl)thieno[3,2-c]pyridin-4-amine;
3-(1-{[2-(methyloxy)phenyl]acetyl}-2,3-dihydro-1H-indol-5-yl)thieno[3,2-c]pyridin-4-amine;
3-[1-(2-naphthalenylacetyl)-2,3-dihydro-1H-indol-5-yl]thieno[3,2-c]pyridin-4-amine;
3-[1-(phenylacetyl)-2,3-dihydro-1H-indol-5-yl]-7-(4-piperidinyl)thieno[3,2-c]pyridin-4-amine;
7-{3-[(dimethylamino)methyl]phenyl}-3-[1-(phenylacetyl)-2,3-dihydro-1H-indol-5-yl]thieno[3,2-c]pyridin-4-amine;
3-{1-[(2,5-dimethylphenyl)acetyl]-2,3-dihydro-1H-indol-5-yl}-1-methyl-1H-pyrazolo[3,4-d]pyrimidin-4-amine;
3-{1-[(3-fluoro-5-methylphenyl)acetyl]-2,3-dihydro-1H-indol-5-yl}-1-methyl-1H-pyrazolo[3,4-d]pyrimidin-4-amine;
3-{1-[(3,5-dimethylphenyl)acetyl]-2,3-dihydro-1H-indol-5-yl}-1-methyl-1H-pyrazolo[3,4-d]pyrimidin-4-amine;

5-{1-[(2,5-difluorophenyl)acetyl]-2,3-dihydro-1H-indol-5-yl}thieno[2,3-d]pyrimidin-4-amine;
3-{1-[(2,3-difluorophenyl)acetyl]-2,3-dihydro-1H-indol-5-yl}-1-methyl-1H-pyrazolo[3,4-d]pyrimidin-4-amine;
7-methyl-5-{1-[(2-methylphenyl)acetyl]-2,3-dihydro-1H-indol-5-yl}-7H-pyrrolo[2,3-d]pyrimidin-4-amine;
5-{1-[(2-fluorophenyl)acetyl]-2,3-dihydro-1H-indol-5-yl}-7-methyl-7H-pyrrolo[2,3-d]pyrimidin-4-amine;
5-{1-[(3-fluorophenyl)acetyl]-2,3-dihydro-1H-indol-5-yl}-7-methyl-7H-pyrrolo[2,3-d]pyrimidin-4-amine;
3-{1-[(2,3-difluorophenyl)acetyl]-2,3-dihydro-1H-indol-5-yl}thieno[3,2-c]pyridin-4-amine;
7-methyl-5-{1-[(3-methylphenyl)acetyl]-2,3-dihydro-1H-indol-5-yl}-7H-pyrrolo[2,3-d]pyrimidin-4-amine;
3-{1-[(3-fluoro-2-methylphenyl)acetyl]-2,3-dihydro-1H-indol-5-yl}thieno[3,2-c]pyridin-4-amine;
3-{2-[5-(4-aminothieno[3,2-c]pyridin-3-yl)-2,3-dihydro-1H-indol-1-yl]-2-oxoethyl}benzonitrile;
3-{1-[(2-fluoro-5-methylphenyl)acetyl]-2,3-dihydro-1H-indol-5-yl}-1-methyl-1H-pyrazolo[3,4-d]pyrimidin-4-amine;
3-{1-[(2,3-dimethylphenyl)acetyl]-2,3-dihydro-1H-indol-5-yl}-1-methyl-1H-pyrazolo[3,4-d]pyrimidin-4-amine;
3-{1-[(3-chlorophenyl)acetyl]-2,3-dihydro-1H-indol-5-yl}-1-methyl-1H-pyrazolo[3,4-d]pyrimidin-4-amine;
1-methyl-3-(1-{[3-(trifluoromethyl)phenyl]acetyl}-2,3-dihydro-1H-indol-5-yl)-1H-pyrazolo[3,4-d]pyrimidin-4-amine;
7-methyl-5-(1-{[3-(trifluoromethyl)phenyl]acetyl}-2,3-dihydro-1H-indol-5-yl)-7H-pyrrolo[2,3-d]pyrimidin-4-amine;
5-{1-[(3-fluoro-5-methylphenyl)acetyl]-2,3-dihydro-1H-indol-5-yl}-7-methyl-7H-pyrrolo[2,3-d]pyrimidin-4-amine;
5-{1-[(3-chlorophenyl)acetyl]-2,3-dihydro-1H-indol-5-yl}-7-methyl-7H-pyrrolo[2,3-d]pyrimidin-4-amine;
5-{1-[(2-chlorophenyl)acetyl]-2,3-dihydro-1H-indol-5-yl}-7-methyl-7H-pyrrolo[2,3-d]pyrimidin-4-amine;
7-methyl-5-(1-{[2-(methyloxy)phenyl]acetyl}-2,3-dihydro-1H-indol-5-yl)-7H-pyrrolo[2,3-d]pyrimidin-4-amine;
1-methyl-3-(1-{[3-(methyloxy)phenyl]acetyl}-2,3-dihydro-1H-indol-5-yl)-1H-pyrazolo[3,4-d]pyrimidin-4-amine;
7-methyl-5-(1-{[3-(methyloxy)phenyl]acetyl}-2,3-dihydro-1H-indol-5-yl)-7H-pyrrolo[2,3-d]pyrimidin-4-amine;
3-{1-[(2-chlorophenyl)acetyl]-2,3-dihydro-1H-indol-5-yl}-1-methyl-1H-pyrazolo[3,4-d]pyrimidin-4-amine;
1-methyl-3-(1-{[2-(methyloxy)phenyl]acetyl}-2,3-dihydro-1H-indol-5-yl)-1H-pyrazolo[3,4-d]pyrimidin-4-amine;
5-{1-[(3-chloro-5-fluorophenyl)acetyl]-2,3-dihydro-1H-indol-5-yl}-7-methyl-7H-pyrrolo[2,3-d]pyrimidin-4-amine;
3-{1-[(2,5-difluorophenyl)acetyl]-2,3-dihydro-1H-indol-5-yl}furo[3,2-c]pyridin-4-amine;
1-methyl-3-{1-[(2,3,5-trifluorophenyl)acetyl]-2,3-dihydro-1H-indol-5-yl}-1H-pyrazolo[3,4-d]pyrimidin-4-amine;
5-{1-[(2,5-dimethylphenyl)acetyl]-2,3-dihydro-1H-indol-5-yl}-7-methyl-7H-pyrrolo[2,3-d]pyrimidin-4-amine;
3-{1-[(2,5-difluorophenyl)acetyl]-2,3-dihydro-1H-indol-5-yl}-7-(1H-pyrazol-4-yl)furo[3,2-c]pyridin-4-amine;
3-{1-[(3,5-dichlorophenyl)acetyl]-2,3-dihydro-1H-indol-5-yl}-1-methyl-1H-pyrazolo[3,4-d]pyrimidin-4-amine;
5-{1-[(2,5-difluorophenyl)acetyl]-2,3-dihydro-1H-indol-5-yl}-7-methyl-7H-pyrrolo[2,3-d]pyrimidin-4-amine; and
3-{1-[(2,5-difluorophenyl)acetyl]-2,3-dihydro-1H-indol-5-yl}-7-(1H-pyrazol-4-yl)thieno[3,2-c]pyridin-4-amine;

or a salt thereof including a pharmaceutically acceptable salt thereof.

5. A compound of claim 1 selected from:
1-methyl-3-[1-(phenylacetyl)-2,3-dihydro-1H-indol-5-yl]-1H-pyrazolo[3,4-d]pyrimidin-4-amine;
3-{1-[(2,5-difluorophenyl)acetyl]-2,3-dihydro-1H-indol-5-yl}-1-methyl-1H-pyrazolo[3,4-d]pyrimidin-4-amine;
3-[1-(phenylacetyl)-2,3-dihydro-1H-indol-5-yl]-1H-pyrazolo[3,4-d]pyrimidin-4-amine;
7-methyl-5-[1-(phenylacetyl)-2,3-dihydro-1H-indol-5-yl]-7H-pyrrolo[2,3-d]pyrimidin-4-amine;
3-[1-(phenylacetyl)-2,3-dihydro-1H-indol-5-yl]thieno[3,2-c]pyridin-4-amine;
3-{1-[(2,5-difluorophenyl)acetyl]-2,3-dihydro-1H-indol-5-yl}thieno[3,2-c]pyridin-4-amine;
1-methyl-4-{1-[(3-methylphenyl)acetyl]-2,3-dihydro-1H-indol-5-yl}-1H-indazol-3-amine;
3-[1-(phenylacetyl)-2,3-dihydro-1H-indol-5-yl]-7-(4-pyridinyl)thieno[3,2-c]pyridin-4-amine;
3-{1-[(2,5-difluorophenyl)acetyl]-2,3-dihydro-1H-indol-5-yl}-7-(3-pyridinyl)thieno[3,2-c]pyridin-4-amine;
3-{1-[(2,5-difluorophenyl)acetyl]-2,3-dihydro-1H-indol-5-yl}-7-(1H-pyrazol-3-yl)thieno[3,2-c]pyridin-4-amine;
4-{1-[(2,5-difluorophenyl)acetyl]-2,3-dihydro-1H-indol-5-yl}-1-methyl-1H-indazol-3-amine;
3-[1-(phenylacetyl)-2,3-dihydro-1H-indol-5-yl]-7-(1H-pyrazol-4-yl)thieno[3,2-c]pyridin-4-amine;
7-(1-methyl-1H-pyrazol-4-yl)-3-[1-(phenylacetyl)-2,3-dihydro-1H-indol-5-yl]thieno[3,2-c]pyridin-4-amine;
3-{1-[(2-fluorophenyl)acetyl]-2,3-dihydro-1H-indol-5-yl}-1-methyl-1H-pyrazolo[3,4-d]pyrimidin-4-amine;
3-{1-[(3-fluorophenyl)acetyl]-2,3-dihydro-1H-indol-5-yl}-1-methyl-1H-pyrazolo[3,4-d]pyrimidin-4-amine;
1-methyl-3-{1-[(2-methylphenyl)acetyl]-2,3-dihydro-1H-indol-5-yl}-1H-pyrazolo[3,4-d]pyrimidin-4-amine;
1-methyl-3-{1-[(3-methylphenyl)acetyl]-2,3-dihydro-1H-indol-5-yl}-1H-pyrazolo[3,4-d]pyrimidin-4-amine;
3-[1-(phenylacetyl)-2,3-dihydro-1H-indol-5-yl]-7-(1,2,3,6-tetrahydro-4-pyridinyl)thieno[3,2-c]pyridin-4-amine;
3-(1-{[3-(trifluoromethyl)phenyl]acetyl}-2,3-dihydro-1H-indol-5-yl)thieno[3,2-c]pyridin-4-amine;
3-{1-[(2-chlorophenyl)acetyl]-2,3-dihydro-1H-indol-5-yl}thieno[3,2-c]pyridin-4-amine;
3-{1-[(3-chlorophenyl)acetyl]-2,3-dihydro-1H-indol-5-yl}thieno[3,2-c]pyridin-4-amine;
3-(1-{[3-(methyloxy)phenyl]acetyl}-2,3-dihydro-1H-indol-5-yl)thieno[3,2-c]pyridin-4-amine;
3-(1-{[2-(methyloxy)phenyl]acetyl}-2,3-dihydro-1H-indol-5-yl)thieno[3,2-c]pyridin-4-amine;
3-[1-(2-naphthalenylacetyl)-2,3-dihydro-1H-indol-5-yl]thieno[3,2-c]pyridin-4-amine;
3-[1-(phenylacetyl)-2,3-dihydro-1H-indol-5-yl]-7-(4-piperidinyl)thieno[3,2-c]pyridin-4-amine;
7-{3-[(dimethylamino)methyl]phenyl}-3-[1-(phenylacetyl)-2,3-dihydro-1H-indol-5-yl]thieno[3,2-c]pyridin-4-amine;
3-{1-[(2,5-dimethylphenyl)acetyl]-2,3-dihydro-1H-indol-5-yl}-1-methyl-1H-pyrazolo[3,4-d]pyrimidin-4-amine;

3-{1-[(3-fluoro-5-methylphenyl)acetyl]-2,3-dihydro-1H-indol-5-yl}-1-methyl-1H-pyrazolo[3,4-d]pyrimidin-4-amine;
3-{1-[(3,5-dimethylphenyl)acetyl]-2,3-dihydro-1H-indol-5-yl}-1-methyl-1H-pyrazolo[3,4-d]pyrimidin-4-amine;
5-{1-[(2,5-difluorophenyl)acetyl]-2,3-dihydro-1H-indol-5-yl}thieno[2,3-d]pyrimidin-4-amine;
3-{1-[(2,3-difluorophenyl)acetyl]-2,3-dihydro-1H-indol-5-yl}-1-methyl-1H-pyrazolo[3,4-d]pyrimidin-4-amine;
7-methyl-5-{1-[(2-methylphenyl)acetyl]-2,3-dihydro-1H-indol-5-yl}-7H-pyrrolo[2,3-d]pyrimidin-4-amine;
5-{1-[(2-fluorophenyl)acetyl]-2,3-dihydro-1H-indol-5-yl}-7-methyl-7H-pyrrolo[2,3-d]pyrimidin-4-amine;
5-{1-[(3-fluorophenyl)acetyl]-2,3-dihydro-1H-indol-5-yl}-7-methyl-7H-pyrrolo[2,3-d]pyrimidin-4-amine;
3-{1-[(2,3-difluorophenyl)acetyl]-2,3-dihydro-1H-indol-5-yl}thieno[3,2-c]pyridin-4-amine;
7-methyl-5-{1-[(3-methylphenyl)acetyl]-2,3-dihydro-1H-indol-5-yl}-7H-pyrrolo[2,3-d]pyrimidin-4-amine;
3-{1-[(3-fluoro-2-methylphenyl)acetyl]-2,3-dihydro-1H-indol-5-yl}thieno[3,2-c]pyridin-4-amine;
3-{2-[5-(4-aminothieno[3,2-c]pyridin-3-yl)-2,3-dihydro-1H-indol-1-yl]-2-oxoethyl}benzonitrile;
3-{1-[(2-fluoro-5-methylphenyl)acetyl]-2,3-dihydro-1H-indol-5-yl}-1-methyl-1H-pyrazolo[3,4-d]pyrimidin-4-amine;
3-{1-[(2,3-dimethylphenyl)acetyl]-2,3-dihydro-1H-indol-5-yl}-1-methyl-1H-pyrazolo[3,4-d]pyrimidin-4-amine;
3-{1-[(3-chlorophenyl)acetyl]-2,3-dihydro-1H-indol-5-yl}-1-methyl-1H-pyrazolo[3,4-d]pyrimidin-4-amine;
1-methyl-3-(1-{[3-(trifluoromethyl)phenyl]acetyl}-2,3-dihydro-1H-indol-5-yl)-1H-pyrazolo[3,4-d]pyrimidin-4-amine;
7-methyl-5-(1-{[3-(trifluoromethyl)phenyl]acetyl}-2,3-dihydro-1H-indol-5-yl)-7H-pyrrolo[2,3-d]pyrimidin-4-amine;
5-{1-[(3-fluoro-5-methylphenyl)acetyl]-2,3-dihydro-1H-indol-5-yl}-7-methyl-7H-pyrrolo[2,3-d]pyrimidin-4-amine;
5-{1-[(3-chlorophenyl)acetyl]-2,3-dihydro-1H-indol-5-yl}-7-methyl-7H-pyrrolo[2,3-d]pyrimidin-4-amine;
5-{1-[(2-chlorophenyl)acetyl]-2,3-dihydro-1H-indol-5-yl}-7-methyl-7H-pyrrolo[2,3-d]pyrimidin-4-amine;
7-methyl-5-(1-{[2-(methyloxy)phenyl]acetyl}-2,3-dihydro-1H-indol-5-yl)-7H-pyrrolo[2,3-d]pyrimidin-4-amine;
1-methyl-3-(1-{[3-(methyloxy)phenyl]acetyl}-2,3-dihydro-1H-indol-5-yl)-1H-pyrazolo[3,4-d]pyrimidin-4-amine;
7-methyl-5-(1-{[3-(methyloxy)phenyl]acetyl}-2,3-dihydro-1H-indol-5-yl)-7H-pyrrolo[2,3-d]pyrimidin-4-amine;
3-{1-[(2-chlorophenyl)acetyl]-2,3-dihydro-1H-indol-5-yl}-1-methyl-1H-pyrazolo[3,4-d]pyrimidin-4-amine;
1-methyl-3-(1-{[2-(methyloxy)phenyl]acetyl}-2,3-dihydro-1H-indol-5-yl)-1H-pyrazolo[3,4-d]pyrimidin-4-amine;
5-{1-[(3-chloro-5-fluorophenyl)acetyl]-2,3-dihydro-1H-indol-5-yl}-7-methyl-7H-pyrrolo[2,3-d]pyrimidin-4-amine;
3-{1-[(2,5-difluorophenyl)acetyl]-2,3-dihydro-1H-indol-5-yl}furo[3,2-c]pyridin-4-amine;
1-methyl-3-{1-[(2,3,5-trifluorophenyl)acetyl]-2,3-dihydro-1H-indol-5-yl}-1H-pyrazolo[3,4-d]pyrimidin-4-amine;
5-{1-[(2,5-dimethylphenyl)acetyl]-2,3-dihydro-1H-indol-5-yl}-7-methyl-7H-pyrrolo[2,3-d]pyrimidin-4-amine;
3-{1-[(2,5-difluorophenyl)acetyl]-2,3-dihydro-1H-indol-5-yl}-7-(1H-pyrazol-4-yl)furo[3,2-c]pyridin-4-amine;
3-{1-[(3,5-dichlorophenyl)acetyl]-2,3-dihydro-1H-indol-5-yl}-1-methyl-1H-pyrazolo[3,4-d]pyrimidin-4-amine;
5-{1-[(2,5-difluorophenyl)acetyl]-2,3-dihydro-1H-indol-5-yl}-7-methyl-7H-pyrrolo[2,3-d]pyrimidin-4-amine;
3-{1-[(2,5-difluorophenyl)acetyl]-2,3-dihydro-1H-indol-5-yl}-7-(1H-pyrazol-4-yl)thieno[3,2-c]pyridin-4-amine;
3-{1-[(3,5-difluorophenyl)acetyl]-2,3-dihydro-1H-indol-5-yl}-1-methyl-1H-pyrazolo[3,4-d]pyrimidin-4-amine;
5-{1-[(3-methylphenyl)acetyl]-2,3-dihydro-1H-indol-5-yl}-7-(4-piperidinyl)-7H-pyrrolo[2,3-d]pyrimidin-4-amine;
5-{1-[(3-methylphenyl)acetyl]-2,3-dihydro-1H-indol-5-yl}-7-(1-methyl-4-piperidinyl)-7H-pyrrolo[2,3-d]pyrimidin-4-amine;
5-{1-[(3-methylphenyl)acetyl]-2,3-dihydro-1H-indol-5-yl}thieno[2,3-d]pyrimidin-4-amine;
3-{1-[(3-fluoro-5-methylphenyl)acetyl]-2,3-dihydro-1H-indol-5-yl}furo[3,2-c]pyridin-4-amine;
3-{1-[(3-chloro-5-fluorophenyl)acetyl]-2,3-dihydro-1H-indol-5-yl}furo[3,2-c]pyridin-4-amine;
3-{1-[(2-fluoro-5-methylphenyl)acetyl]-2,3-dihydro-1H-indol-5-yl}furo[3,2-c]pyridin-4-amine;
1-methyl-3-{1-[(1-methyl-1H-pyrrol-2-yl)acetyl]-2,3-dihydro-1H-indol-5-yl}-1H-pyrazolo[3,4-d]pyrimidin-4-amine;
3-{1-[(3-chlorophenyl)acetyl]-2,3-dihydro-1H-indol-5-yl}furo[3,2-c]pyridin-4-amine;
5-{1-[(2,3-difluorophenyl)acetyl]-2,3-dihydro-1H-indol-5-yl}-7-methyl-7H-pyrrolo[2,3-d]pyrimidin-4-amine;
5-{1-[(2-fluoro-3-methylphenyl)acetyl]-2,3-dihydro-1H-indol-5-yl}-7-methyl-7H-pyrrolo[2,3-d]pyrimidin-4-amine;
5-{1-[(3-fluoro-2-methylphenyl)acetyl]-2,3-dihydro-1H-indol-5-yl}-7-methyl-7H-pyrrolo[2,3-d]pyrimidin-4-amine;
5-{1-[(2-fluoro-5-methylphenyl)acetyl]-2,3-dihydro-1H-indol-5-yl}-7-methyl-7H-pyrrolo[2,3-d]pyrimidin-4-amine;
3-{1-[(2-fluoro-3-methylphenyl)acetyl]-2,3-dihydro-1H-indol-5-yl}-1-methyl-1H-pyrazolo[3,4-d]pyrimidin-4-amine;
3-{1-[(3-fluoro-2-methylphenyl)acetyl]-2,3-dihydro-1H-indol-5-yl}-1-methyl-1H-pyrazolo[3,4-d]pyrimidin-4-amine;
5-{1-[(2,5-difluorophenyl)acetyl]-2,3-dihydro-1H-indol-5-yl}-7-(1-methyl-4-piperidinyl)-7H-pyrrolo[2,3-d]pyrimidin-4-amine;
5-{1-[(3-chloro-4-fluorophenyl)acetyl]-2,3-dihydro-1H-indol-5-yl}-7-methyl-7H-pyrrolo[2,3-d]pyrimidin-4-amine;
5-{1-[(3-chloro-2-fluorophenyl)acetyl]-2,3-dihydro-1H-indol-5-yl}-7-methyl-7H-pyrrolo[2,3-d]pyrimidin-4-amine;
3-{1-[(3-chloro-4-fluorophenyl)acetyl]-2,3-dihydro-1H-indol-5-yl}-1-methyl-1H-pyrazolo[3,4-d]pyrimidin-4-amine;
3-{1-[(3-chloro-2-fluorophenyl)acetyl]-2,3-dihydro-1H-indol-5-yl}-1-methyl-1H-pyrazolo[3,4-d]pyrimidin-4-amine;
5-{1-[(2,3-dimethylphenyl)acetyl]-2,3-dihydro-1H-indol-5-yl}-7-methyl-7H-pyrrolo[2,3-d]pyrimidin-4-amine;
1-(1-methylethyl)-3-{1-[(3-methylphenyl)acetyl]-2,3-dihydro-1H-indol-5-yl}-1H-pyrazolo[3,4-d]pyrimidin-4-amine;

2-(4-amino-3-{1-[(3-methylphenyl)acetyl]-2,3-dihydro-1H-indol-5-yl}-1H-pyrazolo[3,4-d]pyrimidin-1-yl)ethanol;

5-{1-[(3,5-dimethylphenyl)acetyl]-2,3-dihydro-1H-indol-5-yl}-7-methyl-7H-pyrrolo[2,3-d]pyrimidin-4-amine;

5-{1-[(2,5-difluorophenyl)acetyl]-2,3-dihydro-1H-indol-5-yl}-7-(4-piperidinyl)-7H-pyrrolo[2,3-d]pyrimidin-4-amine;

1-ethyl-3-{1-[(3-methylphenyl)acetyl]-2,3-dihydro-1H-indol-5-yl}-1H-pyrazolo[3,4-d]pyrimidin-4-amine;

3-{1-[(2,5-difluorophenyl)acetyl]-2,3-dihydro-1H-indol-5-yl}-7-methylfuro[3,2-c]pyridin-4-amine;

3-{1-[(2,5-difluorophenyl)acetyl]-2,3-dihydro-1H-indol-5-yl}-1-(1-methylethyl)-1H-pyrazolo[3,4-d]pyrimidin-4-amine;

5-{1-[(3,5-difluorophenyl)acetyl]-2,3-dihydro-1H-indol-5-yl}-7-methyl-7H-pyrrolo[2,3-d]pyrimidin-4-amine;

7-methyl-5-{1-[(2,3,5-trifluorophenyl)acetyl]-2,3-dihydro-1H-indol-5-yl}-7H-pyrrolo[2,3-d]pyrimidin-4-amine;

5-{1-[(3,5-dichlorophenyl)acetyl]-2,3-dihydro-1H-indol-5-yl}-7-methyl-7H-pyrrolo[2,3-d]pyrimidin-4-amine;

7-(3-azetidinyl)-5-{1-[(3-methylphenyl)acetyl]-2,3-dihydro-1H-indol-5-yl}-7H-pyrrolo[2,3-d]pyrimidin-4-amine;

5-{1-[(4-fluorophenyl)acetyl]-2,3-dihydro-1H-indol-5-yl}-7-methyl-7H-pyrrolo[2,3-d]pyrimidin-4-amine;

7-methyl-5-{1-[(4-methylphenyl)acetyl]-2,3-dihydro-1H-indol-5-yl}-7H-pyrrolo[2,3-d]pyrimidin-4-amine;

5-{1-[(3-chloro-2,4-difluorophenyl)acetyl]-2,3-dihydro-1H-indol-5-yl}-7-methyl-7H-pyrrolo[2,3-d]pyrimidin-4-amine;

5-(1-{[3-fluoro-5-(trifluoromethyl)phenyl]acetyl}-2,3-dihydro-1H-indol-5-yl)-7-methyl-7H-pyrrolo[2,3-d]pyrimidin-4-amine;

7-[(methyloxy)methyl]-5-{1-[(3-methylphenyl)acetyl]-2,3-dihydro-1H-indol-5-yl}-7H-pyrrolo[2,3-d]pyrimidin-4-amine;

7-methyl-5-{1-[(1-methyl-1H-pyrrol-2-yl)acetyl]-2,3-dihydro-1H-indol-5-yl}-7H-pyrrolo[2,3-d]pyrimidin-4-amine;

5-{1-[(2,5-difluorophenyl)acetyl]-2,3-dihydro-1H-indol-5-yl}-7-(1-methylethyl)-7H-pyrrolo[2,3-d]pyrimidin-4-amine;

5-{1-[(5-chloro-2-fluorophenyl)acetyl]-2,3-dihydro-1H-indol-5-yl}-7-methyl-7H-pyrrolo[2,3-d]pyrimidin-4-amine;

5-{1-[(2,5-difluorophenyl)acetyl]-2,3-dihydro-1H-indol-5-yl}-7-[2-(4-morpholinyl)ethyl]-7H-pyrrolo[2,3-d]pyrimidin-4-amine;

5-{1-[(2,4-difluorophenyl)acetyl]-2,3-dihydro-1H-indol-5-yl}-7-methyl-7H-pyrrolo[2,3-d]pyrimidin-4-amine;

5-{1-[(3,4-difluorophenyl)acetyl]-2,3-dihydro-1H-indol-5-yl}-7-methyl-7H-pyrrolo[2,3-d]pyrimidin-4-amine;

phenylmethyl[2-(4-amino-3-{1-[(2,5-difluorophenyl)acetyl]-2,3-dihydro-1H-indol-5-yl}furo[3,2-c]pyridin-7-yl)ethyl]carbamate;

5-{1-[(2,5-difluorophenyl)acetyl]-2,3-dihydro-1H-indol-5-yl}-7-(3-methylbutyl)-7H-pyrrolo[2,3-d]pyrimidin-4-amine;

5-{1-[(2,5-difluorophenyl)acetyl]-2,3-dihydro-1H-indol-5-yl}-7-[2-(dimethylamino)ethyl]-7H-pyrrolo[2,3-d]pyrimidin-4-amine;

5-{1-[(6-chloro-2-pyridinyl)acetyl]-2,3-dihydro-1H-indol-5-yl}-7-methyl-7H-pyrrolo[2,3-d]pyrimidin-4-amine;

3-{1-[(3-chloro-2,4-difluorophenyl)acetyl]-2,3-dihydro-1H-indol-5-yl}-1-methyl-1H-pyrazolo[3,4-d]pyrimidin-4-amine;

7-(2-aminoethyl)-3-{1-[(2,5-difluorophenyl)acetyl]-2,3-dihydro-1H-indol-5-yl}furo[3,2-c]pyridin-4-amine;

4-amino-3-{1-[(2,5-difluorophenyl)acetyl]-2,3-dihydro-1H-indol-5-yl}furo[3,2-c]pyridine-7-carbonitrile;

5-{1-[(3,5-dimethyl-1H-pyrazol-1-yl)acetyl]-2,3-dihydro-1H-indol-5-yl}-7-methyl-7H-pyrrolo[2,3-d]pyrimidin-4-amine;

5-[4-fluoro-1-(phenylacetyl)-2,3-dihydro-1H-indol-5-yl]-7-methyl-7H-pyrrolo[2,3-d]pyrimidin-4-amine;

5-{4-fluoro-1-[(1-methyl-1H-pyrrol-2-yl)acetyl]-2,3-dihydro-1H-indol-5-yl}-7-methyl-7H-pyrrolo[2,3-d]pyrimidin-4-amine;

5-{1-[(2,5-difluorophenyl)acetyl]-4-fluoro-2,3-dihydro-1H-indol-5-yl}-7-methyl-7H-pyrrolo[2,3-d]pyrimidin-4-amine;

5-{1-[(2,5-difluorophenyl)acetyl]-2,3-dihydro-1H-indol-5-yl}furo[2,3-d]pyrimidin-4-amine;

5-(1-{[3-(trifluoromethyl)phenyl]acetyl}-2,3-dihydro-1H-indol-5-yl)furo[2,3-d]pyrimidin-4-amine;

5-{1-[(3-chloro-5-fluorophenyl)acetyl]-2,3-dihydro-1H-indol-5-yl}furo[2,3-d]pyrimidin-4-amine;

5-{1-[(3-methylphenyl)acetyl]-2,3-dihydro-1H-indol-5-yl}furo[2,3-d]pyrimidin-4-amine;

5-(1-{[3-fluoro-5-(trifluoromethyl)phenyl]acetyl}-2,3-dihydro-1H-indol-5-yl)furo[2,3-d]pyrimidin-4-amine;

5-{1-[(2,5-difluorophenyl)acetyl]-2,3-dihydro-1H-indol-5-yl}-7-[2-(4-piperidinyl)ethyl]-7H-pyrrolo[2,3-d]pyrimidin-4-amine;

7-methyl-5-{1-[(6-methyl-2-pyridinyl)acetyl]-2,3-dihydro-1H-indol-5-yl}-7H-pyrrolo[2,3-d]pyrimidin-4-amine;

5-(1-{[4-fluoro-3-(trifluoromethyl)phenyl]acetyl}-2,3-dihydro-1H-indol-5-yl)-7-methyl-7H-pyrrolo[2,3-d]pyrimidin-4-amine;

5-{1-[(2,5-difluorophenyl)acetyl]-2,3-dihydro-1H-indol-5-yl}-7-(3-oxetanyl)-7H-pyrrolo[2,3-d]pyrimidin-4-amine;

3-{1-[(2,5-difluorophenyl)acetyl]-2,3-dihydro-1H-indol-5-yl}-7-[2-(dimethylamino)ethyl]furo[3,2-c]pyridin-4-amine;

7-methyl-5-(1-{[6-(trifluoromethyl)-2-pyridinyl]acetyl}-2,3-dihydro-1H-indol-5-yl)-7H-pyrrolo[2,3-d]pyrimidin-4-amine;

7-(3-oxetanyl)-5-(1-{[3-(trifluoromethyl)phenyl]acetyl}-2,3-dihydro-1H-indol-5-yl)-7H-pyrrolo[2,3-d]pyrimidin-4-amine;

7-[2-(4-morpholinyl)ethyl]-5-(1-{[3-(trifluoromethyl)phenyl]acetyl}-2,3-dihydro-1H-indol-5-yl)-7H-pyrrolo[2,3-d]pyrimidin-4-amine;

7-(1-methylethyl)-5-(1-{[3-(trifluoromethyl)phenyl]acetyl}-2,3-dihydro-1H-indol-5-yl)-7H-pyrrolo[2,3-d]pyrimidin-4-amine;

7-(3-methylbutyl)-5-(1-{[3-(trifluoromethyl)phenyl]acetyl}-2,3-dihydro-1H-indol-5-yl)-7H-pyrrolo[2,3-d]pyrimidin-4-amine;

4-{1-[(3-methylphenyl)acetyl]-2,3-dihydro-1H-indol-5-yl}-1H-pyrazolo[3,4-c]pyridin-3-amine;

7-chloro-3-{1-[(2,5-difluorophenyl)acetyl]-2,3-dihydro-1H-indol-5-yl}furo[3,2-c]pyridin-4-amine;

7-(3-azetidinyl)-5-(1-{[3-(trifluoromethyl)phenyl]acetyl}-2,3-dihydro-1H-indol-5-yl)-7H-pyrrolo[2,3-d]pyrimidin-4-amine;

7-(1-methyl-3-azetidinyl)-5-(1-{[3-(trifluoromethyl)phenyl]acetyl}-2,3-dihydro-1H-indol-5-yl)-7H-pyrrolo[2,3-d]pyrimidin-4-amine;

7-[2-(dimethylamino)ethyl]-5-(1-{[3-(trifluoromethyl)phenyl]acetyl}-2,3-dihydro-1H-indol-5-yl)-7H-pyrrolo[2,3-d]pyrimidin-4-amine;

5-(4-fluoro-1-{[3-(trifluoromethyl)phenyl]acetyl}-2,3-dihydro-1H-indol-5-yl)-7-methyl-7H-pyrrolo[2,3-d]pyrimidin-4-amine;

5-{4-fluoro-1-[(6-methyl-2-pyridinyl)acetyl]-2,3-dihydro-1H-indol-5-yl}-7-methyl-7H-pyrrolo[2,3-d]pyrimidin-4-amine;

5-(4-fluoro-1-{[6-(trifluoromethyl)-2-pyridinyl]acetyl}-2,3-dihydro-1H-indol-5-yl)-7-methyl-7H-pyrrolo[2,3-d]pyrimidin-4-amine;

5-{1-[(3,5-dimethyl-1H-pyrazol-1-yl)acetyl]-4-fluoro-2,3-dihydro-1H-indol-5-yl}-7-methyl-7H-pyrrolo[2,3-d]pyrimidin-4-amine;

5-(4-fluoro-1-{[4-fluoro-3-(trifluoromethyl)phenyl]acetyl}-2,3-dihydro-1H-indol-5-yl)-7-methyl-7H-pyrrolo[2,3-d]pyrimidin-4-amine;

3-{1-[(2,5-difluorophenyl)acetyl]-4-fluoro-2,3-dihydro-1H-indol-5-yl}furo[3,2-c]pyridin-4-amine;

5-{4-fluoro-1-[(4-fluorophenyl)acetyl]-2,3-dihydro-1H-indol-5-yl}-7-methyl-7H-pyrrolo[2,3-d]pyrimidin-4-amine;

4-(1-{[3-(trifluoromethyl)phenyl]acetyl}-2,3-dihydro-1H-indol-5-yl)-1H-pyrazolo[3,4-c]pyridin-3-amine;

1-methyl-4-(1-{[3-(trifluoromethyl)phenyl]acetyl}-2,3-dihydro-1H-indol-5-yl)-1H-pyrazolo[3,4-c]pyridin-3-amine;

7-(3-azetidinyl)-5-{1-[(2,5-difluorophenyl)acetyl]-2,3-dihydro-1H-indol-5-yl}-7H-pyrrolo[2,3-d]pyrimidin-4-amine;

7-[2-(4-piperidinyl)ethyl]-5-(1-{[3-(trifluoromethyl)phenyl]acetyl}-2,3-dihydro-1H-indol-5-yl)-7H-pyrrolo[2,3-d]pyrimidin-4-amine;

7-(2-aminoethyl)-3-{1-[(2,5-difluorophenyl)acetyl]-4-fluoro-2,3-dihydro-1H-indol-5-yl}furo[3,2-c]pyridin-4-amine;

3-{1-[(3,5-dimethyl-1H-pyrazol-1-yl)acetyl]-2,3-dihydro-1H-indol-5-yl}-1-methyl-1H-pyrazolo[3,4-d]pyrimidin-4-amine;

5-(1-{[3-(trifluoromethyl)phenyl]acetyl}-2,3-dihydro-1H-indol-5-yl)-1H-pyrrolo[2,3-d]pyrimidin-4-amine;

5-{4-chloro-1-[(6-methyl-2-pyridinyl)acetyl]-2,3-dihydro-1H-indol-5-yl}-7-methyl-7H-pyrrolo[2,3-d]pyrimidin-4-amine; and 5-(4-chloro-1-{[6-(trifluoromethyl)-2-pyridinyl]acetyl}-2,3-dihydro-1H-indol-5-yl)-7-methyl-7H-pyrrolo[2,3-d]pyrimidin-4-amine;

or a salt thereof including a pharmaceutically acceptable salt thereof.

6. A pharmaceutical composition comprising a compound of Formula (I) according to claim 1 or a pharmaceutically acceptable salt thereof and a pharmaceutically acceptable excipient.

7. The method of inhibiting PERK activity in a human in need thereof, which comprises administering to such human a therapeutically effective amount of a compound of Formula I, as described in claim 1 or a pharmaceutically acceptable salt thereof.

8. A process for preparing a pharmaceutical composition containing a pharmaceutically acceptable excipient and an effective amount of a compound of Formula (I) as described in claim 1 or a pharmaceutically acceptable salt thereof, which process comprises bringing the compound of Formula (I) or a pharmaceutically acceptable salt thereof into association with a pharmaceutically acceptable excipient.

9. The compound:
5-{4-fluoro-1-[(6-methyl-2-pyridinyl)acetyl]-2,3-dihydro-1H-indol-5-yl}-7-methyl-7H-pyrrolo[2,3-d]pyrimidin-4-amine;
or a pharmaceutically acceptable salt thereof.

10. The compound:
5-(4-fluoro-1-{[6-(trifluoromethyl)-2-pyridinyl]acetyl}-2,3-dihydro-1H-indol-5-yl)-7-methyl-7H-pyrrolo[2,3-d]pyrimidin-4-amine;
or a pharmaceutically acceptable salt thereof.

11. The compound:
5-{1-[(3,5-dimethyl-1H-pyrazol-1-yl)acetyl]-4-fluoro-2,3-dihydro-1H-indol-5-yl}-7-methyl-7H-pyrrolo[2,3-d]pyrimidin-4-amine;
or a pharmaceutically acceptable salt thereof.

12. The compound:
7-methyl-5-(1-{[3-(trifluoromethyl)phenyl]acetyl}-2,3-dihydro-1H-indol-5-yl)-7H-pyrrolo[2,3-d]pyrimidin-4-amine;
or a pharmaceutically acceptable salt thereof.

13. A method of treating or lessening the severity of a disease selected from: Alzheimer's disease, stroke, Parkinson disease, Huntington's disease, and amyotrophic lateral sclerosis, in a mammal in need thereof, which comprises administering to such mammal a therapeutically effective amount of a compound of Formula I, as described in claim 1 or a pharmaceutically acceptable salt thereof.

14. A method of treating or lessening the severity of a disease selected from: Alzheimer's disease, stroke, Parkinson disease, Huntington's disease, and amyotrophic lateral sclerosis, in a mammal in need thereof, which comprises administering to such mammal a therapeutically effective amount of the compound of claim 9 or a pharmaceutically acceptable salt thereof.

15. A method of treating or lessening the severity of a disease selected from: Alzheimer's disease, stroke, Parkinson disease, Huntington's disease, and amyotrophic lateral sclerosis, in a mammal in need thereof, which comprises administering to such mammal a therapeutically effective amount of the compound of claim 10 or a pharmaceutically acceptable salt thereof.

16. A method of treating or lessening the severity of a disease selected from: Alzheimer's disease, stroke, Parkinson disease, Huntington's disease, and amyotrophic lateral sclerosis, in a mammal in need thereof, which comprises administering to such mammal a therapeutically effective amount of the compound of claim 10 or a pharmaceutically acceptable salt thereof.

17. A method of treating or lessening the severity of a disease selected from: Alzheimer's disease, stroke, Parkinson disease, Huntington's disease, and amyotrophic lateral sclerosis, in a mammal in need thereof, which comprises administering to such mammal a therapeutically effective amount of the compound of claim 12 or a pharmaceutically acceptable salt thereof.

* * * * *